US008518000B2

(12) United States Patent
Gray et al.

(10) Patent No.: US 8,518,000 B2
(45) Date of Patent: Aug. 27, 2013

(54) ADHESIVE AND PERIPHERAL SYSTEMS AND METHODS FOR MEDICAL DEVICES

(75) Inventors: Larry B. Gray, Merrimack, NH (US); Eric Yeaton, Epsom, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 744 days.

(21) Appl. No.: 12/395,215

(22) Filed: Feb. 27, 2009

(65) Prior Publication Data

US 2012/0209207 A1      Aug. 16, 2012

Related U.S. Application Data

(63) Continuation of application No. 11/704,886, filed on Feb. 9, 2007, and a continuation of application No. 11/704,899, filed on Feb. 9, 2007, now Pat. No. 8,414,522, and a continuation of application No. 11/704,896, filed on Feb. 9, 2007, and a continuation of application No. 11/704,897, filed on Feb. 9, 2007, now Pat. No. 8,113,244.

(60) Provisional application No. 60/772,313, filed on Feb. 9, 2006, provisional application No. 60/789,243, filed on Apr. 5, 2006, provisional application No. 60/793,188, filed on Apr. 19, 2006, provisional application No. 60/889,007, filed on Feb. 9, 2007.

(51) Int. Cl.
    *A61M 5/32*          (2006.01)
(52) U.S. Cl.
    USPC .......................................... 604/272

(58) Field of Classification Search
    USPC ................................... 604/131, 151, 506, 272
    See application file for complete search history.

(56) References Cited

U.S. PATENT DOCUMENTS

| | | | | | |
|---|---|---|---|---|---|
| 6,093,172 | A  * | 7/2000 | Funderburk et al. | .......... | 604/135 |
| 6,283,943 | B1 * | 9/2001 | Dy et al. | .......... | 604/141 |
| 6,293,925 | B1 * | 9/2001 | Safabash et al. | .......... | 604/136 |
| 6,699,218 | B2 * | 3/2004 | Flaherty et al. | .......... | 604/131 |
| 6,740,059 | B2 * | 5/2004 | Flaherty | .......... | 604/67 |
| 6,749,587 | B2 * | 6/2004 | Flaherty | .......... | 604/151 |
| 6,945,760 | B2 * | 9/2005 | Gray et al. | .......... | 417/417 |
| 7,018,360 | B2 * | 3/2006 | Flaherty et al. | .......... | 604/123 |
| 7,544,185 | B2 * | 6/2009 | Bengtsson | .......... | 604/173 |
| 2006/0253085 | A1 * | 11/2006 | Geismar et al. | .......... | 604/272 |

(Continued)

OTHER PUBLICATIONS

U.S. Appl. No. 12/347,981, filed Dec. 31, 2008.

(Continued)

*Primary Examiner* — Nicholas Lucchesi
*Assistant Examiner* — Diva K Chander
(74) *Attorney, Agent, or Firm* — Michelle Saquet Temple

(57) ABSTRACT

A repeater system may control a pump by using a repeater and a user interface. An adhesive patch system may be used for affixing a pump or other object to a human body. Such an adhesive patch system may include two sets of adhesive members, each member including an adhesive material on at least one side so as to attach to the body. The members of the first set are spaced to allow the members of the second set to attach to the body in spaces provided between the members of the first set, and the members of the second set are spaced to allow members of the first set to detach from the body without detaching the members of the second set. Also, fill stations and base stations are provided for personal pump systems.

14 Claims, 155 Drawing Sheets

(56) References Cited

U.S. PATENT DOCUMENTS

2007/0049865 A1* 3/2007 Radmer et al. ............ 604/93.01
2007/0197889 A1* 8/2007 Brister et al. ................ 600/347
2008/0097381 A1* 4/2008 Moberg et al. ............... 604/506

OTHER PUBLICATIONS

U.S. Appl. No. 12/395,284, filed Feb. 27, 2009.
U.S. Appl. No. 12/395,000, filed Feb. 27, 2009.
U.S. Appl. No. 12/395,339, filed Feb. 27, 2009.
U.S. Appl. No. 12/395,036, filed Feb. 27, 2009.
U.S. Appl. No. 12/429,451, filed Apr. 24, 2009.
U.S. Appl. No. 12/395,098, filed Feb. 27, 2009.
U.S. Appl. No. 12/429,464, filed Apr. 24, 2009.
U.S. Appl. No. 12/395,128, filed Feb. 27, 2009.
U.S. Appl. No. 12/429,590, filed Apr. 24, 2009.
U.S. Appl. No. 12/395,148, filed Feb. 27, 2009.
U.S. Appl. No. 12/429,612, filed Apr. 24, 2009.
U.S. Appl. No. 12/395,168, filed Feb. 27, 2009.
U.S. Appl. No. 12/560,102, filed Sep. 15, 2009.
U.S. Appl. No. 12/395,193, filed Feb. 27, 2009.
U.S. Appl. No. 12/837,193, filed Jul. 15, 2010.
U.S. Appl. No. 12/394,944, filed Feb. 27, 2009.
U.S. Appl. No. 12/981,283, filed Dec. 29, 2010.
U.S. Appl. No. 12/395,258, filed Feb. 27, 2009.
U.S. Appl. No. 13/011,384, filed Jan. 21, 2011

* cited by examiner

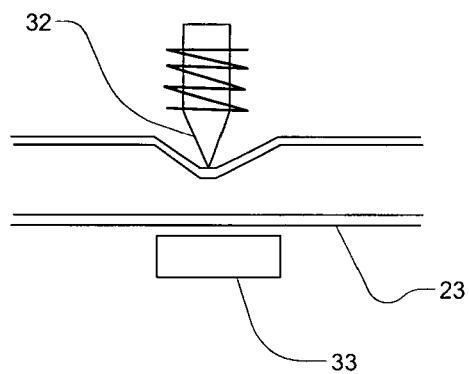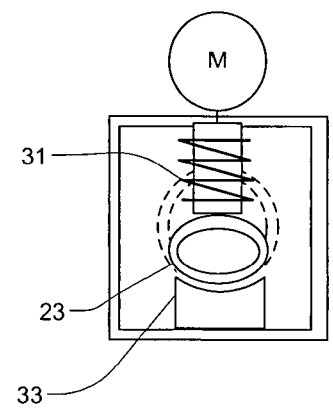
FIG. 22
FIG. 23

| FIG. 70A | FIG. 70B |
|---|---|
| FIG. 70C | FIG. 70D |

FIG. 70

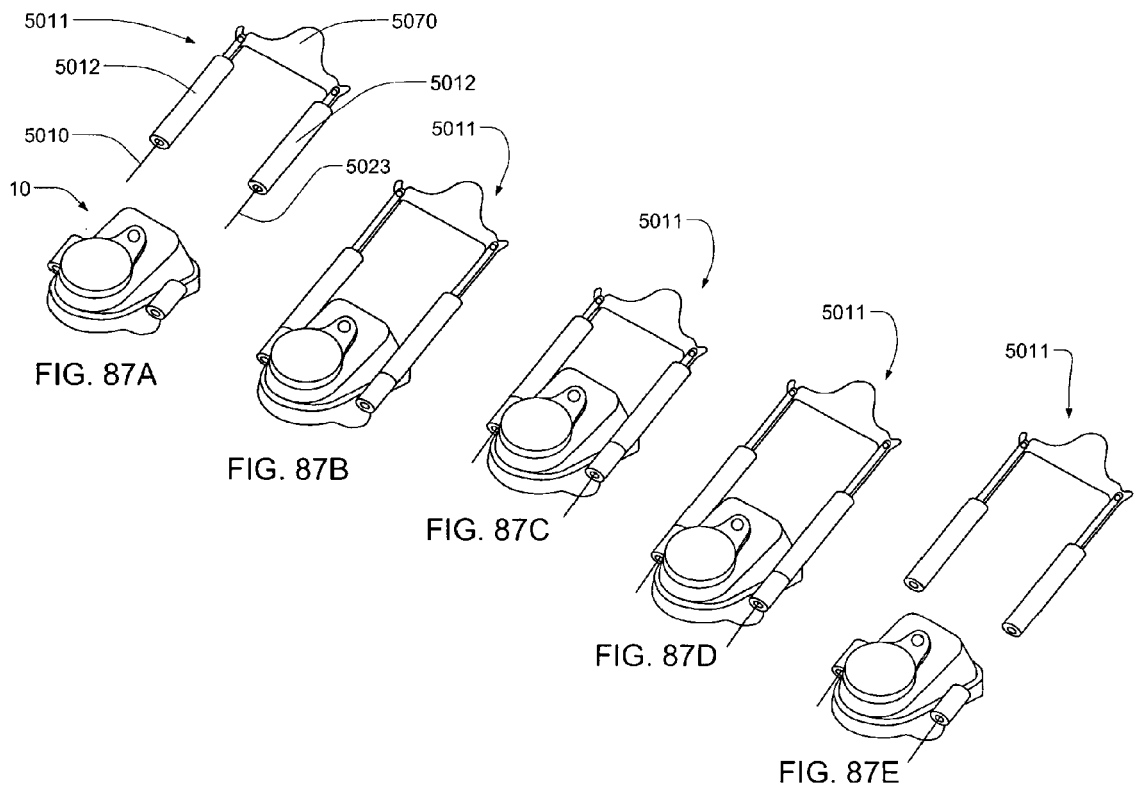

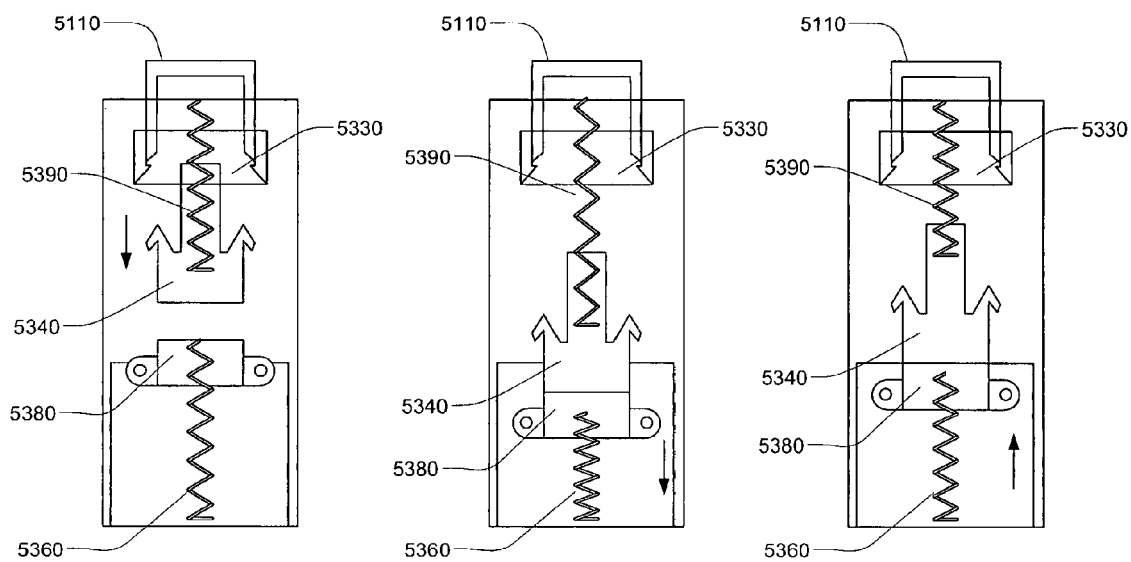

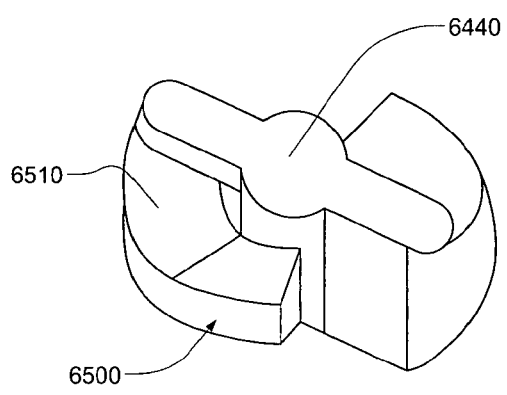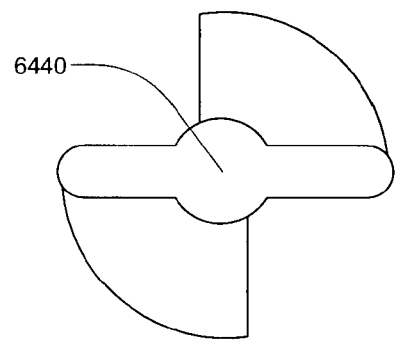
FIG. 103A                    FIG. 103B

ADHESIVE AND PERIPHERAL SYSTEMS AND METHODS FOR MEDICAL DEVICES

CROSS REFERENCE TO RELATED APPLICATIONS

This application is a continuation of U.S. patent application Ser. No. 11/704,886, filed on 09 Feb. 2007, the entire disclosure of which is incorporated herein by reference.

This application also claims the benefit of the following U.S. Provisional Patent Applications, all of which are herein incorporated by reference in their entireties:

Ser. No. 60/772,313 for "Portable Injection System" filed Feb. 9, 2006;

Ser. No. 60/789,243 for "Method of Volume Measurement for Flow Control" filed Apr. 5, 2006;

Ser. No. 60/793,188 for "Portable Injection and Adhesive System" filed Apr. 19, 2006; and Ser. No. 60/889,007 for "Two-Stage Transcutaneous Inserter" filed Feb. 9, 2007.

This application is also a Continuation of the following U.S. Application Serial Numbers, all of which are herein incorporated by reference in their entireties:

Ser. No. 11/704,899 for "Fluid Delivery Systems and Methods" filed Feb. 9, 2007; now U.S. Pat. No. 8,414,522

Ser. No. 11/704,896 for "Pumping Fluid Delivery Systems and Methods Using Force Application Assembly" filed Feb. 9, 2007; and Ser. No. 11/704,897 for "Adhesive and Peripheral Systems and Methods for Medical Devices" filed Feb. 9, 2007 now U.S. Pat. No. 8,113,244.

FIELD OF THE INVENTION

This application relates generally to adhesive and peripheral systems and methods for medical devices.

BACKGROUND

Many potentially valuable medicines or compounds, including biologicals, are not orally active due to poor absorption, hepatic metabolism or other pharmacokinetic factors. Additionally, some therapeutic compounds, although they can be orally absorbed, are sometimes required to be administered so often it is difficult for a patient to maintain the desired schedule. In these cases, parenteral delivery is often employed or could be employed.

Effective parenteral routes of drug delivery, as well as other fluids and compounds, such as subcutaneous injection, intramuscular injection, and intravenous (IV) administration include puncture of the skin with a needle or stylet. Insulin is an example of a therapeutic fluid that is self-injected by millions of diabetic patients. Users of parenterally delivered drugs would benefit from a wearable device that would automatically deliver needed drugs/compounds over a period of time.

To this end, there have been efforts to design portable devices for the controlled release of therapeutics. Such devices are known to have a reservoir such as a cartridge, syringe, or bag, and to be electronically controlled. These devices suffer from a number of drawbacks including the malfunction rate. Reducing the size, weight and cost of these devices is also an ongoing challenge.

SUMMARY OF THE INVENTION

In one embodiment of the invention, a repeater system is provided for controlling a medical device. Such a system may include a repeater and a user interface. The repeater may include circuitry (i) for, over a given range, receiving signals from at least one wearable medical device, (ii) for, over the given range, transmitting signals to the wearable medical device, (iii) for, over a longer range exceeding the given range, transmitting the received signals to a user interface located remotely from the patient, and (iv) for, over the longer range, receiving signals from the user interface. The user interface may include circuitry (i) for receiving signals from the repeater, and (ii) for transmitting signals to the repeater. The medical devices may be wearable or implanted devices.

In some embodiments, the user interface's circuitry may also provide for the reception of signals directly from the wearable device and the transmission of signals directly to the wearable device. Also, the repeater's circuitry may be adapted to receive signals from multiple medical devices.

In some embodiments, the repeater may include one or more of the following: memory for logging received data, a processor for analyzing received data for the presence of a fault condition, and an alarm for notifying a user of the presence of a fault condition. The fault condition may include an occurrence of an event wherein the repeater is separated from the wearable medical device by more than the given range.

In one embodiment of the invention, a repeater is adapted to control a patch-sized pump worn on a subject for delivering fluid to the subject. In this embodiment, the repeater may have circuitry (i) for, over a given range, receiving signals from the pump, the received signals containing data relating to a volume of fluid delivered by the pump and relating to an alarm condition, and (ii) for, over a longer range exceeding the given range, transmitting the received signals to an interface for monitoring the volume of fluid delivered and the alarm condition. Such a repeater's circuitry may also provide for, over the longer range, receiving control signals from the interface, the control signals containing control information for controlling the pump, and for, over the given range, transmitting the control signals to the pump.

Such a repeater may have the characteristics of the repeater described above in connection with the repeater system. In addition to or in instead of having an alarm for an occurrence of an event wherein the repeater is separated from the wearable medical device by more than the given range, the repeater may also include an alarm for a flow occlusion or an air bubble detected in the pump.

In another embodiment of the invention, an adhesive patch system is provided for affixation of an object to a human body. Such an adhesive patch system may include two sets of adhesive members. In a first set of three or more members, each member includes an adhesive material on at least one side so as to attach to the body upon application of pressure, the members disposed around a central region. Similarly, in the second set of three or more members, each member includes an adhesive material on at least one side so as to attach to the body upon application of pressure, the members disposed around the central region. The members of the first set are spaced to allow the members of the second set to attach to the body in spaces provided between the members of the first set, and the members of the second set are spaced to allow members of the first set to detach from the body without detaching the members of the second set.

In one embodiment of the adhesive patch system at least one member is perforated so as to allow facile tearing off of the member. Tearing off of the member may relieve irritation of the underlying skin. Also, the central region is adapted to secure a wearable medical device. The adhesive patch may be semicircular. The adhesive patch may include a peelable backing strip. The members of the adhesive patch system may be attached to the central region by a fiber. The members of the first set may be a first color while the members of the second set may be a second color different from the first color.

Such an adhesive patch system may be used to attach an object to a human body by a method that includes the steps of: providing the first set of three or more members (each member of which, as noted above, includes an adhesive material on at least one side so as to attach to the body upon application of pressure, the members being disposed around a central region); attaching the first set of members to the body so that spaces are left between each of the members, so as to hold the object against the body; providing a second set of three or more members (each member of which includes an adhesive material on at least one side so as to attach to the body upon application of pressure, the members being disposed around the central region); attaching the second set of members to the body in the spaces between the members of the first set, so as to hold the object against the body with the second set of members; and after attaching the second set of members to the body, removing the first set of members from the body.

The object being attached may be a pump for therapeutic of fluid to the body through the skin. A cannula of such a pump may be passed through the skin to permit delivery of the fluid from the pump through the skin. In a preferred embodiment of the method, the cannula is not moved and is left passing through the skin while the second set of members is attached to the body and while the first set of members is removed from the body.

Similarly, the object being attached may be a probe for measuring a parameter in the body through the skin. Such a probe may be passed through the skin. In a preferred embodiment of the method, the probe is not moved and is left passing through the skin while the second set of members is attached to the body and while the first set of members is removed from the body.

The object being attached in such an adhesive patch system may be provided with air passages to permit airflow to the body under the object when the object is attached to the body.

An alternative adhesion system for affixing an object to a human body includes a central member adapted to secure a wearable object and having an adhesive material on at least one side so as to attach to the body upon application of pressure, and includes a plurality of peripheral members, each member including an adhesive material on at least one side so as to attach to the body upon application of pressure, wherein fibrous connectors are provided for connecting each of the peripheral members to the central member. In a preferred embodiment, the fibrous connectors are elastic.

In one embodiment of the invention, a method is provided for filling a reservoir with a liquid therapeutic. Such a method may include providing a fill station having a substantially rigid fill-station base for holding the reservoir at a tilt, and a substantially rigid fill-station cover attached to the fill-station base. The fill-station cover has a filling aperture for receiving fluid from a syringe. The fill-station cover and the fill-station base define a volume so as to prevent over-filling of the reservoir. Such a method also includes placing a reservoir in the fill station, closing the fill-station cover over the reservoir, applying a syringe containing the liquid therapeutic to the filling aperture, and ejecting the liquid therapeutic from the syringe through the filling aperture into the reservoir. In a preferred embodiment, any air in the reservoir after the ejection step is removed. A window may be provided in the fill station cover to view the amount of liquid in the reservoir. The amount of liquid may be estimated by comparing the liquid level viewed through the window to a fluid-level indicia.

In one embodiment of the invention, a base station is provided for a patch-sized infusion device, wherein the infusion device includes a disposable portion and a reusable portion, and the disposable portion and the reusable portion are connectable to each other via an attachment mechanism associated with the reusable portion. The base station includes a receptacle for holding the reusable portion of the infusion device, the receptacle including a member for cooperating with the reusable portion's attachment mechanism. The base station may also include a recharger for recharging a battery in the reusable portion. The base station may also include a communication interface between a separate computer and the reusable portion, in order to upload information to or download information from the reusable portion.

These aspects of the invention are not meant to be exclusive and other features, aspects, and advantages of the present invention will be readily apparent to those of ordinary skill in the art when read in conjunction with the appended claims and accompanying drawings.

BRIEF DESCRIPTION OF THE DRAWINGS

The foregoing features of the invention will be more readily understood by reference to the following detailed description, taken with reference to the accompanying drawings, in which:

FIGS. 22 and 23 show pumping mechanisms employing a finger;

FIGS. 87A-87E shows a sequence of an embodiment of the infusion and sensor assembly being inserted into a device;

FIGS. 92A-92F schematically shows a temporal sequence for the operation of one embodiment of an inserter mechanism;

FIG. 103A shows a perspective view of a cam guide for use in assembling a fluid delivery device;

FIG. 103B shows a top view of the cam guide of FIG. 103A;

FIG. 107 shows a reservoir filling station in accordance with one embodiment;

FIGS. 108A-108B shows an embodiment of a reservoir filling station in both the open (108A) an closed (108B) positions;

FIG. 109A shows a block diagram of one embodiment of a data acquisition and control scheme for an embodiment of the fluid delivery system;

FIG. 109B shows a block diagram of one embodiment of a data acquisition and control scheme for an embodiment of the fluid delivery system FIG. 110A shows a flow chart describing the operation of a fluid delivery device according to one embodiment;

FIG. 110B shows a flow chart describing the operation of a fluid delivery device according to one embodiment;

FIG. 111 shows a block diagram of a user interface and fluid delivery component in wireless communication with each other;

FIG. 112 shows a data flow diagram showing the use of an intermediate transceiver in accordance with one embodiment;

FIG. 113 shows a block diagram for an intermediate transceiver in accordance with one embodiment;

FIG. 114 shows a data flow diagram for a universal patient interface in accordance with one embodiment;

FIG. 115 shows a non-disposable portion of the fluid delivery device and a battery recharger in an uncoupled state in accordance with one embodiment;

FIG. 116 shows the non-disposable portion of the fluid delivery device and battery recharger of FIG. 115 in a docked state in accordance with one embodiment; and FIG. 117 is a flowchart depicting a process for measuring the volume of liquid delivered in a pump stroke, in accordance with an embodiment of the invention.

Figure 1:
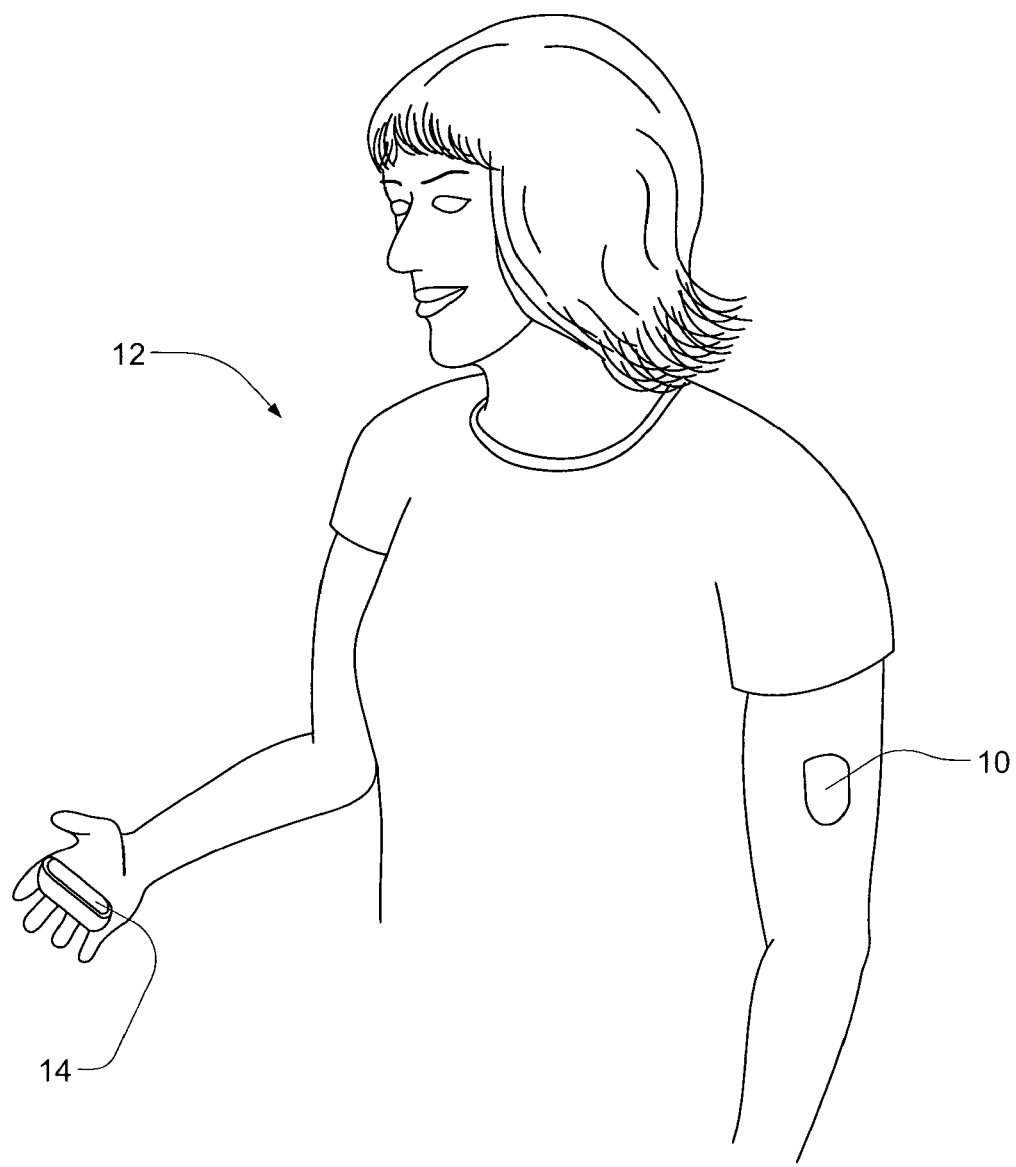
FIG. 1 depicts a patient with a patch and a wireless handheld user interface assembly.

It should be noted that the foregoing figures and the elements depicted therein are not necessarily drawn to a consistent scale or to any scale.

DETAILED DESCRIPTION OF SPECIFIC EMBODIMENTS

Definitions. As used in this description and the accompanying claims, the following terms shall have the meanings indicated, unless the context otherwise requires: A "user input" of a device includes any mechanism by which a user of the device or other operator can control a function of the device. User inputs may include mechanical arrangements (e.g., switches, pushbuttons), wireless interfaces for communication with a remote controller (e.g., RF, infrared), acoustic interfaces (e.g., with speech recognition), computer network interfaces (e.g., USB port), and other types of interfaces.

A "button" in the context of a user input such as the so-called "bolus button" discussed below may be any type of user input capable of performing a desired function, and is not limited to a pushbutton.

An "alarm" includes any mechanism by which an alert can be generated to a user or third party. Alarms may include audible alarms (e.g., a speaker, a buzzer, a speech generator), visual alarms (e.g., an LED, an LCD screen), tactile alarms (e.g., a vibrating element), wireless signals (e.g., a wireless transmission to a remote controller or caretaker), or other mechanism. Alarms may be generated using multiple mechanisms simultaneously, concurrently, or in a sequence, including redundant mechanisms (e.g., two different audio alarms) or complementary mechanisms (e.g., an audio alarm, a tactile alarm, and a wireless alarm).

"Fluid" shall mean a substance, a liquid for example, that is capable of flowing through a flow line.

"Impedance" shall mean the opposition of a device or flow line to the flow of fluid therethrough.

"Wetted" describes a component that comes into direct contact with the fluid during normal fluid delivery operations. Since a fluid is not limited to a liquid, a "wetted" component will not necessarily become wet.

A "patient" includes a person or animal who receives fluid from a fluid delivery device, whether as part of a medical treatment or otherwise.

"Cannula" shall mean a disposable device capable of infusing fluid to a patient. A cannula as used herein can refer to a traditional cannula or to a needle.

"Analyte sensor" shall mean any sensor capable of determining the presence of an analyte in a patient. The embodiments of analyte sensors include, but are not limited to, sensors capable of determining the presence of any viral, parasitic, bacterial or chemical analyte. The term analyte includes glucose. An analyte sensor may communicate with other components within the fluid delivery device (e.g., a controller in a non-disposable portion) and/or with a remote controller.

"Dispensing assembly sensor" shall mean a mechanism for determining the volume of fluid present in the dispensing chamber.

A "sharp" shall mean anything that is capable of puncturing or poking an animal's skin, especially a human's skin. A Sharp may include a cannula, a cannula insertion device, an analyte sensor, or an analyte sensor insertion device. Sharps may be provided individually or may be provided together, for example, in a cartridge.

"Disposable" refers to a part, device, portion or other that is intended to be used for a fixed duration of time, then discarded and replaced.

"Non-disposable" refers to a reusable portion that is intended to have an open-ended duration of use.

"Patch-sized" shall mean of a size sufficiently small as to be secured, by means such as adhesive or straps, to the skin of a patient and worn as a medical device over a course of administration of substance contained within the device. A medical device small enough to function as an implant is within the scope of this definition.

"Normally present finite fluid impedance" shall mean a finite fluid impedance that is present in the routine course of fluid delivery, i.e., when a fault condition (e.g., an occlusion) is absent.

A "passive" impedance is one that is not actively controlled during a pumping cycle.

"Acoustic volume measurement" shall mean quantitative measurement of a relevant volume using acoustical techniques such as described in U.S. Pat. Nos. 5,349,852 and 5,641,892, as well as the techniques described herein.

A "temperature sensor" includes any mechanism for measuring temperature and communicating temperature information to a controller. The device may include one or more temperature sensors for measuring such things as skin temperature, AVS temperature, ambient temperature, and fluid temperatures.

Embodiments of the device, pumping mechanism, system and methods described herein relate to fluid delivery including pumping and volume measurement of fluid as well as the actuation and control of same. Embodiments of the device include a portable or non-portable device for fluid delivery. Some embodiments of the device include a base portion that is disposable and a top portion that is non-disposable. The device includes embodiments where an infusion device is inserted through the base portion and directly into a patient. These device embodiments are patch pump devices. The patch pump may be adhered to the patient using an adhesive, a strap, or other suitable arrangement. The adhesive may have a protective peelable strip which may be removed to expose the adhesive prior to use.

However, in other embodiments, the fluid delivery device is a portable device where tubing is connected to a fluid line. The tubing is typically connected to a patient through a cannula.

In some embodiments where a disposable base and non-disposable top are implemented, the base portion includes parts that are wetted, while the parts included in the non-disposable top portion are typically non-wetted parts.

Various embodiments of the pumping mechanism include an upstream inlet valve, a pumping actuation member, a downstream exit valve and a moveable member. In some embodiments, the pumping actuation member and downstream valve functions are implemented using the same device. The pumping mechanism pumps fluid from a reservoir through a fluid line to an exit. The pumping mechanism is typically employed with a non-pressurized reservoir, however, the scope of the present invention is not limited accordingly.

In one embodiment of the fluid delivery system, the device includes an analyte sensor housing. An analyte sensor is introduced into the patient through the analyte sensor housing of the base portion of the device. In these embodiments, an infusion device is also introduced through a cannula housing on the base portion of the device. In these embodiments, the device is worn by the user as a patch pump.

The system typically includes a controller, which may include a wireless transceiver. Thus, the device may be controlled exclusively or in part through a wireless controller device. The controller device may receive information through wireless communication from the analyte sensor and/or the fluid delivery device. The patient or a third party can control the function of the fluid delivery device using the controller device.

In one embodiment of the fluid delivery device, the device is an insulin pump and the analyte sensor is a blood glucose sensor. The controller, receiving information relating both to the volume of insulin delivered (or the number of pump strokes over time) and blood glucose data, assists the user in programming the actuation schedule for the pump mechanism.

An exemplary dispensing assembly and volume sensing device is described herein. The dispensing assembly includes at least one microphone and a loudspeaker. The assembly determines the volume change in a dispensing chamber to determine the volume of fluid pumped. The volume sensing data is used to determine the status of the fluid delivery device. Thus, various controls may rely on the volume sensing data.

In an embodiment of the invention, a user configures the fluid-delivery device via a user interface in order to cause the fluid-delivery device to deliver a fluid in an appropriate manner. In one embodiment, the user interface resides on a separate hand-held user-interface assembly that may communicate wirelessly with the patch. The patch may be disposable, or partially disposable.

An exemplary use of embodiments of the device is for the delivery of insulin to diabetic patients, but other uses include delivery of any fluid, as described above. Fluids include analgesics to those in pain, chemotherapy to cancer patients and enzymes to patients with metabolic disorders. Various therapeutic fluids may include small molecules, natural products, peptide, proteins, nucleic acids, carbohydrates, nanoparticulate suspensions, and associated pharmaceutically acceptable carrier molecules. Therapeutically active molecules may be modified to improve stability in the delivery device (e.g., by pegylation of peptides or proteins). Although illustrative embodiments herein describe drug-delivery applications, embodiments may be used for other applications including liquid dispensing of reagents for high throughput analytical measurements such as lab-on-chip applications and capillary chromatography. For purposes of description below, terms "therapeutic" or "fluid" are used interchangeably, however, in other embodiments, any fluid, as described above, can be used. Thus, the device and description included herein are not limited to use with therapeutics.

Typical embodiments include a reservoir for holding a supply of fluid. In the case of insulin, the reservoir may be conveniently sized to hold an insulin supply sufficient for delivery over one or more days. For example, a reservoir may hold about 1 to 2 ml of insulin. A 2 ml insulin reservoir may correspond to about 3 days supply for about 90% of potential users. In other embodiments, the reservoir can be any size or shape and can be adapted to hold any amount of insulin or other fluid. In some embodiments, the size and shape of the reservoir is related to the type of fluid the reservoir is adapted to hold. The fluid reservoir may be eccentrically or irregularly shaped and/or may be keyed in order to deter incorrect installation or usage.

Some embodiments of the fluid delivery device are adapted for use by diabetics, thus, in these embodiments, the device delivers insulin which supplements or replaces the action of the patient's pancreatic islet beta cells. Embodiments adapted for insulin delivery seek to mimic the action of the pancreas by providing both a basal level of fluid delivery as well as bolus levels of delivery. Basal levels, bolus levels and timing can be set by the patient or another party by using a wireless handheld user interface. Additionally, basal and/or bolus levels can be triggered or adjusted in response to the output of an integral or external analyte sensor, such as a glucose monitoring device or blood glucose sensor. In some embodiments, a bolus can be triggered by a patient or third party using a designated button or other input means located on the fluid-delivery device. In still other embodiments, the bolus or basal can be programmed or administered through a user interface located on the fluid delivery device.

FIG. 1 shows a patient 12 wearing a fluid-delivery device 10 and holding a wireless user interface assembly 14 for monitoring and adjusting operation of the fluid-delivery device 10, in accordance with an exemplary embodiment of the present invention. The user interface assembly 14 typically includes apparatus for entering information (such as touch-screen or keypad) and for transmitting information to the user (such as an LCD display, a speaker or a vibrating alarm). The fluid delivery device is typically small and lightweight enough to remain comfortably adhered to the patient for several days.

The fluid delivery device 10 is shown worn on the arm of a patient 12 in FIG. 1. In other embodiments, the fluid-delivery device 10 may be worn at other positions on the patient where the particular fluid being delivered can be utilized advantageously by the patient's body. For example, fluid may be delivered advantageously to the patient's abdominal area, kidney area, leg or otherwise.

Figure 2A:
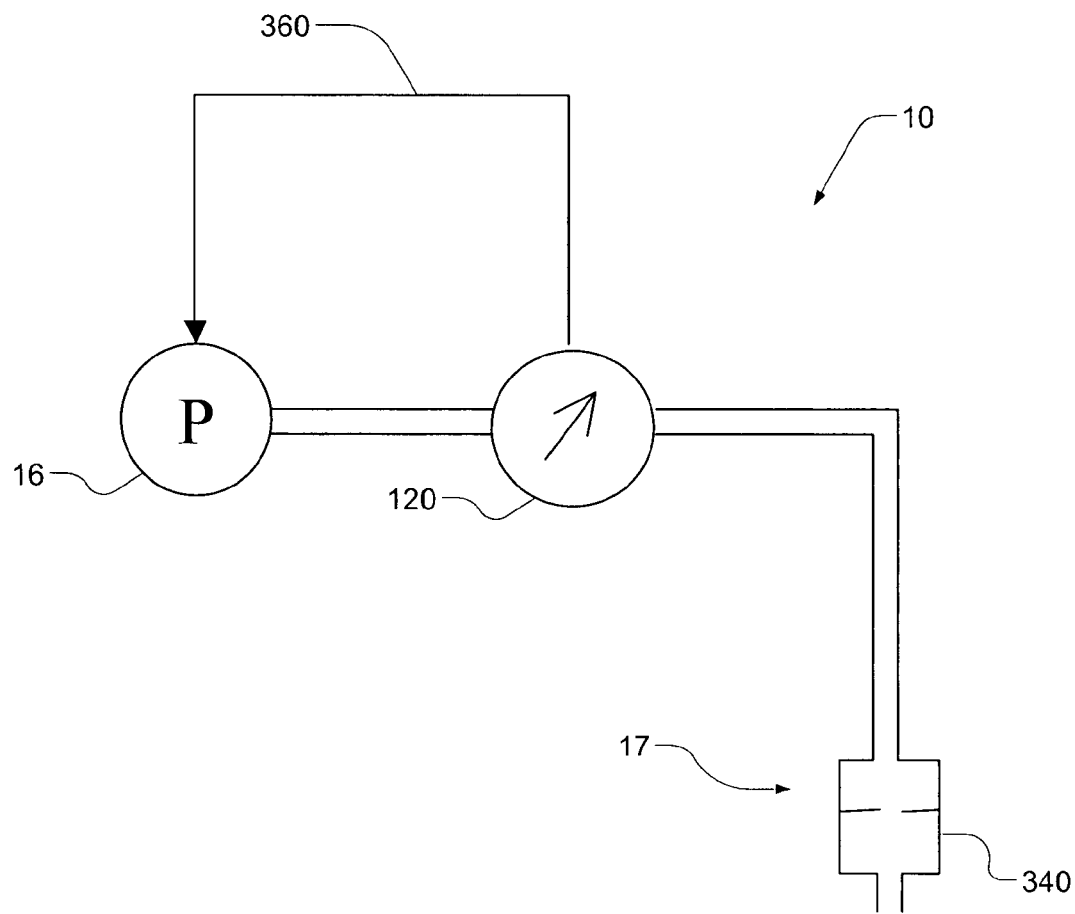
FIG. 2A is a schematic diagram of a fluid-delivery device with feedback control.
Figure 2B:
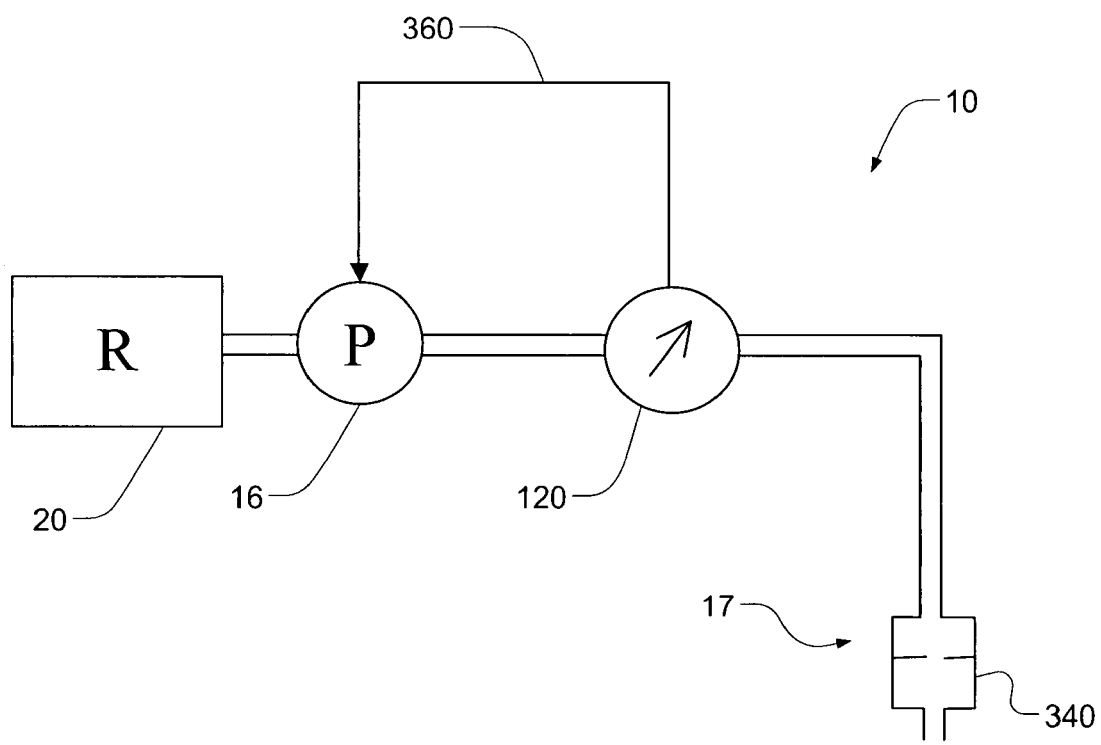
FIG. 2B is a schematic diagram of a fluid-delivery device with feedback control and a reservoir.

Referring now to FIG. 2A, a schematic representation of a fluid delivery device 10 having a feedback loop 360 from a dispensing assembly 120 to a pumping assembly 16 is shown. The pumping assembly 16 pumps fluid to the dispensing assembly 120; the fluid then exits through an exit assembly 17, which includes a flow restrictor 340 and an output. The output typically includes a cannula and leads to a patient. The dispensing assembly 120 may include a resilient, variable-volume dispensing chamber and at least one microphone and a loudspeaker for measuring parameters related to flow through the output over time. The feedback loop 360 allows adjustment of the operation of the pumping assembly 16 based on repeated measurements made by the sensor. The flow restrictor 340 creates high impedance between the dispensing assembly 120 and the output of the flow line 5010. The flow restrictor 340 could be, for example, a section of narrow-bore tubing or microtubing. Referring now to FIG. 2B, in one embodiment, the pumping assembly 16 pumps fluid from a reservoir 20 to a dispensing assembly 120.

Figure 3:
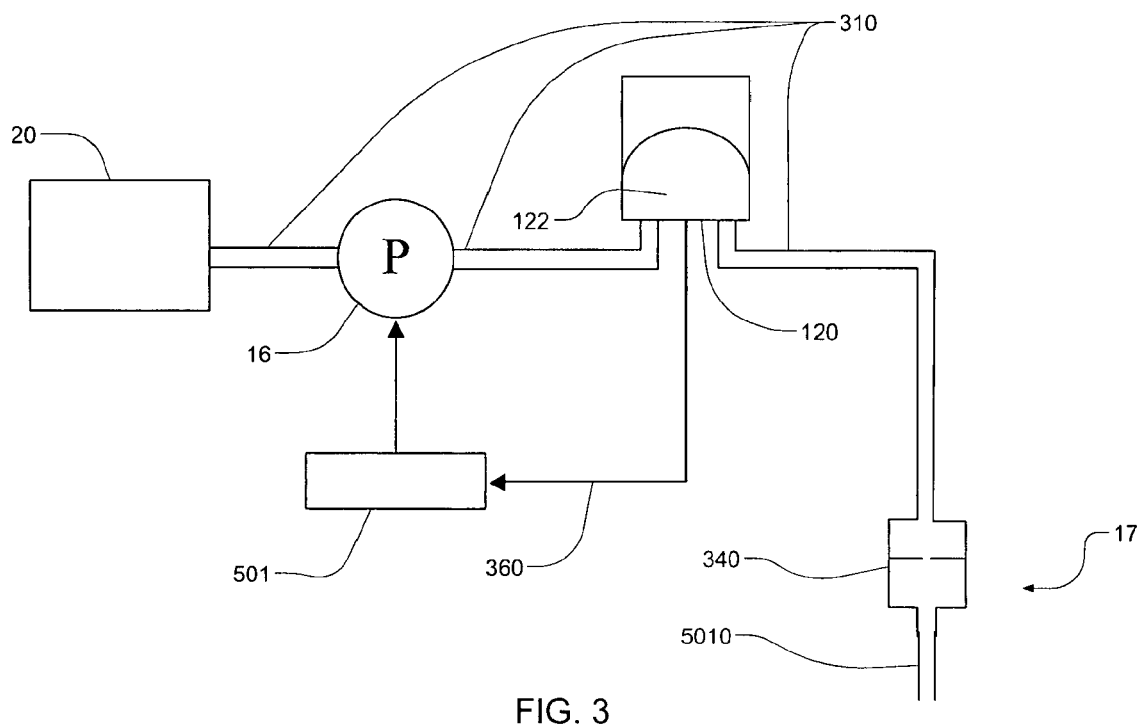
FIG. 3 is a schematic diagram of a fluid-delivery device having an un-pressurized reservoir.

Referring now to FIG. 3, a block diagram of a further embodiment employing fluidic principles is shown. A flow line 310 couples a reservoir 20, a pumping assembly 16, a dispensing assembly 120, and an exit assembly 17. The exit assembly 17 may include a high impedance flow restrictor 340 and an infusion device 5010—for example, a cannula. The output of the flow restrictor 340 is sent to the infusion device 5010 for delivery to a patient. The flow restrictor 340 has a higher flow impedance than that of the portion of the flow line 310 upstream of the dispensing assembly 120. Therefore, the pumping assembly 16 is capable of pumping fluid into the dispensing assembly 120 faster than the fluid can exit the exit assembly 17. The dispensing assembly 120 may include a variable volume dispensing chamber 122 having a resilient wall. In embodiments presented below, the resilient wall is a membrane. Examples of membrane materials include silicone, NITRILE, and any other material having desired resilience and properties for functioning as described herein. Additionally, other structures could serve the same purpose. Upon receiving a charge of fluid as a result of the action of the pumping assembly 16, the resilience of the membrane will allow the chamber 122 to first expand and then to provide the delivery pressure required to drive the fluid contents of the dispensing assembly 120 past the flow restrictor 340 to a patient. When equipped with an appropriate sensor (examples of which are described below), the dispensing assembly 120 may measure fluid flow through the variable volume dispensing chamber 122 and may provide feedback through the feedback loop 360 to control the timing and/or rate at which the pumping assembly 16 pumps or partially fills the dispensing chamber 122, thereby delivering a desired dose at a desired rate to a patient.

Referring again to FIG. 3, additionally, the flow restrictor 340 prevents fluid flow above a specified flow rate. Furthermore, since pressurized fluid delivery is accomplished through the interaction of the pumping assembly 16, the dispensing assembly 120, and the flow restrictor 340, a non pressurized reservoir 20 can be employed.

Still referring to FIG. 3, the feedback loop 360 may include a controller 501. The controller 501 may include a processor and control circuitry for actuating a pumping assembly 16 to pump fluid to the dispensing assembly 120. The controller 501 repeatedly receives a parameter related to fluid flow from a sensor, which may be integral to the dispensing assembly 120, and uses this parameter to control the pumping assembly 16 to achieve a desired flow through the output. For example, the controller 501 can adjust the timing or extent of actuation of the pumping assembly 16 to achieve a desired basal or bolus flow rate and/or to deliver a desired basal or bolus cumulative dose. In determining the timing or extent of pumping, the controller 501 may use the output of the sensor (not shown) to estimate (amongst other things) the rate of fluid flow, cumulative fluid flow, or both, and then, based on the estimation, determine an appropriate compensatory action. In the various embodiments, pumping may occur in pulses which can deliver anywhere between 10–9 liters per pulse to microliters per pulse. A basal or bolus dose may be achieved by delivering multiple pulses. (Examples of basal and bolus dosing are shown and described below).

The use of a partially collapsible non pressurized reservoir 20 may advantageously prevent the buildup of air in the reservoir as the fluid in the reservoir is depleted. The reservoir 20 may be connected to the fluid line 310 through a septum (not shown). Air buildup in a vented reservoir could prevent fluid egress from the reservoir 20, especially if the system is tilted so that an air pocket intervenes between the fluid contained in the reservoir and the septum of the reservoir 20. Tilting of the system is expected during normal operation as a wearable device. FIGS. 104-106C depict various embodiments and views of one embodiment of the reservoir. Additionally, further description of the reservoir is included below.

Figure 4A:
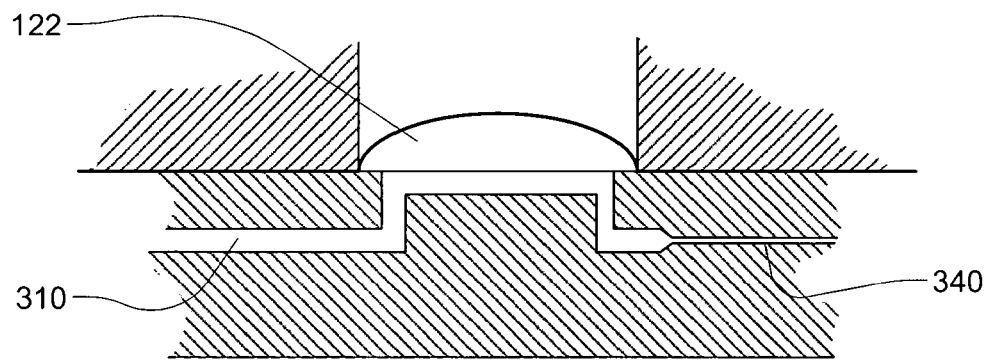
FIGS. 4A-4C are schematic sectional diagrams of various embodiments of a flow restrictor.
Figure 4B:
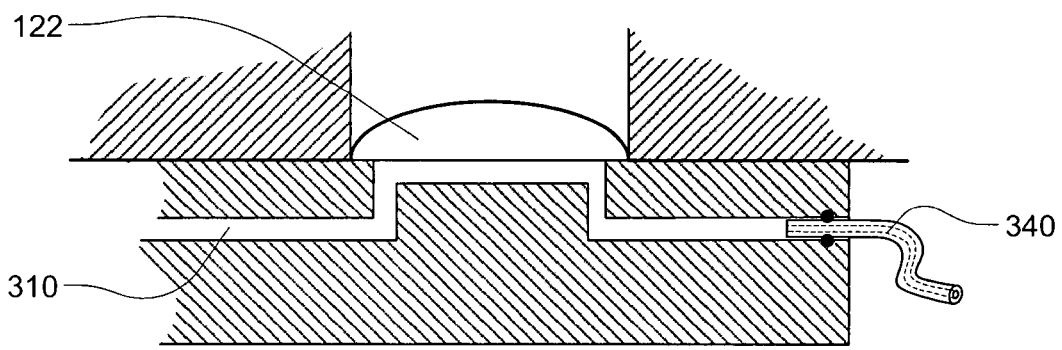
Figure 4C:
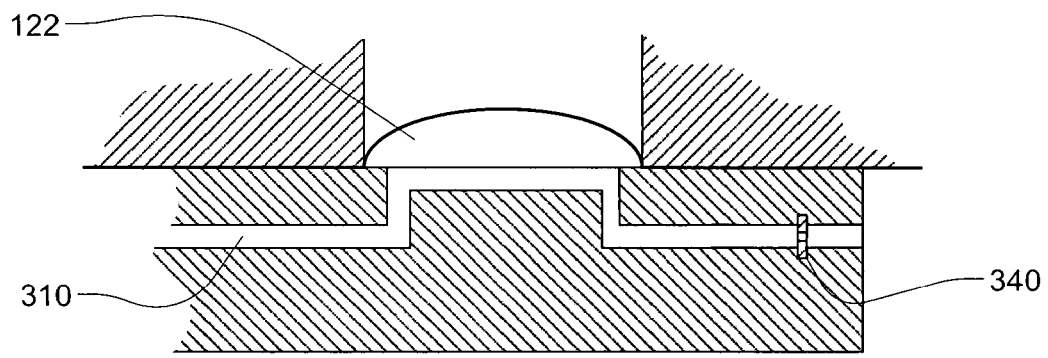

Referring now to FIGS. 4A-4C, various embodiments of the flow restrictor 340 are shown. Referring now to FIG. 4A, the flow restrictor is a molded flow channel 340, which may be a molded groove in a base (not shown). In one embodiment, the cross section of the molded flow channel 340 is approximately 0.009 inches. In this embodiment, the flow restrictor 340 is molded into an apparatus. Referring now to FIG. 4B, microtubing 340 is shown as an alternate embodiment flow restrictor. In one embodiment, the microtubing has an internal diameter of approximately 0.009 inches. Both the molded flow channel and the microtubing use a long path having a small internal diameter or cross section to impart flow impendence. Referring now to FIG. 4C, a precision orifice is shown as a flow restrictor 340. In one embodiment, the precision orifice is a plate with a laser drilled hole. In alternate embodiments, any flow impendence device or method known in the art can be used.

In contrast to prior-art fluid delivery systems that have an active downstream valve, which may be generally considered to create, in a functional sense, an infinite fluid impedance, the flow restrictor 340 creates a finite fluid impedance. The impedance is also normally present; in contrast to prior-art systems than may occasionally be impeded due to an occlusion. As a result of the finite nature of the fluid impedance, in embodiments that include a dispensing chamber 122, fluid may leak through the exit even while the dispensing chamber 122 is expanding.

Figure 5:
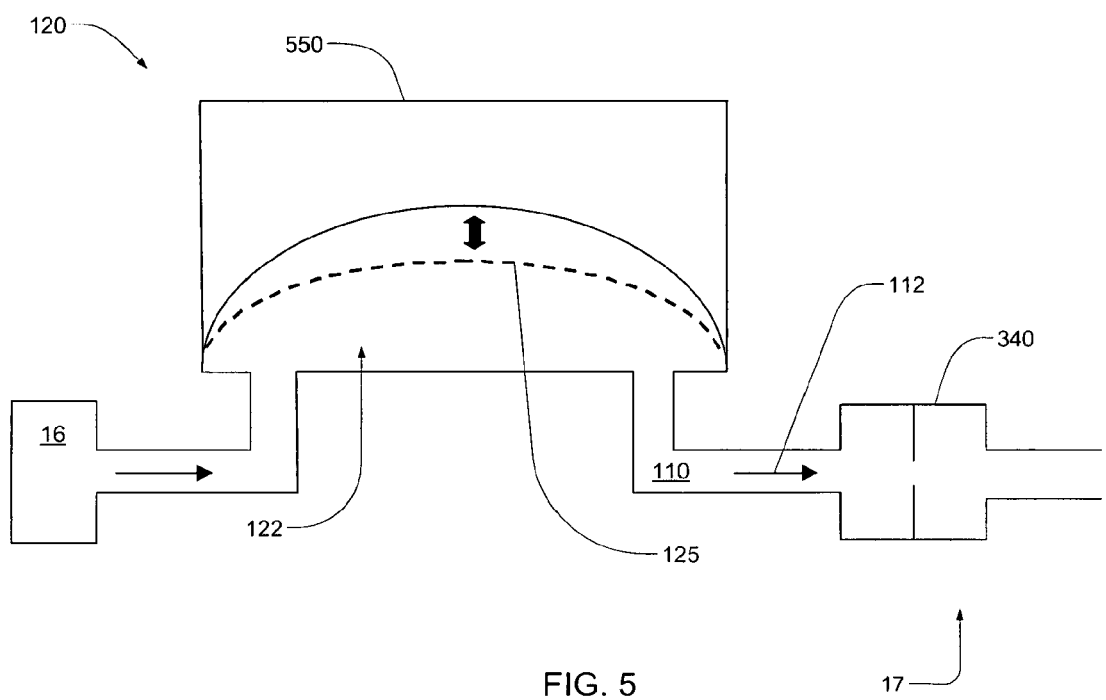
FIG. 5 shows a resilient dispensing assembly in series with a flow restrictor.

FIGS. 5-8 schematically show sectional views of illustrative embodiments of the dispensing assembly 120. It is to be understood that the delivery of fluid for other purposes, such as industrial processes, is within the scope of the present invention, and that the description in particular terms is by way of example only. As shown in FIG. 5, the dispensing assembly 120 may include the variable volume dispensing chamber 122 and a sensor 550. The variable volume dispensing chamber 122 includes a resilient dispensing diaphragm 125, which allows the chamber 122 to expand and contract depending on the flow of fluid into and out of the dispensing assembly 120. In certain embodiments of the invention, the variable-volume dispensing chamber 122 may be detachable from other elements of the dispensing assembly 120, as further discussed herein. The concept of the resilient dispensing diaphragm 125 allowing the chamber 122 to expand and contract is illustrated by the double headed arrow. Metering chamber 122 is considered to comprise a portion of a line 110 characterized by a fluid flow, which is designated, in FIG. 5, by arrow 112. Neither the position nor the nature of the termination of fluid flow 112 or line 110 need limit the scope of the present invention as claimed in certain of the claims appended hereto. The flow restrictor 340 causes fluid to leave the dispensing chamber 122 more slowly than fluid enters the chamber 122 when pumped into the chamber 122 by the pumping assembly 16. As a consequence, the dispensing chamber 122 expands and is pressurized as a fluid charge enters. Dispensing diaphragm 125, deformed by virtue of the expansion of dispensing chamber 122, provides the force needed to deliver the metered volume past the flow restrictor 340 to the exit assembly 17. As discussed above, the sensor 550 repeatedly measures a parameter, such as a displacement, or a thermodynamic variable or capacitance, that can be related to the volume of the resilient dispensing chamber 122. The volume measurements produced by the sensor 550 may be used to control, through a feedback loop, the timing and rate at which the pumping assembly pumps fluid to the dispensing chamber 122 so that the proper flow of fluid is delivered to exit assembly 17 and to a subsequent line, and thence, for example, to the patient. The sensor 550 may employ, for example, acoustic volume sensing (described in more detail below), or other methods (optical, or capacitive, for other examples) for determining a volume, or a volume-related parameter. Acoustic volume measurement technology is the subject of U.S. Pat. Nos. 5,575,310 and 5,755,683 assigned to DEKA Products Limited Partnership, as well as the co-pending provisional U.S. patent application entitled "METHOD OF VOLUME MEASUREMENT FOR FLOW CONTROL", Ser. No. 60/789,243, filed Apr. 5, 2006, all of which are hereby incorporated herein by reference. Fluid volume sensing in the nanoliter range is possible with this embodiment, thus contributing to highly accurate and precise monitoring and delivery. Other alternate techniques for measuring fluid flow may also be used; for example, Doppler-based methods; the use of Hall-effect sensors in combination with a vane or flapper valve; the use of a strain beam (for example, related to a flexible member over a fluid chamber to sense deflection of the flexible member); the use of capacitive sensing with plates; or thermal time of flight methods.

Figure 6:
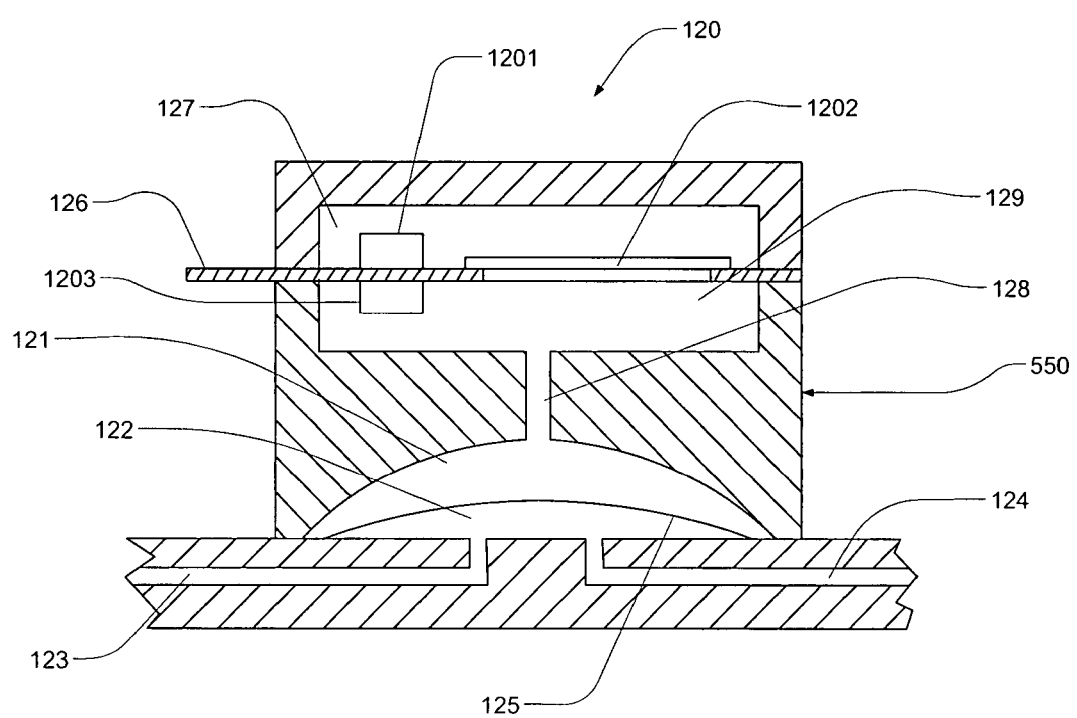
FIG. 6 shows a dispensing assembly having a metering chamber and a sensor.
Figure 7:
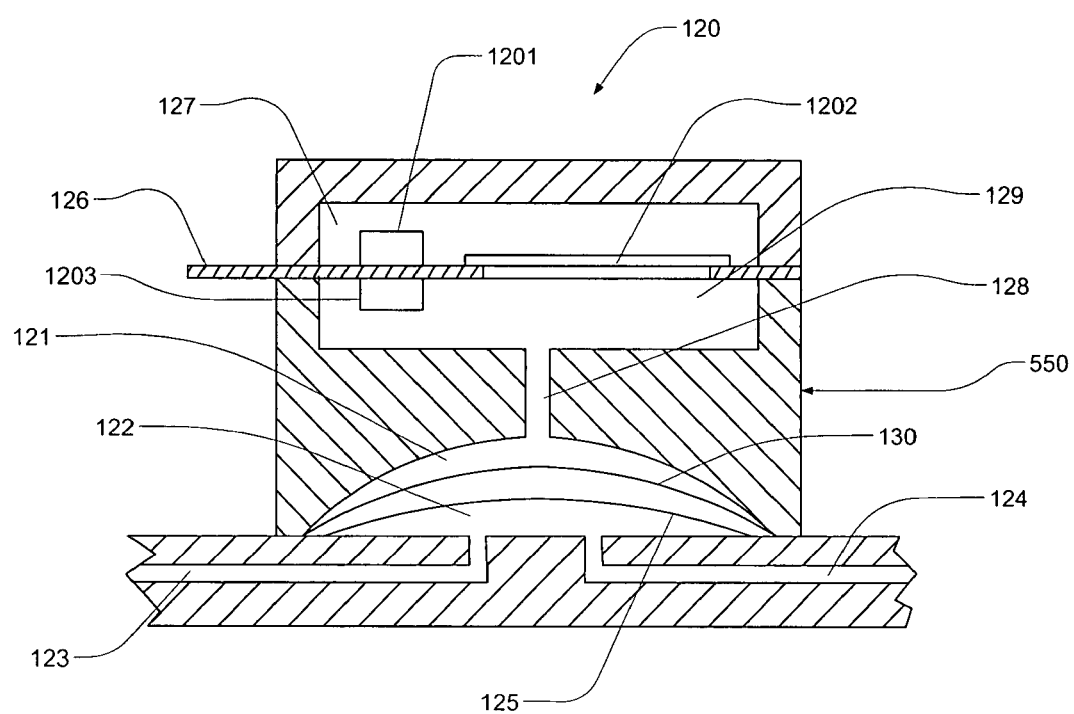
FIG. 7 shows a dispensing assembly having a metering chamber with a dispensing spring and a sensor.

Referring now to FIGS. 6 through 9, embodiments are shown in which a sensor utilizes acoustic volume sensing (AVS) technology. A first discussion refers to embodiments depicted in FIGS. 6 and 7. The dispensing assembly 120 has a sensor that includes a reference chamber 127, and a variable volume measurement chamber 121 that is coupled by a port 128 to a fixed-volume chamber 129. While the invention may be practiced with a reference chamber 127, as shown in FIGS. 6 and 7, in certain other embodiments of the invention, no reference volume is provided. It is to be understood that volume 129 is referred to, herein, as "fixed" as a matter of terminology, but that the actual volume may vary slightly, on the time scale of acoustic excitation, as when the region referred to as fixed volume 129 is driven by a speaker diaphragm. Fluid flows from the pumping assembly 16 to an input 123, through the resilient dispensing chamber 122, and out of an exit channel 124. Due to the high downstream impedance, as fluid enters the dispensing chamber 122, the dispensing diaphragm 125 expands into the variable volume chamber 121. An electronics assembly, which may be arranged on a printed circuit board 126, has a loudspeaker 1202, a sensing microphone 1203, and a reference microphone 1201 for measuring acoustic parameters associated with a gas (typically air) in the variable volume chamber 121, the volume of which is defined by the position of the dispending diaphragm 125. Sound waves induced by the loudspeaker 134 travel through the fixed volume chamber 129 to the variable volume chamber 121 via the port 128; sound waves also travel to the reference chamber 127. As the dispensing diaphragm 125 moves with the flow of fluid through the flow line, the volume of air in the variable volume chamber 121 varies, causing related changes in its acoustic characteristics, which may be detected by the loudspeaker and microphone 1203. For the same acoustic stimulations, the reference microphone 1201 may detect acoustic characteristics of the fixed reference volume 127. These reference measurements may, for example, be used to factor out imprecision and to reject common-mode inaccuracies in acoustic stimulation, and other errors. The volume of fluid displaced may be determined by comparing the measured volume of the variable volume chamber 121 to an initial volume of the variable volume chamber 121. Since the total combined volume of the dispensing chamber 122 and variable volume chamber 121 stays constant, the absolute volume of the dispensing chamber 122 can also be estimated.

The embodiment shown in FIG. 6 utilizes an inherently resilient dispensing diaphragm 125, while the embodiment shown in FIG. 7 utilizes a resilient dispensing spring 130, which when combined with a dispensing diaphragm 125, increases the resiliency of the dispensing chamber 122 and may allow the use of a more compliant (i.e., less resilient) dispensing diaphragm 125 than would be required in the embodiment shown in FIG. 5. The dispensing spring 130 is typically positioned adjacent to the dispensing diaphragm 125 on a side of the diaphragm 125 opposite to the dispensing chamber 122.

Figure 8:
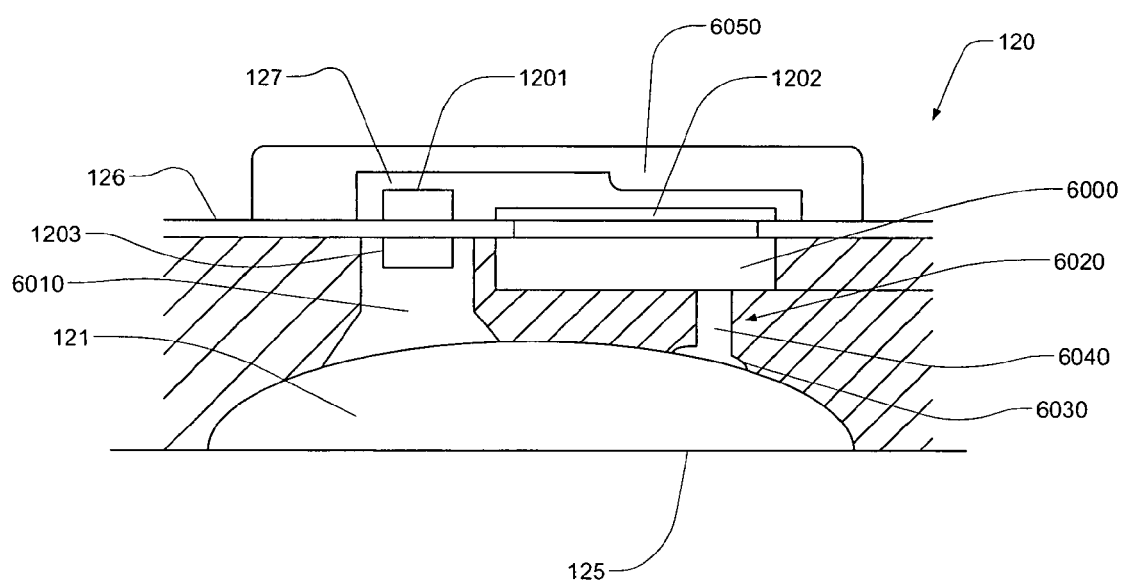
FIG. 8 shows a sectional view of a dispensing assembly with an alternate acoustic path.

Alternately, to reduce background noise from the microphone, the loudspeaker 1202 and the sensing microphone 1203 may be coupled to the variable volume chamber 121 via separate ports. As schematically shown in FIG. 8, a loudspeaker 1202 generates pressure waves in a fixed loudspeaker volume 6000 which is acoustically coupled with the variable volume chamber 121 via a loudspeaker port 6020. Pressure waves travel from the loudspeaker 1202, through the loudspeaker port 6020 to the variable volume chamber 121 and then through a microphone port 6010 before being recorded by the sensing microphone 1203. The loudspeaker port 6020 may include a tube portion 6040 with a flared aperture 6030. The flared aperture 6030 serves to create a uniform length along which sound waves travel for all axial paths of the tube portion 6040. For example, the tube portion 6040 can have the geometry of a cylinder, such as a right cylinder or right circular cylinder. A similarly flared aperture may also adjoin a tube portion to define the microphone port 6010. In contrast to the AVS sensor of FIGS. 6 and 7, in the embodiment of FIG. 8, pressure waves traveling from the loudspeaker 1202 do not have a direct path to the sensing microphone 1203. Thus, pressure waves from the loudspeaker 1202 are prevented from directly impacting the sensing microphone 1203 without first passing through the variable volume 121. A lower background signal is therefore received by the microphone and a better signal/noise ratio is achieved. Additionally, an upper shelf 6050 may be included in any of the embodiments of FIGS. 6-8 advantageously reducing the volume of the reference chamber 127.

In embodiments to be further described, it may be convenient to separate the sensor and metering chamber portions of the dispensing assembly such that the dispensing chamber is detachable and disposable. In this case, the dispensing chamber resides in a disposable section of the patch, while the sensor resides in the reusable section. The dispensing chamber may be bounded by a resilient fluid dispensing diaphragm (as shown in FIGS. 6 as 122 and 124). Alternately, as in FIG. 7, the dispensing chamber 122 may be bounded by a compliant diaphragm 125. In this case, a dispensing spring 130 can be used to impart resiliency on the dispensing chamber 122. When the sensor 550 and dispensing chamber 122 are brought together, the dispensing spring 130 covers the compliant dispensing diaphragm 125. The dispensing spring 130 and dispensing diaphragm 125 may alternately be employed as a single part defining the dispensing chamber 122.

Figure 9:
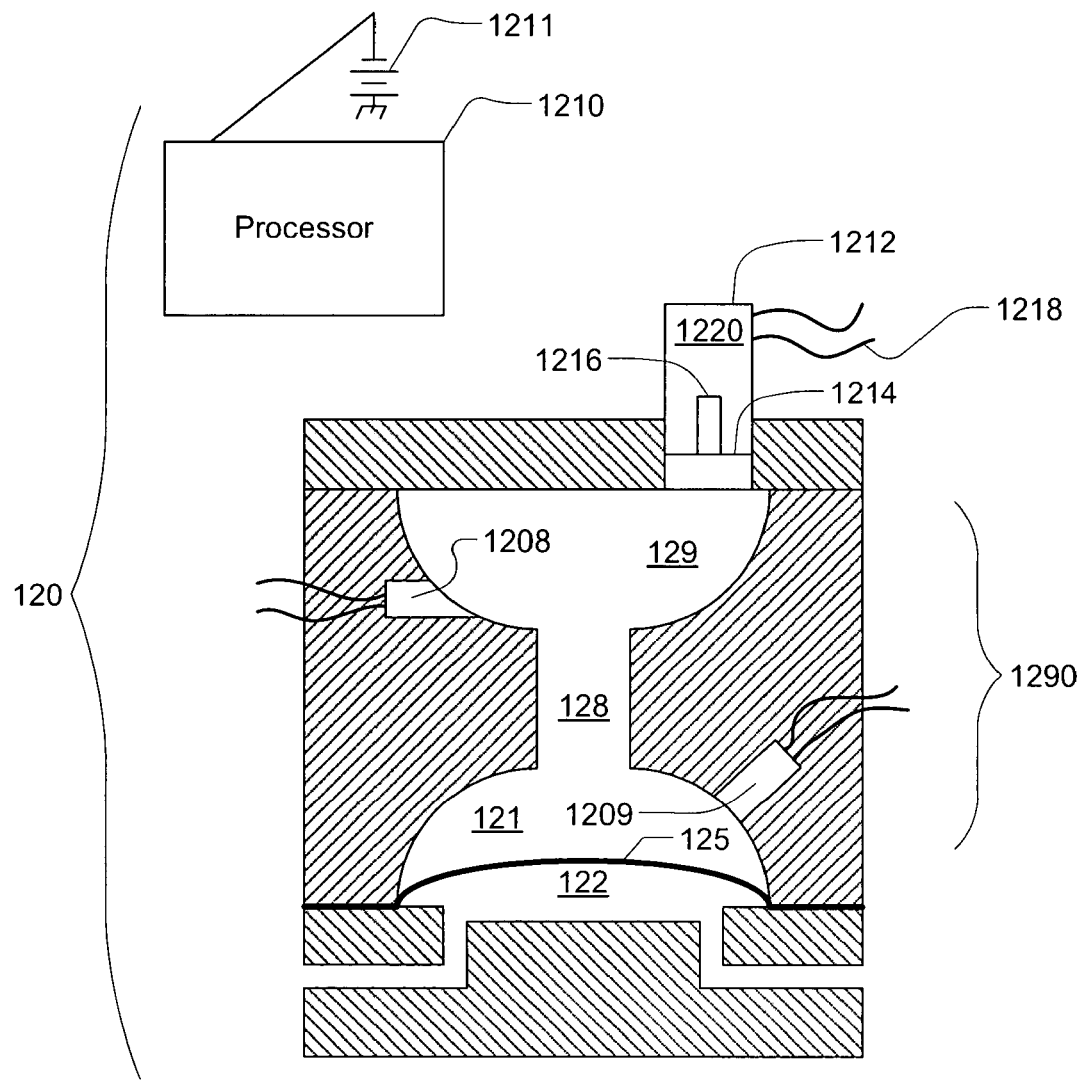
FIG. 9 shows a schematic view of a dispensing assembly.

As shown in FIG. 9, an alternate embodiment of the dispensing assembly is shown. In an embodiment of dispensing assembly 120 depicted in FIG. 9, variable-volume measurement chamber 121 shares a compliant wall (here shown as compliant diaphragm 125) with dispensing chamber 122. Port 128 acoustically couples measurement chamber 121 to fixed volume chamber 129, so as to form an acoustically contiguous region designated generally by numeral 1290. A compressible fluid (typically, air, or another gas) fills the acoustically contiguous region 1290 and is excited by a driving member 1214, itself driven by an actuator 1216. Driving member 1214 may be a diaphragm of a speaker, such as a hearing aid speaker, where actuator 1216 is a voice coil solenoid or piezoelectric element, for example. Within the scope of the invention, driving member 1214 may also be coextensive with actuator 1216, such as where driving member 1214 may, itself, be a piezoelectric element. Driving member 1214 may be contained within a driver module 1212 that may contain, on a side of driving member 1214 distal to fixed volume 129, a reference volume 1220. However, reference volume 1220 is typically not employed in practice of the invention.

A reference microphone 1208 is shown in acoustic communication with fixed volume 129, while a signal microphone 1209 is acoustically coupled to measurement chamber 121. The volume of measurement region 121 may be determined from electronic signals provided by one or more microphones 1208, 1209 on the basis of pressure variations (or, equivalently, acoustic signal) measured at their respective positions within the acoustically contiguous region 1290. Phase measurements may be performed by comparing the phase of response at one or more microphones relative to the phase of acoustic excitation or relative to the phase of response at a position of another microphone. The volume of measurement region 121, and, by implication, of dispensing chamber 122, is determined, on the basis of phase and/or amplitude measurements, as discussed below, by a processor 1210, which derives power from power source 1211, shown, representatively, as a battery.

For the purposes of precise delivery of minute amounts of therapeutic agents, the delivery of small, but very accurately metered, quantities per pump stroke is desirable. However, if minute volumes of fluid are to be pumped through line 110 during the course of each pump stroke, extremely high resolution is required of the metering process. Consequently, in accordance with embodiments of the present invention, changes in volume are measured by sensor 550 with a resolution of at least 10 nanoliters. Measurements of resolution 0.01% of the empty volume of measurement region 121 may be achieved in some embodiments of the invention. In accordance with other embodiments of the invention, sensor 550 provides resolution of better than 13 nanoliters. In other embodiments yet, sensor 550 provides resolution of better than 15 nanoliters, and in yet further embodiments, resolution of better than 20 nanoliters is provided. In such cases, the total volume of acoustically contiguous region 1290 may be less than 130 µl, and, in other embodiments, less than 10 µl.

In accordance with various embodiments of the present invention, use may be made of a priori modeling of the response of the volume of dispensing chamber 122, and, consequently of variable-volume chamber 121 (which may also be referred to, herein, as a "metering volume"), based upon the filling of the dispensing chamber due to a pumped volume of fluid entering through input 123. While other models are within the scope of the present invention, one model that may be employed expresses the volume of fluid within dispensing chamber 122, in response to a pumped influx of fluid and a outlet of fixed flow impedance, as the sum of a baseline volume $V_B$ and an exponentially decaying volume characterized by a peak displacement $V_D$, such that the metering chamber volume during a measurement is characterized as a function of time t, as:

$$V = V_D \exp\left(\frac{-t}{\tau}\right) + V_B.$$

In order to fit a parameterization of the modeled exponential decay (or other functional model) to a succession of acoustic measurements, the response of systems such as depicted in FIGS. 6 through 9 is developed as follows. For purposes of modeling the response, port 128 is characterized by a length l and a diameter d. The pressure and volume of an ideal adiabatic gas can be related by $PV^\gamma = K$, where K is a constant defined by the initial conditions of the system.

The ideal adiabatic gas law can be written in terms of a mean pressure, P, and volume, V, and a small time-dependent perturbation on top of those pressures, p(t), v(t):

$$(P+p(t))(V+v(t))^\gamma = K.$$

Differentiating this equation yields $$\dot{p}(t)(V+v(t))^\gamma + \gamma(V+v(t))^{\gamma-1}(P+p(t))\dot{v}(t) = 0$$

Or, simplifying, $$\dot{p}(t) + \gamma \frac{P+p(t)}{V+v(t)} \dot{v}(t) = 0$$

If the acoustic pressure levels are much less than the ambient pressure the equation can be further simplified to:

$$\dot{p}(t) + \frac{\gamma P}{V} \dot{v}(t) = 0.$$

Applying the ideal gas law, $P=\rho RT$, and substituting in for pressure gives the result:

$$\dot{p}(t) + \frac{\gamma RT \rho}{V} \dot{v}(t) = 0.$$

This can be written in terms of the speed of sound, $a=\sqrt{\gamma RT}$, as:

$$\dot{p}(t) + \frac{\rho a^2}{V} \dot{v}(t) = 0.$$

Also, an acoustic impedance for a volume is defined as:

$$Z_v = \frac{p(t)}{\dot{v}(t)} = -\frac{1}{\left(\frac{V}{\rho a^2}\right)s} = -\frac{\rho a^2}{V} \cdot \frac{1}{s}.$$

In accordance with one set of models, the acoustic port is modeled assuming that all of the fluid in the port essentially moves as a rigid cylinder reciprocating in the axial direction. All of the fluid in the channel (port 128) is assumed to travel at the same velocity, the channel is assumed to be of constant cross section, and the "end effects" resulting from the fluid entering and leaving the channel are neglected.

Assuming laminar flow friction of the form $\Delta p = R \rho \dot{v}$, the friction force acting on the mass of fluid in the channel can be written: $F = R \rho A^2 \dot{x}$.

A second order differential equation can then be written for the dynamics of the fluid in the channel:

$$\rho L A \ddot{x} = \Delta p A - R \rho A^2 \dot{x}$$

or, in terms of volume flow rate:

$$\ddot{v} = -\frac{RA}{L}\dot{v} + \Delta p \frac{A}{\rho L}.$$

The acoustic impedance of the channel can then be written:

$$Z_p = \frac{\Delta p}{\dot{v}} = \frac{\rho L}{A}\left(s + \frac{RA}{L}\right).$$

Using the volume and port dynamics define above, the acoustic volume sensor system can be described by the following system of equations (with index k denoting the speaker, and r denoting the resonator):

$$\dot{p}_0 - \frac{\rho a^2}{V_0} \dot{v}_k = 0.$$

Following the same convention, $$\dot{v}_k > 0 \Rightarrow \dot{p}_1 < 0 \text{ and } \dot{v}_r > 0 \Rightarrow \dot{p}_1 > 0,$$

$$\dot{p}_1 + \frac{\rho a^2}{V_1}(\dot{v}_k - \dot{v}_r) = 0.$$

In addition, $$\dot{v}_r > 0 \Rightarrow \dot{p}_2 < 0,$$

$$\dot{p}_2 + \frac{\rho a^2}{V_2}\dot{v}_r = 0.$$

The volume tends to accelerate in a positive direction if $p_2$ is larger than $p_1$.

$$\ddot{v}_r = -\frac{RA}{L}\dot{v}_r + \frac{A}{\rho L}(p_2 - p_1).$$

Reducing the number of equations (treating $p_0$ as input), and substituting $$\dot{v}_k = \frac{V_0}{\rho a^2}\dot{p}_0,$$

$$\dot{p}_1 + \frac{V_0}{V_1}\dot{p}_0 - \frac{\rho a^2}{V_1}\dot{v}_r = 0$$

$$\dot{p}_2 + \frac{\rho a^2}{V_2}\dot{v}_r = 0$$

$$\ddot{v}_r = -\frac{RA}{L}\dot{v}_r + \frac{A}{\rho L}p_1 - \frac{A}{\rho L}p_2.$$

This leads to one simple expression using these equations:

$$\frac{\rho a^2}{V_2}\dot{v}_r = \frac{V_1}{V_2}\cdot\left(\frac{\rho a^2}{V_1}\dot{v}_r\right) = \frac{V_1}{V_2}\dot{p}_1 + \frac{V_0}{V_2}\dot{p}_0$$

$$\dot{p}_2 + \frac{V_0}{V_2}\dot{p}_0 + \frac{V_1}{V_2}\dot{p}_1 = 0$$

$$V_0 \dot{p}_0 + V_1 \dot{p}_1 = -V_2 \dot{p}_2$$

$$-\frac{V_0 \dot{p}_0 + V_1 \dot{p}_1}{\dot{p}_2} = V_2,$$

or $$V_0 p_0 + V_1 p_1 = -V_2 p_2$$

$$-\frac{V_0 p_0 + V_1 p_1}{p_2} = V_2$$

These equations can also be expressed in transfer function form. The "cross-speaker" transfer function, $p_1/p_0$, is:

$$s\cdot p_1 + \frac{V_0}{V_1}s\cdot p_0 - \frac{\rho a^2}{V_1}s\cdot v_r = 0$$

$$s\cdot p_2 + \frac{\rho a^2}{V_2}s\cdot v_r = 0$$

-continued $$s^2 \cdot v_r = -\frac{RA}{L}s\cdot v_r - \frac{A}{\rho L}p_1 + \frac{A}{\rho L}p_2$$

$$p_2 = -\frac{\rho a^2}{V_2}v_r$$

$$s^2 v_r = -\frac{RA}{L}s\cdot v_r + \frac{A}{\rho L}\left(-\frac{\rho a^2}{V_2}\right)v_r - \frac{A}{\rho L}p_1$$

$$\left(s^2 + \frac{RA}{L}s + \frac{Aa^2}{LV_2}\right)v_r = -\frac{A}{\rho L}p_1$$

$$v_r = \frac{-\frac{A}{\rho L}}{s^2 + \frac{RA}{L}s + \frac{Aa^2}{LV_2}}p_1$$

or $$\frac{p_1}{p_0} = -\frac{V_0}{V_1}\frac{s^2 + 2\zeta\omega_n s + \alpha\omega_n^2}{s^2 + 2\zeta\omega_n s + \omega_n^2}$$

where $$\omega_n^2 = \frac{a^2 A}{L}\left(\frac{1}{V_1} + \frac{1}{V_2}\right);$$

$$\zeta = \frac{RA}{2L\omega_n}; \text{ and}$$

$$\alpha = \frac{V_1}{V_1 + V_2}.$$

Similarly, the "cross system" transfer function, based on measurements on either end of port 128, is $p_2/p_0$, is given by:

$$s\cdot p_1 + \frac{V_0}{V_1}s\cdot p_0 - \frac{\rho a^2}{V_1}s\cdot v_r = 0$$

$$s\cdot p_2 + \frac{\rho a^2}{V_2}s\cdot v_r = 0$$

$$s^2 \cdot v_r = -\frac{RA}{L}s\cdot v_r - \frac{A}{\rho L}p_1 + \frac{A}{\rho L}p_2$$

$$p_1 = \frac{\rho a^2}{V_1}v_r - \frac{V_0}{V_1}p_0$$

$$s^2 v_r = -\frac{RA}{L}s\cdot v_r - \frac{A}{\rho L}\cdot\frac{\rho a^2}{V_1}v_r - \frac{A}{\rho L}\left(-\frac{V_0}{V_1}p_0\right) + \frac{A}{\rho L}p_2$$

$$v_r = \frac{\frac{AV_0}{\rho L V_1}}{s^2 + \frac{RA}{L}s + \frac{Aa^2}{LV_1}}p_0 + \frac{\frac{A}{\rho L}}{s^2 + \frac{RA}{L}s + \frac{Aa^2}{LV_1}}p_2$$

$$s\cdot p_2 + \frac{\rho a^2}{V_2}s\cdot\left[\frac{\frac{AV_0}{\rho L V_1}}{s^2 + \frac{RA}{L}s + \frac{Aa^2}{LV_1}}p_0 + \frac{\frac{A}{\rho L}}{s^2 + \frac{RA}{L}s + \frac{Aa^2}{LV_1}}p_2\right] = 0$$

$$\left[s^2 + \frac{RA}{L}s + \frac{Aa^2}{LV_1} + \frac{Aa^2}{LV_2}\right]p_2 = -\frac{Aa^2}{LV_2}\cdot\frac{V_0}{V_1}p_0$$

$$\frac{p_2}{p_0} = -\frac{V_0}{V_1}\frac{\frac{Aa^2}{LV_2}}{s^2 + \frac{RA}{L}s + \frac{Aa^2}{LV_2}\cdot\frac{V_1 + V_2}{V_1}}$$

$$\frac{p_2}{p_0} = -\frac{V_0}{V_1}\frac{\alpha\omega_n^2}{s^2 + 2\zeta\omega_n s + \omega_n^2}$$

Volume Estimation Using Cross-System Phase

Similarly, using the same principles, a transfer function is readily derived, expressing a pressure in the fixed volume chamber 129 in terms of the pressure in the variable volume chamber 121 to which it is coupled via port 128. In particular, the transfer function is:

$$\frac{p_2}{p_1} = \frac{1}{\frac{V_2 L_p}{a^2 A_p} s^2 + \frac{RV_2}{a^2} s + 1}$$

$$= \frac{\frac{a^2 A_p}{V_2 L_p}}{s^2 + \frac{RV_2}{a^2} \frac{a^2 A_p}{V_2 L_p} s + \frac{a^2 A_p}{V_2 L_p}}$$

$$= \frac{\omega_n^2}{s^2 + \frac{RA_p}{L_p} s + \omega_n^2}.$$

In either of the foregoing cases, the resonant frequency of the system may be expressed as a function of the variable volume, $V_2$:

$$\omega_n^2 = \frac{a^2 A}{L}\left(\frac{1}{V_1} + \frac{1}{V_2}\right), \text{ or } \frac{1}{V_2} = \frac{\omega_n^2 L}{a^2 A} - \frac{1}{V_1}.$$

Since all of the other parameters are known, variable volume $V_2$ can be calculated based, for example, on the resonant frequency, although other methods of deriving $V_2$ may be advantageous, and are described further in the course of the present application. The one parameter that is not a constant in this equation is the speed of sound, a, which may be calculated, based on a knowledge of the pertinent temperature, or otherwise derived or measured.

As stated, various strategies may be employed to interrogate the system so as to derive volume $V_2$. In accordance with certain embodiments of the current invention, the system is excited by driving member 1214 at a single frequency, while monitoring the response of one or more transducers (microphones 1208 and 1209, in FIG. 9). The response is captured as a complex signal, retaining both amplitude and phase of the pressure variation. It is advantageous that the single interrogating frequency lie close to the resonance of the system in mid-stroke, since the largest phase changes with volume over the range of a full to empty chamber is thereby achieved.

The response of the signal microphone 1208 may be corrected to reject common-mode effects due to the frequency-dependent characteristics of the exciting loudspeaker 1202 (shown in FIG. 6) or driving member 1214 (shown in FIG. 9). The corrected signal, obtained as a complex ratio of the microphone signals, may be expressed as $m_i$, where the index i denotes successive time samples of the signal.

Expressed, in transfer function form, in analogy, to a second-order mechanical Helmholtz resonator, the signal may be represented as:

$$m_i \approx -\frac{V_0}{V_1} \frac{\frac{A\gamma RT}{LV_2}}{s_i^2 + \frac{\lambda A}{L} s_i + \frac{A\gamma RT}{LV_2} \cdot \frac{V_1 + V_2}{V_1}}$$

$$= \frac{-\frac{V_0}{V_1} \cdot \frac{A\gamma R}{L\omega_c^2} \cdot \frac{T_i}{V_2} \cdot \frac{\alpha}{\varepsilon_{v,i}}}{\frac{s_i^2}{\omega_c^2} + \frac{A\lambda}{L\omega_c} \cdot \varepsilon_\lambda \cdot \frac{s_i}{\omega_c} + \frac{A\gamma R}{L\omega_c^2} \cdot \frac{T_i}{V_1} \cdot \frac{(\varepsilon_{v,i} + \Psi_{1,2})}{\varepsilon_{v,i}}}$$

$$= \frac{-\kappa_{0,i} \frac{\alpha}{\varepsilon_{v,i}}}{\bar{s}_i^2 + \psi_1 \cdot \bar{s}_i \cdot \varepsilon_\lambda + \psi_{0,i} \frac{\Psi_{1,2} + \varepsilon_{v,i}}{\varepsilon_{v,i}}}$$

$$= \frac{-\kappa_{0,i} \alpha}{\bar{s}_i^2 \varepsilon_{v,i} + \psi_1 \bar{s}_i \varepsilon_\lambda \varepsilon_{v,i} + \psi_{0,i}(\Psi_{1,2} + \varepsilon_{v,i})}$$

$$= \frac{-\kappa_{0,i} \alpha}{[\psi_{0,i}(\Psi_{1,2} + \varepsilon_{v,i}) - \bar{\omega}_i^2 \varepsilon_{v,i}] + \iota \cdot \psi_1 \bar{\omega}_i \varepsilon_\lambda \varepsilon_{v,i}} \cdot$$

$$\frac{[\psi_{0,i}(\Psi_{1,2} + \varepsilon_{v,i}) - \bar{\omega}_i^2 \varepsilon_{v,i}] - \iota \cdot \psi_1 \bar{\omega}_i \varepsilon_\lambda \varepsilon_{v,i}}{[\psi_{0,i}(\Psi_{1,2} + \varepsilon_{v,i}) - \bar{\omega}_i^2 \varepsilon_{v,i}] - \iota \cdot \psi_1 \bar{\omega}_i \varepsilon_\lambda \varepsilon_{v,i}}$$

$$= \frac{-\kappa_{0,i} \alpha [\psi_{0,i} \Psi_{1,2} + (\psi_{0,i} - \bar{\omega}_i^2) \varepsilon_{v,i}] + \iota \cdot \kappa_{0,i} \alpha \psi_1 \bar{\omega}_i \varepsilon_\lambda \varepsilon_{v,i}}{[\psi_{0,i} \Psi_{1,2} + (\psi_{0,i} - \bar{\omega}_i^2) \varepsilon_{v,i}]^2 + \psi_1^2 \bar{\omega}_i^2 \varepsilon_\lambda^2 \varepsilon_{v,i}^2}$$

Here, normalization variables have been introduced so as to maintain relevant parameters within a computationally useful dynamic range of order unity. The final expression is expressed in terms of the real and imaginary parts over a common denominator. Taking the ratio of the real μ to the imaginary ν parts, (i.e., the phase cotangent), $$\frac{\mu_i}{\nu_i} \approx -\frac{(\psi_{0,i} - \bar{\omega}_i^2)\varepsilon_{v,i} + \psi_{0,i}\Psi_{1,2}}{\psi_1 \bar{\omega}_i \varepsilon_\lambda \varepsilon_{v,i}},$$

the error may be defined as:

$$E = \frac{1}{M}\sum [\mu_i D_i + \nu_i N_i]^2,$$

with N and D denoting the numerator and denominator, respectively of the model.

If the error is minimized with respect to each of the model parameters, a best-fit has been achieved. Any method may be employed for fitting the model parameters. In one embodiment of the invention, a gradient-descent method is employed to find the minima:

$$\frac{\partial E}{\partial \varepsilon_\lambda} = \frac{2}{M}\sum \psi_1 \bar{\omega}_i \varepsilon_{v,i} D_i e_i$$

$$\frac{\partial E}{\partial \varepsilon_b} = \frac{2}{M}\sum \left(\mu_i \frac{\partial D_i}{\partial \varepsilon_b} + \nu_i \frac{\partial N_i}{\partial \varepsilon_b}\right)e_i$$

$$= 2\sum \left(\mu_i \frac{\partial D_i}{\partial \varepsilon_{v,i}} + \nu_i \frac{\partial N_i}{\partial \varepsilon_{v,i}}\right)e_i \frac{\partial \varepsilon_{v,i}}{\partial \varepsilon_b}$$

$$\frac{\partial D_i}{\partial \varepsilon_{v,i}} = \psi_1 \bar{\omega}_i \varepsilon_\lambda$$

$$\frac{\partial N_i}{\partial \varepsilon_{v,i}} = \psi_{0,i} - \bar{\omega}_i^2$$

$$\frac{\partial \varepsilon_{v,i}}{\partial \varepsilon_b} = 1$$

$$\frac{\partial E}{\partial \delta_d} = \frac{2}{M}\sum \left(\mu_i \frac{\partial D_i}{\partial \varepsilon_{v,i}} + \nu_i \frac{\partial N_i}{\partial \varepsilon_{v,i}}\right)e_i \frac{\partial \varepsilon_{v,i}}{\partial \delta_d}$$

$$\frac{\partial \varepsilon_{v,i}}{\partial \delta_d} = \exp\left(\frac{-t_i \varepsilon_\tau}{\tau}\right)$$

-continued $$\frac{\partial E}{\partial \varepsilon_\tau} = \frac{2}{M} \sum \left( \mu_i \frac{\partial D_i}{\partial \varepsilon_{v,i}} + v_i \frac{\partial N_i}{\partial \varepsilon_{v,i}} \right) e_i \frac{\partial \varepsilon_{v,i}}{\partial \varepsilon_\tau}$$

$$\frac{\partial \varepsilon_{v,i}}{\partial \varepsilon_\tau} = \delta_d \frac{-t_i}{\tau} \exp\left(\frac{-t_i \varepsilon_\tau}{\tau}\right)$$

The intervals over which each successive temporal sample is obtained, and the number of intervals sampled in order to fit the parameters of the temporal model are advantageously optimized for each specific application of the invention. Where fluid flows at a slow but relatively constant rate, as in basal insulin delivery, sampling over a period from $\tau/3$ to $3\tau$ has been found efficacious. On the other extreme, where a relatively large bolus of fluid is to be delivered, the fluid may reside in dispensing volume 122 for only a short period of time, on the time scale of the exponential decay time constant. In that case, sampling is performed over a shorter fraction of the characteristic decay time.

Figure 117:
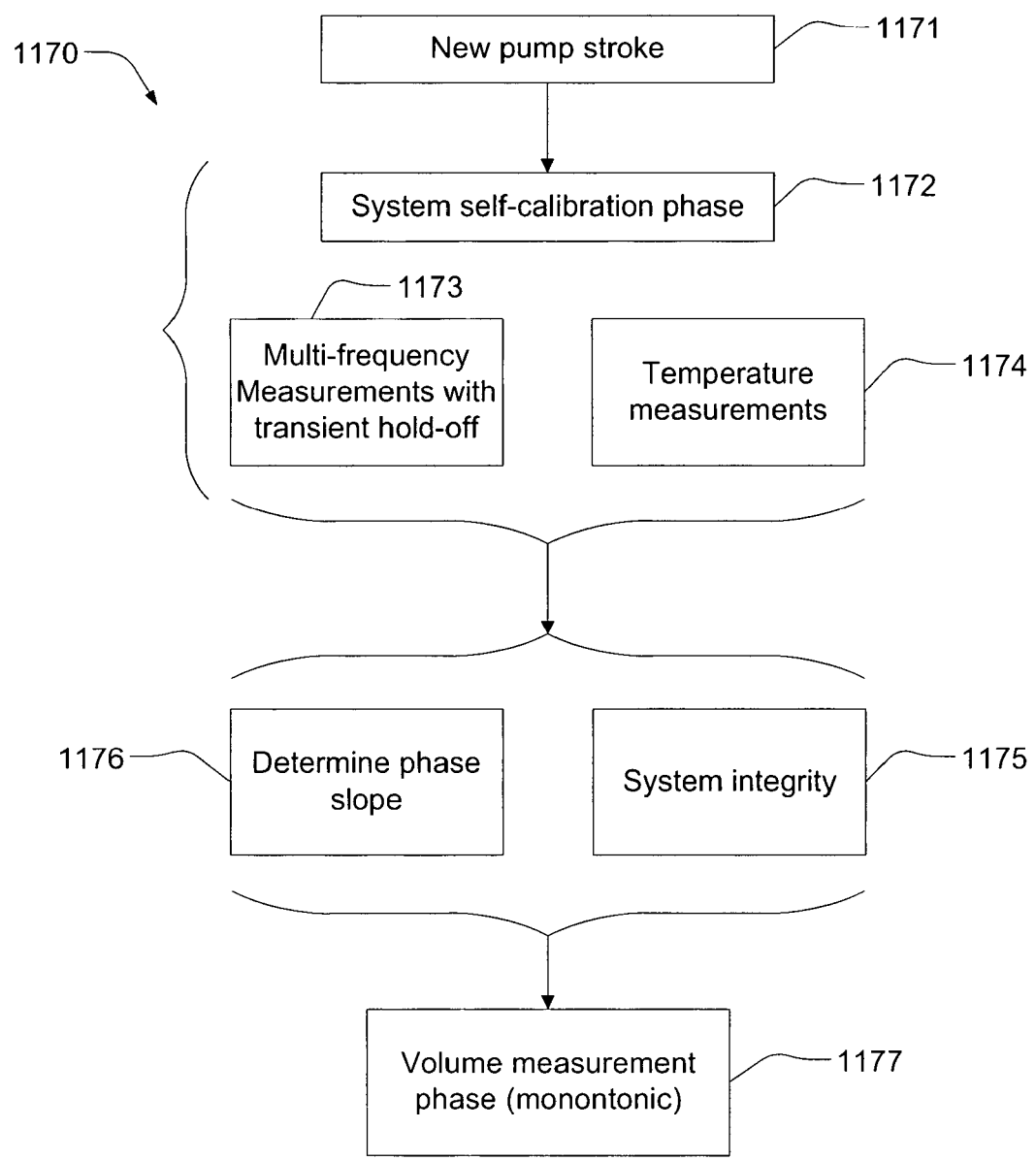

In accordance with preferred embodiments of the invention, volume of fluid dispensed through dispensing volume 122 is determined on the basis of a fit to a model of volume vs. time, based on cross-system phase measurements made at monotonic frequency of excitation. During the initial portion of a pump stroke, moreover, preliminary measurements are made in order to calibrate system operation, as now described, in conjunction with the measurement protocol, with reference to the flowchart shown in FIG. 117. The metering process, denoted generally by numeral 1170, advantageously conserves computer resources and minimizes power consumption, thereby extending the useful time between charges or replacement of power source 1211 (shown in FIG. 9), while providing, through frequent calibration, the measurement accuracy required for delivery of fluid with the resolution per stroke described above.

Either prior to, or at the beginning 1171 of, each pump stroke, or both, processor 1210 initiates a Self-Calibration Phase 1172 of the AVS system. Measurements are held-off until electronic transients due to activation of the pump have substantially decayed. Microphone and speaker gains are set, and driving member 1214 is actuated, in step 1173, at a succession of frequencies, where typically five frequencies are employed, in the general proximity of the resonance of contiguous acoustic region 1290 (otherwise referred to herein as the "acoustic chamber"). Frequencies in the range of 6-8 kHz are typically employed, though the use of any frequencies is within the scope of the present invention. At the onset of activation of each successive frequency, data collection is delayed, for a period of approximately 5 ms, until acoustic transients have substantially decayed.

For a duration of approximately 64 acoustic cycles, data are collected as follows: the temperature reading provided by temperature sensor 132 (shown in FIG. 70B) is sampled in step 1174, and the real and imaginary portions of the ratio of output signals of signal microphone 1209 with respect to reference microphone 1208, denoted ρ and i, respectively, are sampled. The complex ratio of signals, or other functional combination of the microphone signals with respect to the reference, may be referred to herein as the "signal," for purposes of describing the AVS system.

On the basis of measurements at each frequency, taken over the course of approximately 200 ms per frequency, a set of means and variances are derived for each of the real and imaginary parts of the signal at each frequency and for the temperature readings. Analysis, in step 1175, of these values, permits a determination of whether errors are within specified bounds. An anomalous transfer function may advantageously indicate system faults that include, but are not limited to, faults in the microphones or other sensors, speaker, transducer, electronics, mechanical components, fluid ingress, poor acoustic seal, excessive ambient noise, and excessive shock and vibration. Additionally, the functional dependence of the phase angle of the signal as a function of frequency is determined in step 1176. The phase angle of the signal, namely the arctangent of the ratio of imaginary to real portions thereof, may be used as a measure of phase, however any measure of phase may be used within the scope of the invention. The functional dependence may be derived by polynomial fit of the phase to the frequency, or otherwise. On the basis of the polynomial fit, or otherwise, the slope of phase vs. frequency is determined at the volume measurement frequency, and volume measurement proceeds, in step 1177. Additionally, and significantly, an anomalous slope of phase vs. frequency is indicative of a gaseous bubble in the fluid contained within dispensing chamber 122.

For a succeeding portion of each pump stroke, driving member 1214 is actuated at substantially a single frequency, thereby acoustically exciting the gas within acoustically contiguous region 1290 at that frequency. Signal data, based typically on the complex ratio of output signals of signal microphone 1209 with respect to reference microphone 1208 are collected and averaged over specified sampling intervals of approximately 64 cycles. Real and imaginary components of the signal, as well as temperature data, are recorded for each sampling interval. Based on the sampled and collected data, a fit is performed to a temporal model. In various embodiments of the invention, a gradient-descent method is employed, as described above, in order to minimize error in fitting the model parameters, namely the baseline volume $V_B$, peak displacement $V_D$, and decay time $\tau$, of the variable volume chamber 121 during the course of each pump stroke, thereby providing the volume of fluid delivered through dispensing chamber 122.

Figure 10:
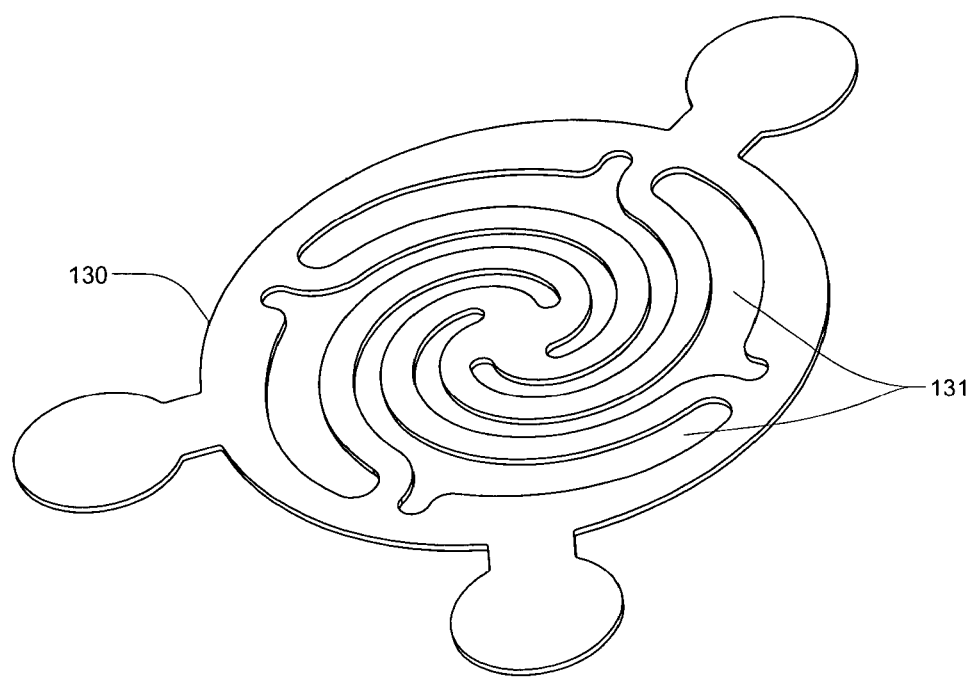
FIG. 10 shows a diaphragm spring for use with a resilient variable-volume dispensing chamber.

Referring now to FIG. 10, the dispensing spring 130 may have a spiral or fan shape that is complementary to the diaphragm and may have multiple helical grooves 131. Embodiments of the spring as shown can apply an approximately even force over the diaphragm. This approximately even force helps the diaphragm to retain an approximately concave shape as it expands. The grooves 131 allow air to pass freely through the spring, thus most air is not trapped between the spring and the diaphragm.

Figure 11A:
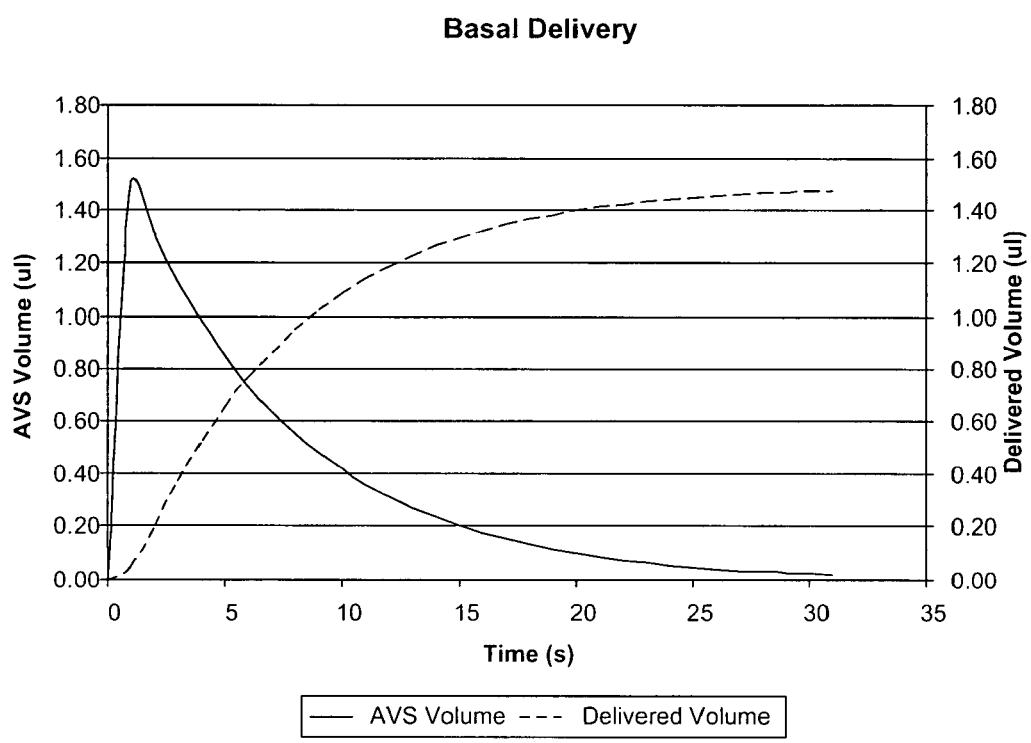
FIG. 11A shows a kinetic profile of an exemplary basal fluid delivery.
Figure 11B:
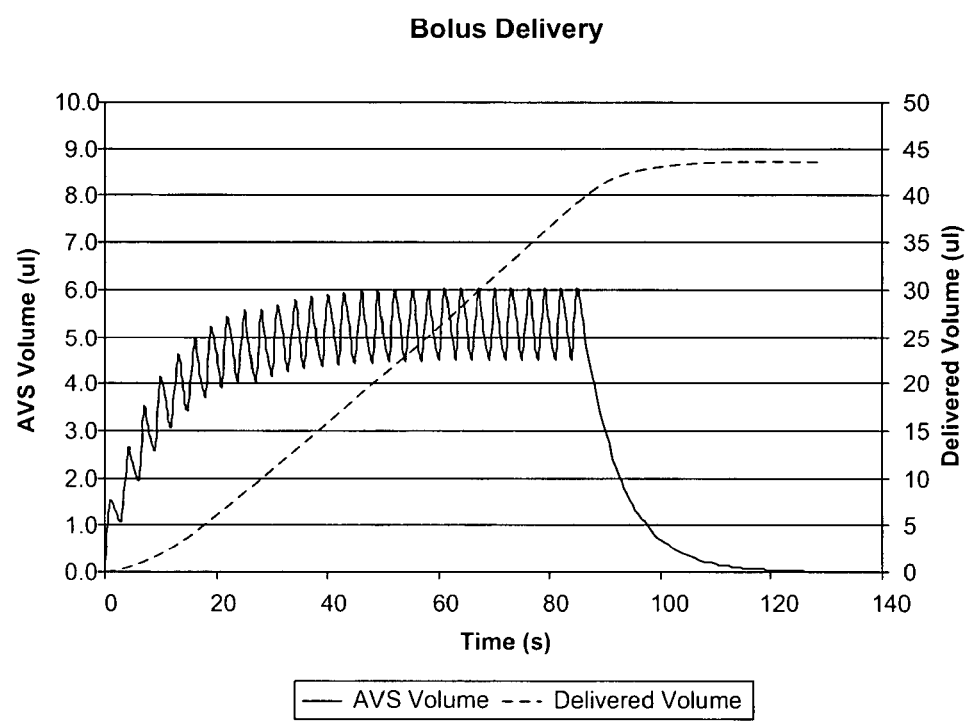
FIG. 11B shows a kinetic profile of an exemplary bolus fluid delivery.

Referring now to FIGS. 11A and 11B, examples of kinetic measurements of the volume of the dispensing chamber 122 (shown in FIG. 5) and of the calculated cumulative volume expelled from the dispensing chamber 122 are shown for a typical basal delivery pulse (FIG. 11A) and for a typical bolus delivery (FIG. 11B). As can be seen in FIG. 11A, actuation of the pumping assembly 16 causes an expansion of the dispensing chamber 122, as measured by the acoustic volume sensor 550, from about 0 to about 1.5 µl in about 2 seconds. The resilient dispensing chamber 122 is seen to contract and expel its fluid from the chamber 122 through the high impedance output over a course of about 30 seconds with an exponential decay kinetic characterized by a half-life ($t_{1/2}$) of about 6 seconds. The cumulative volume of output from dispensing chamber 122 is calculated from the measurements made by the sensor 550 and seen also to rise exponentially to about 1.5 µl. It can be seen that the high impedance output introduces a delay between actuation of the pump assembly and delivery of the majority of the displaced fluid. The $t_{1/2}$ characteristic of the system can be chosen with attention to the resilient force exerted by the dispensing chamber 122 and the degree of impedance of the output. In various embodiments, the time constant may vary to save power and eliminate drift issues. The time constant may be, for example, $t_{1/2}$=2 seconds, or $t_{1/e}$=2 seconds.

FIG. 11B shows a kinetic profile of a bolus delivery of fluid by the fluid delivery device 10. A rapid succession of about 29 pump actuations (i.e., pulses) each displace fluid from a fluid source into the resilient dispensing chamber 122, thus causing corresponding changes in the parameter measured by the acoustic volume measurement sensor 550. It can be seen that the volume of the dispensing chamber 122 expands on the first pump pulse to about 1.5 µl, a value similar to that observed in FIG. 11A. The dispensing chamber 122 volume further expands upon additional pulsatile pumping at pulse intervals shorter than the time period required to achieve full discharge of the dispensing assembly 120; the expansion reaches a maximum of about 6 µl. Cessation of the pump pulsing occurs after about 85 seconds and the volume of the chamber 122 is seen to decrease with an exponential decay kinetic resulting in complete discharge of its contents by about 30 seconds after cessation of pumping. The $t_{1/2}$ for this final discharge is approximately the same as for the basal delivery shown in FIG. 11A. The calculated cumulative output volume is seen to rise during pumping with an approximately linear kinetic and plateau upon cessation of pumping.

In the described system, fault conditions are detected by volume measurements rather than by pressure measurements, thus, faults may be determined in seconds. FIGS. 11C-11F illustrate the sensor 550 of FIGS. 5-7 detection various types of fault conditions. All description with respect to FIGS. 11C-11F are described with reference to FIGS. 5-7.

Figure 11C:
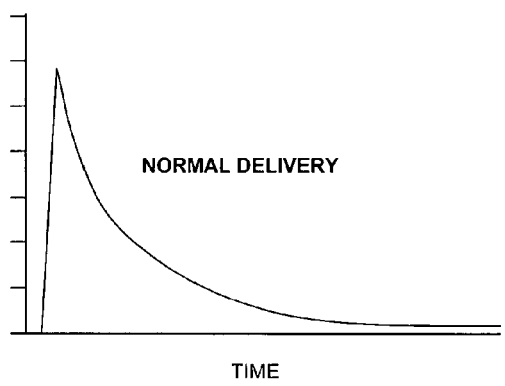
FIG. 11C shows kinetic data representing a normal fluid delivery.
Figure 11D:
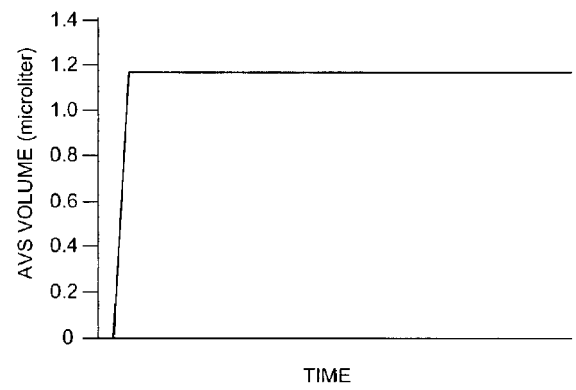
FIGS. 11D-11F show kinetic data representing various fault conditions.

FIG. 11C shows a kinetic profile of sensor 550 output over time for a pumping pulse under normal operating conditions. In contrast, FIG. 11D shows an expected result of an occlusion downstream of the dispensing assembly 120; the increasing (or not decreasing) volume of fluid in the dispensing chamber 122 is quickly detected by the sensor 550.

Figure 11E:
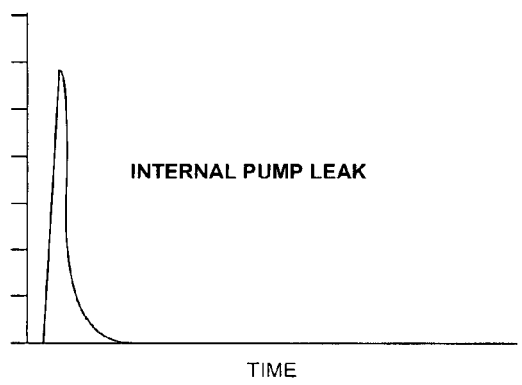
Figure 11F:
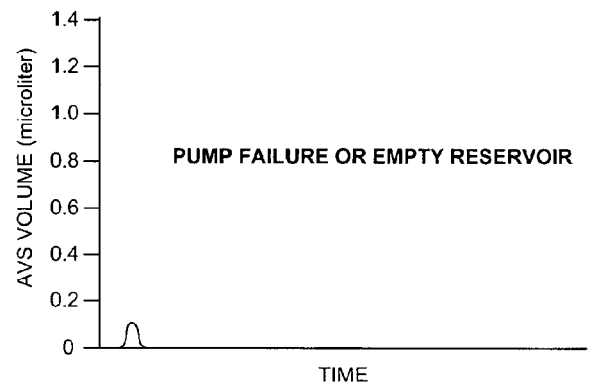

Low volume conditions are shown in FIGS. 11E-11F. In FIG. 11E, an approximate maximum sensor signal is reached, followed by an overly fast decay; this condition may indicate an internal leak in the pump 16, line 310, or dispensing assembly 120. The kinetic profile of FIG. 11F has a low peak volume signal and may be representative of a pump failure, an empty reservoir 20, or an occlusion that is upstream of the dispensing chamber 122. Delayed expansion of the dispensing chamber 122 in response to pump actuation may also indicate a problem in the flow line 310. The sensor 550 may also be capable of detecting bubbles in the fluid. An alarm can be activated in response to detection of a fault condition.

Figure 12:
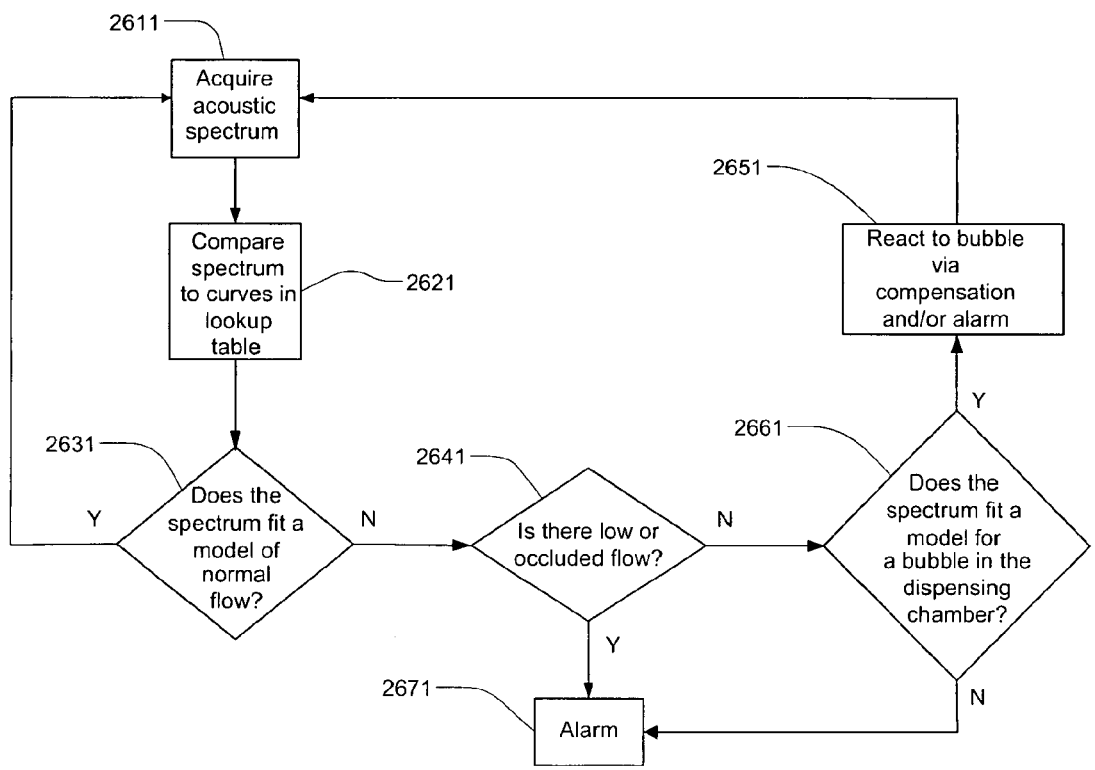
FIG. 12 shows a flow chart of a sensing and reacting process of an embodiment of the fluid delivery device.

FIG. 12 shows a flow chart depicting a cycle of acoustic volume sensing and compensation (corresponding to control loop 360 of FIGS. 2A-3). The sensor may measure the amount of fluid dispensed from the device 10 based on measures of the magnitude of the cyclical changes in the variable volume chamber 121 induced by the pumping cycles. For example, the sensor 550 may repeatedly acquire acoustic spectra of the resonant variable volume 121 and the reference volume chamber 127 (step 2611) and maintains a parameter, which, for each pumping pulse, is updated to incorporate the decrease in volume of gas in the variable volume chamber 121.

Accordingly the updated parameter indicates the net quantity of fluid that has entered the dispensing chamber 122. The fluid entering the dispensing chamber 122 is approximately equal to the volume that has been dispensed by the device 10 if there is sufficient delay between pulses. Alternately, the sensor 550 can repeatedly measure the increase in the volume of gas in the variable volume chamber 121 to determine the amount dispensed by the device (if there is a sufficient delay between pulses). Acoustic spectra are compared to model spectra in a lookup table that may correspond to any or all of a dispensing chamber 122 with a bubble, without a bubble, or with bubbles of varying sizes (step 2621). The lookup table may hold data acquired experimentally, determined using a model, or determined to work empirically. The lookup table may contain data representing varying bubble containing and/or normal conditions for multiple degrees of expansion of dispensing chamber 122. If the spectrum and updated sum fit a model of normal flow (step 2631), another acoustic spectrum is acquired and the cycle is repeated at step 2611. If the spectrum and/or the updated sum do not fit a model of normal flow, the presence of a low or occluded flow will be determined (step 2641). A low or occluded flow may be indicated by a persistently out-of-range volume of the variable volume chamber 121, by an updated sum that is lower than a predicted or set value, or both. If a low or occluded flow condition is detected, an alarm will be triggered (step 2671). Alarms may include audible signals, vibrations, or both. If no condition of low or occluded flow is found, the device determines if the spectrum fits a model corresponding to a condition of a bubble in the dispensing chamber 122 (step 2661). If a bubble is determined to be present, a reaction is initiated that may include an alarm and/or compensatory action which may include temporarily increasing the rate of pumping (step 2651) and the cycle will begin again at step 2611. If it is determined that no bubble is present, an alarm is triggered to indicate an undetermined fault condition (step 2671). Embodiments of the present invention may also utilize bubble detection using AVS technology as disclosed in co-pending U.S. Patent Application Ser. No. 60/789,243, which is incorporated herein by reference.

The pumping assembly 16 of FIGS. 2A-3 urges fluid from the reservoir 20 to the dispensing assembly 120. When a dispensing assembly according to FIGS. 6-7 is used, it is not necessary to use a high precision pump, because the feedback provided from the dispensing assembly 120 to the pumping assembly 16 allows adjustment of the pumping assembly 16 based on exact measurements of the volume being delivered. The individual pumping pulses may be of sufficiently low volume to allow precise compensation based on the feedback. Many different pumping assembly 16 implementations can therefore be employed. Various possible embodiments of the pumping assembly 16 are described below.

Figure 13:
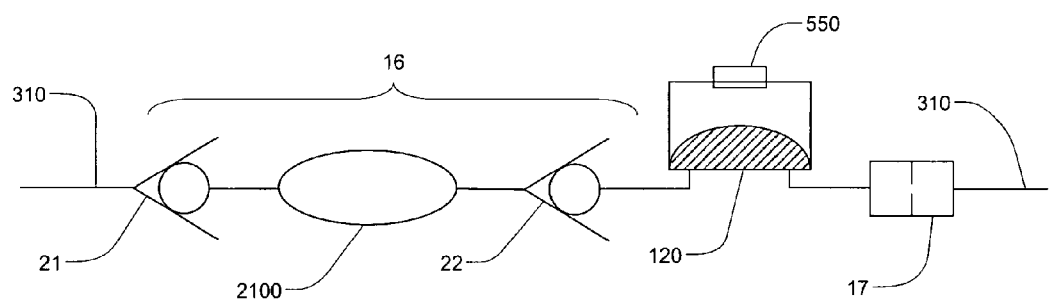
FIG. 13 shows a block diagram of a fluidic line with a pressure generation assembly.
Figure 14:
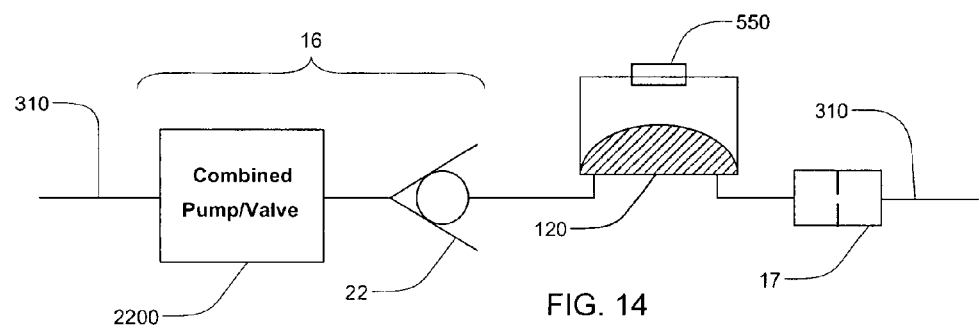
FIG. 14 shows a block diagram of a fluidic line with a valving pump.

FIGS. 13 and 14 schematically show alternate embodiments of some of the components in a fluid delivery device according to an embodiment of the invention. FIG. 13 shows a flow line 310 with a pumping assembly 16 having a pumping element 2100 located between an upstream one way valve 21 and a downstream one way valve 22. The pumping element 2100 may use an actuator to deform a portion of the flow line to generate pressure in the flow line 310. The upstream one way valve 21 inhibits retrograde flow from the pumping element 2100 toward a fluid source (not shown), while the downstream one way valve 22 inhibits retrograde flow from the volume-sensing chamber 120 to the pumping element 2100. As a result, fluid is driven in the direction of the exit assembly 17, which, in one embodiment, includes a high-impedance passage.

In an alternate embodiment shown in FIG. 14, the functions of the pumping element, i.e., generating pressure in the flow line 310, and the upstream one way valve 21 are performed by a combined valving pump 2200. Thus, the pumping assembly 16 in the FIG. 14 embodiment is made up of two components—the combined valving pump 2200 and the downstream one way valve 22—instead of the three components used in the FIG. 13 embodiment. Other embodiments of the pumping assembly 16 may be used. The combination of valving and pumping functions in valving pump 2200 may be accomplished by a variety of mechanisms, some of which are described below with reference to FIGS. 15A-16 and 22-56.

In many of the embodiments described below, the poppet for the inlet valve 21, the poppet for the exit valve 22 and the pumping actuation member 54 are all either directly or indirectly (e.g., as in FIGS. 50-56) in communication with the fluid line 310 such that each of these elements are able to create or react to various fluid pressures. As noted above, the upstream and downstream valves—which may also be referred to herein as the inlet and exit valves—are one way valves. The valves can be volcano, flapper, check or duck-bill valves, amongst other types of one way valves, or other types of valves that bias the flow toward the device output. An example of volcano valves are disclosed in U.S. application No. 5,178,182 issued Jan. 12, 1993 to Dean L. Kamen, and incorporated herein by reference.

In the embodiment shown in FIGS. 15A-15D, the pumping assembly includes both an inlet valve 21 and an exit valve 22, each of which includes a fluid inlet, a fluid exit, and a moveable member (which is, for each valve, a portion of membrane 2356). The pumping assembly also includes a pumping element 2100. The pumping element is located downstream from the inlet valve 21 and upstream from the exit valve 22. In the following description, the exit valve will be starting from the closed position, i.e., fluid is not flowing through the exit valve. However, at a time when the fluid presents enough pressure, the fluid pressure opens the exit valve by placing pressure on the membrane and the exit valve's poppet 9221 to open the valve, and the fluid can then flow through the exit valve 22. The embodiment of FIGS. 15A through 15D may be considered to be a combined valving-pump (like item 2200 in FIG. 14), in the sense that a single mechanical action both occludes a pump inlet and then urges flow through a pump outlet.

This pumping arrangement has the advantage of partitioning the moving parts and wetted line components to opposite sides of a flexible barrier membrane 2356. As a result, the moving parts may be located in a reusable component and the wetted parts (fluidic line 310) may be located in a disposable component.

In a preferred embodiment of the pumping mechanism, the fluid source is a non-pressurized reservoir. When the moveable member of the inlet valve is in the open position, and a negative pressure exists in the pumping chamber, a pressure differential exists that pulls the fluid from the reservoir towards the inlet valve. This negative pressure may be created by the resiliency of the membrane in the pumping chamber. In one alternative embodiment, a spring—which may be built into the membrane—may be used to assist in the recoil of the membrane in the pumping chamber. The non-pressurized reservoir may be collapsible, so that when fluid is drawn from it, a corresponding collapse in the reservoir reduces its volume. As a result, build-up of negative pressure, or air in the reservoir is prevented.

In a preferred embodiment of the pumping mechanism, after the inlet valve is closed, pressure is applied to the pumping chamber forcing fluid from the pumping chamber towards the exit valve. Pressure created by the pumping motion opens the exit valve and allows fluid to flow through the exit valve's fluid exit.

The moveable member can be anything capable of functioning as described above. In some embodiments, the moveable member is a flexible membrane or a resilient pumping diaphragm. In other embodiments, the moveable member is a ball-shaped rigid structure or another object capable of preventing fluid from flowing out of an opening in the fluid path.

In practice, the pumping mechanism may be primed prior to use. Thus, the pumping mechanism cycles through a number of strokes, purging air from the fluid line, until most or all of the air in the fluid line is purged. Many of the pumping mechanisms disclosed herein have the ability to "self-prime" because the fluid volume contained outside the pumping chamber, but between the valves, is small. When the pump squeezes air in the pump chamber, it generally builds up enough pressure to blow past the exit valve. The subsequent return stroke can therefore develop sufficient negative pressure for the pump to pull liquid from the reservoir. If the "dead" volume of the pump is too large, the air in the pumping chamber may not build up enough pressure to escape the exit valve. As a result, the pump may stall.

FIGS. 15A-15D, 16 and 22-56 show several embodiments of the pumping mechanism. Referring now to FIGS. 15A-15D, one embodiment of the pumping mechanism is shown exemplifying several steps in the pumping process: 1. fluid passing through the inlet valve 21 (as shown in FIG. 15B); 2. the inlet valve closed (as shown in FIG. 15C); and 3. the pumping actuation member 54 forcing fluid downstream, with fluid pressure opening the exit valve 22 and flowing through the fluid exit (as shown in FIG. 15D).

The pumping mechanism of FIGS. 15A-15D includes a moveable member, which, in this embodiment, is a portion of the flexible membrane 2356. The inlet and exit valves include poppets 9221, 9222 that function as valve occluders. Each of the poppets 9221, 9222 and the pump actuation member 54 include a spring 8002, 8004, 8006. The pump plate 8000 is attached to both the pump actuation member 54 and the inlet poppet 9221 and serves as a terminus to their respective springs 8004, 8002.

The term "poppet" is used to denote a member that applies pressure against the moveable member (i.e., the membrane) to affect the position of the membrane. Although other designs may be used, some specific examples of spring-loaded poppet valves that utilize structures and principles of mechanical advantage are described below (in connection with FIGS. 50-56). However, mechanisms other than poppets can be used to perform the same function. In FIGS. 15B-15D, the inlet valve 21 includes a fluid inlet and fluid exit, part of the membrane 2356, and a poppet 9221. The exit valve 22 includes a fluid inlet a fluid exit, part of the membrane and a poppet 9222.

Figure 15A:
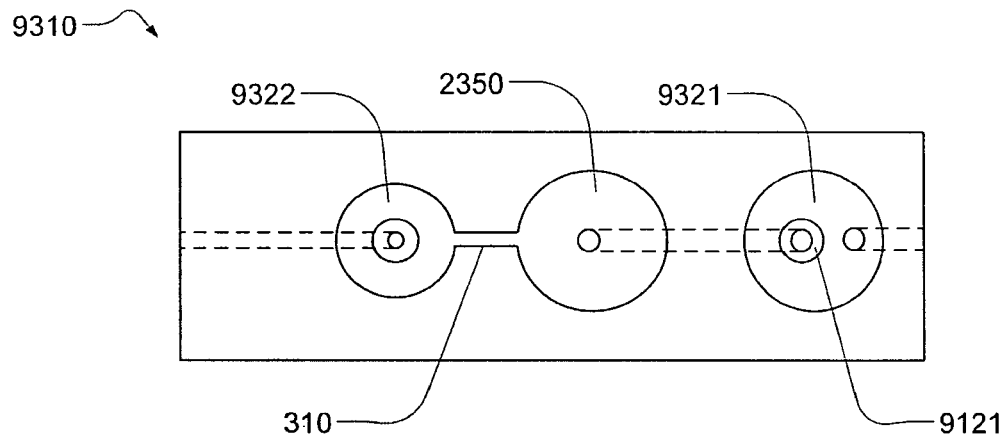
FIGS. 15A-15D show schematic diagrams of a pumping mechanism.
Figure 15B:
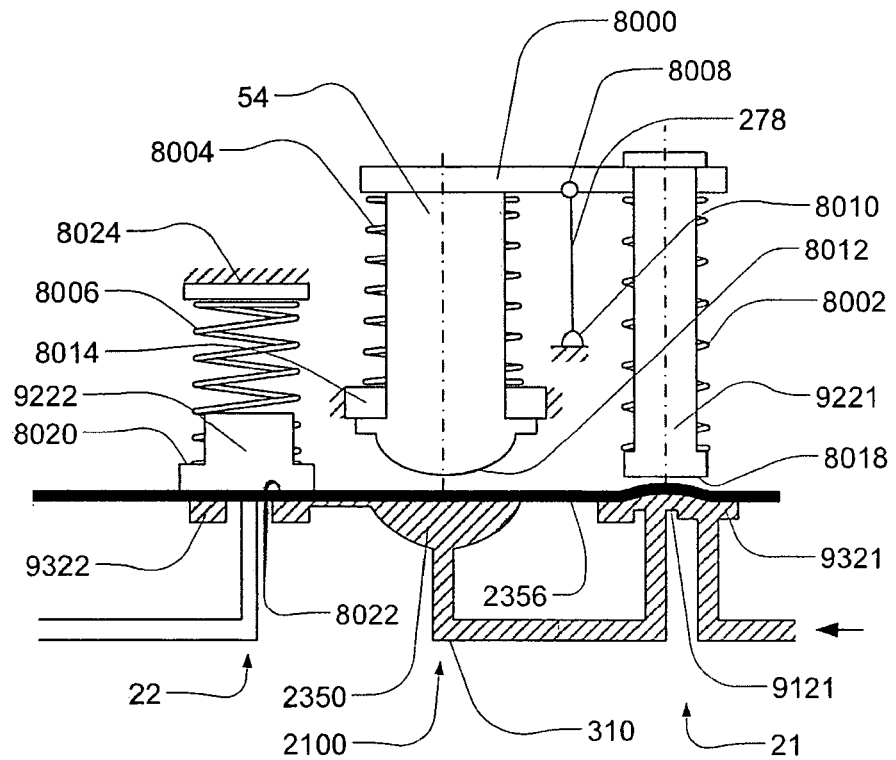
Figure 15C:
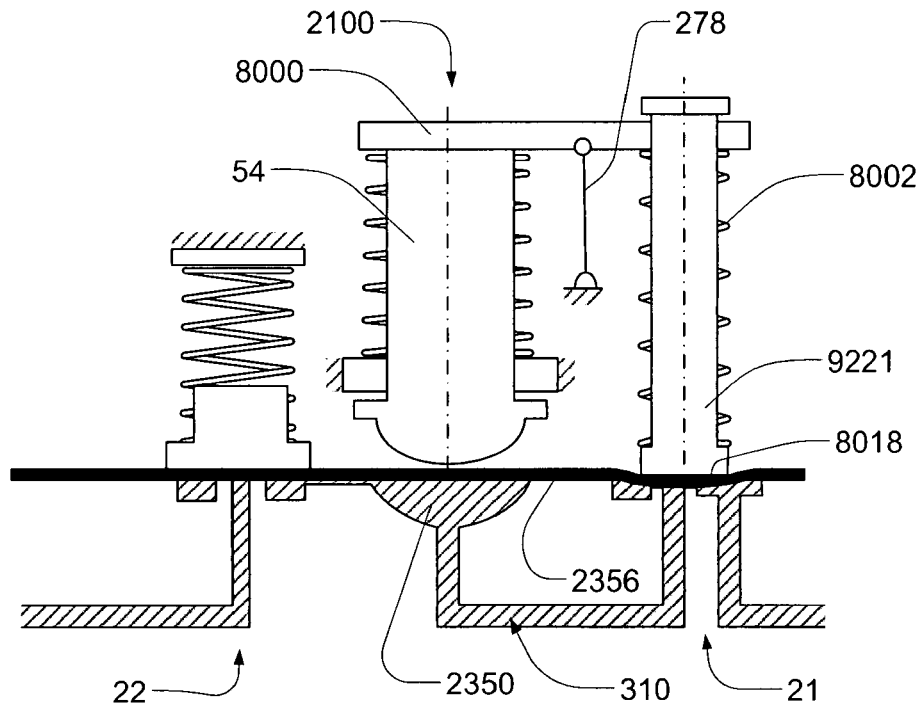
Figure 15D:
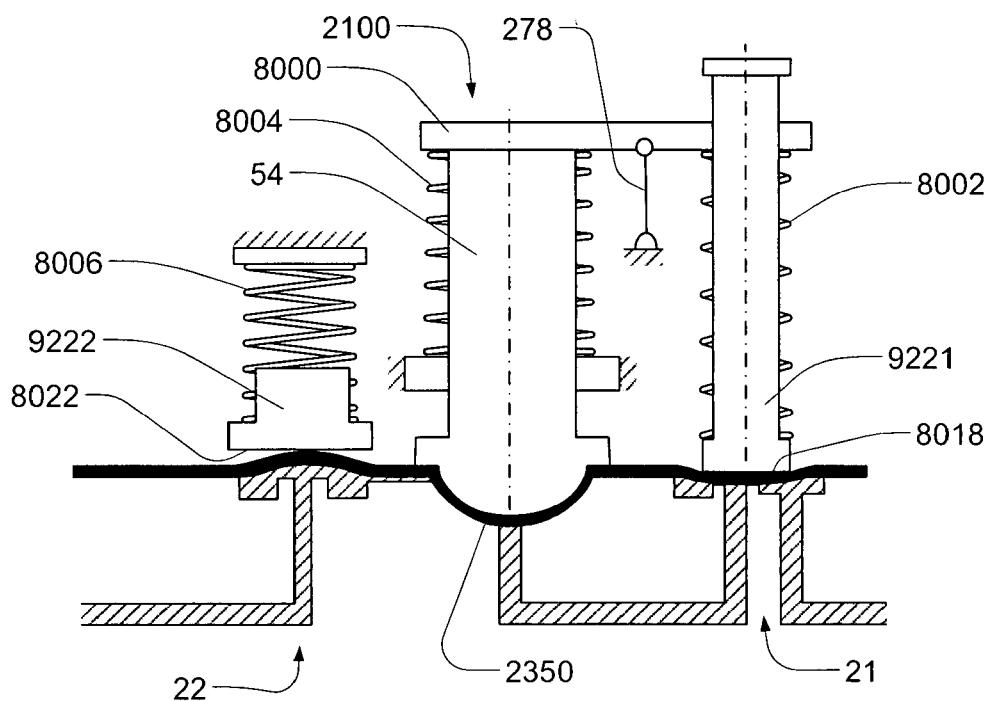

In the embodiment shown in FIGS. 15A-15D, the fluid path 310 is defined by a structure (item 9310 in FIG. 15A), which may be rigid or have some flexibility (preferably less flexibility than membrane 2356. As shown in FIG. 15A, the housing structure 9310 defines the valving chambers 9321, 9322 and the pumping chamber 2350; all three of these chambers are in the fluid path 310.

Referring now to FIGS. 15B-15D, the inlet valve 21, exit valve 22 and pump element 2100 each have a fluid inlet and a fluid exit. The pumping actuation member 54 has a pumping chamber 2350 where the fluid flows after exiting the inlet valve. Pumping actuation member 54 applies pressure onto the membrane 2356, creating positive pressure in the fluid line.

As shown in FIGS. 15B-15D (and similarly for the valve seat 4070 for the outlet valve shown in FIGS. 50-56), the valve seat 9121 in the inlet valve 21 is preferably spaced away from the membrane 2356, when the membrane is not being actuated by the poppet 9221 of the inlet valve.

The fluid line 310 is partially defined by a membrane 2356. In this embodiment, the membrane 2356 separates parts of the pumping mechanism from the fluid. Thus, the fluid line 310 is wetted and the pumping actuator 54 and the valve poppets 9221, 9222 are not wetted. However, alternative embodiments of the pumping assembly do not need to include a membrane 2356 that is in contact with the fluid line 310. Instead, a different moveable member may be used for the valves and/or pump. In still other embodiments, only parts of the fluid line 310 are separated from the pumping mechanism, thus partially wetting the pumping assembly.

The inlet poppet 9221 includes an end 8018 referring to the surface area of the inlet poppet that contacts the membrane portion of the fluid line 310. The pumping actuation member 54 includes an end 8012 that contacts the membrane portion of the fluid line 310. Likewise, the exit poppet 22 includes an end 8022 that contacts the membrane portion of the fluid line 310. The ends 8018, 8022 of the valve poppets apply pressure onto their respective areas of the membrane 2356, blocking or unblocking the respective portions of the flow path 310. The end 8012 of the pressure actuation member also applies pressure onto its respective area of the membrane, so as to cause flow through the fluid line 310.

The pumping actuation member 54 is surrounded by a plunger biasing spring 8004. The plunger biasing spring 8004 has both a terminus at the pump plate 8000 and at 8014, a support structure that also holds the pumping actuation member.

The inlet poppet 21 is surrounded by an inlet poppet spring 8002, although in alternate embodiments, the inlet poppet itself is resilient and so serves the function of the spring. The inlet poppet spring 8002 has both a terminus at the pump plate 8000 and near the end 8018 of the inlet poppet 9221.

The exit poppet 9222 is surrounded by a passive exit poppet spring 8006. The exit poppet spring 8006 has both a terminus at an exit poppet plate 8024 and the lip 8020 near the end of the exit poppet 9222.

In each case, the springs 8002, 8004, 8006 terminate before the respective ends and do not interfere with the surface areas 8018, 8012, 8022 that contact the membrane 2356.

In a preferred embodiment, the fluid pumping device also includes at least one shape memory actuator 278 (e.g., a conductive shape-memory alloy wire) that changes shape with temperature. The temperature of the shape-memory actuator(s) may be changed with a heater, or more conveniently, by application of an electric current. FIGS. 15B-15D show an embodiment with one shape memory actuator 278, however, in other embodiments (described below) there may be more than one shape memory actuator 278. In one embodiment, the shape memory actuator is a shape memory wire constructed of nickel/titanium alloy, such as NITINOL™ or FLEXINOL®. However, in other embodiments, any device capable of generating a force, such as a solenoid, could also be used. In certain embodiments, the shape memory actuator 278 has a diameter of about 0.003 inches and is about 1.5 inches in length. However, in other embodiments, the shape memory actuator 278 may be made from any alloy capable of contraction with heat (and expansion may be aided by a mechanism that imparts force on the alloy so as to stretch the alloy to the original length, i.e., a spring, although such a mechanism is not required) so as to actuate the pumping mechanism as described in the embodiments herein. In certain embodiments, the diameter of the shape memory actuator 278 can be from 0.001 inches to any diameter desired and the length can be any length desired. Generally speaking, the larger the diameter, the higher the available contraction force. However, the electrical current required to heat the wire generally increases with diameter. Thus, the diameter, length and composition of the shape memory alloy 278 may affect the current necessary to actuate the pumping mechanism. Irrespective of the length of the shape memory actuator 278, the actuation force is approximately constant. Increase in actuation force can be imparted by increasing the diameter of the shape memory actuator 278.

The shape memory actuator 278 connects to the pump plate 8000 through connector 8008. Connector 8008 is described in more detail below. The shape memory actuator 278 connects to a fluid pumping device by way of terminus connector 8010. Depending on the device or system in which the pumping mechanism is used, the terminus connection location will vary. The terminus connector 8010 is described in more detail below.

FIGS. 15B-15D show the pumping mechanism and fluid line 310 having already been primed as discussed above. Referring now to FIG. 15B, the inlet valve 21 is open, and the pumping actuation member 54 is not pressing against the membrane 2356. The exit valve 22 is in the closed position. The shape memory actuator 278 is in an expanded position. In this configuration, fluid is pulled from a reservoir (not shown) to the inlet valve 21 fluid inlet. (Although shown as a bulge in the membrane in the inlet valve region, the pulling of fluid in this step may cause a depression in the membrane, or no deformation of the membrane). When the inlet poppet is in the open position, the fluid can flow from the fluid inlet to the fluid exit and into the pumping chamber 2350. At this point, the exit poppet end 8022 is firmly pressed against the membrane 2356 and seals the exit valve 22.

Referring next to FIG. 15C, electrical current has been applied to the shape memory actuator 278, and the shape memory actuator is contracting from a starting length towards the desired end length. The contracting of the shape memory actuator 278 pulls the pump plate 8000 towards the fluid line 310. The inlet poppet 9221 and the pumping actuation member 54 are both connected to the pumping plate 8000. The motion of the plate 8000 pulls both the inlet poppet 9221 and pumping actuation member 54 towards the membrane 2356. As shown in FIG. 15C, the inlet poppet end 8018 is pressed firmly against the membrane 2356, sealing the membrane against the valve seat 9121 and, closing the inlet valve 21. (The motion of the inlet poppet can force a small amount of fluid in the inlet valving chamber, item 9321 in FIG. 15A, through either the fluid inlet or the fluid exit of the inlet valve 21.)

Simultaneously, the pumping actuation member 54 begins its path towards the pumping chamber 2350. During this process, as the inlet poppet spring 8002 is compressed (at this point, the inlet poppet end 8018 is pressing firmly against the fluid line 310), the pump plate 8000 and pumping actuation member 54 continue traveling towards the fluid line 310. The inlet poppet spring 8002 allows the pump plate 8000 to continue moving toward the fluid line 310 with the pump actuation member 54 even when the inlet poppet 9221 can not travel any further.

Referring now to FIG. 15D, the pumping actuation member 54 presses against the area of the membrane 2356 over the pumping chamber 2350 and the fluid is pumped so as to increase the pressure of the fluid in the pumping chamber 2350. The exit poppet end 8022 remains pressing firmly (aided by the exit poppet spring 8006) on the membrane 2356 sealing the fluid inlet and fluid exit of the exit valve 22 until the pressure from the fluid flowing from the pumping chamber 2350 forces exit valve 22 open. Upon reaching a sufficient pressure, the fluid exits through the fluid exit of the exit valve 22, thus overcoming the pressure exerted against the membrane 2356 by the exit valve 22. Upon cessation of flow, the exit valve 22 is forced closed by the passive spring 8006.

During the work stroke, the pump actuation member spring 8004 is loaded. Eventually, the pump actuation member spring 8004 will pull the pump actuation member 54 away from the membrane 2356. As a result, during the relaxation stroke, the spring 8004 returns the pump actuation member 54, and pumping plate 8000 to the relaxed position of FIG. 15C; the loaded inlet poppet spring 8002 may also contribute energy to the return stroke. As the pumping plate 8000 nears its relaxed position, it engages a cap of the inlet poppet 9221 to lift and unseat the inlet poppet so as to open the inlet valve 21. The pump actuation member spring 8004 also unloads during the return stroke.

The pump plate 8000, reaching a threshold distance where the inlet poppet spring 8002 is at the same level as the pump plate 8000, will unload with the pump actuation member spring 8004. The membrane 2356 in the pumping chamber 2350, being resilient, will return to its starting position. This creates a negative pressure and as the inlet valve opens, fluid will flow through the inlet valve's fluid inlet to the fluid exit and towards the pumping chamber 2350. Thus, the pumping mechanism will now be in the state as shown in FIG. 15B.

The entire pump sequence described with respect to FIGS. 15B-15D will repeat each time the pump is actuated through application of current onto the shape memory actuator 278.

The membranes referred to herein, including membrane 2356, may be made from any resilient material capable of imparting the necessary characteristics to function as described herein. Additionally, the membrane material may include a biocompatible material so as not to impede operation of the pump or diminish the therapeutic value of the fluid. Multiple biocompatible resilient materials may be suitable, including nitrile and silicone. However, different therapeutic fluid compositions may require different choices of resilient material.

The pumping mechanism described above and also various embodiments as described herein can be described in terms of stroke length. One way to determine stroke length is by the total change in the length of the shape memory actuator during one cycle of contraction and expansion of the shape memory actuator. This difference will determine the total distance the pump rod travels and thus, the total amount of fluid that flows out of the inlet chamber 2354 to the pumping chamber 2350, to the exit chamber 2352 and finally, out the exit chamber 2352. Another way to determine stroke length is the travel distance of the pump plate 8000. For a partial stroke, the pump plate 8000 will not reach its maximum travel distance. In one embodiment, very small or micro-strokes are initiated continuously, pumping micro-liter volumes of fluid on a continuous or regular basis, from the reservoir to the exit. For example, a micro-stroke may displace less than 20%, 10% or 1% of the volume of the pumping chamber 2350.

Figure 16:
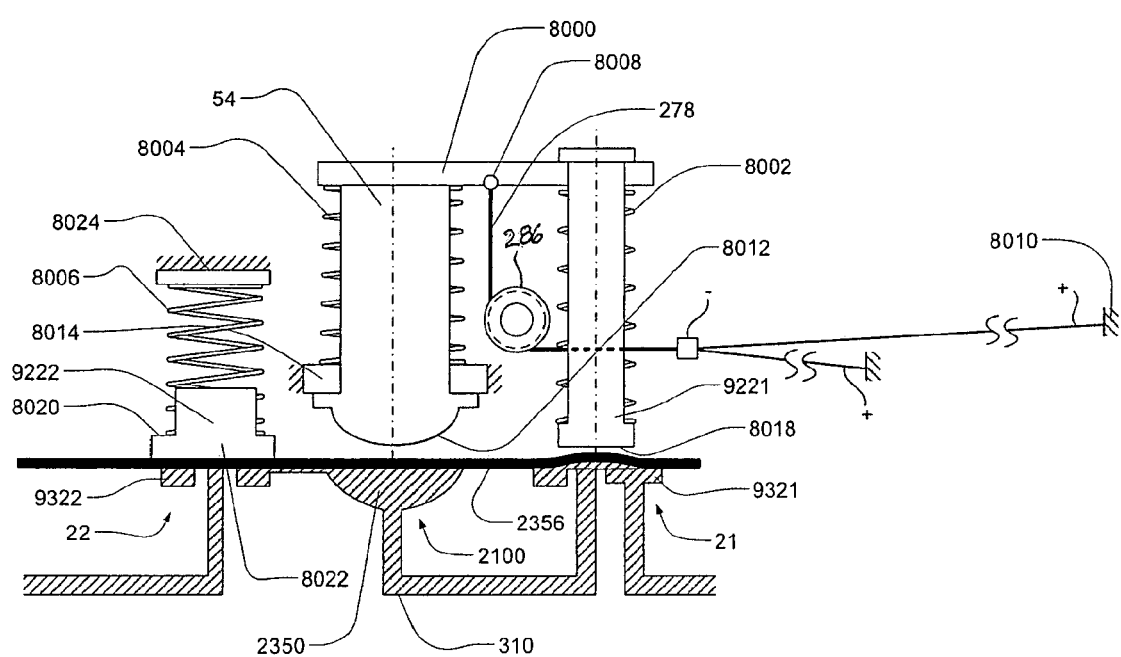
FIG. 16 shows a schematic diagram of a pumping mechanism.

FIG. 16 shows a variation of the pumping mechanism embodiment shown in FIG. 15B. In FIG. 16, two different shape memory actuators—a longer one and a shorter one— are used. FIG. 16 shows an embodiment of the pumping mechanism shown in FIG. 15B in which the shape memory wire 278 is tensioned around a pulley 286 and splits into longer and shorter strands. A common juncture serving as a negative terminal may be located where the longer and shorter strands split off. Completion of a circuit with either or both of the alternate paths allows adjustment of the pumping force and/or stroke length. In an alternative embodiment, a piece of material, such as Kevlar material, extends from the common junction around the pulley to the force plate 8000, while two separate pieces of shape memory wire extend from the common junction to their respective supports. These embodiments provide both a pumping mode and an air purging mode, as described below, by using two wires with different lengths.

Figure 17:
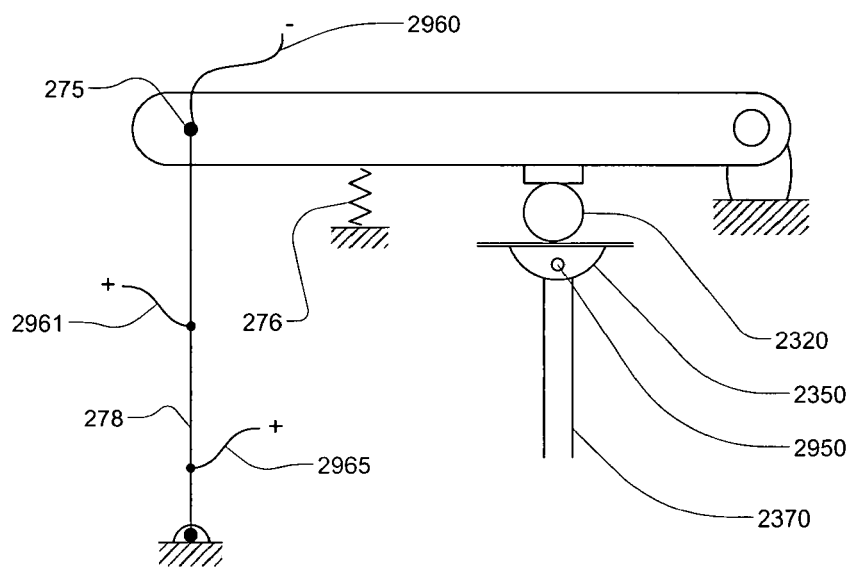
FIG. 17 schematically shows a sectional view of an embodiment that includes a shape-memory-wire actuator capable of multiple pumping modes.
Figure 18:
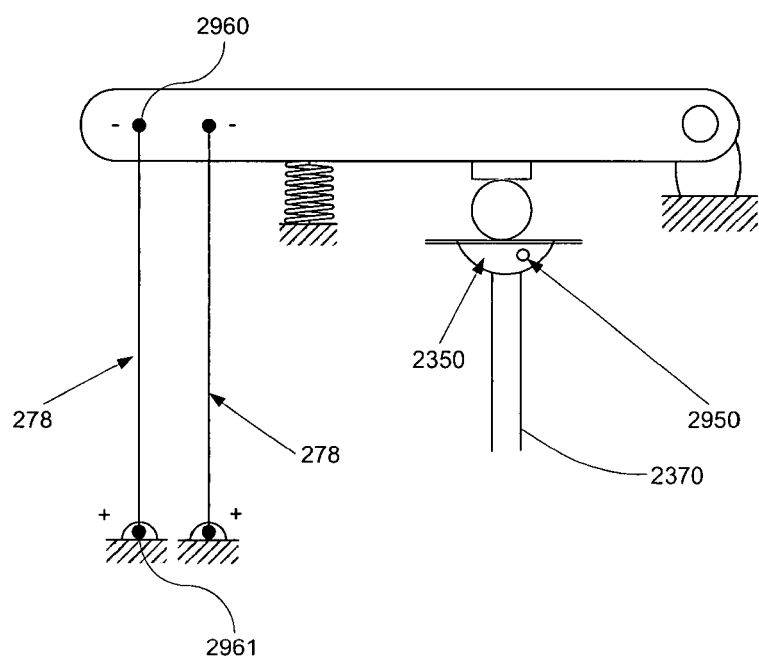
FIG. 18 schematically shows a sectional view of an embodiment that includes two shape-memory actuators and is capable of multiple pumping modes.
Figure 19:
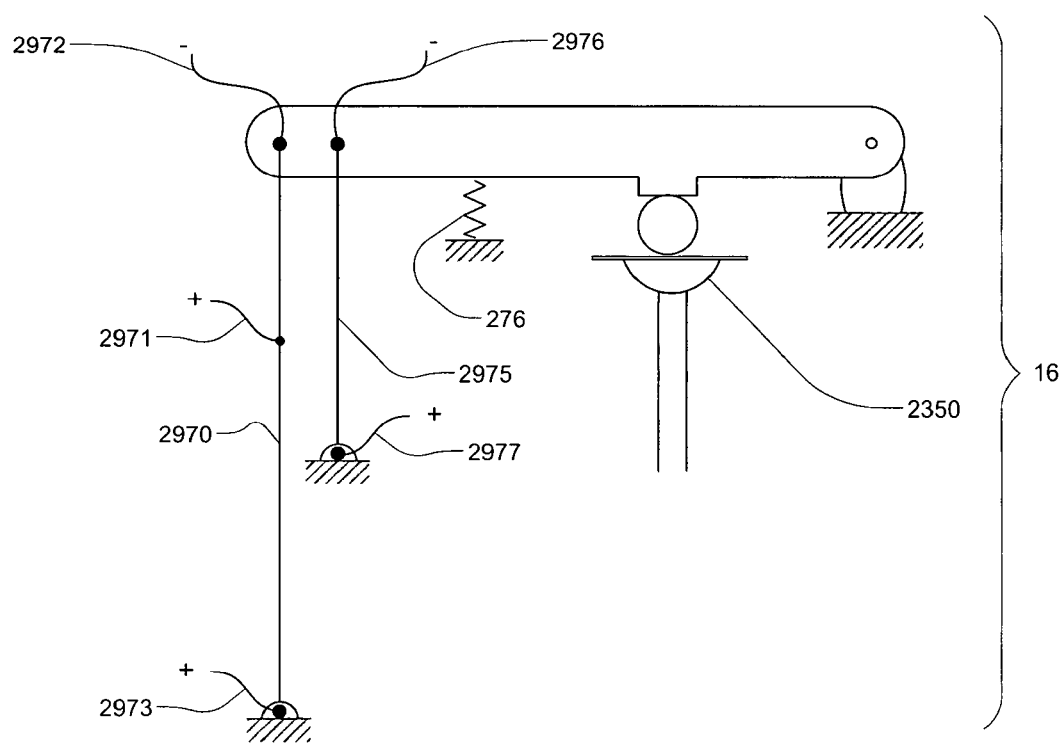
FIG. 19 schematically shows a sectional view of an embodiment that includes shape-memory actuators of differing lengths.

With respect to varying stroke using the shape memory actuator variables, for a given length of shape memory actuator, the stroke is dependent on a number of variables: 1. total time electricity/heat is applied; 2. total voltage of the electricity; and 3. the diameter of the shape memory actuator. Some variable embodiments are shown in FIGS. 17-19. However, in some embodiments, the stroke can be varied while maintaining the length, electricity time and voltage. These embodiments include multiple shape memory actuators (see FIG. 19) and multiple switches on a single shape memory wire (see FIG. 17). As discussed above, the desired stroke length can also be attained by modifying any one or more of the variables.

Additionally, the timing of the application of heat or electric current to the shape memory actuation can vary to control the stroke. Each time the shape memory actuator is heated can be termed a pulse. Factors such as the pulse frequency, pulse duration, and stroke length may affect the amount of fluid delivered over time.

FIGS. 17-19 additionally depict embodiments of pumping assemblies which have both a fluid pumping mode and an air purging mode. When activated, the air purging mode applies a compression stroke of increased displacement and/or increased application of force by a force application member. The air purging mode may be activated based on the likelihood or knowledge of air being present in the pumping assembly. For example, the air purging mode may be activated when the line is attached to a reservoir, when a bubble is detected by a sensor or sensing apparatus, or when insufficient flow is detected by a sensor or sensing apparatus. Alternately, the two modes may be used to select between displacing a smaller and a larger volume of fluid for a given pumping pulse.

Referring now to FIG. 17, a schematic shows a pumping assembly actuated by a shape memory actuator 278 and having multiple modes of operation. When a pumping chamber 2350 is filled with fluid, the pumping assembly operates in a fluid pumping mode. During fluid pumping mode, electrical current flows between a negative electrical lead 2960 and a positive electrical lead 2961, causing resistive heating of the alloy shape memory actuator 278 and a resultant phase change and power stroke. In one embodiment, during priming of the pumping mechanism or when a bubble 2950 is suspected to be in the pumping chamber 2350, the air purging mode is activated and electrical current flows along a path of extended length between a negative electrical lead 2960 and a positive electrical lead 2965; the result is a compression stroke of greater force on and displacement of force application member 2320 which should be sufficient to displace air 2950 from the pumping chamber 2350 to the pump outlet 2370. In alternate embodiments, the positive and negative leads may be reversed.

Referring now to FIG. 18, a schematic shows an alternate pumping assembly having a plurality of shape memory actuators 278 having the same length. The additional actuators may be used to increase the actuating pressure on the pumping chamber 2350, for example, to remove an occlusion or air bubble in the fluid line, pumping chamber or other area of the pumping mechanism. The additional actuators may also provide a redundancy to any pumping device. A single shape memory actuator may be capable of imparting sufficient force to remove an air-bubble from the pumping chamber. Additionally, in the embodiment shown in FIG. 18, an additional return spring may be necessary depending on the length of the second shape memory actuator.

When a reservoir is first attached to a flow line having a pumping assembly, the pumping mechanism (item 16 in FIGS. 13-14) is typically filled with air. Air can also enter the pumping mechanism during normal operation for various reasons. Since air is more compressible than fluid, application of a compression stroke of a length that is sufficient to displace a fluid may be insufficient to generate enough pressure to overcome the cracking pressure of a one way valve of the pumping mechanism if there is a substantial amount of air in the fluid line. Accordingly, the pumping mechanism may stall. However, it may be desired to force air through the line during priming or when an innocuously small amount of air is present in the pumping assembly. Thus, the embodiments shown in FIG. 18 can be used to impart additional force in this situation.

FIG. 19 schematically shows an alternative pumping assembly 16 having a plurality of shape memory actuators. A first, shorter, shape memory actuator 2975 has a first electrical lead 2976 and a second electrical lead 2977. The shorter actuator 2975 is capable of generating compression strokes that are sufficient to displace fluid in the pumping chamber 2350; the shorter shape memory alloy actuator 2975 is used during normal fluid pumping mode operations. When an air purging mode is indicated, or a larger pumped fluid volume is required, a second longer shape memory alloy actuator 2970 may be used by sending a current along an actuator length disposed between a first electrical lead 2973 and a second electrical lead 2972. The longer shape memory alloy actuator 2970 may also be used as a backup actuator for fluid pumping mode operation by creating a shorter circuit which includes an electrical path between a first electrical lead 2972 and a second electrical lead 2971. The shorter shape memory actuator 2975 may also be used to vary the stroke volume to provide better control at lower fluid volume rates. The multiple mode actuators of FIGS. 17-19 are not limited to use with the pump components shown and may be employed with any of the various embodiments of pumping mechanisms described herein including those using fluid pumping devices as described below and those employing valving pumps as described below. Thus, the desired stroke length can be initiated by applying electricity/heat to the length shape memory actuator that will provide the desired stroke length.

Figure 20A:
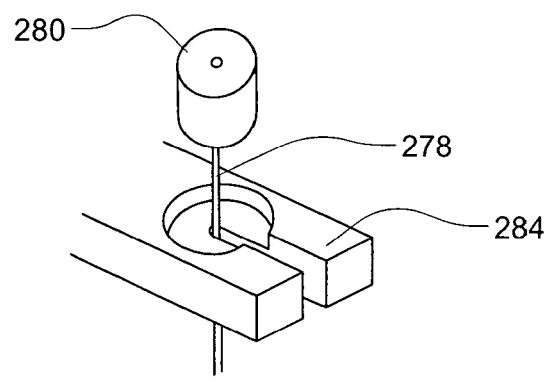
FIG. 20A-20B schematically show embodiments for attaching a shape memory actuator.
Figure 20B:
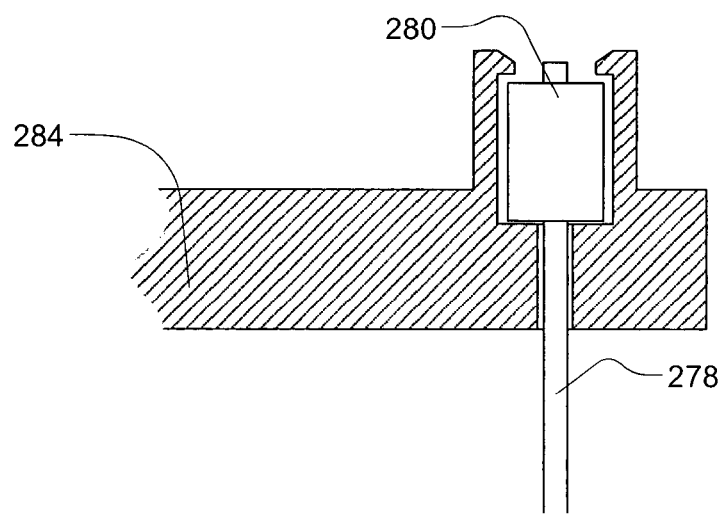

Referring now to FIGS. 20A and 20B, each shows one embodiment for attaching the shape memory actuator. These various embodiments can be used in any of the mechanisms or devices described herein which employ a shape memory actuator 278. Referring to both FIG. 20A and FIG. 20B, the shape memory actuator 278 is fed into a grommet 280. The grommet 280 is then attached to a part 284. Although only two embodiments of this mode of attachment are shown, various other modes are used in other embodiments. Other modes of attaching a grommet to a part or any fixed location can be used.

Figure 21A:
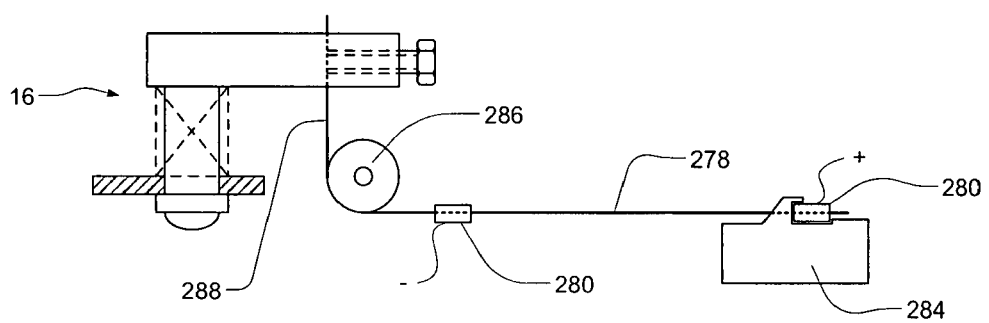
FIGS. 21A-21B schematically show embodiments for attaching a shape memory actuator to a pumping mechanism.
Figure 21B:
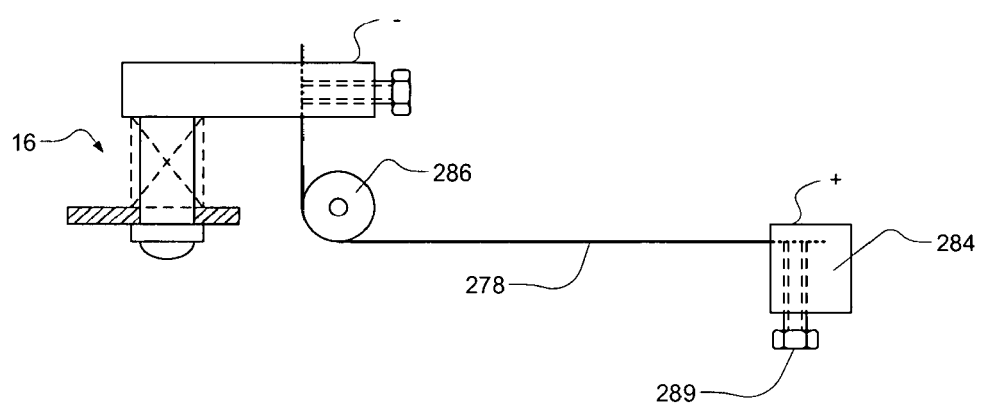

Referring now to FIGS. 21A and 21B, two exemplary embodiments of attaching the shape memory actuator 278 for use with a pumping mechanism 16 are shown. In each of these embodiments, the shape memory actuator 278 is designed to turn around a pulley 286. Referring to FIG. 21A, the shape memory actuator 278 is attached to a piece 288, preferably made of KEVLAR material, by way of grommet 280. One end of the shape memory actuator 278 is shown attached to a part 284 by way of a set screw attachment 289. Referring now to FIG. 21B, one end of the shape memory actuator is shown attached to a part 284 by a grommet 280.

Various embodiments of the pumping mechanism are shown in herein. The pumping mechanisms may include an inlet valve, a pumping actuation member and an exit valve. As discussed above, different types of one way valves may be used in alternative embodiments. Although the schematic shown in FIGS. 15A-15D shows one embodiment, the following figures show alternate embodiments.

Referring now to FIG. 22 and FIG. 23, a side view and a cross section of a section of a pumping mechanism is shown. In this embodiment, the pumping actuation member is a pumping elongate finger 32. When force is exerted onto the finger 32, the finger 32 depresses the moveable member and reduces the internal volume of the fluid line. The section of the pumping mechanism in FIGS. 22 and 23 shows only the pumping chamber. When combined with one way valves (items 21 and 22 of FIG. 13), application of a deforming force to moveable member 23 urges fluid to flow toward an exit assembly (not shown). As shown in FIGS. 22 and 23, the finger 32 is pointed for focusing of force, but in other embodiments, the finger 32 may be flat, or of any other suitable shape. A spring 31 serves to bias the finger 32 toward a retracted position with respect to the resilient member 23 so that the finger 32 returns to the retracted, non depressing position in the absence of application of force. As shown in FIG. 23, a motor can be used to apply force onto the finger 23. However, in other embodiments, a shape memory actuator is used. Various types of motors will be suitable including electric motors and piezoelectric motors.

Referring to both FIGS. 22 and 23, a backstop 33 limits the potential travel of the finger 32, supports the moveable member 23, and ensures a reduction of volume in the fluid line or pumping chamber by preventing the moveable member 23 from moving out of position in response to application of force by the finger 32. As seen in FIG. 22, the backstop 33 may advantageously have a shape complementary to the resilient member 23. In various embodiments, the pumping assembly 16 may include a lever or crank driven on one end by a motor, compressing the resilient member 23 at another end.

Figure 24:
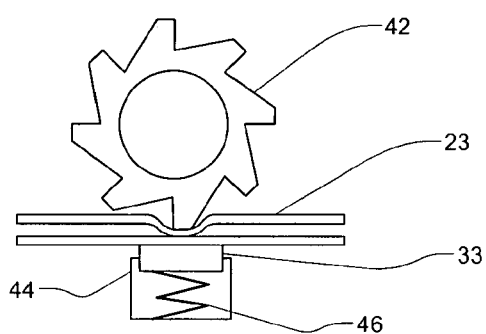
FIG. 24 shows a pumping mechanism employing rotating projections.

Referring now to FIG. 24, another embodiment of the pumping actuation member is shown in relation to one section of the pumping assembly. A motor or shape memory actuator (not shown) applies a rotating force to a grouping of coupled projections 42. These projects 42 serve as the pumping actuation member and, in turn, apply force to the moveable member 23 in turn. Accordingly, intermittent pulses of force are applied to the moveable member 23. The backstop 33, as shown, can travel within a housing 44 and is upwardly biased toward the resilient member 23 by a spring 46.

Figure 25:
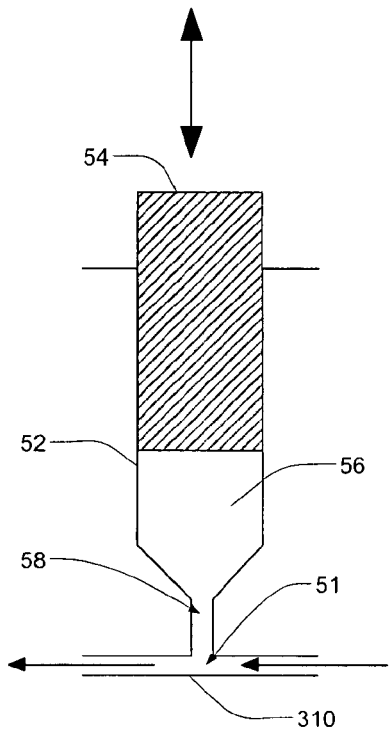
FIG. 25 shows a pumping mechanism employing a plunger and barrel.

Referring now to FIG. 25, an embodiment of a force application assembly with a pumping actuation member (here, a plunger) 54 inside a barrel 52 is shown. A motor causes the plunger 54 to be alternately withdrawn and inserted into the barrel. When the plunger 54 is withdrawn, a negative pressure draws fluid from the reservoir (not shown) into a channel 51 and a lumen 56. When the plunger 54 is inserted, the increased pressure in combination with the one way valves (not shown) drives fluid towards the dispensing assembly (not shown). The lumen 56 is connected to the channel 51 via a connecting channel 58 and the volume of the barrel lumen 56 decreases with the plunging action of the plunger 54 thereby urging fluid through the flow line 310.

Figure 26:
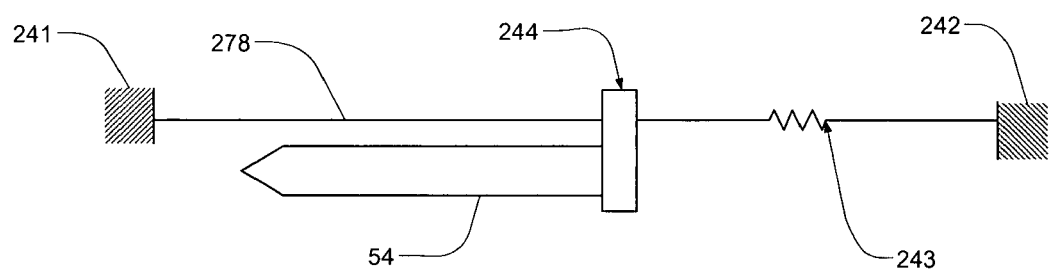
FIG. 26 shows a view of a shape-memory actuator in an expanded state.
Figure 27:
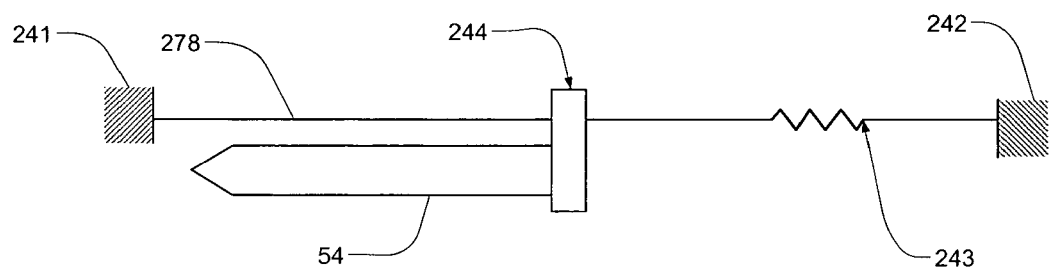
FIG. 27 shows a view of a shape-memory actuator in a contracted state.

FIGS. 26 and 27 show another embodiment where the pumping actuation member is a plunger 54. A force application assembly and a linear actuator, that includes a shape memory actuation 278, drive the plunger 54. In FIG. 26, a shape memory wire 278 is in a cool, expanded state and is attached to a first support 241 and a plunger attachment cap 244. The cap 244 is in turn attached to a biasing spring 243 which is in turn attached to a second support 242. When the wire 278 is in an expanded state, the biasing spring 243 is in a relaxed state. FIG. 27 shows the shape memory actuator 278 in a contracted state due to application of an electric current to the wire 278 and coincident heating. Upon contraction, a force is exerted on the cap 244 causing an inserting movement of a plunger 54 and a corresponding pumping action. In the contracted state, the biasing spring 243 is in a high potential energy state. Upon cessation of application of the electric field, the Nitinol wire 278 cools and expands again, allowing the biasing spring 243 to return the plunger 54 to its retracted state. As shown in FIG. 21A-21B, a shape memory actuator 278 may be wound around one or more pulleys.

Figure 28:
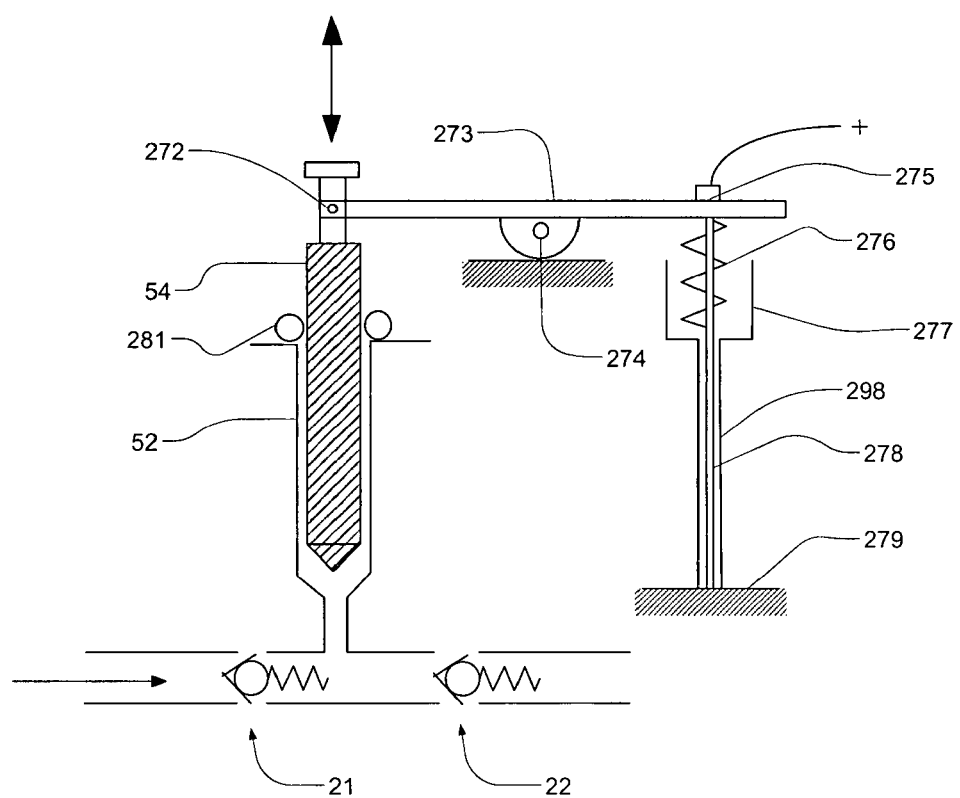
FIG. 28 shows a view of a pumping assembly employing a plunger and barrel, and a shape-memory motor having a lever.
Figure 29:
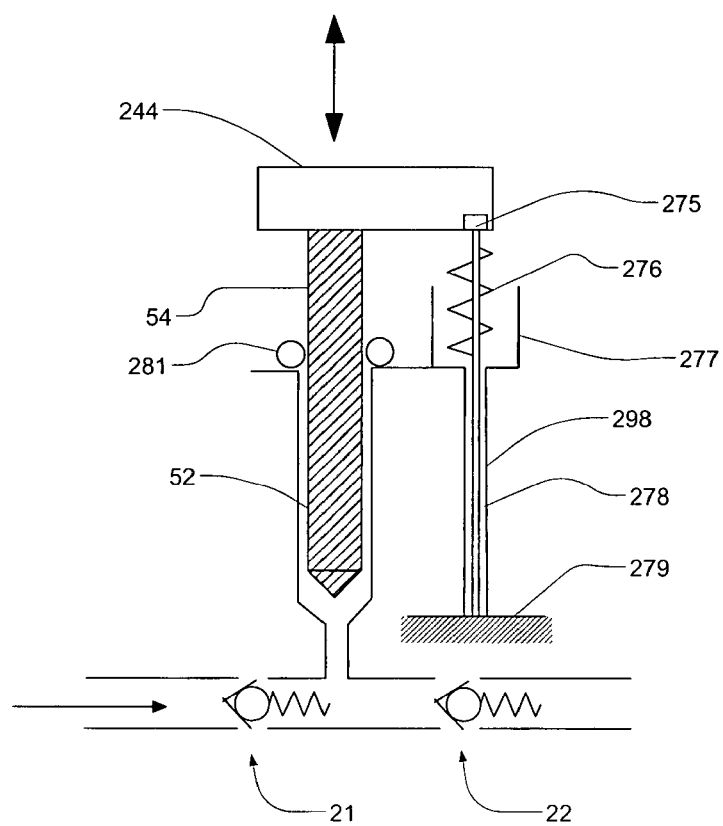
FIG. 29 shows a view of a pumping assembly employing a plunger and barrel, and a shape-memory motor.
Figure 30:
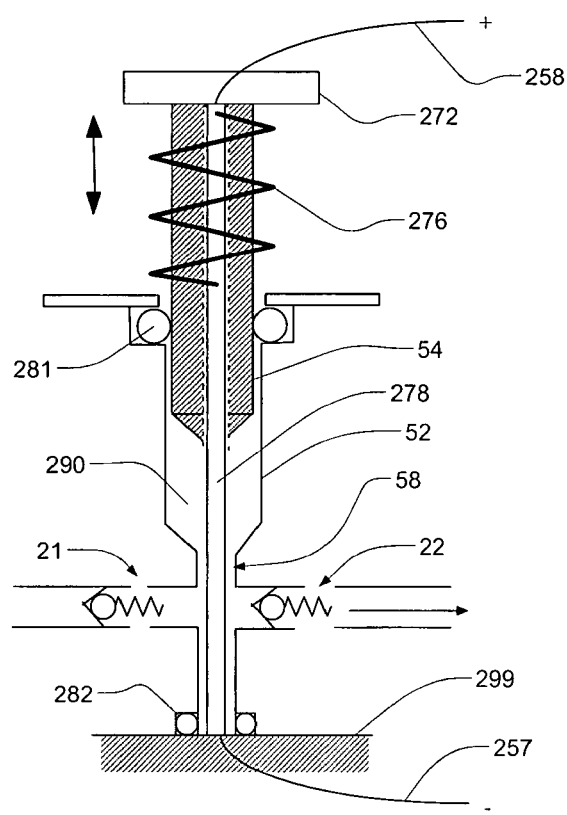
FIG. 30 shows a view of a pumping device employing a plunger and barrel and a shape-memory motor having a wire in a shaft of the plunger.

FIGS. 28-30 show a variety of embodiments in which pumping is accomplished by a pumping actuation member 54 using a shape memory actuator 278 to compress a moveable member forming a pumping chamber. The pumping chamber is bounded by one way valves 21, 22. FIG. 28 shows an embodiment including a pumping mechanism where the pumping actuation member is a plunger 54 in a barrel 52. The mechanism also includes a lever 273, a fulcrum 274, and a shape memory actuator 278. A shape memory actuator 278 is held within a housing 298 and is attached at one end to a conductive support 279 and at the other end to a positive terminal 275 of a lever 273. The lever 273 is in turn attached at its center to a fulcrum 274 and at a second end to a plunger 54. An electric current is applied to cause current to flow through the terminal 275, the shape memory actuator 278, and the conductive support 279, thereby causing the shape memory actuator 278 to contract, causing lever 273 to pivot about the fulcrum 274 and effect withdrawal of the plunger 54. Cessation of the current allows cooling of the shape memory actuator 278, allowing it to expand. The return spring 276 acts via the lever 273 to return the plunger 54 to an inserted position within the barrel 52. The return spring 276 is held in a housing 277. An o-ring 281 prevents leaking of fluid from the plunger 54-barrel 52 assembly. The insertion and withdrawal of plunger 54 causes fluid to flow through the flow line in a direction determined by the orientation of two check valves: a first one way valve 21 and a second one way valve 22. Any suitable backflow prevention device may be used, which include one way valve, check valves, duck bill valves, flapper valves, and volcano valves.

FIG. 29 shows another embodiment of a pumping mechanism having a plunger 54, a barrel 52, and a force application assembly that includes a shape memory actuator 278. However, this embodiment, unlike the embodiment shown in FIG. 28, does not include a lever. A shape memory actuator 278 is held within a housing 298 and is attached at one end to a conductive support 279 and at the other end to a plunger cap 244 by way of contact 275. The plunger cap 244 is attached to the plunger 54. Once ample electric current is applied through a contact 275, the shape memory actuator 278 contracts. This contraction causes a pulling on the plunger cap 244 to effect insertion of the plunger 54 into the barrel 52. Cessation of the current allows cooling and of the shape memory actuator 278, thereby allowing it to expand. Upon expansion of the wire, the return spring 276 acts to return the plunger 54 to a withdrawn position within the barrel 52. The return spring 276 is held in a housing 277. O-rings 281 prevent fluid from leaking plunger 54-barrel 52 assembly. The insertion and withdrawal of the plunger 54 causes fluid to flow through the flow line in a direction determined by the orientation of a first one way valve 21 and a second one way valve 22.

Referring now to FIG. 30, an embodiment of a pumping device using a plunger 54 and a barrel 52 is shown. In this embodiment, a shape memory actuator 278 in the form of a wire positioned in a shaft within the plunger 54 is used to impart force on the plunger. The shape memory actuator 278 extends from a plunger cap 272 through a shaft in a plunger 54 and through a channel 58 to a supporting base 299. O-rings 281 and 282 seal the plunger 54, barrel 52, and channel 58. Application of electrical current to a first lead 258 and a second lead 257 causes heating of the shape memory actuator 278 which results in contraction of the shape memory actuator 278. Contraction of the shape memory actuator 278 causes a downward force sufficient to overcome the upward bias of a return spring 276 to be exerted on the plunger cap 272, thereby driving the plunger 54 into the lumen 290 of the barrel 52. Expansion of the shape memory actuator 278 allows the return spring 276 to return the plunger 54 to a withdrawn position. The insertion and withdrawal of plunger 54 causes fluid to flow through the flow line in a direction determined by the orientation of a first one way valve 21 and a second one way valve 22.

Figure 31:
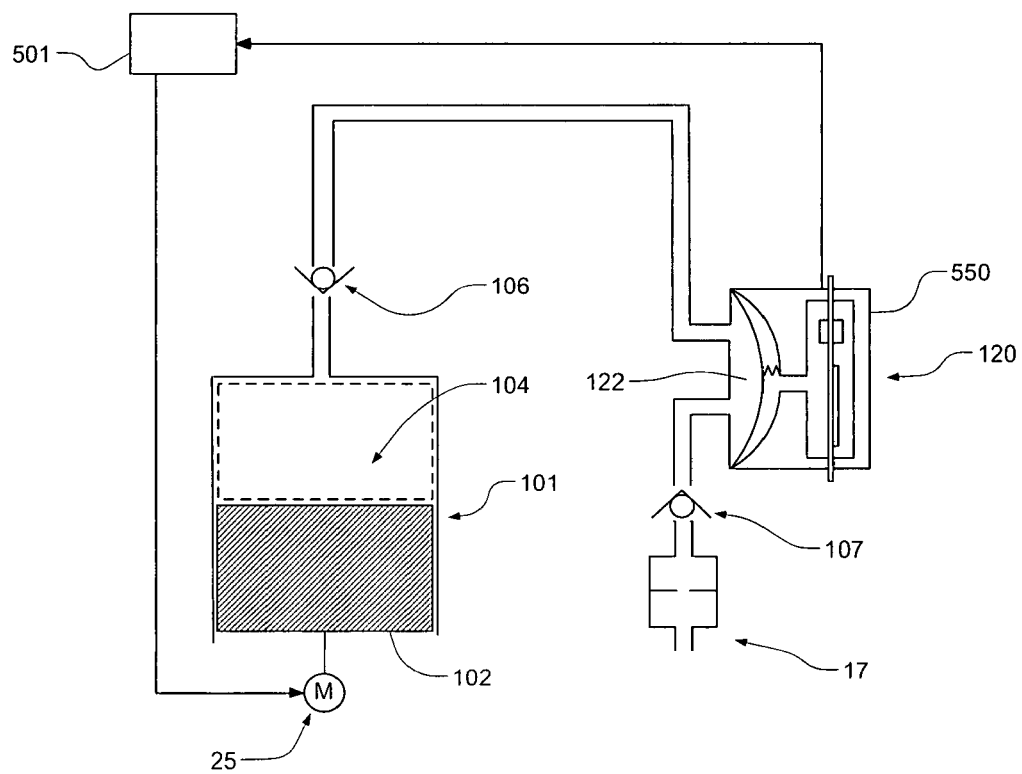
FIG. 31 shows a flow line embodiment with a combined pump and reservoir.

An alternate embodiment of the pumping mechanism is shown in FIG. 31. The pumping actuation member is an assembly 101 that combines the functions of a reservoir and pumping mechanism. Under the command of a controller 501, a motor 25 drives a plunger 102 to create pressure in a reservoir 104, thereby forcing fluid through a first one way valve 106. Fluid then enters the resilient dispensing chamber 122 of a volume sensing assembly 120 with a sensor 550, and to an exit assembly 17. An optional second one way valve 107 may be included. Feedback control between the sensor 550 and the motor 25 via the controller 501 assures the desired flow of fluid to the patient. The first one way valve 106 serves to prevent reverse flow of fluid due to the resilient force of the dispensing chamber 122 of the volume sensing assembly 120 when the chamber is filled and extended. The second one way valve 107 serves to prevent reverse flow of fluid from the exit assembly 17 or patient 12 into the dispensing chamber 122. In this embodiment, the sensor 550 can immediately detect the volume in the dispensing chamber 122.

Figure 32:
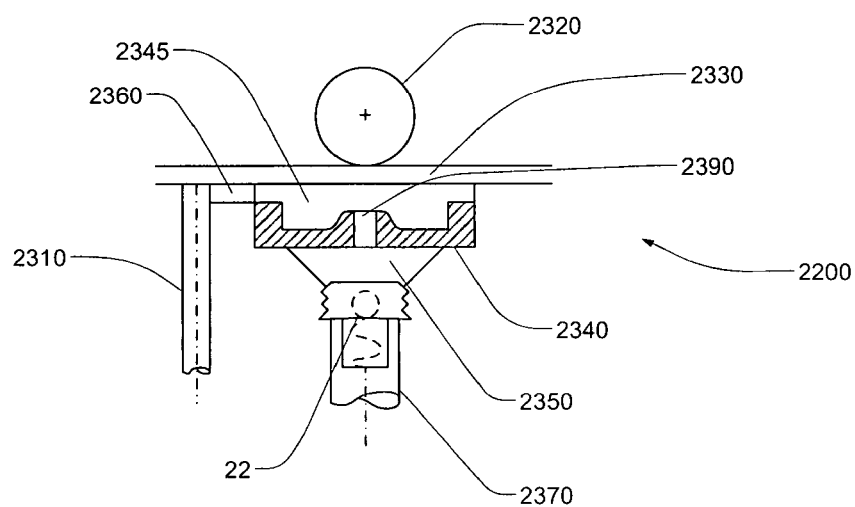
FIG. 32 schematically shows a sectional view of a valving pump in a resting position.
Figure 33:
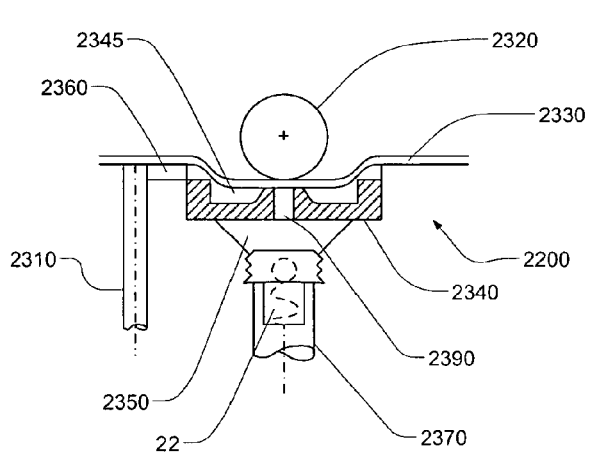
FIG. 33 schematically shows a sectional view of the valving pump of FIG. 32 in an intermediate position.
Figure 34:
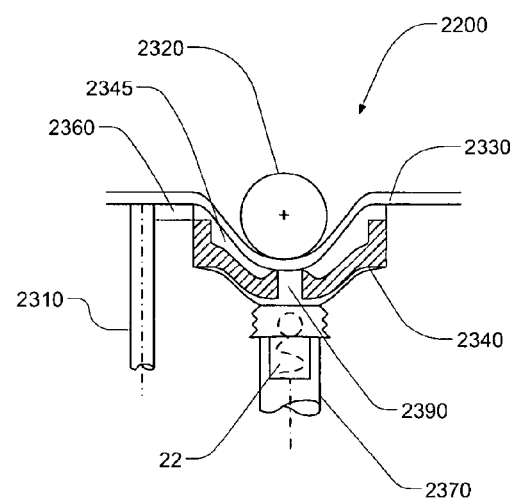
FIG. 34 schematically shows a sectional view of the valving pump of FIG. 32 in an actuated position.

FIGS. 32-34 schematically show sectional views of a combined valving pump 2200. FIG. 32 shows the valving pump 2200 with a collection chamber 2345 and a pumping chamber 2350 in a resting position, prior to actuation; FIG. 33 shows the valving pump 2200 in an actuating state during a compression stoke; and FIG. 34 shows the pump in an actuated state at the end of a compression stroke. A pump inlet 2310 is in fluid communication with an upstream fluid source, such as a reservoir, and connects to a first end of a channel 2360. The channel 2360 connects at a second end to the collection chamber 2345, which is in fluid communication with a diaphragm aperture 2390 disposed in a resilient pumping diaphragm 2340. The collection chamber 2345 is bounded on a first side by the resilient pumping diaphragm 2340 and on a second side by a resilient pumping membrane 2330. The pumping membrane 2330 may be made from, among other things, latex or silicone rubber. The downstream side of the diaphragm aperture 2390 opens into the pumping chamber 2350. During priming of the pump and between actuation cycles, fluid travels from a fluid source such as a reservoir, through the pump inlet 2310, the channel 2360, the collection chamber 2345, and the diaphragm aperture 2390, and then arrives in the pumping chamber 2350. A one way valve 22 prevents fluid from leaving the pumping chamber 2350 via a pump outlet 2370 until and unless ample fluid pressure is exerted against the one way valve 22 such that the one way valve 22 is open. In FIG. 32 a pumping actuation member 2320 is shown in a resting position, and the resilient pumping membrane 2330 is shown in a relaxed configuration of minimal surface area, thereby maximizing the volume of the collection chamber 2345. Although in this embodiment, the pumping actuation member is shown as a ball, in other embodiments, the pumping actuation member can be anything capable of actuation and applying ample force against the resilient pumping membrane 2330 in order to actuate the pumping mechanism.

As can be seen from FIG. 33, when the pumping actuation member 2320 is actuated during a compression stroke, the pumping actuation member 2320 begins to travel toward the diaphragm aperture 2390 of the resilient pumping diaphragm 2340 and distends the resilient pumping membrane 2330, causing retrograde flow of fluid that has collected in the collection chamber 2345. Later in the force application stroke, as shown in FIG. 34, the pumping actuation member 2320 will sealingly lodge the resilient pumping membrane 2330 against the diaphragm aperture 2390. To aid in sealing, the pumping actuation member 2320 may have a shape that is complementary to the shape of the diaphragm aperture 2390. For example, the pumping actuation member 2320 may be spherical or conical and the diaphragm aperture 2390 may be a cylindrical through-hole. At this stage of the force application stroke, retrograde flow from the pumping chamber 2350 will be inhibited. Continued travel of the pumping actuation member 2320 will deform the resilient pumping diaphragm 2340 and increase the pressure in the pumping chamber 2350, while continuing to seal the diaphragm aperture 2390 against retrograde flow from the pumping chamber 2350. When the pressure within the pumping chamber 2350 provides ample fluid pressure against the one way valve one way valve 22, fluid will flow from the pumping chamber 2350 through the pump outlet 2370. During the return stroke, the pumping actuation member 2320, resilient pumping membrane 2330 and resilient pumping diaphragm 2340 return to the relaxed positions shown in FIG. 32. During the return stroke, the internal pressure of pumping chamber 2350 and collection chamber 2345 will drop, which should encourage refilling of the valving pump 2200 by inducing flow of fluid from the fluid source through the pump inlet 2310 and channel 2360.

Figure 35:
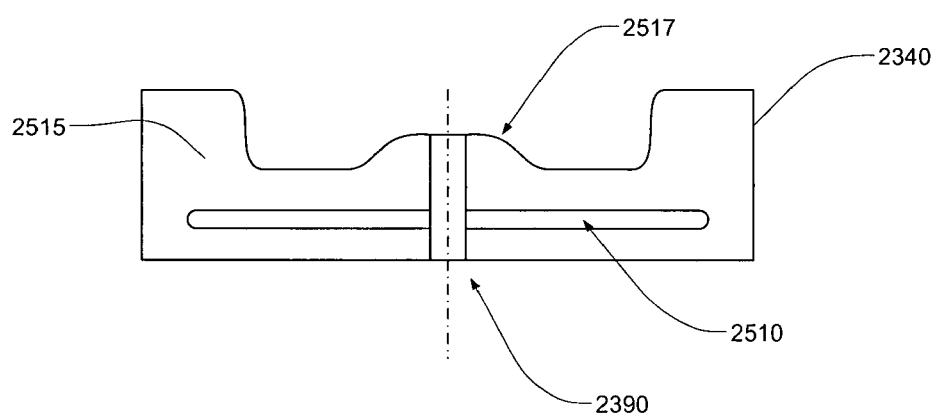
FIG. 35 schematically shows a sectional view of a pumping diaphragm for use in a valving pump.

Referring now to FIG. 35, a schematic sectional view of one embodiment of a resilient pumping diaphragm 2340 is shown. A diaphragm body 2515 may be constructed of a resilient material such as silicone rubber. A diaphragm spring 2510 may also be included to impart resiliency to a flexible, or already resilient, body 2515. The diaphragm spring 2510 may be embedded within the resilient pumping diaphragm 2340 or disposed adjacent to the resilient pumping diaphragm 2340. An example of one embodiment of a diaphragm spring 2510 can be seen in FIG. 36. A combination of a diaphragm body 2515 that includes a compliant material, and a diaphragm spring 2510 that includes a resilient material may be used; the result is a pumping diaphragm 2340 that will exhibit a high degree of sealing when contacted with the resilient pumping membrane 2330 deformed by a pumping actuation member (not shown, see FIGS. 32-34) and also have a high degree of resiliency. A valve seat 2517 may be positioned around the diaphragm aperture 2390. The valve seat 2517 may function as a receptacle for the deformed portion of the resilient pumping membrane 2330 The force application member 2320 may deform the pumping membrane 2330, causing the membrane 2330 to deform and sealingly contact the valve seat 2517. If sufficient force is applied, the valve seat may be resiliently deformed to ensure a thorough seal against retrograde flow of fluid. The ratio of the section height to the section width of the valve seat 2517 can generally be selected differently and matched to the circumstances of the flow.

Figure 36:
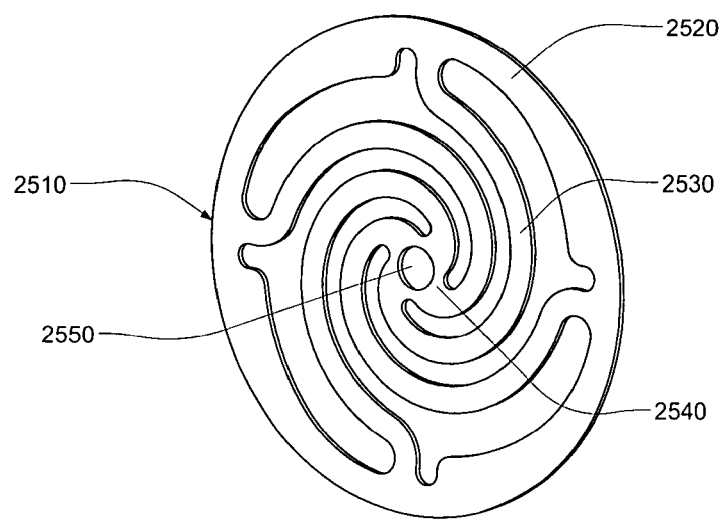
FIG. 36 shows a perspective view of a diaphragm spring for use in a pumping diaphragm.

Now referring to FIG. 36, an example of a diaphragm spring 2510 for use in the pumping diaphragm 2340 of FIG. 35 is shown. An outer annulus 2520 and an inner annulus 2540 are connected by at least three resilient arms 2530. The center of the inner annulus 2540 has a spring aperture 2550, which may be aligned with the diaphragm aperture 2390 of the pumping diaphragm 2340 as shown in FIG. 35.

Figure 37:
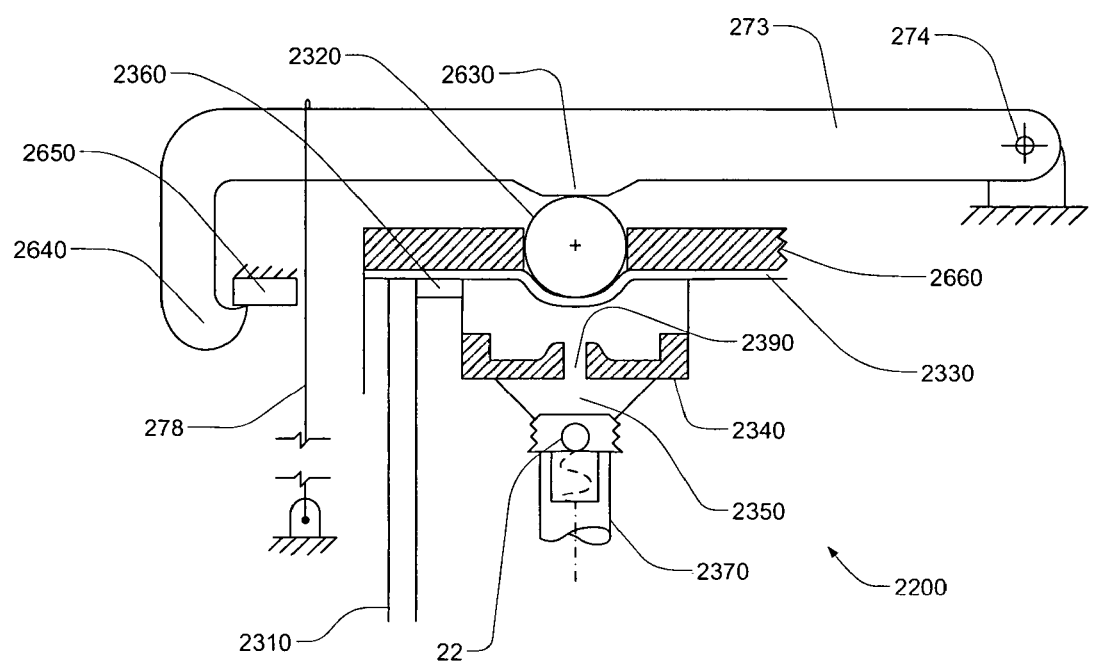
FIG. 37 schematically shows a sectional view of a valving pump employing a lever and a shape memory wire actuator.

Referring now to FIG. 37, a schematic is shown representing a sectional view of the valving pump 2200 previously shown in FIGS. 32-34 in combination with a force application assembly which includes a pumping actuation member 2320, an actuator, and a lever 273. When energized by an actuator, such as a shape memory actuator 278, the lever 273 pivots around a fulcrum 274 to initiate a compression stroke. A hammer 2630 protrudes from the lever 273. During the compression stroke, the hammer 2630 contacts a rounded pumping actuation member 2320, causing the pumping actuation member to travel within a void in a support structure 2660, and pushing the pumping actuation member 2320 against a resilient pumping membrane 2330 until the pumping actuation member 2320 is held sealingly against a diaphragm aperture 2390 located in the resilient pumping diaphragm 2340. As the lever 273 continues travel, the pumping actuation member 2320 causes deformation of a pumping diaphragm 2340. When enough fluid pressure is exerted onto the one way valve 22, the one way valve 22 opens. This allows the fluid to flow from a pumping chamber 2350 through a pump outlet 2370. Upon cooling of the shape memory actuator 278, the resiliency of the pumping diaphragm 2340 and the resilient pumping membrane 2330 will cause return of the lever 273 to a starting position determined by a lever stop 2650 and lever catch 2640. Alternately, a return spring (not shown) may be used to return the lever 273 to the starting position. Although shown as a sphere, the force application member 2320 may alternately be a piston, a protrusion of the lever 273 or other suitable form.

Figure 38:
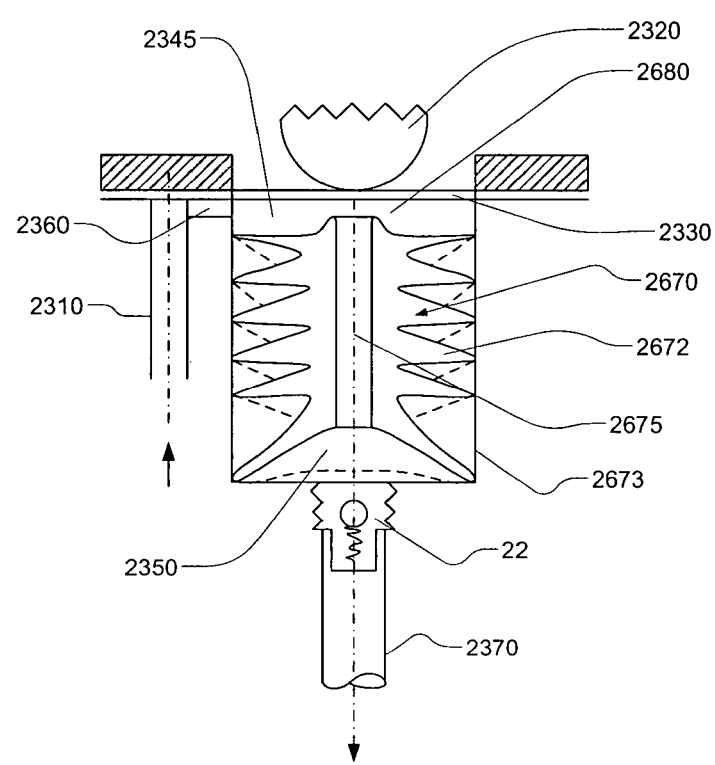
FIG. 38 schematically shows a sectional view of an embodiment that includes a valving pump which employs a resilient cylindrical flexure.

FIG. 38 schematically shows a sectional view of an embodiment of a valving pump using a resilient cylindrical flexure 2670. In one embodiment, the resilient cylindrical flexure is made from rubber, but in other embodiments, it can be made from any resilient material. The cylindrical flexure 2670 has a central passageway 2675, and a plurality of resilient radial fins 2672 that are sealingly arranged against a housing 2673. Fluid entering through a pump inlet 2310 passes through a channel 2360 and collects in regions upstream of a one way valve 22: a collection chamber 2345, the central passageway 2675 of the cylindrical flexure 2670, and a pumping chamber 2350. The pumping chamber is coupled in fluid communication with the collection chamber 2345 through the central passageway 2675. During the pumping mechanism's compression stroke, a pumping actuation member 2320 applies force to, and deforms, a resilient pumping membrane 2330 until the resilient pumping membrane 2330 is sealingly held against a valve seat 2680 of the cylindrical flexure 2670; retrograde flow to the pump inlet 2310 from the collection chamber 2345 is thereby blocked. Continued travel of the pumping actuation member 2320 causes deformation of the cylindrical flexure 2670; the pressure within the pumping chamber 2350 increases until such time that it is ample to open the one way valve 22. Fluid can then flows through a pump outlet 2370.

The pumping actuation member 2320 is shown as a ball shape in FIG. 38. However in other embodiments, the pumping actuation member 2320 can be any shape that can function as described above.

Figure 39:
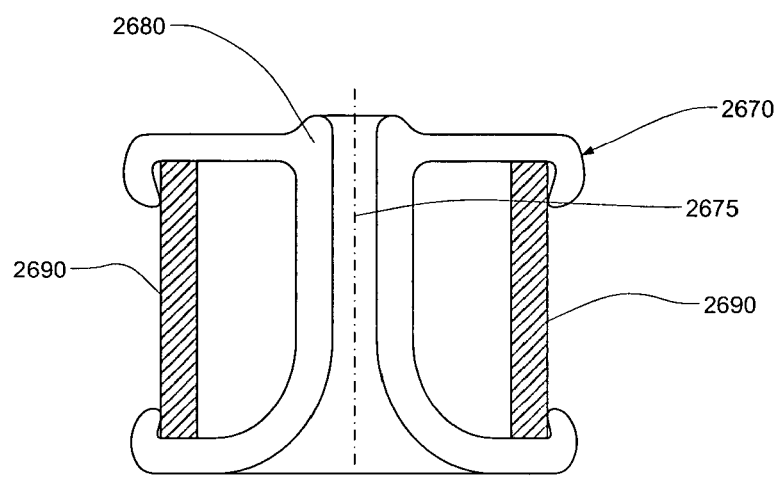
FIG. 39 schematically shows a sectional view of an embodiment that includes a valving pump flexure having a resilient member and a rigid support.

Referring now to FIG. 39, an alternate embodiment of the cylindrical flexure 2670 (shown in FIG. 38) employing a resilient portion 2680 and a rigid cylindrical support 2690 is shown. Like the cylindrical flexure 2680 of FIG. 38, the resilient portion of the cylindrical flexure 2670 includes a valve seat 2680 which seals the central passageway 2675 upon application of force by a pumping actuation member 2320. Thus, the resilient portion 2680 of the cylindrical flexure 2670 deforms to transmit pressure to the pumping chamber 2350.

Figure 40:
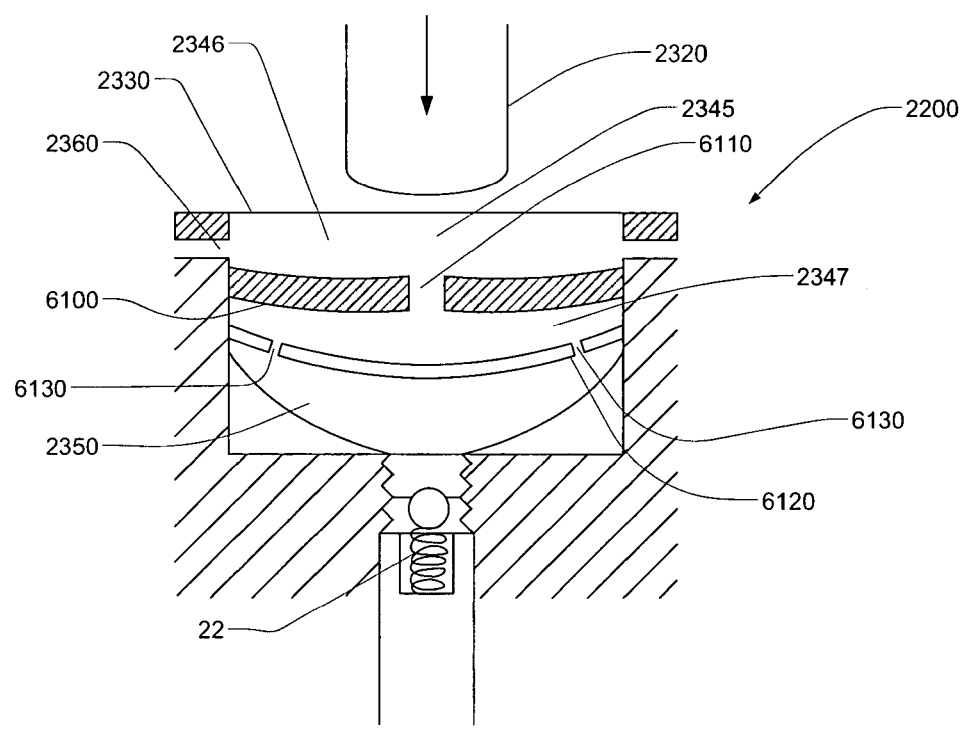
FIG. 40 schematically shows a sectional view of a valving pump, in a resting state, with a diaphragm spring upstream of a flexible membrane.

FIGS. 40-44 schematically show sectional views of an alternate embodiment of a valving pump in various states of actuation. The valving pumps 2200 of FIGS. 40-44 have a resilient diaphragm spring 6100 and a resilient sealing membrane 6120 which together serve a function that is similar to that of the resilient pumping diaphragm 2340 of the valving pump 2200 shown in FIGS. 32-34. FIG. 40 shows the valving pump 2200 in a resting state. In the resting state, fluid may flow from the inlet 2360, into an upper portion 2346 of the collection chamber 2345, through an aperture 6110 in the diaphragm spring 6100 and into a lower portion 2347 of the collection chamber 2345. Fluid then may proceed through one or more openings 6130 in a sealing membrane 6120 and into the pumping chamber 2350. Under low-pressure conditions, further fluid flow is hindered by a one way valve 22. The spring diaphragm 6100 and sealing membrane 6120 may both be constructed from resilient, biocompatible materials. The spring diaphragm 6100 may have a greater resiliency than the sealing membrane 6120. For example, the spring diaphragm 6100 may be a circular piece of flexible bio-inert plastic and the sealing membrane 6120 may be a sheet of silicone or fluorosilicone elastomer.

Figure 41:
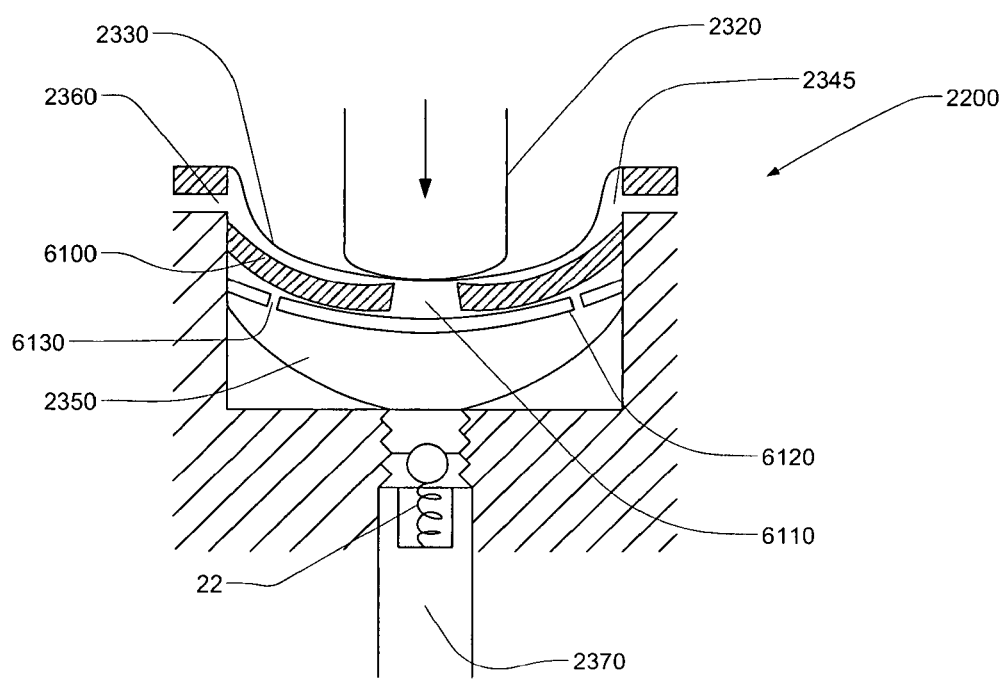
FIG. 41 schematically shows a sectional view of the valving-pump of FIG. 40, in an intermediate state.
Figure 42:
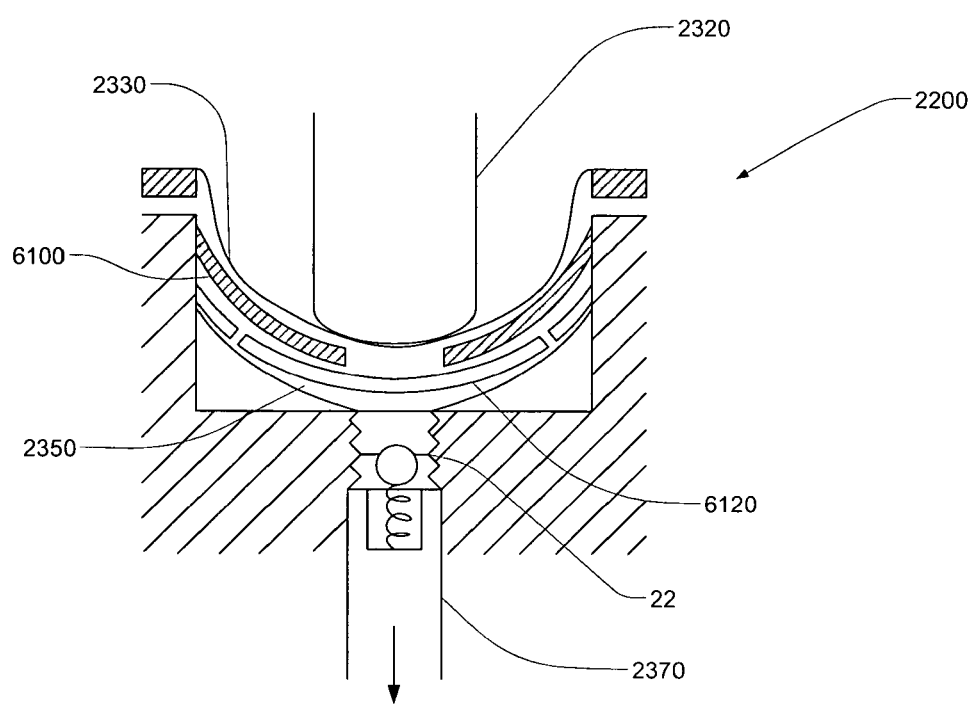
FIG. 42 schematically shows a sectional view of the valving-pump of FIG. 40, in an actuated state.

FIGS. 41 and 42 show the valving pump 2200 in two intermediate, partially actuated states. The pumping actuation member 2320 deforms the pumping membrane 2330 and forces it through the collection chamber 2345 and against the spring diaphragm 6100, which, in turn, is deformed and forced against the sealing membrane 6120. At this point in the compression stroke, retrograde flow through either the aperture 6110 of the spring diaphragm 6100, or through openings 6130 in the sealing membrane 6120, or both, are suppressed. Offset placement of the sealing membrane openings 6130 relative to the spring aperture 6100 allows a seal to be created between the spring diaphragm 6100 and the sealing membrane 6120. In some embodiments this seal may be supplemented with a redundant seal between the fill chamber resilient pumping membrane 2330 and the spring diaphragm 6100 (the embodiments of FIGS. 43-44, for example, lack this redundant seal). A circumferential ridge (not shown) around the spring diaphragm aperture 6110 may act as a valve seat to enhance the seal.

Referring now to FIG. 42, continued travel of the pumping actuation member 2320 causes further deformation of the pumping membrane 2330, spring diaphragm 6100, and sealing membrane 6120. As a result, fluid in the pumping chamber 2350 is compressed until the fluid pressure forces the one way valve 22 open; further compression causes fluid egress through the outlet 2370.

Figure 43:
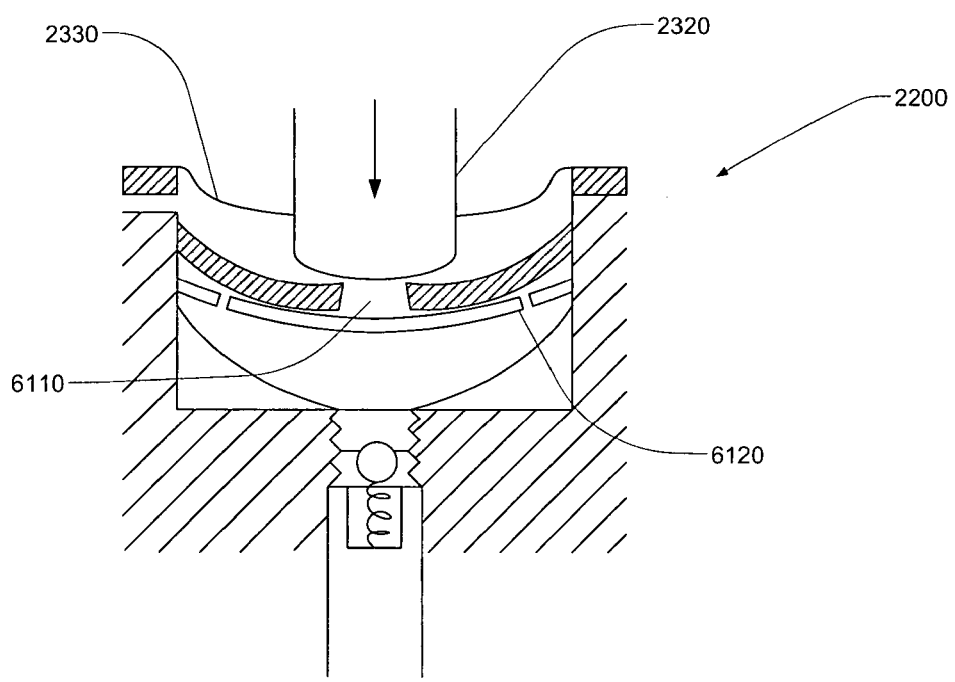
FIG. 43 schematically shows a sectional view of a valving-pump with a diaphragm spring upstream of a flexible membrane, in which a flexible membrane is circumferentially attached to a force application member.
Figure 44:
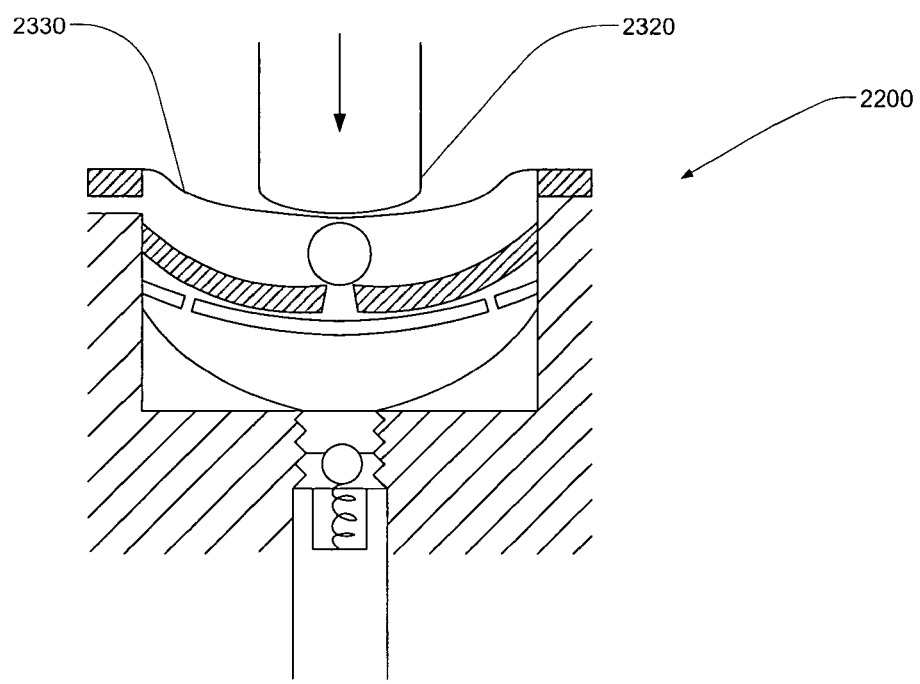
FIG. 44 schematically shows a sectional view of a valving-pump with a diaphragm spring upstream of a flexible membrane, which includes a rigid ball for transmitting force.

An alternate embodiment of the valving pump 2200 of FIGS. 40-42 is shown schematically in FIG. 43. In this embodiment, a pumping actuation member 2320 traverses the resilient pumping membrane 2330. The pumping membrane 2330 is sealingly attached to the circumference of the pumping actuation member 2320 at a midpoint along the length of the pumping actuation member 2320. When actuated, the diaphragm spring aperture 6110 is sealed against backflow by the sealing membrane 6120 alone; the resilient pumping membrane 2330 will not contact the aperture 6110. An alternate embodiment of the device shown in FIG. 40 is shown in FIG. 44.

Figure 45:
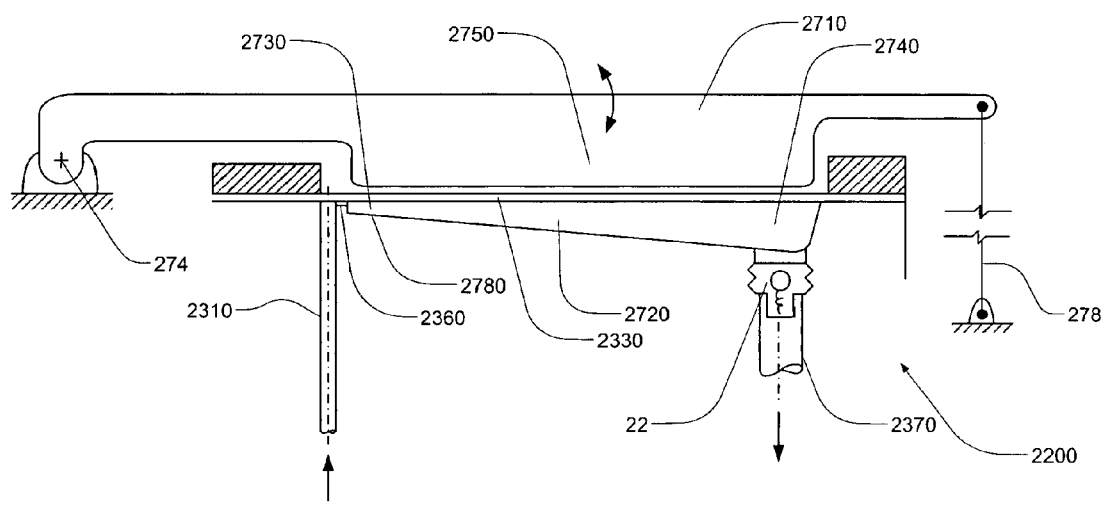
FIG. 45 schematically shows a sectional view of an embodiment that includes a valving pump having a resilient pump blade.

Referring now to FIG. 45, a sectional view of an alternate embodiment of a combined valving pump 2200 is shown. A shape memory actuator 278 actuates a compression stroke which causes a resilient pump blade 2710 to lever about a fulcrum 274, causing the resilient pumping membrane 2330 to be deformed. The resilient pump blade 2710 and resilient pumping membrane 2330 apply pressure to fluid in a graded pumping chamber 2720 having a shallow region 2730 and a deeper region 2740. Early in the compression stroke, the pump blade 2710 induces the resilient pumping membrane 2330 to obstruct a channel 2360 that connects a pump inlet 2310 to the graded pumping chamber 2720. As the compression stroke continues, force is applied to the fluid in the graded pumping chamber 2720 until the fluid pressure in the graded pumping chamber 2720 is great enough to open a one way valve 22. Fluid then exits a pump outlet 2370. The pump blade 2710 may be constructed entirely or partly from a resilient material such as rubber. In some embodiments, the resilient material includes a non-resilient spline. Alternately, in some embodiments, the resiliency is imparted through a resilient region 2750, thus, the resilient region 2750 is the only resilient part of the pump blade 2710 in these embodiments. In these embodiments, the resilient region 2750 contacts the bottom of the graded pumping chamber 2720. The resiliency of pump blade 2710 allows the compression stroke to continue after the pumping blade 2710 contacts the base 2780 of the shallow region 2730. A return spring (not shown) returns the pump blade 2710 to a starting position during the return stroke.

Figure 46:
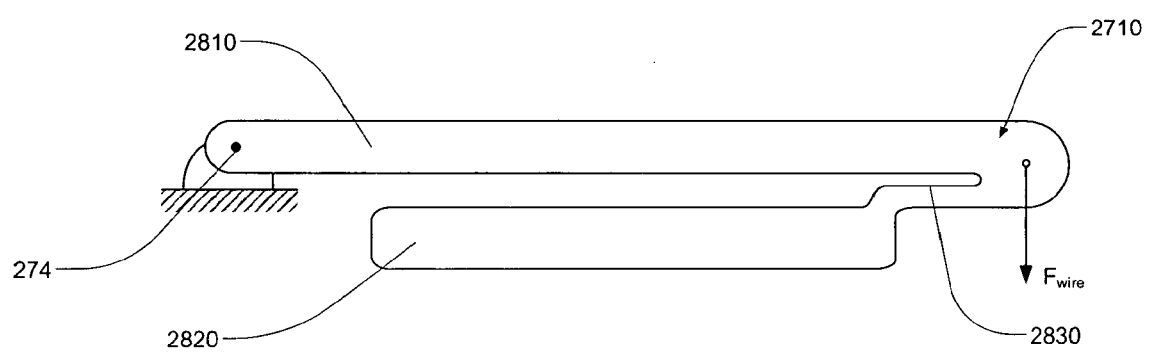
FIG. 46 schematically shows a sectional view of an embodiment that includes an alternative version of a resilient pump blade for use with a valving pump.

Referring now to FIG. 46, a sectional view of an alternate embodiment of a pumping mechanism is shown. This embodiment includes a resilient pump blade 2710. The resilient pump blade 2710 includes a resilient region 2830 which provides resiliency to the pump blade 2710. The resilient region 2830 joins a pumping actuation member 2820 to a pump blade 2810. When used with a valving pump (not shown) the resilient pump blade 2710 of FIG. 42 will occlude the inlet channel (not shown, shown in FIG. 45 as 2360) and then bend at the flexible region 2830 to allow the force application member 2820 to apply further pressure to the fluid in the graded pumping chamber (not shown, shown in FIG. 45 as 2720). The force application member 2820 may be constructed entirely of a resilient material such as rubber. However, in alternate embodiments, only a region that contacts the bottom of the pumping chamber (not shown) is made from resilient material. The resilient pump blade 2710 will return to its relaxed conformation during the return stroke.

Figure 47:
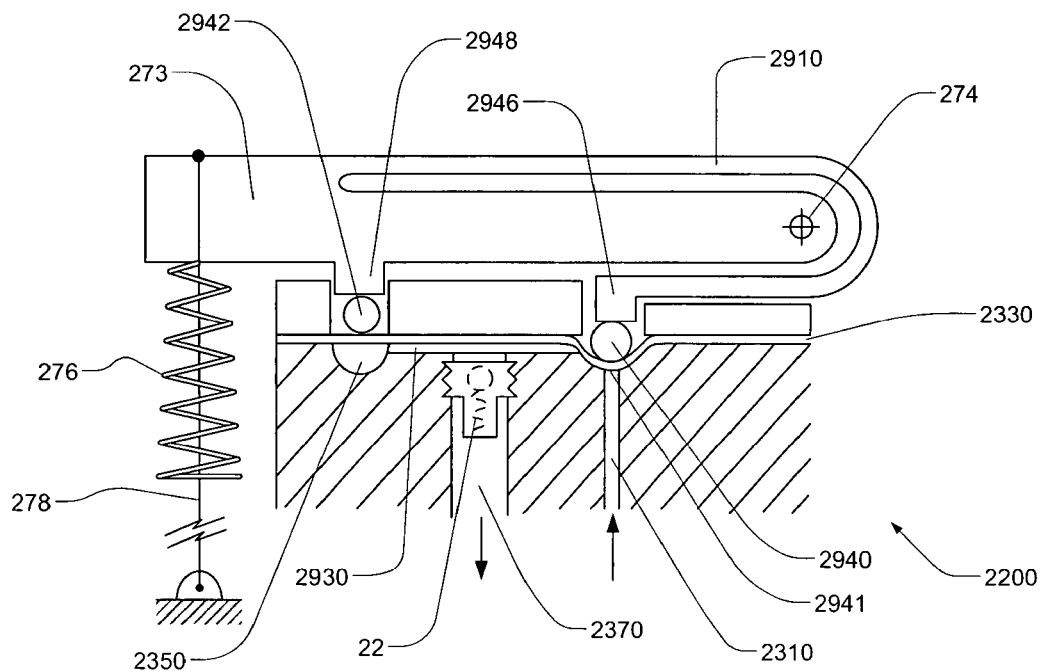
FIG. 47 schematically shows a sectional view of an embodiment that includes a valving pump having multiple force application members.

Referring now to FIG. 47, a sectional view of another embodiment of pumping mechanism is shown. The pumping mechanism is shown where the lever is at the intermediate stage of actuation with the inlet valve 2941 closed. The pumping mechanism includes a fluid line 2930, a moveable member 2330, which is a membrane in this embodiment, an inlet valve 2941 poppet 2940, a pumping actuation member 2942, a pumping chamber 2350, and an exit valve 22. The inlet valve 2941 and the pumping actuation member 2942 are each actuated by the shape memory actuator 278 which is surrounded by return spring 276 and connected to a lever 273. The lever 273 actuates both the inlet valve 2941 and the pumping actuation member 2942. The lever 273 includes an elongate and spring member 2910 that is attached to the lever 273 hinged to fulcrum 274 and terminated in a valve actuation hammer 2946. The spring member 2910 may be curved. The spring member 2910 biases the position of the valve actuation hammer 2946 away from the lever 273 and toward the inlet valve 2941. The lever 273 has a pump actuation hammer 2948, which is not attached to the spring member 2910, and is positioned adjacent to the pumping actuation member 2942.

Electric current causes the shape memory actuator 278 to contract and the lever 273 pivots about the fulcrum 274. The pivoting places the valve actuated hammer 2946 in position to force the inlet valve 2941 closed. As the shape memory actuator 278 continues to contract, the lever 273 continues pivoting and the pump actuation hammer 2948 forces the pump actuation member 2942 against the pumping chamber 2350, even while further compressing the elongate spring member 2910. Upon achieving sufficient pressure, the fluid pressure opens the exit valve 22, and fluid exits through the valve.

During the relaxation stroke, the return spring 276 unloads and returns the lever 273 to the starting position, releasing the pumping actuation member 2942. The inlet valve 2941 opens. The resiliency of the pumping chamber 2350 causes the pumping chamber 2350 to refill.

Figure 48:
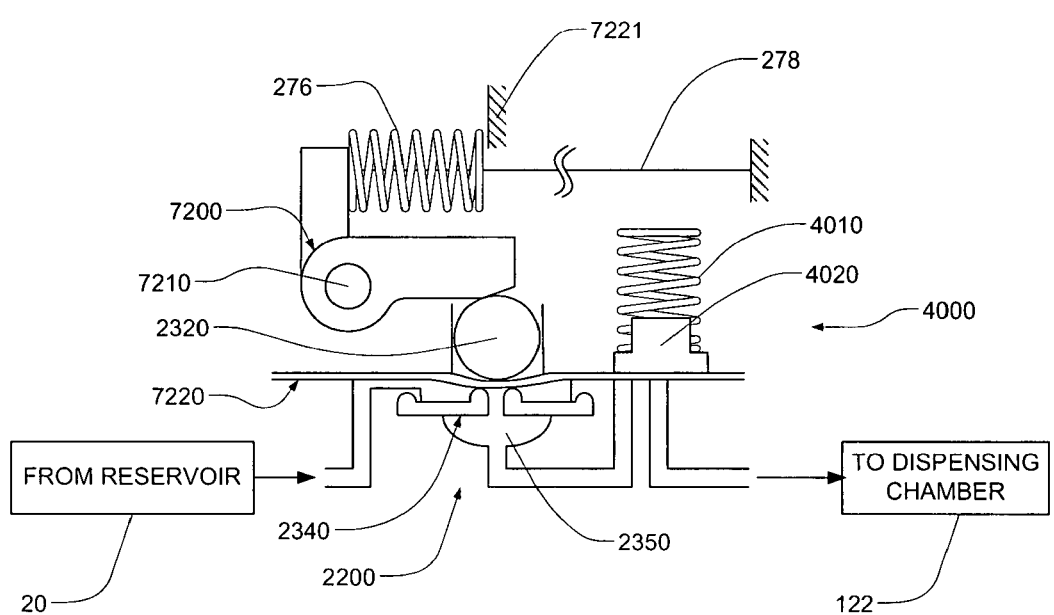
FIG. 48 schematically shows, in a resting or filling mode, a pumping mechanism including a bell-crank driven valving-pump and a flow-biasing valve.
Figure 49:
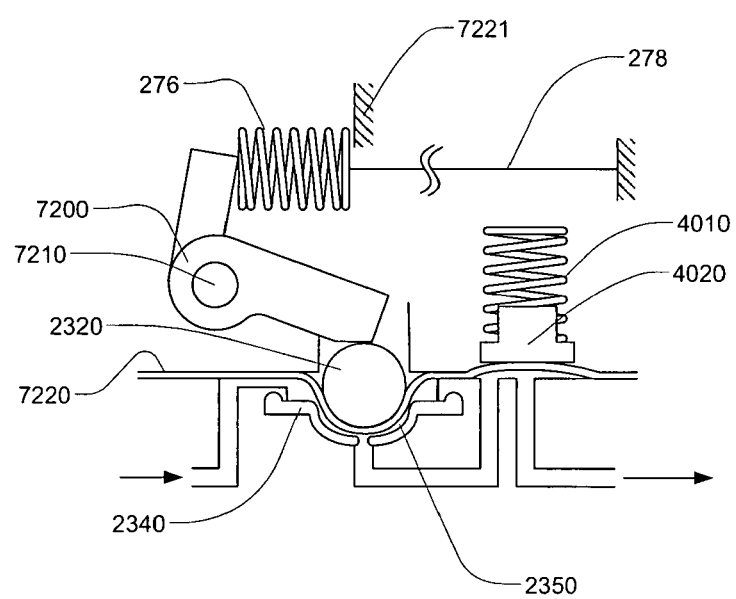
FIG. 49 schematically shows the pumping mechanism of FIG. 48 in an actuated state.

Referring now to FIGS. 48 and 49 schematically show a cross section of an embodiment in which a pumping mechanism employs a bell crank 7200 and combines a valving pump 2200 with a flow biasing valve. The bell crack 7200 converts force produced by the linear shape memory actuator 278 into a transverse pumping force. FIG. 48 shows the mechanism in a resting or refilling mode and FIG. 49 shows the mechanism in an actuated state. Contraction of the actuator 278 causes the bell crank 7200 to rotate around a shaft 7210 and press upon the force application member 2320, which drives a resilient membrane 7220 to seal against the resilient pumping diaphragm 2340 and urge fluid from the pumping chamber 2350 toward the dispensing chamber 122. The return spring 276 cooperates with a return spring support 7221 to release the pumping force, causing the pumping chamber 2350 to expand and draw fluid from the reservoir 20. Still referring to FIGS. 48 and 49, the flow biasing valve 4000 is also shown, having a valve spring 4010, a poppet or plunger 4020.

Figure 50:
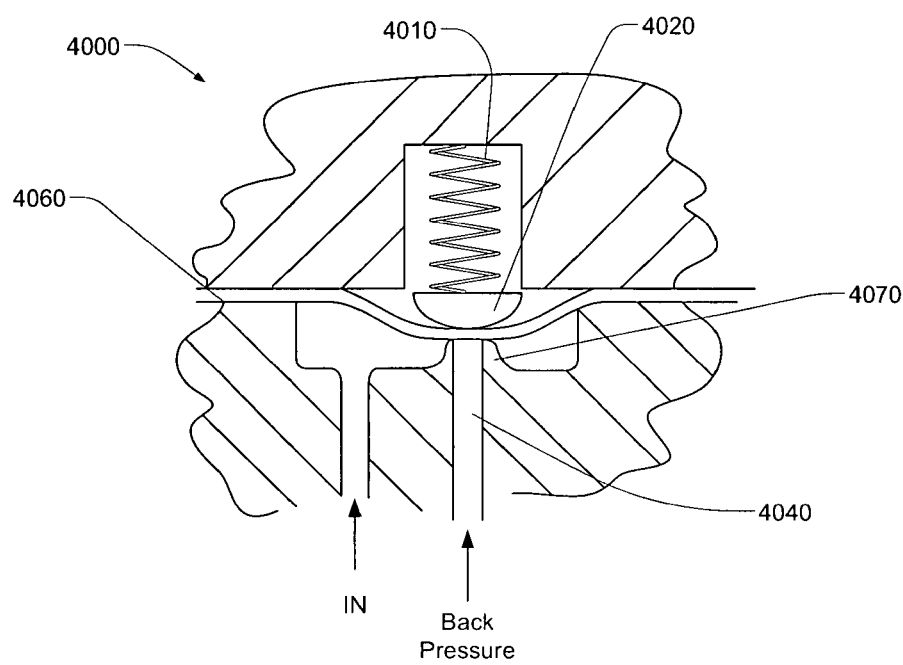
FIG. 50 schematically shows a sectional view of a flow-biasing valve in accordance with an embodiment of the invention having a raised valve seat and in a closed position.
Figure 51:
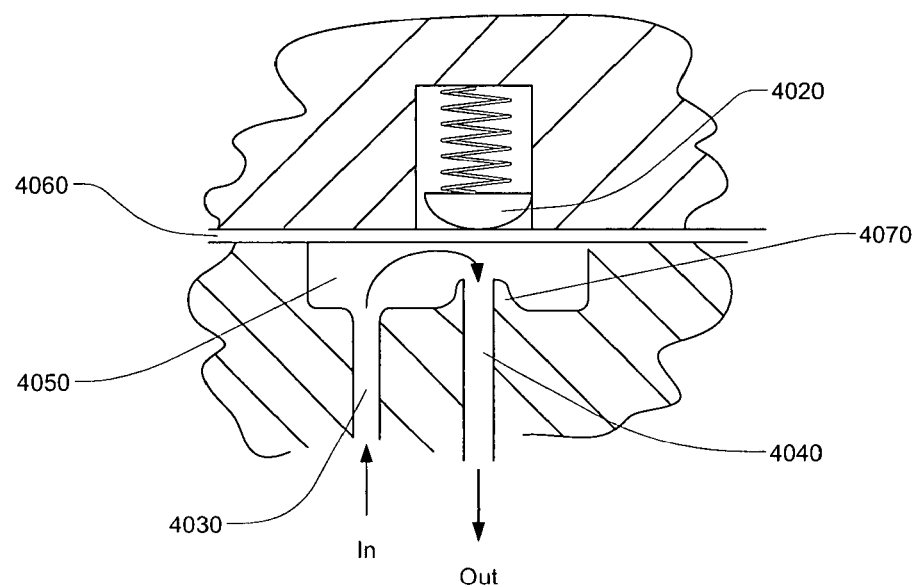
FIG. 51 schematically shows a sectional view of the flow-biasing valve of FIG. 50 in an open position.
Figure 52:
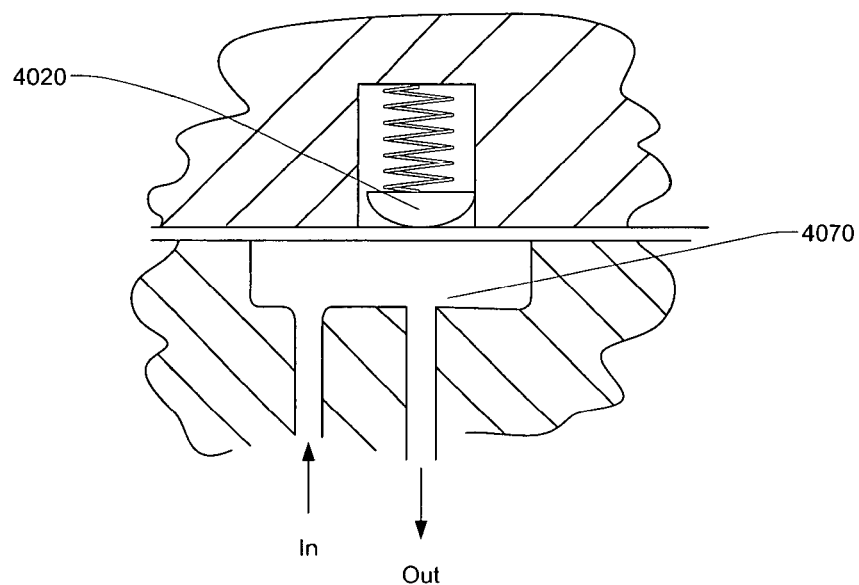
FIG. 52 schematically shows a sectional view of a flow-biasing valve in accordance with an embodiment of the invention without a raised valve seat and in an open position.
Figure 53:
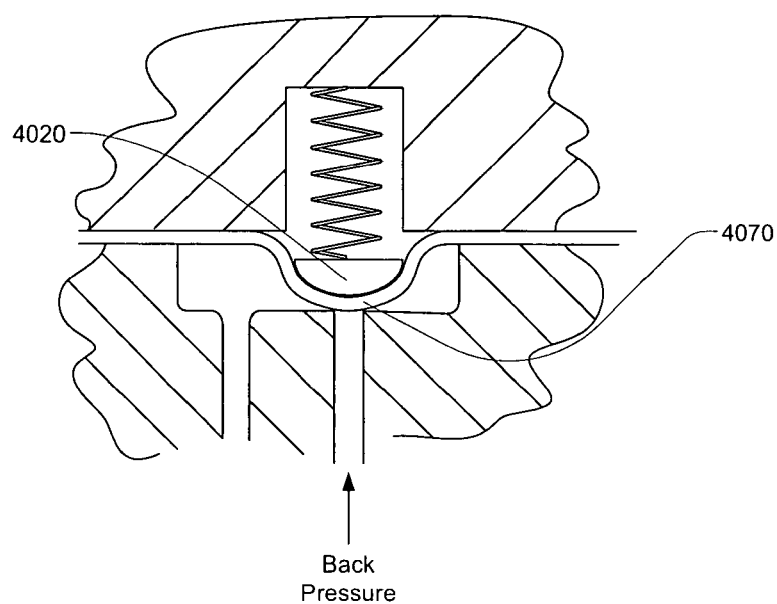
FIG. 53 schematically shows a sectional view of the flow-biasing valve of FIG. 52, in a closed position.

In some of the embodiments of the pumping mechanism described above, one or more aspects of the following valving operation description is relevant. Referring now to FIG. 50, an example of a flow biasing valve 4000 is shown, closed. A valve spring 4010 exerts force on a poppet 4020 to sealingly press a valve membrane 4060 against a valve seat 4070 surrounding a terminal aperture of a valve outlet 4040. The valve seat 4070 may include a circumferentially raised portion to improve sealing. As explained below with references to FIGS. 54-55, back pressure created by the action of a resilient dispensing assembly should be insufficient to cause retrograde flow through the flow biasing valve 4000. As shown in FIG. 51, when the pumping assembly is actuated, sufficient pressure should be generated to unseat the membrane 4060 and the poppet 4020 from the valve seat 4070 thereby allowing fluid to flow from the valve inlet 4030, through an inlet chamber 4050 and to the valve outlet 4040. FIGS. 52-53 shows an alternate valve that has a valve seat 4070 without a circumferentially raised portion.

Figure 54:
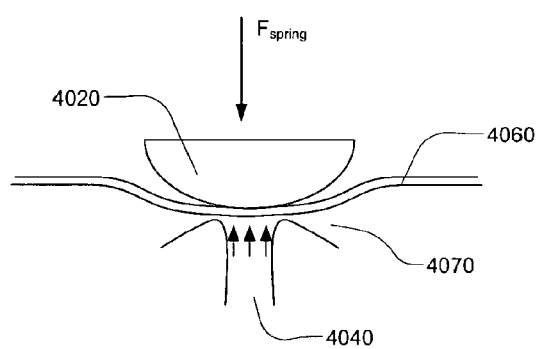
FIG. 54 schematically shows forces that act upon a poppet in the vicinity of a valve outlet in accordance with embodiments of the invention.
Figure 55:
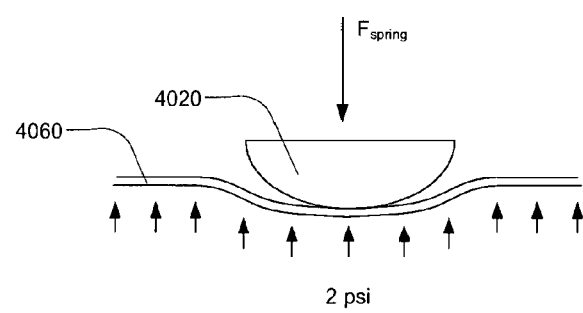
FIG. 55 schematically shows, in close-up view, forces that act upon a poppet in the vicinity of a valve inlet in accordance with embodiments of the invention.

Referring now to FIGS. 54 and 55, illustrations of how an exemplary flow biasing valve discriminates between forward and retrograde flow are shown. FIG. 54 schematically represents the valve in a closed position. Back pressure in the outlet 4040 applies force to a relatively small area of the flexible valve membrane 4060 adjacent to the valve seat 4070 and is thus unable to dislodge the poppet 4020. Referring now to FIG. 55, this FIG. schematically represents the valve during the actuation of a pumping actuation member. The pressure of the pumped fluid applies force over an area of the membrane 4060 that is larger than the area adjacent to the valve seat. As a result, inlet pressure has a larger mechanical advantage for unseating the poppet 4020 and forward flow should ensue in response to the action of the pumping actuation member. Thus, the critical pressure needed to displace the poppet 4020 is lower in the inlet than in the outlet. Accordingly, the spring biasing force and the size of the force application areas associated with both the fluid inlets and fluid exits may be chosen so that flow is substantially in the forward direction.

Figure 56:
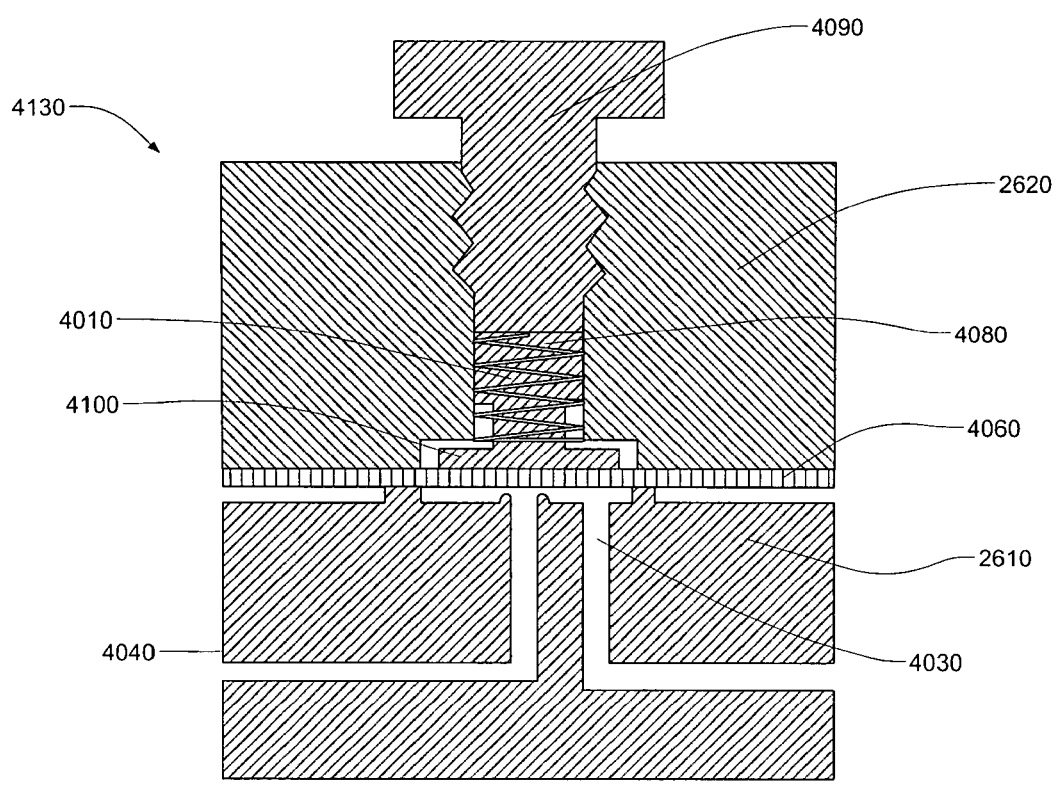
FIG. 56 schematically shows a flow-biasing valve with an adjustable cracking pressure in accordance with an embodiment of the invention.

Referring now to FIG. 56, a sectional view of an adjustable flow biasing valve 4130 which operates on a principal similar to the flow biasing valve in FIG. 50, but allows adjustment of the pressure necessary to open the valve, i.e., "cracking pressure" (which, in some embodiments, can be from 0.2 to 20 pounds per square inch or "psi") is shown. The cracking pressure is adjusted by turning a spring tensioning screw 4090, which alters the volume of the recess 4080 to compress or decompress the valve spring 4010 thereby altering the spring 4010 biasing force. The valve spring 4010 biases a plunger 4100 against the valve membrane 4060 to force it against the valve seat. The plunger 4100 serves a force application function similar to the fixed force poppet of the flow biasing valve (shown as 4020 and 4000 respectively, in FIGS. 50-53). Compressing the valve spring 4010 will increase its bias, thereby increasing the cracking pressure. Conversely, decompressing the spring 4010 will decrease its bias and the associated cracking pressure. The valve spring 4010 is positioned coaxially around the shaft of a plunger 4100 and exerts its biasing force on the plunger 4100. In some embodiments, the shaft of the plunger 4100 may be shorter than both the length of the valve spring 4010 and the recess 4080 to allow it to be freely displaced in response to increased fluid pressure in the fluid inlet 4030. The plunger 4100 may be any size necessary to function as desired. As in the embodiment of FIGS. 50-53, the wetted parts may reside in a disposable portion 2610 and the force application components (e.g., the plunger and spring) may reside in the reusable portion 2620. The principal of operation is also similar; a larger mechanical advantage in the fluid inlet 4030 relative the outlet 4040 favors forward flow versus retrograde flow. Alternately, the plunger 4100 may be replaced by the poppet (shown as 4020 in FIGS. 50-55). In some embodiments, it may be desirable to eliminate the raised valve seat; in these embodiments, the plunger may be ball shaped or another shape capable of concentrating the force.

The flow biasing valve 4000 substantially reduces or prevents retrograde flow from the dispensing chamber 122 into the pumping chamber 2350. As in FIGS. 50-56, a valve spring 4010 biases a poppet or plunger 4040 to press the membrane 7220 against a valve seat 4070 in a way that provides mechanical advantage to forward flow through the line 310. By serving the function of the pumping membrane 2330 and the valve membrane, membrane 7220 allows the line 310, pumping chamber 2350 and pumping diaphragm 2340 to reside in one component (e.g., the disposable portion 2610) and the remainder of the pumping mechanism in a second, removable component (e.g., the reusable portion 2620). By placing the more durable and expensive components in the reusable portion 2620, economy and convenience may be realized.

The pumping mechanism described in the various embodiments above can be used in various devices to pump fluid. As an exemplary embodiment, the pumping mechanism described in FIGS. 59A-59E, FIGS. 60A-60D and FIGS. 60A-60C will be described as integrated into a fluid pumping device.

Figure 57:
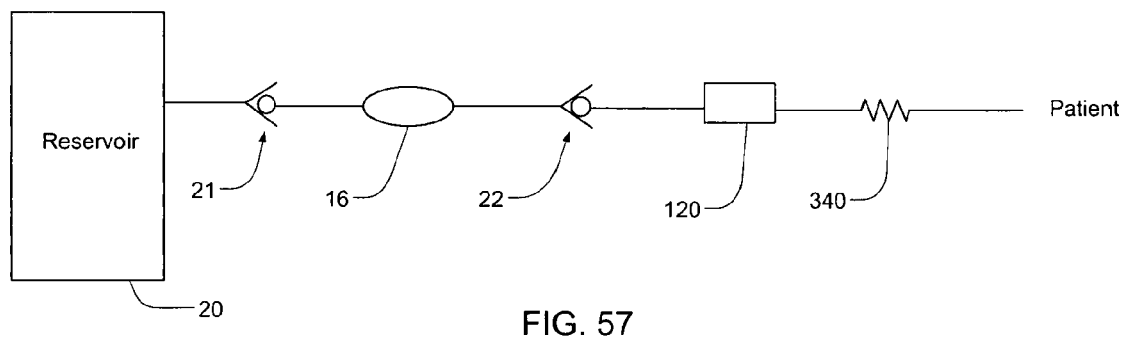
FIGS. 57 and 58 show schematics for flow lines utilizing un-pressurized reservoirs.
Figure 58:
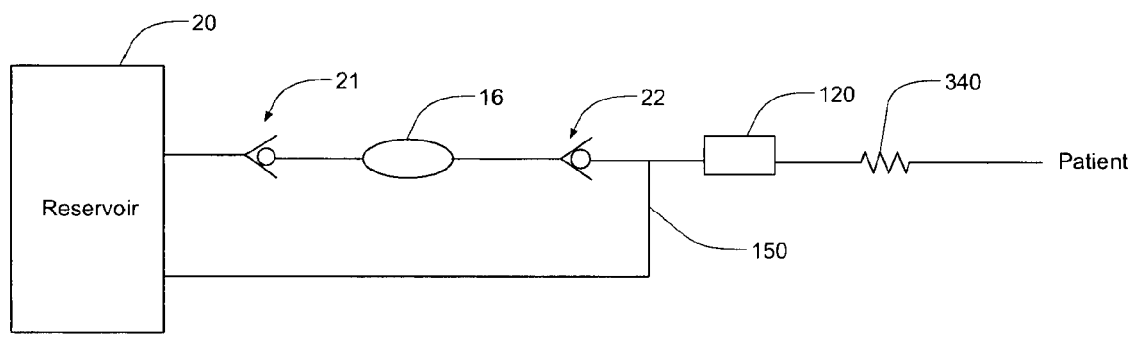

Referring FIGS. 57 and 58, alternate ways are shown for the fluid schematic. These are two schematics where the reservoir 20 and pumping assembly 16 are coupled to the dispensing assembly 120. In the embodiment shown in FIG. 57, the reservoir and pumping assembly are coupled in series to the dispensing assembly 120. In the embodiment shown in FIG. 58, a shunt line 150 is coupled from the output of the pumping assembly 16 back to the reservoir 20. Since much of the fluid output of the pumping assembly 16 is returned to the reservoir 20 via the shunt line 150, the pumping assembly 16 can accommodate varieties of pumping mechanisms 16 that may not function as desired in the embodiment shown in FIG. 57. Thus, in some embodiments, where a large volume pumping mechanism is employed, the shunt line 150 can impart small volume functionality to a large volume pumping mechanism. One way valves 21 and 22 are oriented in the same direction and included to prevent unwanted backflow.

Figure 59A:
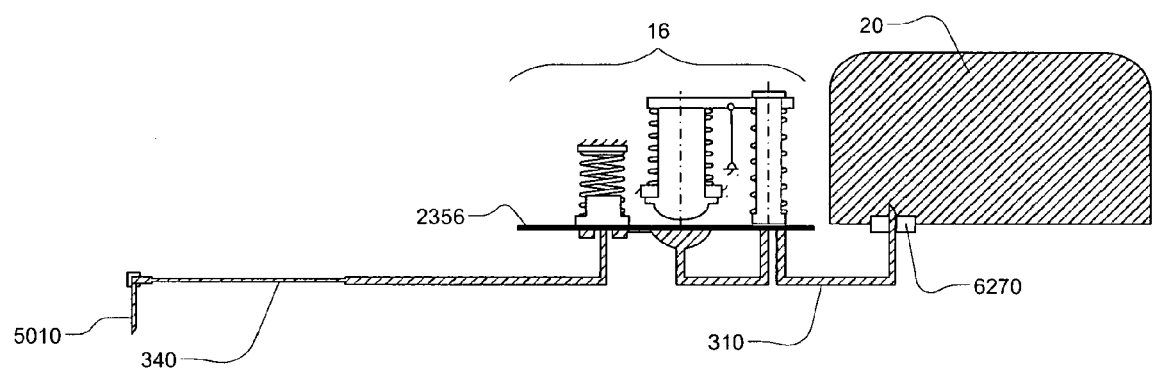
FIGS. 59A-59E shows schematics of a fluid flow in a fluid delivery device.

Referring now to FIG. 59A, a fluid schematic of one embodiment of a fluid pumping device is shown. In this embodiment, fluid is located in a reservoir 20 connected to a fluid line 310. Fluid line 310 is in communication with pumping mechanism 16, separated by a membrane 2356. The fluid is pumped through a flow restrictor 340 to an infusion device or cannula 5010 for delivery to a patient. It should be understood that the infusion device or cannula 5010 is not part of the device as such, but is attached to a patient for delivery of the fluid. System embodiments are described in more detail below and these include an infusion device or cannula 5010.

Figure 59B:
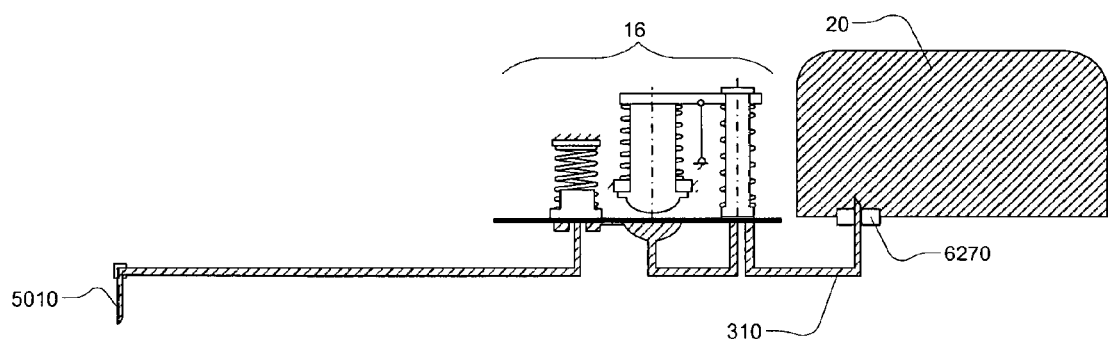

Referring now to FIG. 59B, an alternate embodiment of the schematic shown in FIG. 59A is shown. In the embodiment shown in FIG. 59A, the fluid is pumped through a flow restrictor 340 then through a cannula 5010. However, in FIG. 59B, the fluid is not pumped through a flow restrictor; rather, the fluid is pumped, having the same impedance, through the cannula 5010.

In both FIGS. 59A and 59B, the volume of fluid pumped to the patient, in one embodiment, is calculated roughly by pump strokes. The length of the stroke will provide for a rough estimate of the volume pumped to the patient.

Figure 59C:
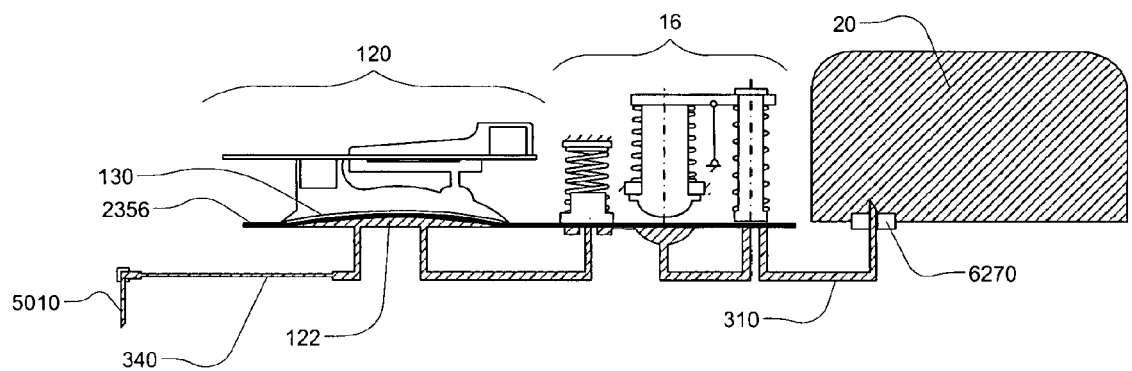

Referring now to FIG. 59C, a fluid schematic of one embodiment of a fluid pumping device is shown. In this embodiment, fluid is located in a reservoir 20 connected to a fluid line 310 by a septum 6270. Fluid line 310 is in communication with pumping mechanism 16, separated by a membrane 2356. The fluid is pumped to a variable volume delivery chamber 122 and then through a flow restrictor 340 to a cannula 5010 for delivery to a patient.

The volume of fluid delivered is determined using the dispensing assembly 120 which includes an acoustic volume sensing (AVS) assembly, as described above, a variable volume delivery chamber 122, and a dispensing spring 130. Similarly to the pumping mechanism, a membrane 2356 forms the variable volume dispensing chamber 122. The membrane is made of the same material (or, in some embodiments, different material) from the membrane 2356 in the pumping mechanism 16 (described in detail above). The AVS assembly is described in greater detail above.

Figure 59D:
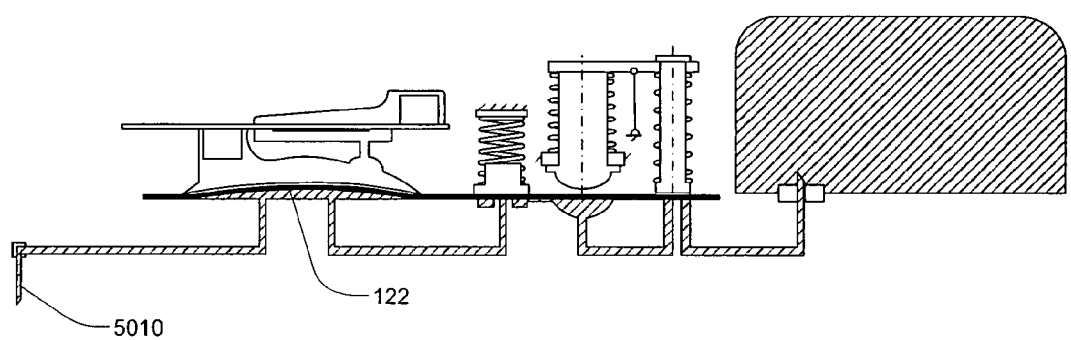
Figure 59E:
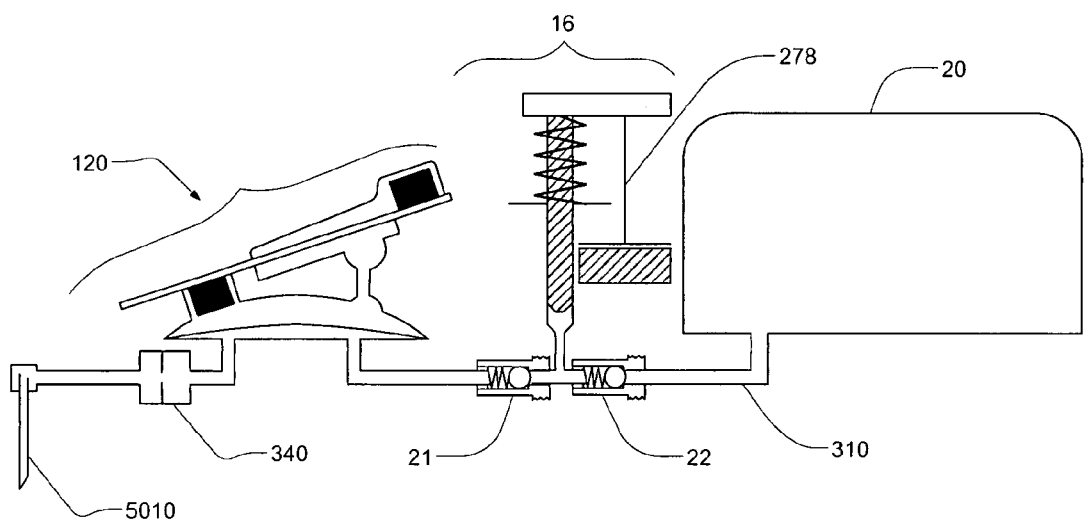
Figure 60A:
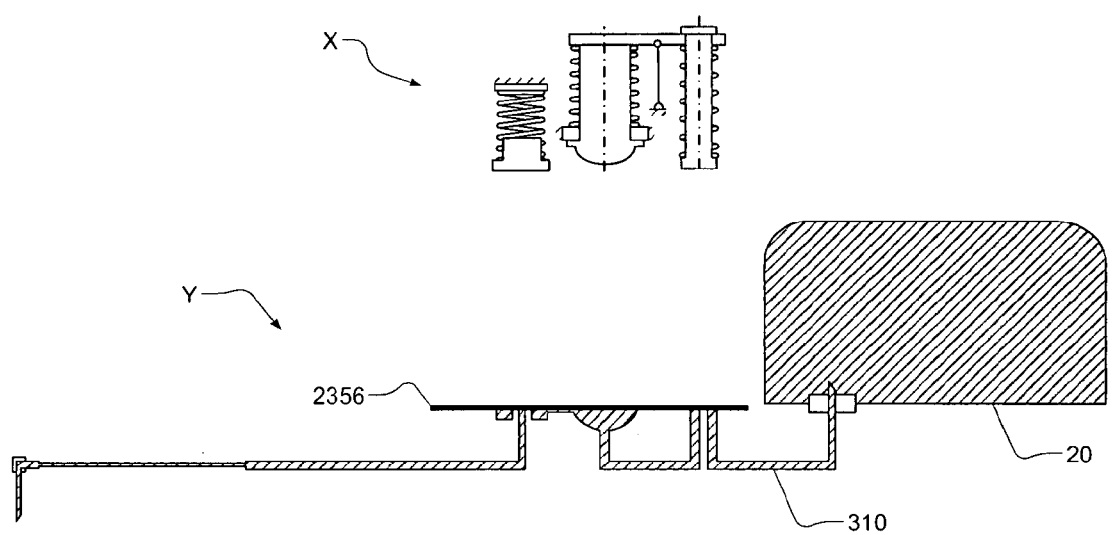
FIGS. 60A-60D shows exploded schematics of the fluid flow in a fluid delivery device.
Figure 60B:
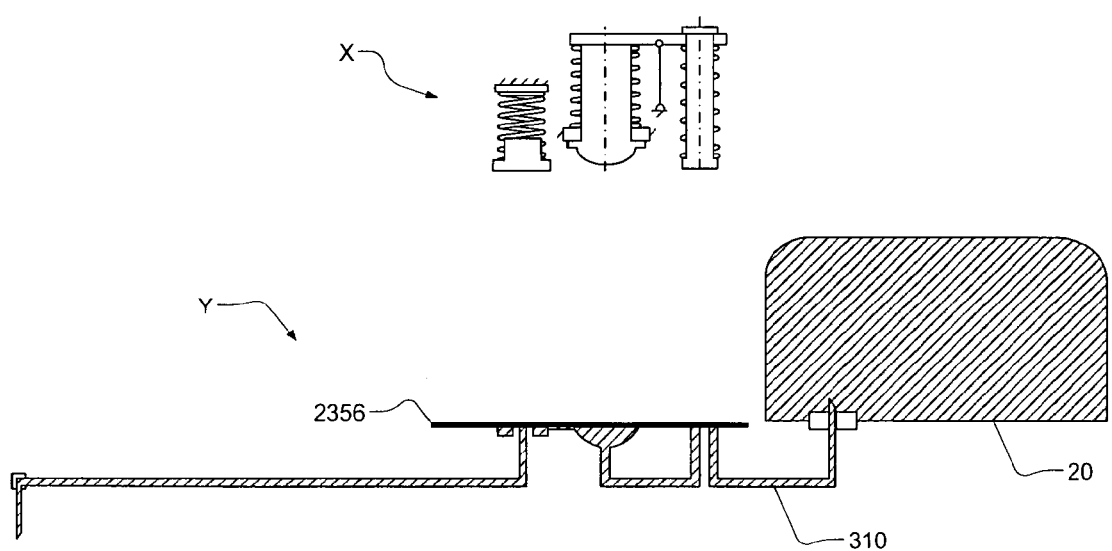
Figure 60C:
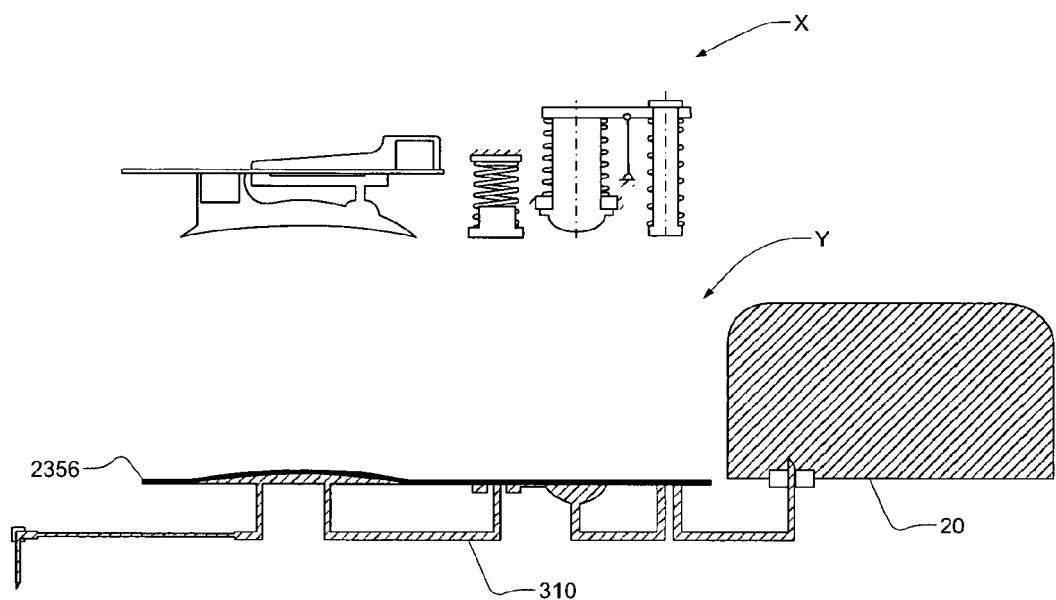
Figure 60D:
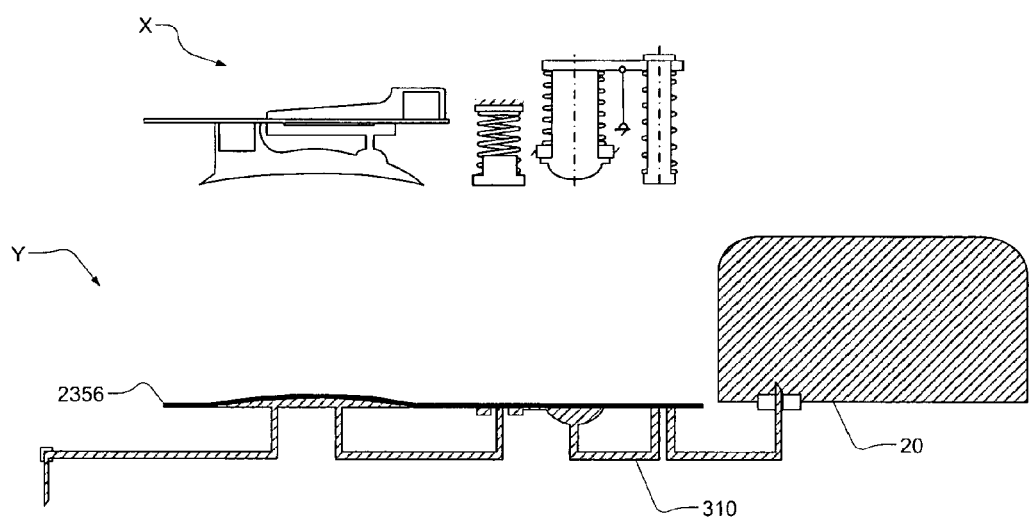

Referring now to FIG. 59D, an alternate embodiment to the embodiment shown in FIG. 59C, in this embodiment, there is no flow restrictor between the variable volume delivery chamber 122 and the cannula 5010. Referring now to FIG. 59E, an alternate embodiment to the embodiment shown in FIG. 59C is shown, with an alternate pumping mechanism 16.

Referring now to FIGS. 59A-59E, the reservoir 20 can be any source of a fluid, including but not limited to a syringe, a collapsible reservoir bag, a glass bottle, a glass vile or any other container capable of safely holding the fluid being delivered. The septum 6270 is the connection point between the fluid line 310 and the reservoir 20. Various embodiments of the septum 6270 and the reservoir 20 are described in more detail below.

The fluid delivery device embodiment shown in FIGS. 59A-59E can be used for the delivery of any type of fluid. Additionally, the embodiments can be used as one, two or three separate mating parts. Referring now to FIGS. 60A-60D, the same embodiments described with respect to FIGS. 59A-59D are shown as separated into mating parts. Part X includes the movable parts while part Y includes the fluid line 310 and the membrane 2356. In some embodiments of this design, part Y is a disposable portion while part X is a non-disposable portion. Part X does not come into contact directly with the fluid, part Y is the only part having wetted areas. In the above embodiments, the reservoir 20 can any size and is either integrated into the disposable or a separate disposable part. In either embodiment, the reservoir 20 can be refillable. In embodiments where the reservoir 20 is integrated into the disposable part Y, the reservoir 20 can either be manufactured filled with fluid, or, a patient or user fills the reservoir 20 using a syringe through the septum 6270. In embodiments where the reservoir 20 is a separate mating part, the reservoir 20 can either be manufactured filled with fluid, or, a patient or user fills the reservoir 20 using a syringe (not shown) through the septum 6270 as part of a reservoir loading device (not shown, described in more detail below) or manually using a syringe through the septum 6270. Further detail regarding the process of filling a reservoir 20 is described below.

Figure 61A:
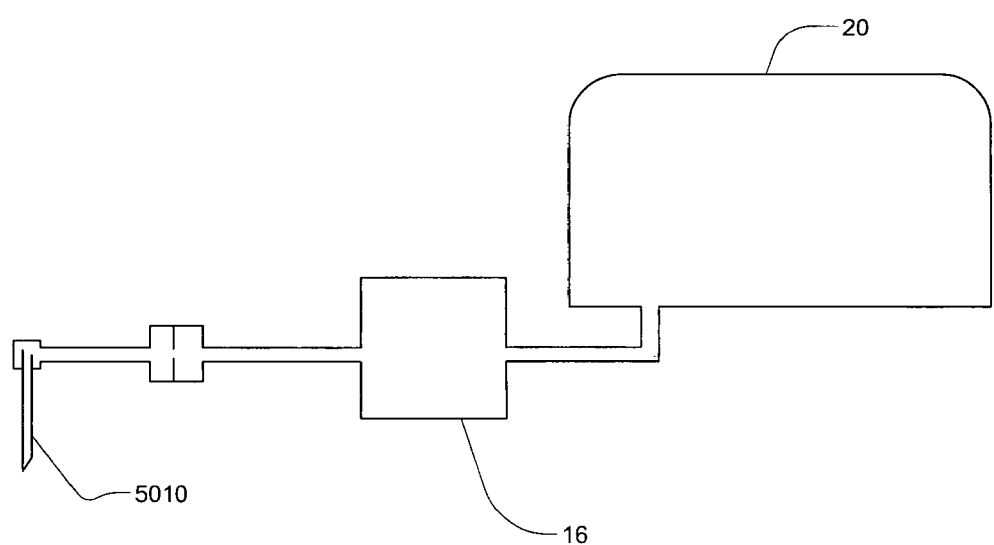
FIGS. 61A-61C show schematics of a fluid flow in a fluid delivery device.
Figure 61B:
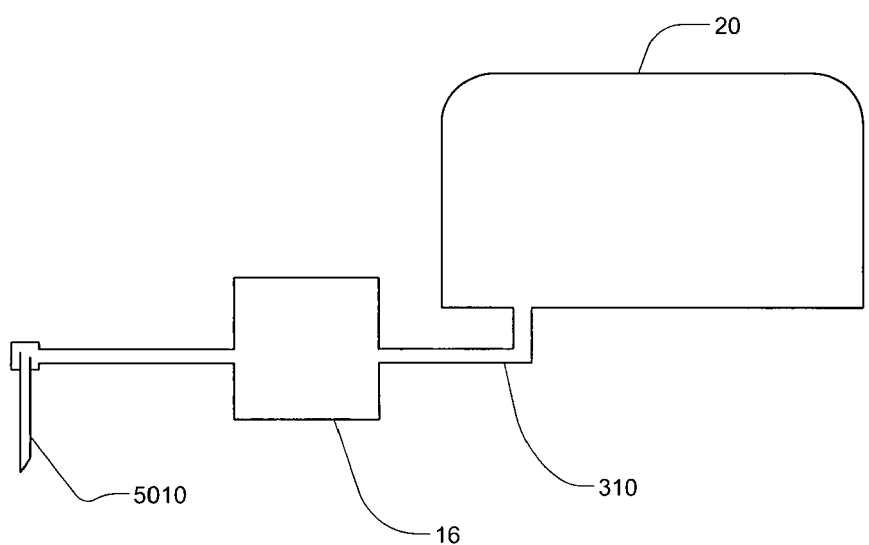
Figure 61C:
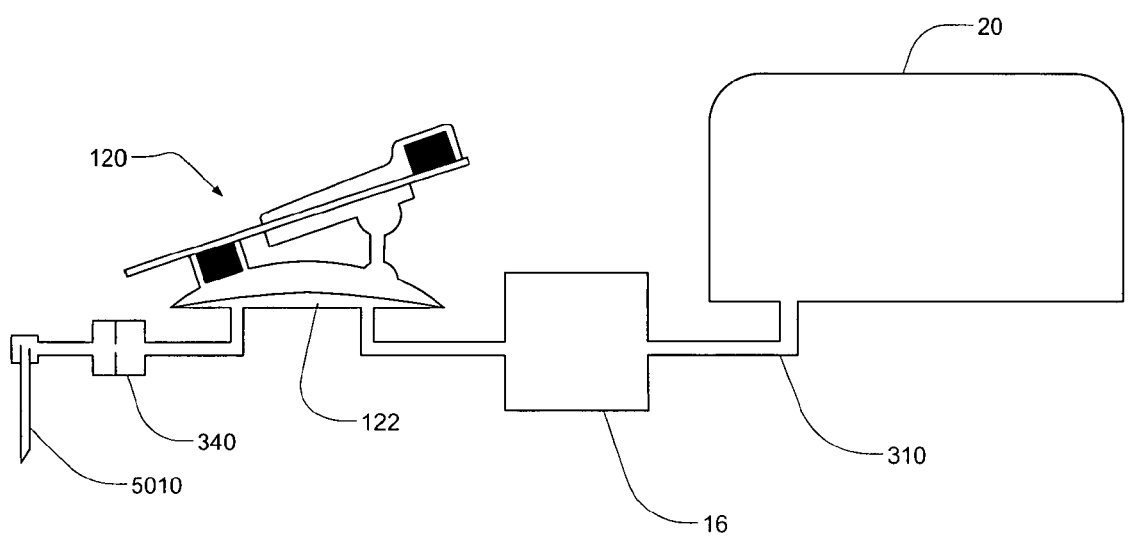

Although various embodiments have been described with respect to FIGS. 59A-59E and FIGS. 60A-60D, the pumping mechanism can be any pumping mechanism described as embodiments herein or alternate embodiments having similar function and characteristics. For example, referring now to FIG. 61A, a similar embodiment as that shown in FIG. 59A is shown having a representative block that includes pumping mechanism 16. This is to show that any pumping mechanism 16 described herein or functioning similarly can be used in the fluid pumping device. Likewise, FIG. 61B and FIG. 61C are representations of systems encompassing the embodiments FIG. 59B and FIG. 59C respectively.

The schematics of a fluid pumping device described above can be implemented in a device usable by a patient. There are a number of embodiments. The device can be a stand-alone device or be integrated into another device. The device can be any size or shape. The device can be either portable or non-portable. The term "portable" means a patient can, transport the device either in a pocket area, strapped to the body, or otherwise. The term "non-portable" means that the device is in a healthcare institution or in the home, but the patient does not carry the device almost everywhere they move. The remainder of this description will focus on portable devices as the exemplary embodiment.

With respect to portable devices, the device can be worn by a patient or carried by a patient. In the embodiments where the device is worn by a patient, this is referred to as a "patch pump" for purposes of this description. Where the device is carried by a patient, this is referred to as a "portable pump" for purposes of this description.

The following description is applicable to various embodiments for either the patch pump embodiments or the portable pump embodiments. In various embodiments, the device includes a housing, a pumping mechanism, a fluid line, a moveable member, a reservoir, a power source and a microprocessor. In various embodiments, a dispensing assembly, for example a volume sensing device, which in some embodiments includes an AVS assembly, are included in the device. Also, an embodiment can also include a fluid restrictor, although it is not depicted in the following figures, as the fluid line is shown as homogeneous to simplify the illustration. For purposes of this description, where a dispensing assembly is included, the exemplary embodiment will include an AVS assembly. Although an AVS assembly is a preferred embodiment, in other embodiments, other types of volume sensing device can be used. In some embodiments, however, no volume sensing device is used, but rather, either the reservoir itself will determine the volume of fluid delivered, the pump stroke is used to roughly determine the amount of volume delivered. It should be understood that the schematic devices shown herein are meant to illustrate some of the variations in the device. The embodiments represented by these schematics can each also include a sensor housing, a vibration motor, an antenna, a radio, or other components that are described with respect to FIGS. 70-70D. Thus, these depictions are not meant to limit the components but rather to illustrate how various components could interrelate in a device.

Figure 62A:
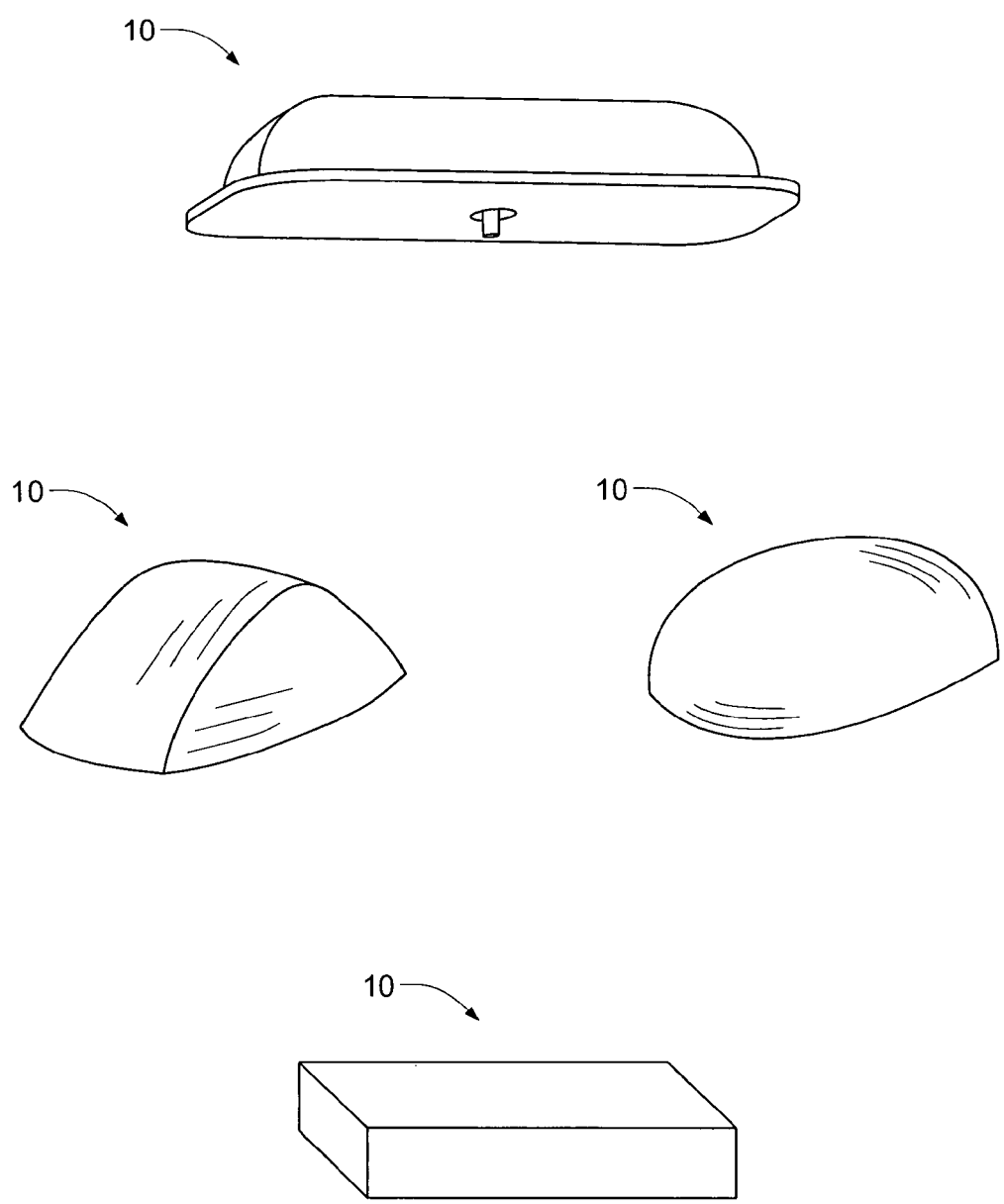
FIGS. 62A and 62B show schematics of a stand alone device.

Referring now to FIG. 62A, schematics of a stand alone device 10 are shown. The housing 10 can be any shape or size and accommodates the intended use. For example, where the device is used as a patch, the device will be compact enough to be worn as such. Where the device is used as a portable pump, the device will be compact enough to be used accordingly. In some embodiments, the housing is made from plastic, and in some embodiments, the plastic is any injection molded fluid-compatible plastic, for example, polycarbonate. In other embodiments, the housing is made from a combination of aluminum or titanium and plastic or any other material, in some embodiments the materials are light and durable. Additional materials may include, but are not limited to, rubber, steel, titanium, and alloys of the same. As shown in FIG. 62A, the device 10 can be any size or shape desired.

FIGS. 62A-69B are schematics showing representative embodiments. The exact design is dependant on many factors, including, but not limited to, size of the device, power restrictions and intended use. Thus, FIGS. 62A-69B are intended to describe the various features of a device and the possible combinations, however, actual devices can be readily designed and implemented by one or ordinary skill in the art. As examples, embodiments of devices are described and shown below. However, these are not intended to be limiting, but rather, are intended to be examples.

Figure 62B:
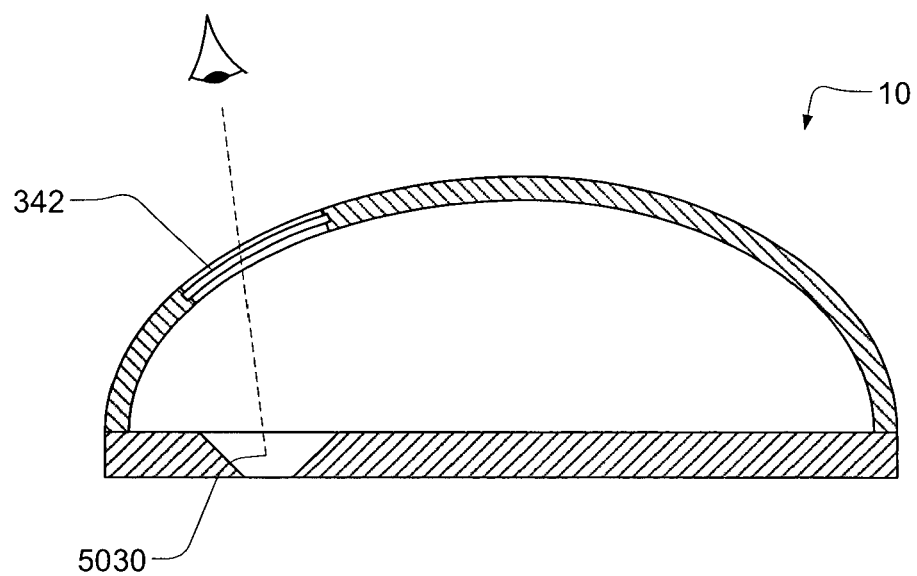

Referring now to FIG. 62B, with respect to the patch device, in some embodiments, the housing 10 includes an insertion area viewing window 342. This allows for the area on a patient where the infusion device or cannula (not shown) is inserted to be viewed. Shown here is the cannula housing 5030 area of the device 10. The viewing window 342 is made from any material capable of being transparent, including, but not limited to, plastic. Although the viewing window 342 is shown to be in one particular location on one particular shaped device, a viewing window 342 can be integrated in any location desired in any housing embodiment.

Figure 63A:
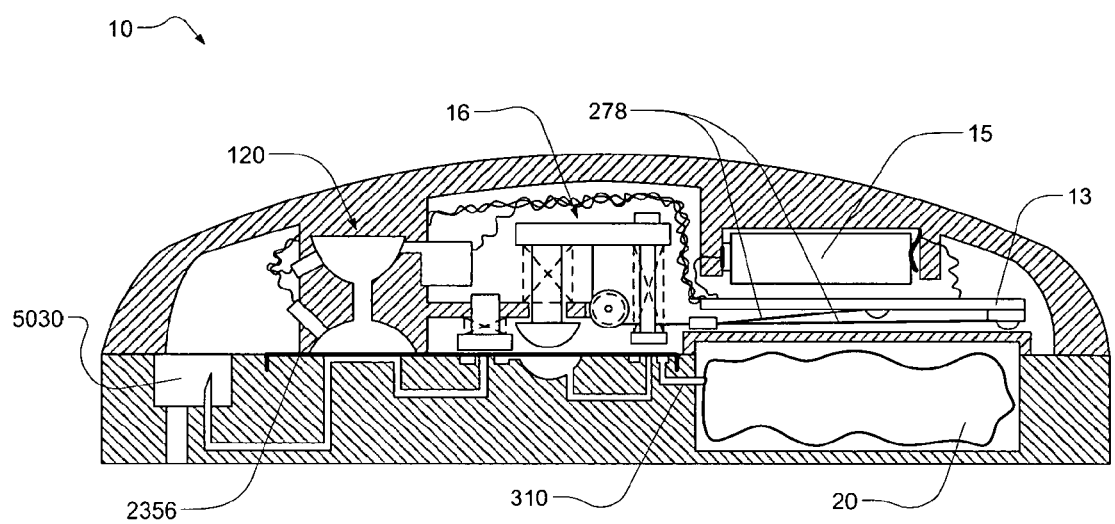
FIGS. 63A-63C show cross sectional schematics of embodiments of a device.

Referring now to FIG. 63A, a device 10 is shown. A reservoir 20 is shown connected to a fluid line 310, which is then connected to a pumping mechanism 16. A dispensing assembly 120 is shown connected to the fluid line 310. The pumping mechanism 16 and dispensing assembly 120 are separated from the fluid line 310 by a membrane 2356. The cannula housing 5030 is downstream from the volume measuring device. Shape memory actuators 278 are shown connected to the pumping mechanism 16. A microprocessor on a printed circuit board 13 as well as a power source or battery 15 are included. A flow impedance as described above can also be implemented between the dispensing assembly 120 and the cannula housing 5030.

Figure 63B:
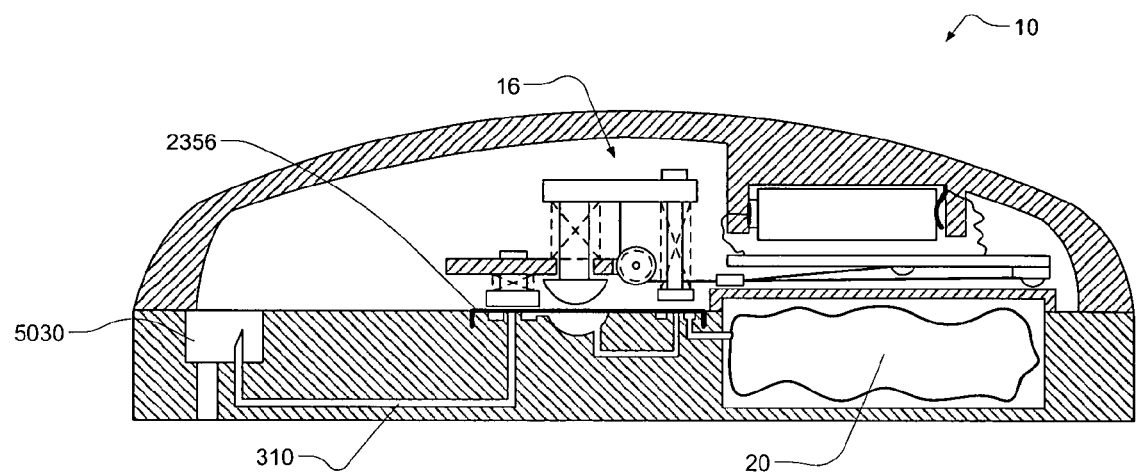

Referring now to FIG. 63B, a similar device 10 as shown in FIG. 63A is shown, except in this embodiment, a dispensing assembly is not included. In this embodiment, the volume of fluid delivered will depend on either the pump strokes (number and length), the reservoir 20 (volume and time), both, or any other method described previously with respect to monitoring the volume of fluid delivered.

Figure 63C:
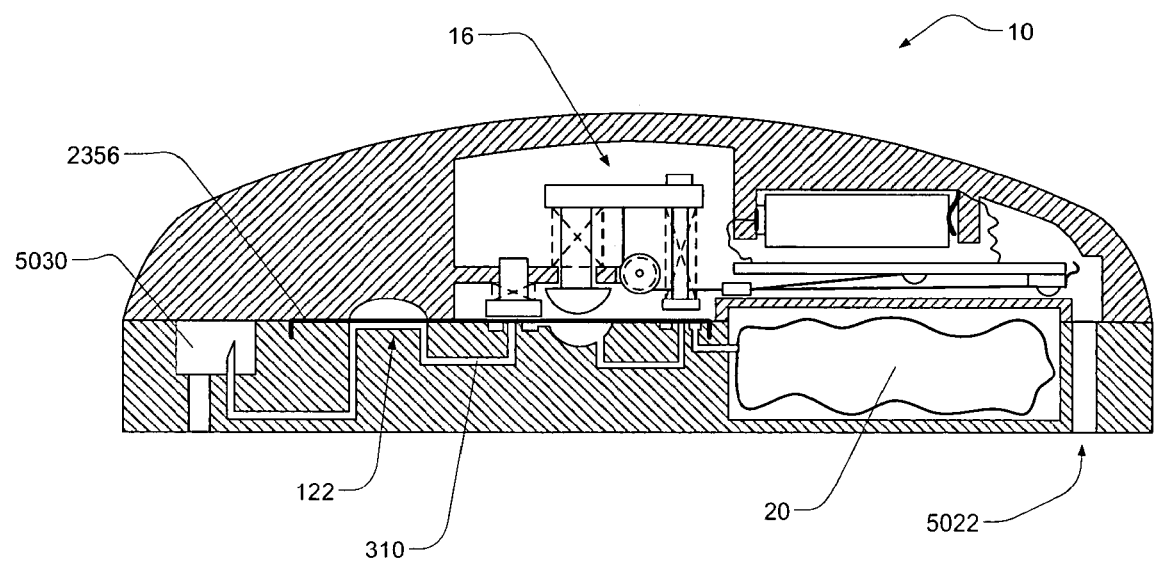

Referring now to FIG. 63C, a similar device 10 as shown in FIG. 63B is shown, except the device 10 includes a dispensing chamber 122 and sensor housing 5022.

Figure 64A:
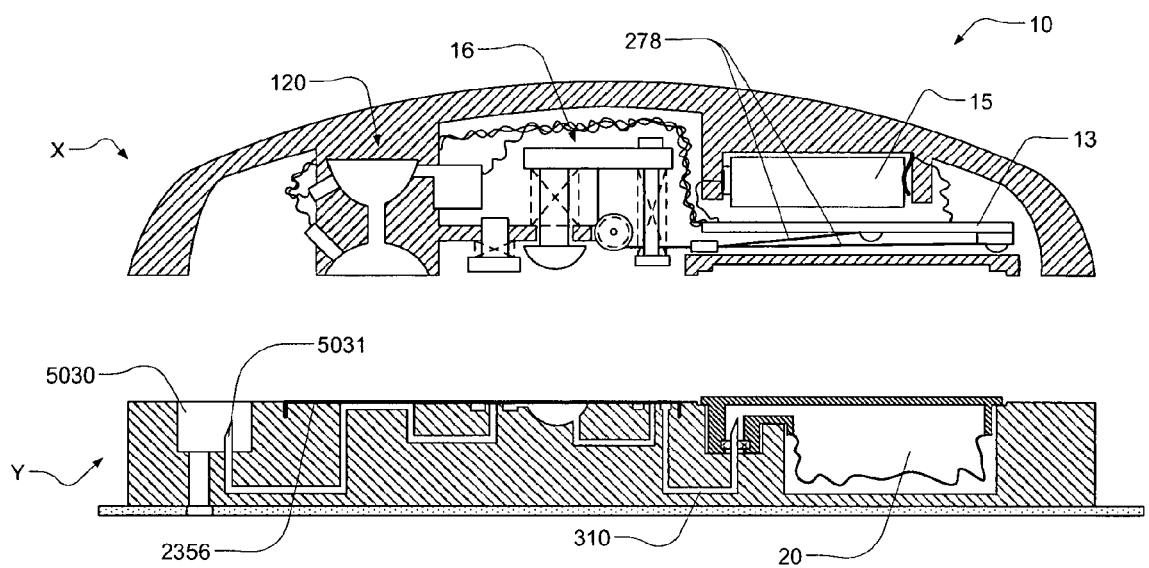
FIGS. 64A-64D show cross section schematics of embodiments of a device.

Referring now to FIG. 64A, one embodiment of the patch pump device 10 is shown. This embodiment is based on the embodiment of the device 10 shown in FIG. 63A. In this embodiment, the patch pump device 10 is divided into two sections: a top X and a base Y. The top X contains the pumping mechanism 16, a dispensing assembly 120 (which is optional, but is shown as an exemplary embodiment), the power supply 15, and the microprocessor and printed circuit board 13. These are the non-wetted elements, i.e., they do not come into direct contact with the fluid. The base Y contains the fluid line 310 and the membrane 2356. Where the reservoir 20 is built into the device, the reservoir is also contained on the base Y. However, in embodiments where the reservoir 20 is a separate mating part, the reservoir 20 is connected to the fluid line when fully assembled (see FIG. 66A-66D and description referring thereto), however, is not built into the device.

The patch pump device also includes a cannula housing 5030. This is the area the cannula line 5031 is located. Part of the fluid line 310, the cannula line 5031 allows a cannula (or other infusion device) to receive the fluid and deliver the fluid to a patient (not shown).

Figure 64B:
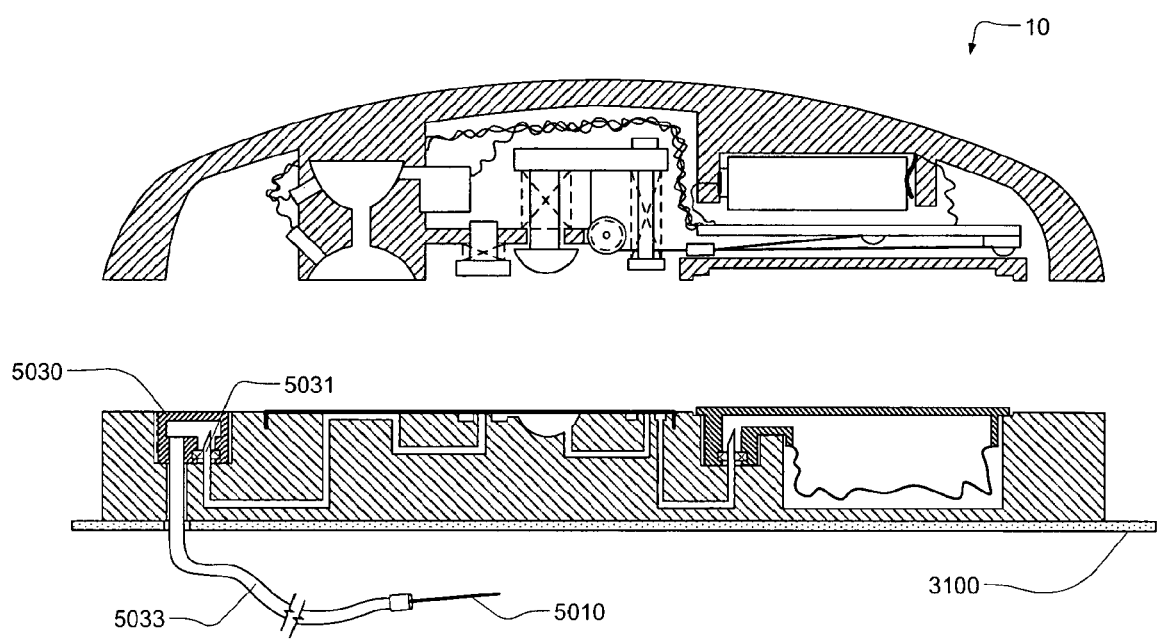
Figure 65A:
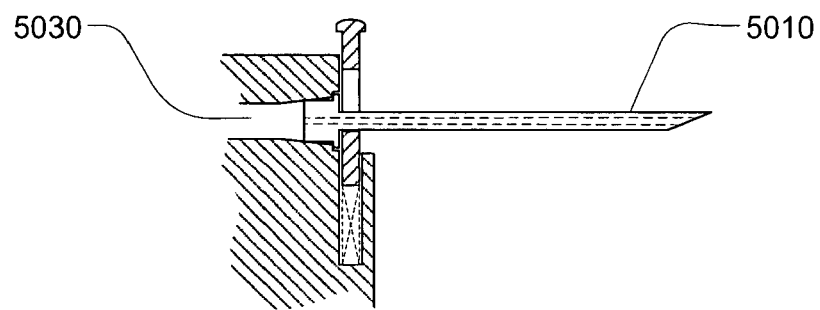
FIGS. 65A-65B show cross section schematics of embodiments of an infusion device connected to a fluid line.
Figure 65B:
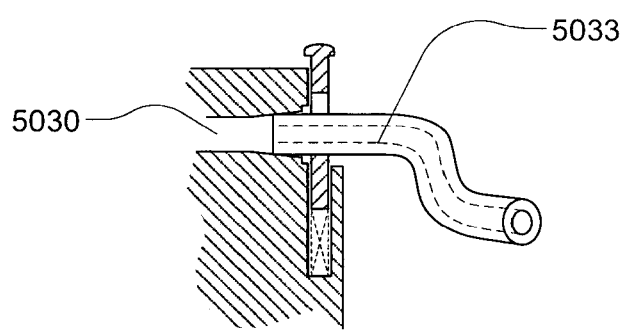

Referring now to FIG. 65A, in some embodiments, the cannula 5010 is inserted through the housing 5030 directly into the patient. The cannula 5010 is connected to a septum (not shown) connecting the cannula line 5031 to the cannula 5010. Referring now to FIG. 65B, in other embodiments, an insertion set, (including the cannula and tubing, not shown in FIG. 65B, but shown in FIG. 64B as items 5033 and 5010) is used; thus, the tubing 5033 of the insertion set will connect to the cannula line 5030 on one end and will connect to the cannula (not shown) on the opposite end of the tubing.

Referring again to FIG. 64A, in use, the reservoir 20, having fluid contained inside (which, as described above, is either molded into the base Y or is separate and attached to the base Y) is connected to the fluid line 310. The microprocessor on the printed circuit board 13 sends a signal to activate the pumping mechanism 16 and a stroke is initiated through electrical current being applied to the shape memory actuators 278. The fluid flows from the reservoir 20, in the fluid line 310 to the dispensing assembly 120, or AVS assembly. There, the exact volume of fluid inside the AVS chamber is determined and the fluid is forced out of the AVS chamber, to the cannula line 5031 and the cannula housing 5030.

Figure 64C:
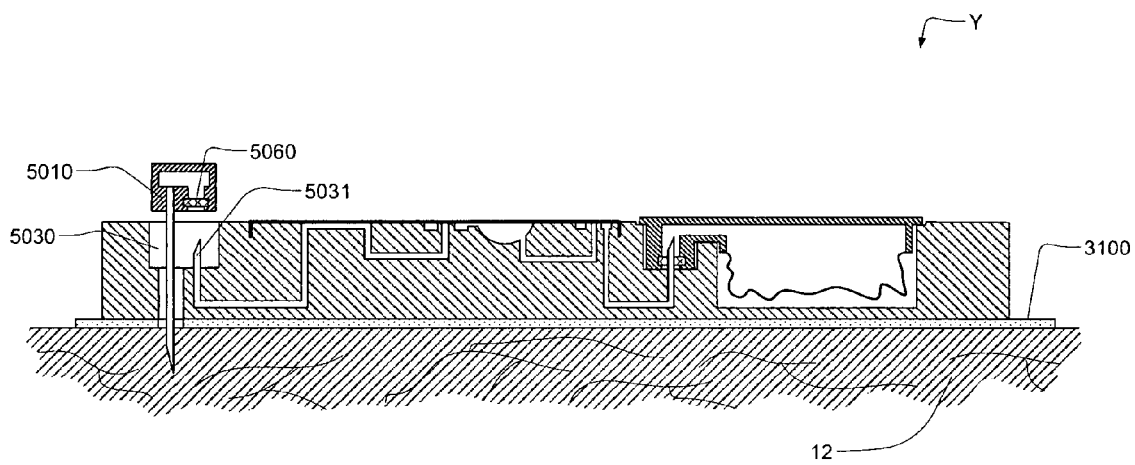

Referring now to FIG. 64B, the device shown in FIG. 64A is shown connected to an insertion set, tubing 5033 and cannula 5010. In FIG. 64C, the base Y of the device is shown using an adhesive patch or pad 3100 to the body of a patient 12. It should be noted that in this embodiment, the element 3100 can be either a pad or patch. However, as described in more detail below, item 3100 is called a patch, and item 3220 is called a pad. For simplicity purposes only, item 3100 is used; however, in some embodiments, a pad is used, thus item 3220 would be appropriate in those circumstances.

Figure 64D:
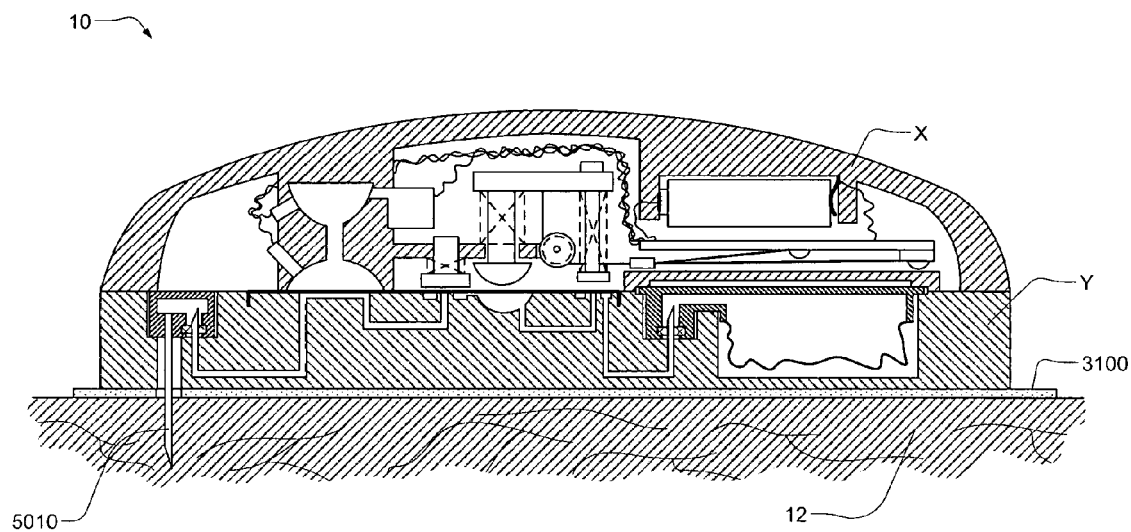

The cannula 5010, which is inserted through the cannula housing 5030 so that it mates by way of the cannula septum 5060 to the cannula line 5031, is inserted into a patient 12. However, as shown and described above with respect to FIG. 2B, the base Y can be fluidly attached to a patient through an insertion set, which includes a tubing 5033 and a cannula 5010. In both FIGS. 64B and 64C, the base Y can be adhered to a patient either before or after insertion of the cannula 5010. Referring again to FIG. 2C, the cannula 5010, once inserted into to the patient 12, will receive fluid from the device directly without an infusion set tubing (shown in FIG. 64B). The base Y is adhered to the patient 12 with an adhesive patch 3100 either before or after insertion of the cannula 5010. Referring now to FIG. 64D, the top X of the device 10 is then attached to the base Y of the device 10 after the cannula 5010 has been inserted into the patient 12.

As described below, the adhesive patch can have many embodiments and in some cases, the patch is placed on top of the device. Thus, the patch shown in these embodiments is only one embodiment. As described above, a pad, if used, would be placed in the same location as the patch in FIGS. 64A-64D.

Figure 66A:
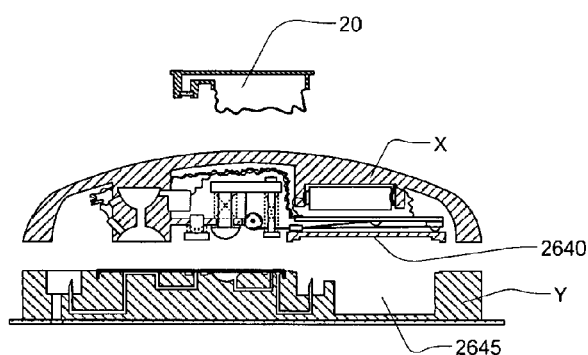
FIGS. 66A-66D show cross section schematics of a sequence of inserting a reservoir into a device.
Figure 66B:
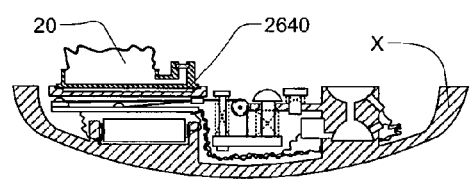
Figure 66C:
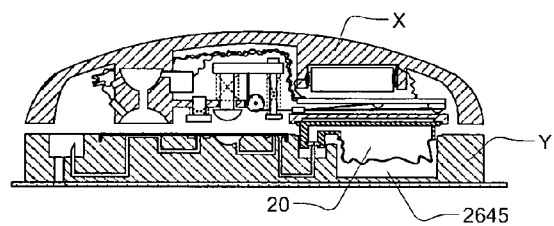
Figure 66D:
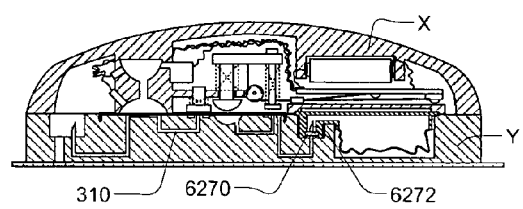

Referring now to FIGS. 66A-66D, in this embodiment, the reservoir 20 is shown as a separate part. As shown in FIG. 66A, the base Y includes a reservoir cavity 2645 with a septum needle 6272. Shown in FIG. 66B, the reservoir 20 is first placed in a top reservoir cavity 2640. At this point, the reservoir 20 is not attached to the device. Now, referring to FIG. 66C, when the top X is placed over the base Y, the reservoir 20 is sandwiched into the base reservoir cavity 2645. Shown in FIG. 66D, the force created by the attachment of the top to the base Y push the septum needle 6272 into the septum 6270 of the reservoir 20 connecting the reservoir 20 to the fluid line 310 of the base Y.

Figure 69A:
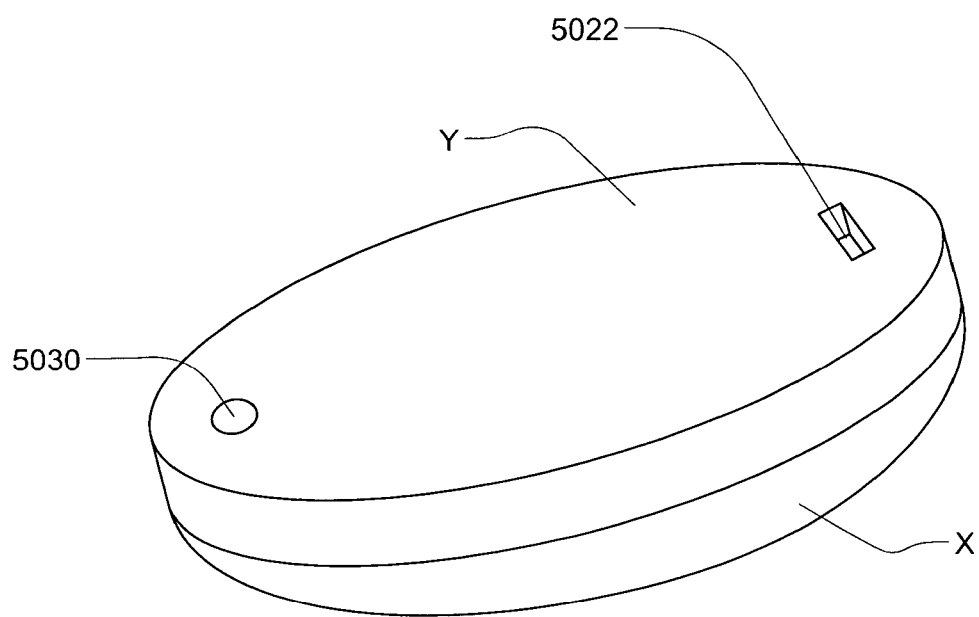
FIGS. 69A-69B show schematic views of the underside of the housing of a device.
Figure 69B:
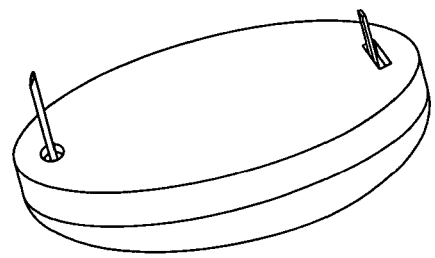

Referring now to FIGS. 67A-F, alternate embodiments of the embodiments shown in FIGS. 64A, 64C and 66A-66D are shown. In these alternate embodiments, in addition to a cannula housing 5030, the base Y includes a sensor housing 5022. Referring now to FIGS. 69A-69B, both the sensor housing 5022 and the cannula housing 5030 include an exit to the underside of the base Y, shown in FIG. 69A as 5022 and 5030 respectively. FIG. 69B depicts the embodiment shown in FIG. 69A with the sharps protruding through the housings. The sensor housing accommodates a sensor. In some embodiments, the sensor is an analyte sensor. Analytes sensed include blood glucose, but in other embodiments, this analyte sensor can be any type of analyte sensor desired.

Figure 67A:
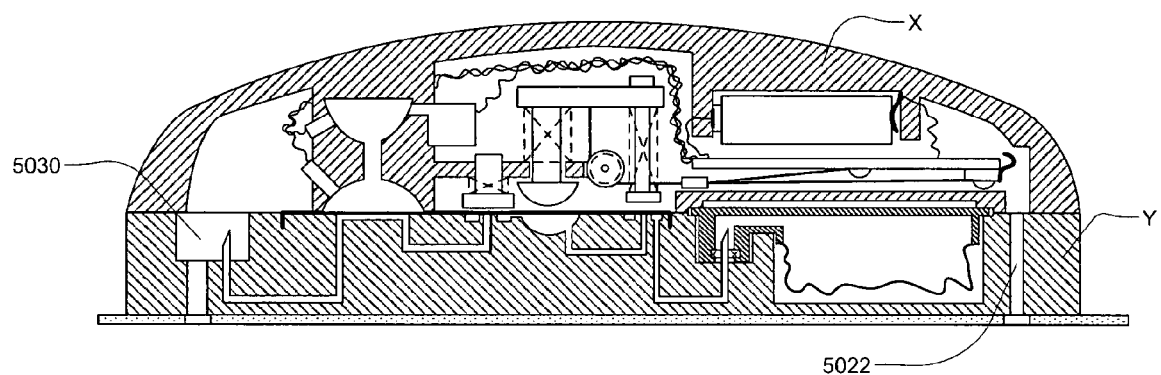
FIGS. 67A-67F show schematics of embodiments of the fluid delivery device.
Figure 67B:
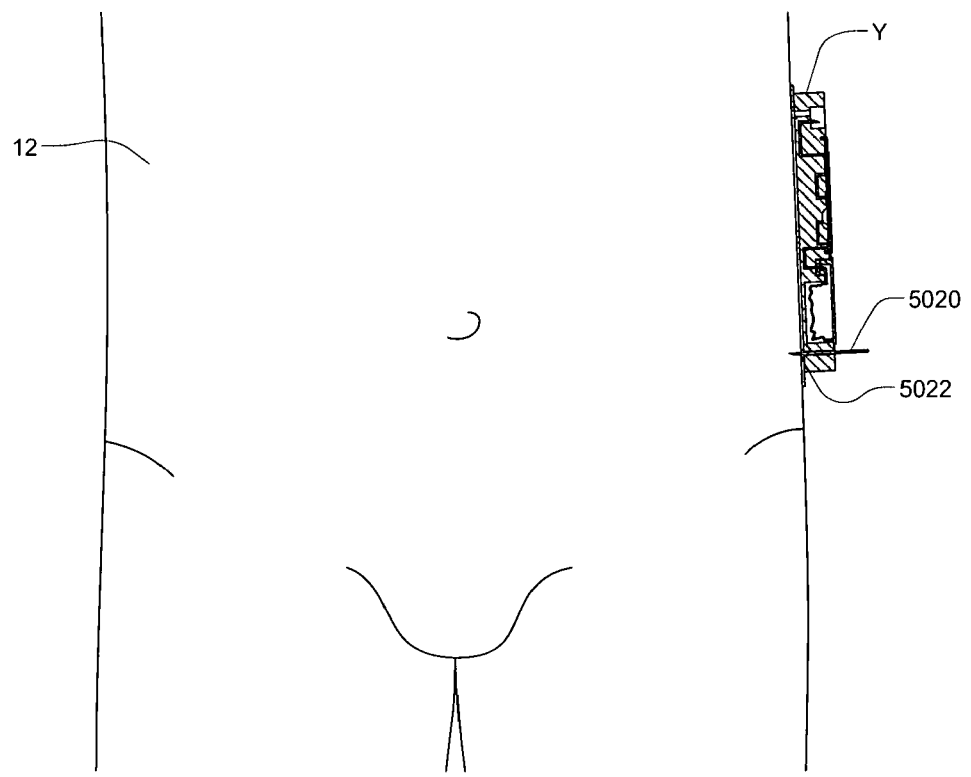
Figure 67C:
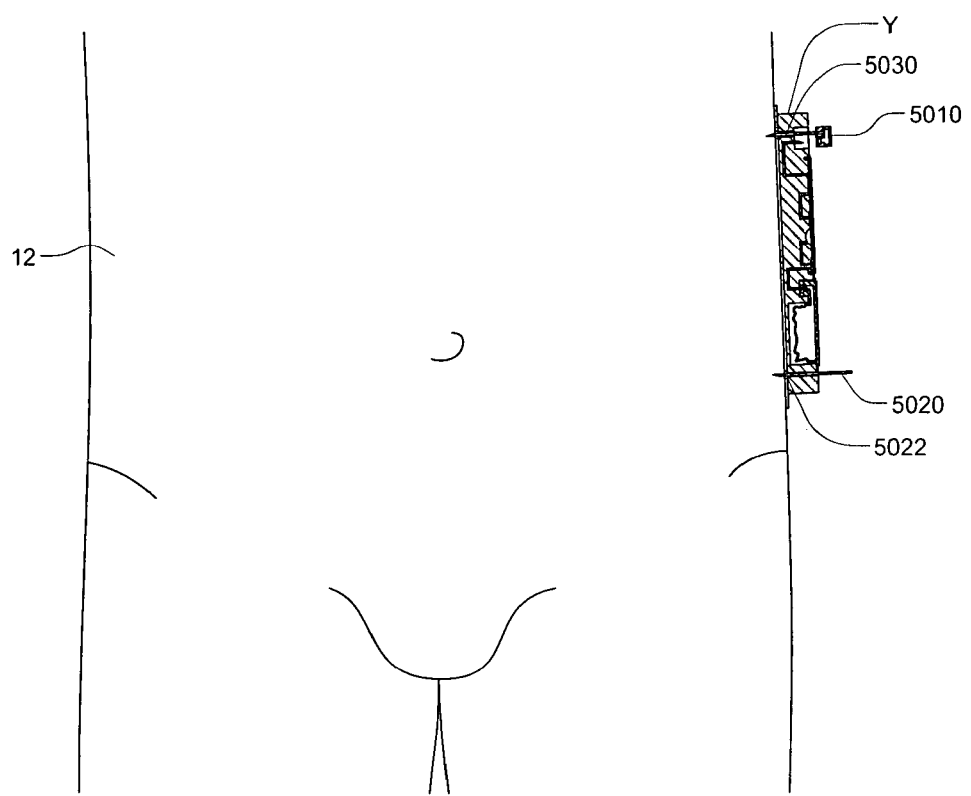
Figure 67D:
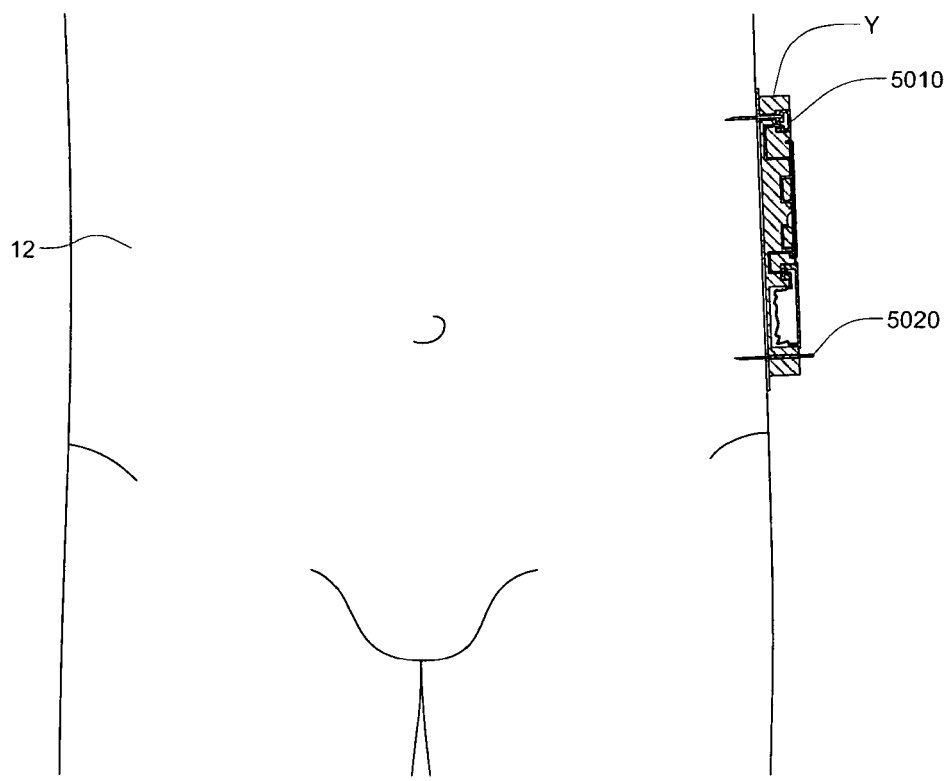

Referring now to FIG. 67B, the base Y is shown on the body of a patient 12. The sensor 5020 is shown having been inserted through the base Y sensor housing 5022 and into the patient 12. Referring now to FIG. 67C, in some embodiments, the cannula 5010 and sensor 5020 are inserted though their respective housing (5030 and 5022) and into the patient 12 simultaneously. Referring next to FIG. 67D, the base Y is shown attached to the patient with both a cannula 5010 and sensor 5020 attached to the patient 12 through the base Y.

Figure 67E:
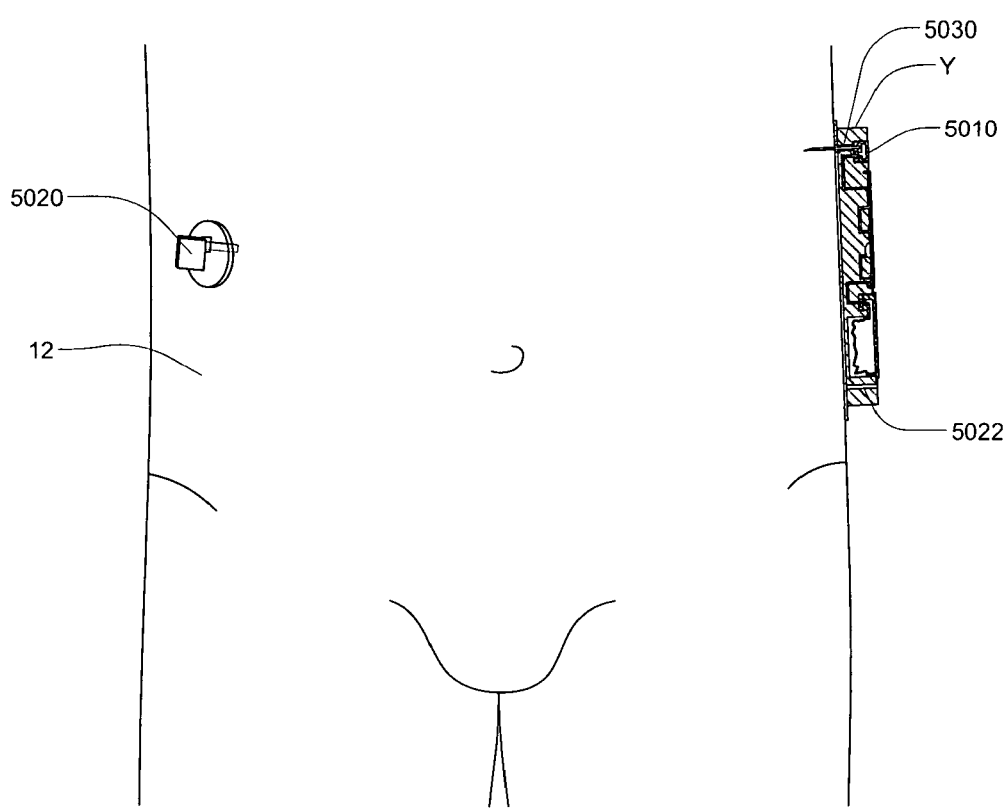

Referring now to FIG. 67E, the base Y is shown attached to a patient 12 and the cannula 5010 inserted through the cannula housing 5030. In this embodiment, the sensor housing 5022 is shown without a sensor. However, a sensor 5020 is shown inserted into the patient 12 in another location. Thus, the sensor 5020 is not required to be inserted through the base Y, but embodiments described below relating to monitoring blood glucose and pumping insulin through a cannula can be implemented in this way. Additionally, other embodiments relating to administering a fluid in response or relation to an analyte level can be administered this way.

Figure 67F:
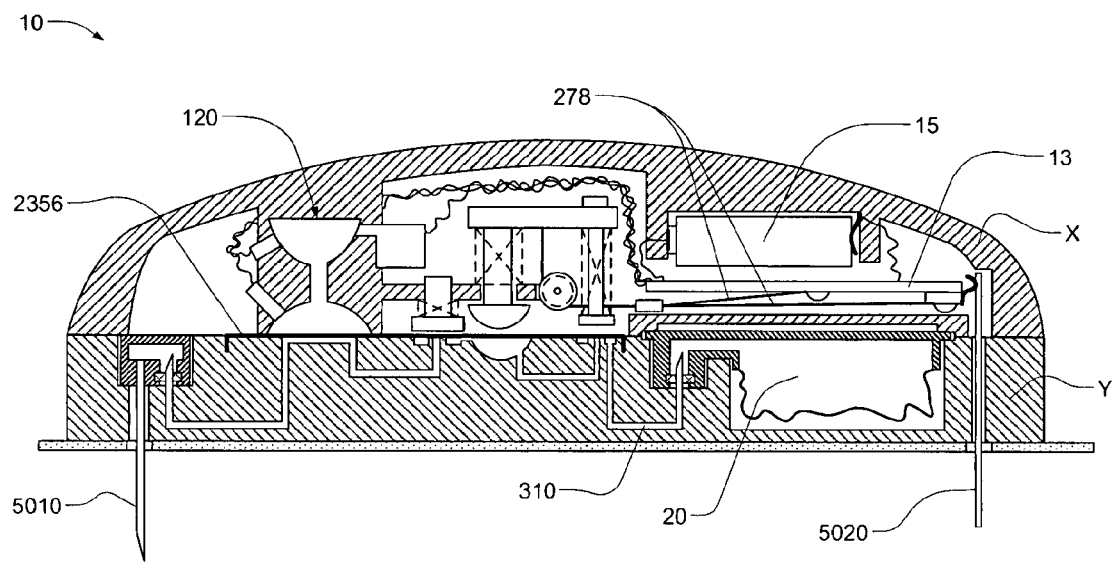

Referring now to FIG. 67F, the device 10, having both a sensor 5020 and a cannula 5010 through the base Y is shown with the top X placed on. Again, in the embodiments shown in FIGS. 66A-66D, once the top X is placed onto the base Y, the reservoir 20 is fluidly connected to the fluid line 310.

Figure 68:
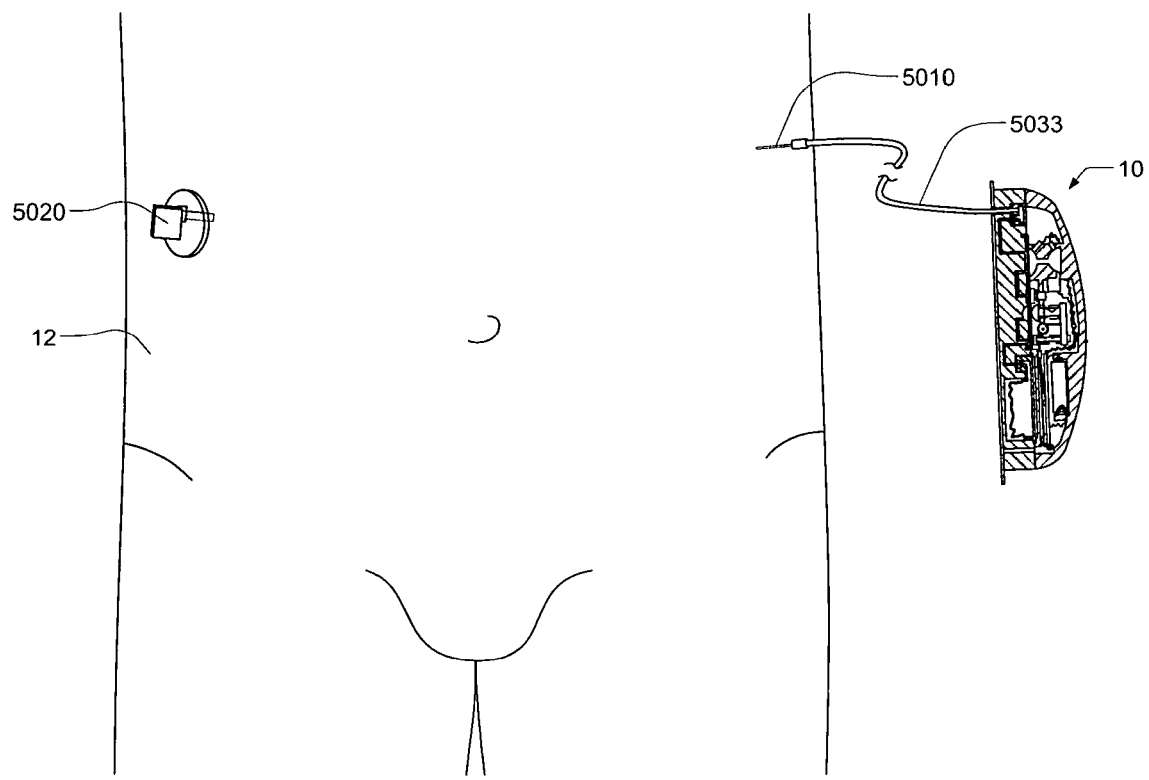
FIG. 68 is schematic of one embodiment of the portable pump embodiment of the device connected to a patient.

Referring now to FIG. 68, one embodiment of the portable pump embodiment of the device 10 is shown. In this device 10, an insertion set, including a cannula 5010 and tubing 5033, is necessary to connect the fluid line in the device 10 to the patient 12. Thus, the cannula 5010 is not connected, in this embodiment, through the portable pump device 10 to the patient 12 directly. Additionally, although this embodiment can function as described below with respect to an analyte sensor and a fluid pump, the sensor 5020 will be located outside the portable pump device 10 similar to the embodiment of the sensor 5020 shown in FIG. 5F.

Figure 70A:
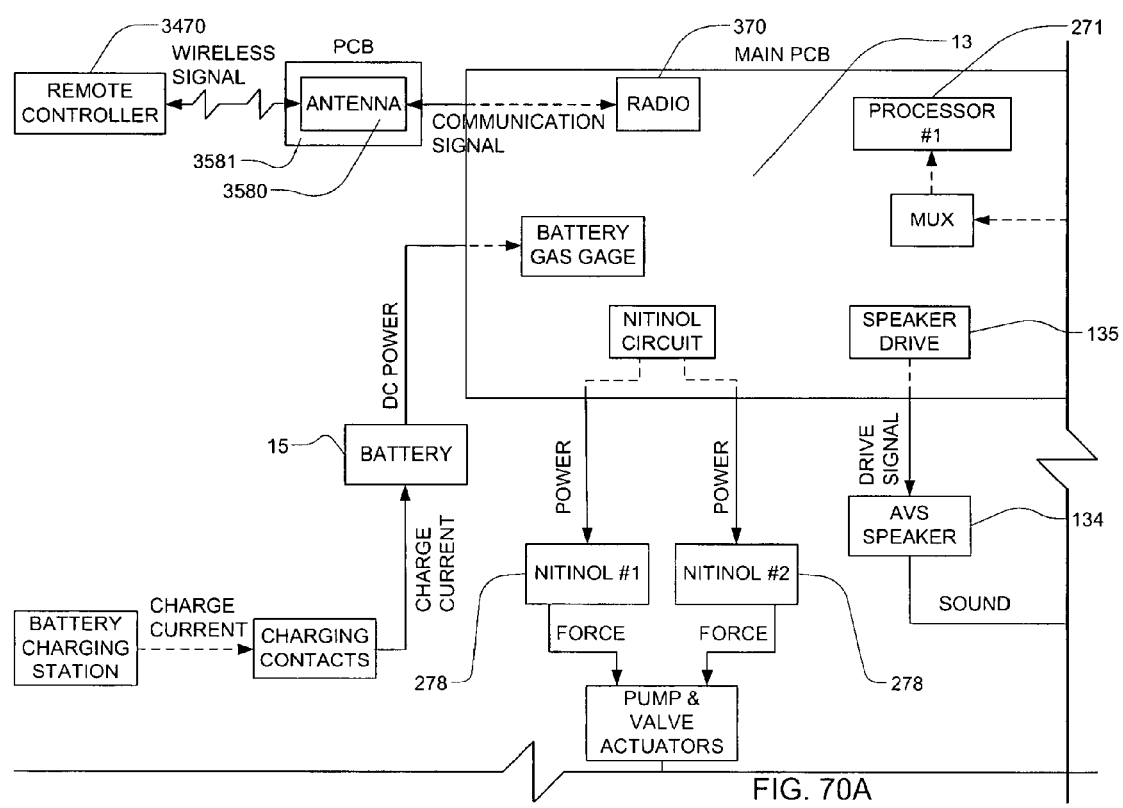
FIGS. 70-70D are a diagram depicting the various components available in embodiments of the fluid delivery device.
Figure 70B:
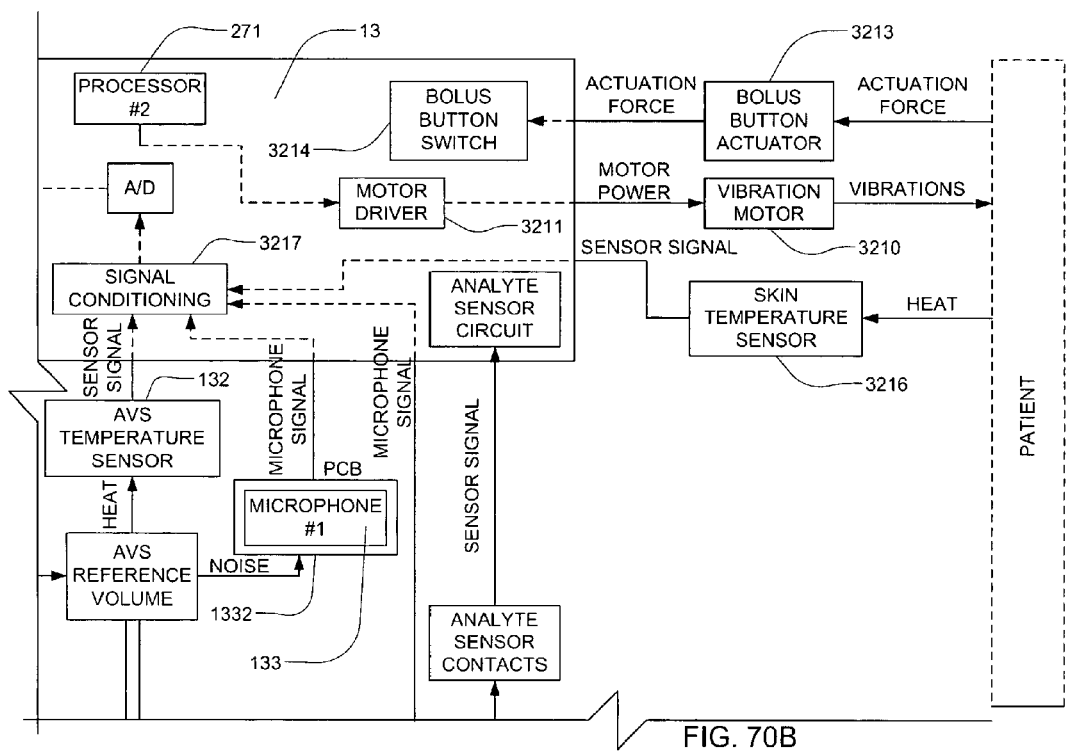
Figure 70C:
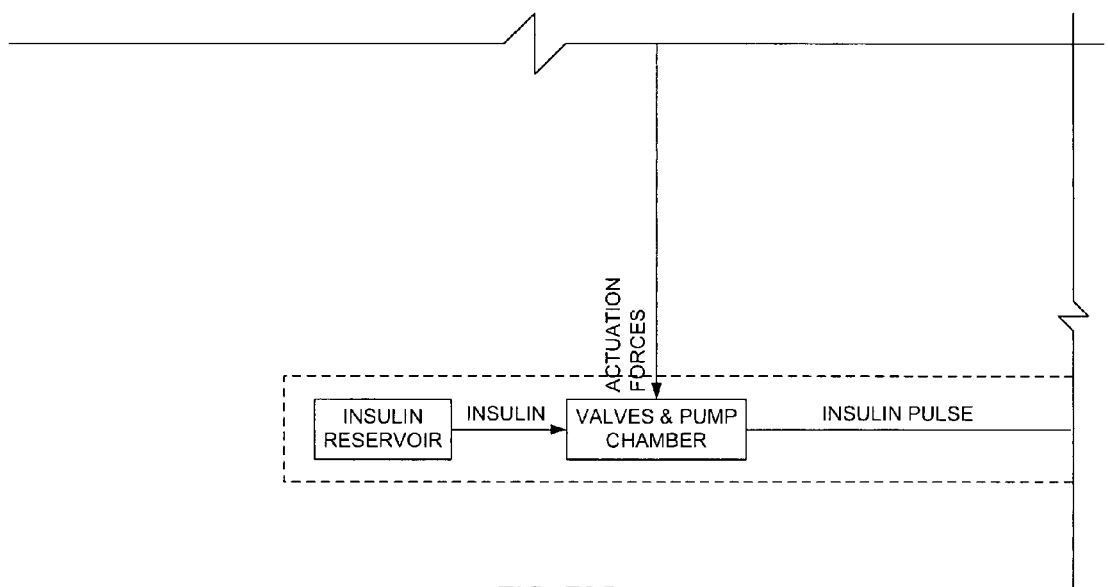
Figure 70D:
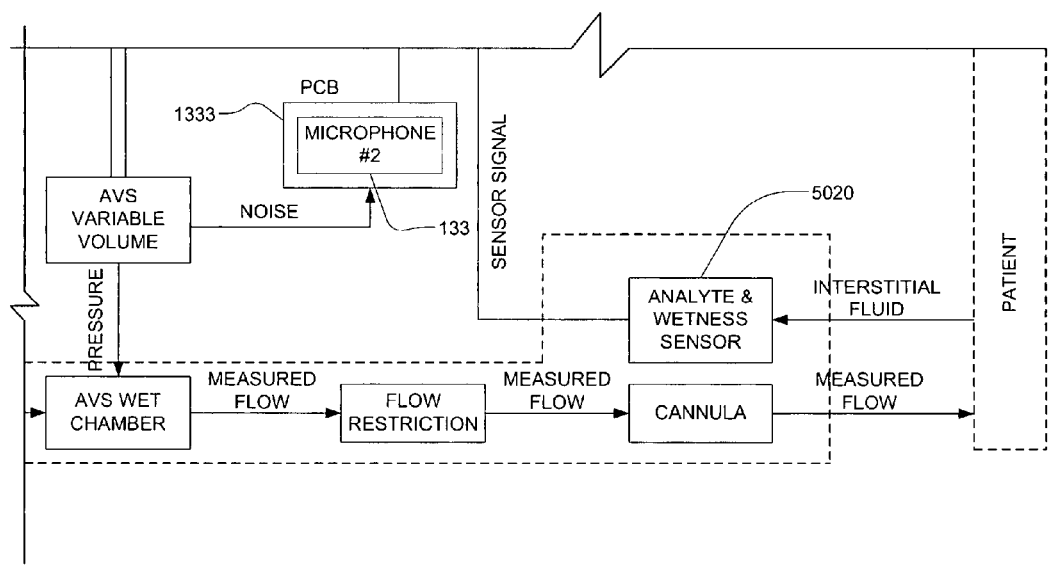

Referring now to FIGS. 70-70D, both the patch pump and portable pump embodiments as described additionally contain various components of the dispensing assembly (in applicable embodiments) and for embodiments including the AVS assembly, the various components thereof, including, at least one microphone, a temperature sensor, at least one speaker, a variable volume dispensing chamber, a variable volume chamber, a port and a reference chamber. In some embodiments, the device contains one or more of the following: a vibrator motor (and, in those embodiments, a motor driver), an antenna, a radio, a skin temperature sensor, a bolus button, and in some embodiments, one or more additional buttons. In some embodiments, the antenna is a quarter-wavelength trace antenna. In other embodiments the antenna may be a half-wavelength or quarter wavelength trace, dipole, monopole, or loop antenna. The radio, in some embodiments, is a 2.4 GHz radio, but in other embodiments, the radio is a 400 MHz radio. In still other embodiments, the radio can be any frequency radio. Thus, in some embodiments, the device includes a radio strong enough to communicate to a receiver within a few feet in distance from the device. In some embodiments, the device includes a second radio. In some embodiments, the second radio may be a specific long-range radio, for example, a 433 or 900 MHz radio or, in some embodiments, any frequency within the ISM band or other bands, Not shown in FIGS. 70-70D, the device, in some embodiments, contains a screen and/or a user interface.

The following description of these components and the various embodiments thereof are applicable to both device types, and further, to the various embodiments described with respect to each device type. Referring now to FIG. 67F, for illustration purposes only, both the cannula 5010 and the sensor 5020 have been inserted into the device 10. Also, referring to FIGS. 70-70D, the various components, some of which will not necessarily be included in all embodiments, are shown in a schematic representing the electrical connections of those components. FIGS. 70-70D therefore represent the various elements that could be included in the device. These can be mixed and matched depending on size requirements, power restrictions, usage and preferences, as well as other variables. FIG. 70 shows the relation of FIGS. 70A-70D.

The device contains at least one microprocessor 271. This can be any speed microprocessor capable of processing, at a minimum, the various electrical connections necessary for the device to function. In some embodiments, the device contains more than one microprocessor, as seen in FIGS. 70A-70B, the device is shown having two microprocessors 271.

The microprocessor 271 (or in some embodiments, microprocessors) is connected to the main printed circuit board (hereinafter, the "PCB" refers to the term "printed circuit board") 13. A power source, which in some embodiments is a battery 15, is connected to the main PCB 13. In one embodiment, the battery 15 is a lithium polymer battery capable of being recharged. In other embodiments, the battery can be a replaceable battery or a rechargeable battery of any type.

In some embodiments, the device includes a radio 370 connected to the main PCB 13. The radio 370 communicates to a remote controller 3470 using the antenna 3580. The communication between the device 10 and the remote controller 3470 is therefore wireless.

In some embodiments, the device contains a vibration motor 3210. The vibration motor 3210 is connected to a motor driver 3211 on the main PCB 13 motor driver 3211.

Some embodiments include a bolus button 3213. The bolus button 3213 functions by a user applying force to a button form 3213, which can be made from rubber or any other suitable material. The force actuates the bolus button actuation, which is attached to a bolus button switch 3214 on the main PCB 13. The switch 3214 activates a single bolus which will indicate a particular pre-determined volume of fluid is to be delivered to the patient. After the user presses the bolus button 3213, in some embodiments, the device 10 will generate an alarm (e.g., activate the vibration motor 3210 and/or send a signal to the remote controller) to signal to the user that the button 3213 was pressed. The user will then need to confirm the bolus should be delivered, for example, by depressing the button 3213. In still other embodiments, the remote controller 3470 queries the user to confirm the bolus should be delivered.

A similar query/response sequence may be used in various embodiments to test and report on patient responsiveness. For example, the device may be configured to test patient responsiveness by generating an alarm (e.g., an audible and/or tactile alarm) and awaiting a response from the patient (e.g., actuation of the button 3213). Such a test may be performed at various times (e.g., every five minutes) or upon detection of a condition such as an abnormal analyte level monitored via an analyte sensor or an abnormal body temperature monitored via a temperature sensor. If the patient does not provide an appropriate response within a predetermined amount of time, the reusable portion may send an alarm to a remote controller or caretaker. Such testing and reporting might be particularly valuable for patients who could become unconscious or incapacitated, either from a device malfunction or otherwise.

The NITINOL circuit (referring to the shape memory actuator, which in some embodiments, is a NITINOL strand) 278 on the main PCB 13 provides electrical current to the NITINOL connectors. As shown in FIG. 67F and FIG. 70A, the device can include two NITINOL connectors 278 (and two NITINOL strands). However, as described above, in some embodiments, the device includes one NITINOL connector (and one NITINOL strand).

In some embodiments, the device includes a temperature sensor 3216 shown on FIG. 70B The temperature sensor 3216 is located on the underside of the base Y and senses the temperature of the patient's skin. The skin temperature sensor 3216 is connected to a signal conditioner, represented by 3217. As shown in FIG. 70B, the signal conditioning 3217 is represented as one block, however the device includes multiple signal conditioners, as needed, each filtering different the signals. Following, the AVS temperature sensor 132, AVS microphones 133, and analyte sensor 5020 are all connected to a signal conditioner, represented in one block as 3217.

The AVS speaker 134 is connected to the speaker drive 135 on the main PCB 13. The AVS speaker 134, in one embodiment, is a hearing aid speaker. However, in other embodiments, the speaker 134 (a speaker containing a voice coil, a magnet with an electromagnetic coil) is a piezo speaker (shown in FIG. 50, representing one embodiment of the device).

Referring still to FIGS. 70-70D, in some embodiments, the antenna 3580 has a dedicated PCB 3581, which is then connected to the main PCB 13. Also, in some embodiments, the AVS microphones 133 each have a dedicated PCB 1332, 1333, connected to the main PCB 13. The various PCBs may be connected to the main PCB 13 using conventional methods, for example, flexible circuits or wires.

Referring to FIG. 67F, the device 10 is shown as an exemplary embodiment for description purposes. However, the layout of the various parts can vary and many of the embodiments are shown below. However, additional alternate embodiments are not shown but can be determined based on size, power and use.

In accordance with an alternate embodiment, the disposable portion 2610 may include the reservoir 20 and optionally, a battery. The reservoir 20 may be integral to the disposable portion or otherwise coupled to the disposable portion. The battery may be the primary or sole power source for the device or may be a backup power source, and may be used to provide electrical power to electronics on the reusable portion and/or the disposable portion. Both the reservoir 20 and the battery will typically require regular replacement, so including both of these components in the disposable portion 2610 may provide to the user the increased convenience of simultaneous replacement. Additionally, by replacing the battery every time the reservoir is changed, the user may be less likely to allow the battery to run down.

The disposable portion 2610 could additionally or alternatively include a processor that may be used, for example, to continue certain device operations in the event of a failure (e.g., a failure of a main controller in the reusable portion), to generate an alarm in the event of a failure, or to provide status information to the reusable portion. With regard to status information, the processor could keep track of the operation history and various characteristics of the disposable and hold status information for access by the user, the fluid delivery device 10, and/or the user interface 14 including during installation of the disposable portion 2610. For instance, the processor can store status related to shelf life, maximum exposure or operation temperature, manufacturer, safe dispensing limits for the therapeutic, etc. If any of these status indicators is determined by the device to be unacceptable, the device can refuse to power the pumping assembly and dispensing assembly and indicate to the user that the disposable is not usable. The processor may be powered by a battery in the reusable portion or the disposable portion.

More generally, the device may be configured to obtain status information from any of the disposables (including, for example, the disposable portion 2610 and any disposable component used therewith, such as the fluid reservoir, battery, or sharps cartridge or individual sharps component), for example, from a processor disposed in disposable portion, via bar code reader, or via RFID technology. If the device detects a problem with the disposables (e.g., invalid model number for use with the reusable portion or an expiration date of the fluid has passed), then the device may take remedial action, such as, for example, preventing or terminating operation of the device and generating an appropriate alarm.

Additional components may be included in some embodiments. For example, redundant failure detection and announcement mechanisms can be employed. The device may employ an audible alarm. The loudspeaker 1202 of the sensor 550 may be used for the audible alarm or an additional speaker may be included loudspeaker and used for the audible alarm. The device vibrating mechanism 3210 can also be used as an alarm. If a system failure is detected that requires immediate attention, both alarms can be activated. Additionally, a secondary battery or supercapacitor may be employed as a backup to the primary battery. If either battery fails, the controller can activate one or more alarms so that at least one announcement of battery failure occurs.

The alarms can also be used to indicate to a user that the device is working properly. For example, a user might program the device for a bolus delivery over a certain period of time. The user may desire to know that the programmed delivery is occurring properly. The processor can use the vibrating motor or an audio sound to indicate successful programmed delivery. Thus, some mechanisms can be employed in some embodiments of the device to provide feedback, whether positive or negative, to the patient or user.

A microphone may also be used to detect any abnormal vibration or lack of normal vibrations and trigger an alarm condition. In various embodiments, a microphone of the acoustic volume sensing system may be used to perform such monitoring, or a separate microphone may be included for such monitoring. Periodic checks can also be performed to determine that the device is operating by checking for expected pump vibrations with the microphone. If improper vibrations are detected, or if proper vibrations are not detected by the microphone, an alarm can be activated.

Figure 71:
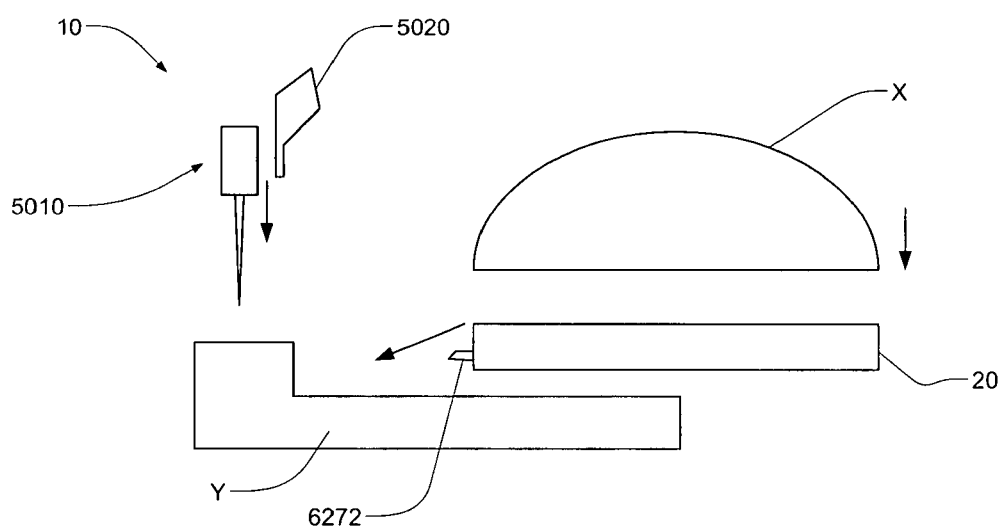
FIG. 71 schematically shows components which may be assembled to create a fluid delivery device in accordance with an embodiment of the device.

Referring now to FIG. 71, various components of a device 10 are shown schematically. In one embodiment of the device 10, a top X portion mates with a base portion Y and a reservoir 20 is sandwiched between the top X and base Y. The force of the sandwiching allows the reservoir septum 6272 to mate with the base portion Y. In some embodiments, both an infusion device 5010 and an analyte sensor 5020 are inserted through the base Y and into a patient (not shown).

In many embodiments, the base Y and the reservoir 20 are disposable portions and the top X is a non-disposable portion. Both the infusion device 5010 and the analyte sensor are also disposable.

Figure 72:
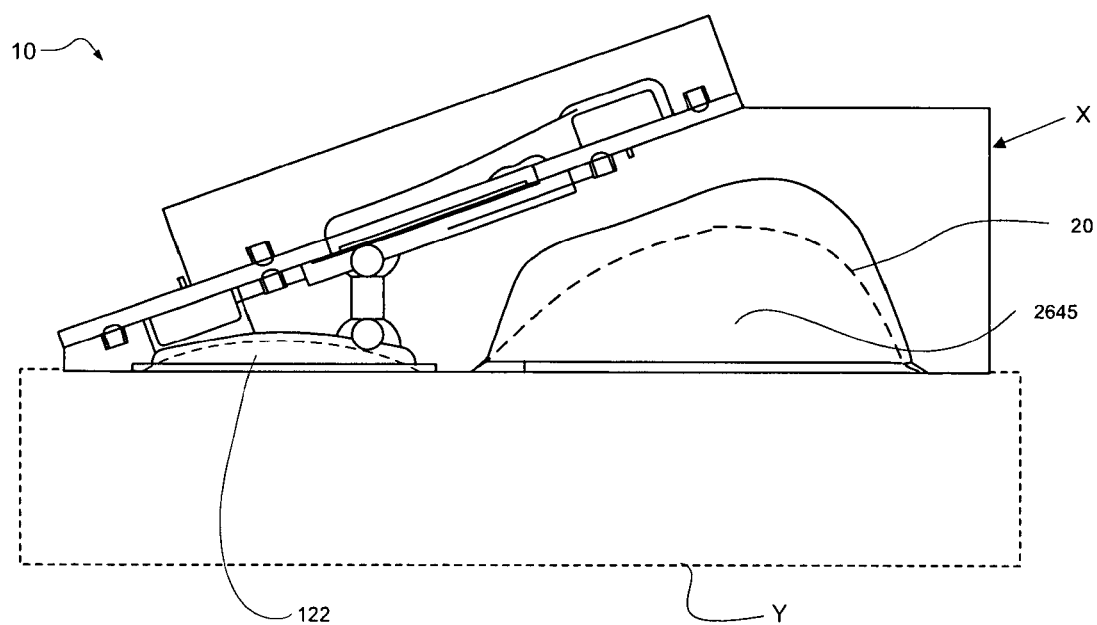
FIG. 72 shows a side view of a fluid-delivery device with an acoustic volume-measurement component.

As previously discussed, the patch pump device may be entirely or partially disposable. FIG. 72 shows an embodiment of a fluid delivery device 10 having disposable and non-disposable portions. In this embodiment, the disposable portion Y contains components that come into direct contact with the fluid, including the collapsible reservoir 20, pumping assembly (not shown), the variable volume dispensing chamber 122 (part of the dispensing assembly 120, located on the top X) and the flow restrictor (not shown), as well as one way valves (not shown) and a fluid path (not shown) connecting the reservoir to the pumping mechanism to the variable volume dispensing chamber 122. Additionally, the disposable portion Y includes a reservoir cavity 2645

Figure 73:
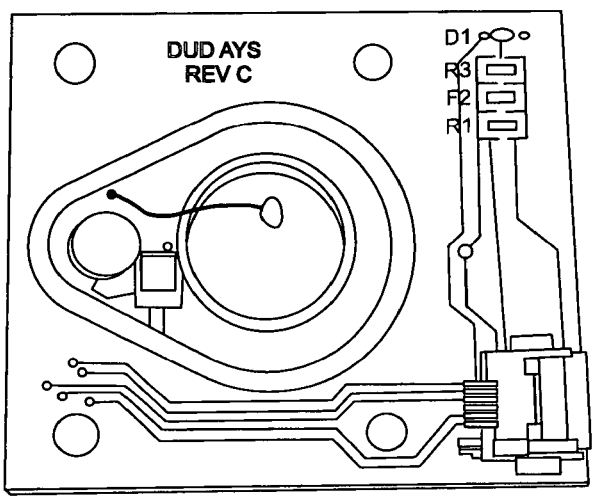
FIG. 73 shows a printed circuit board for acoustic volume measurement.

The reusable portion X includes elements of the dispensing assembly 120 except the variable volume dispensing chamber 122, which is located on the disposable portion Y. In some embodiments, the dispensing assembly 120 is an AVS assembly. The AVS assembly is described in detail above. Referring now to FIG. 73, an integrated acoustic volume measurement sensor is shown on a PCB.

Figure 74:
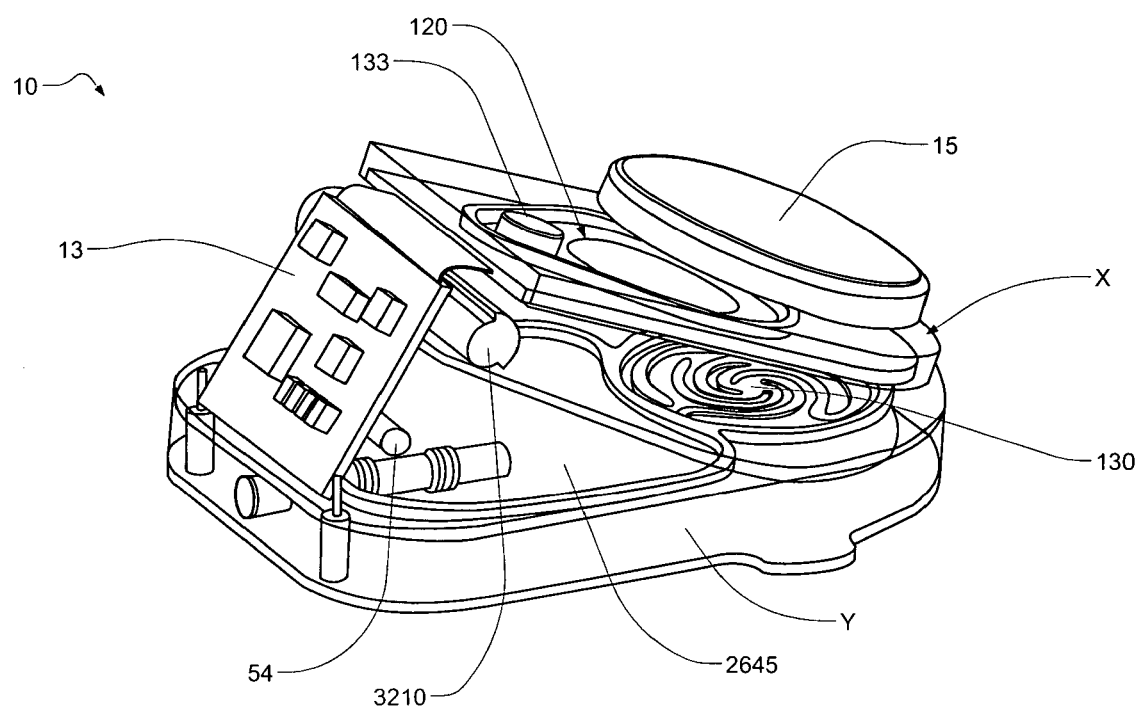
FIG. 74 shows a pictorial view of an embodiment of a device.

Referring now to FIG. 74, the device 10 shown in FIG. 49 is shown. The base disposable portion Y includes a reservoir cavity 2645. The top non-disposable portion X includes battery 15 and a dispensing assembly 120. A microphone 133 is shown as well as a diaphragm spring 130. In some embodiments, the dispensing assembly 120 includes more than one microphone. Although throughout this description, each microphone is referred to as 133, this does not infer that the microphones are always identical. In some embodiments, the microphones are the same, in other embodiments, the microphones are different.

In the FIG. 74, the top non-disposable portion X also includes main PCB 13, a vibration motor 3210 and a pumping actuation member 54. The top, non-disposable portion X includes the AVS assembly or dispensing assembly 120. In FIG. 74, a microphone 133 is shown. The top, non-disposable portion X also includes a battery 15, which may be used to provide electrical power to electronics on the non-disposable portion and/or the disposable portion. In some embodiments, this battery 15 is rechargeable. Recharging can be done by methods described below. The disposable portion Y includes the wetted components including a fluid line (not shown) and the pumping assembly. In FIG. 74, only the pumping plunger 54 can be seen. This embodiment of the device 10 can also include many of the elements described above, including, but not limited to, a fluid impedance, a flexible membrane, a cannula housing and a sensor housing. Any pumping mechanism can be used.

Figure 75:
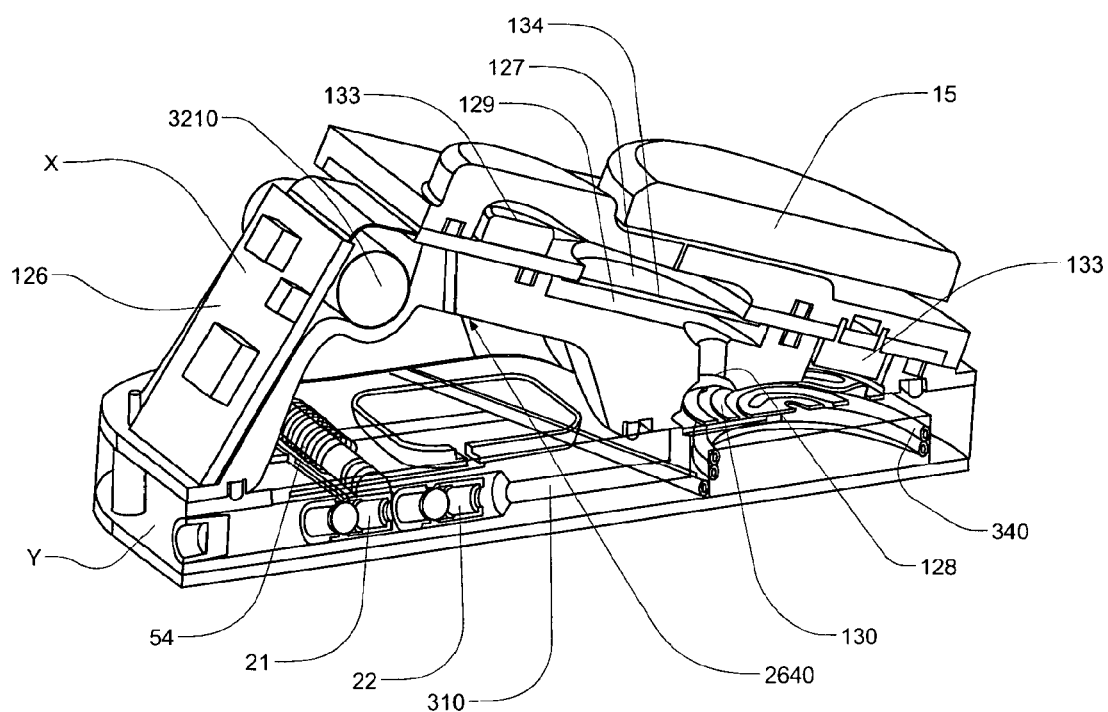
FIG. 75 shows a pictorial sectional view of an embodiment of fluid delivery device.

Referring now to FIG. 75, the device 10 is shown in another view where more elements are visible. In FIG. 75, the device 10 is shown with base disposable portion Y including a coiled microtubing flow restrictor 340 and a fluid line 310 connecting the inlet 21 and outlet 22 valves. The pumping actuation member 54 is also shown. The top X includes a main PCB 13, a vibration motor 3210, two microphones 133, a speaker 134, a reference chamber 127 and a fixed volume chamber 129. A battery 15 is also shown. Since choosing a very small diameter for the flow restrictor 340, may cause occlusion of the line 310 (for example, due to protein aggregates in a therapeutic fluid), it may be desirable to use a longer length of tubing with a larger diameter. However, in order to pack a longer length of tubing within a patch-sized housing, it may be necessary to bend the tubing in to form a tortuous path, e.g., a coiled or serpentine shape.

Figure 76:
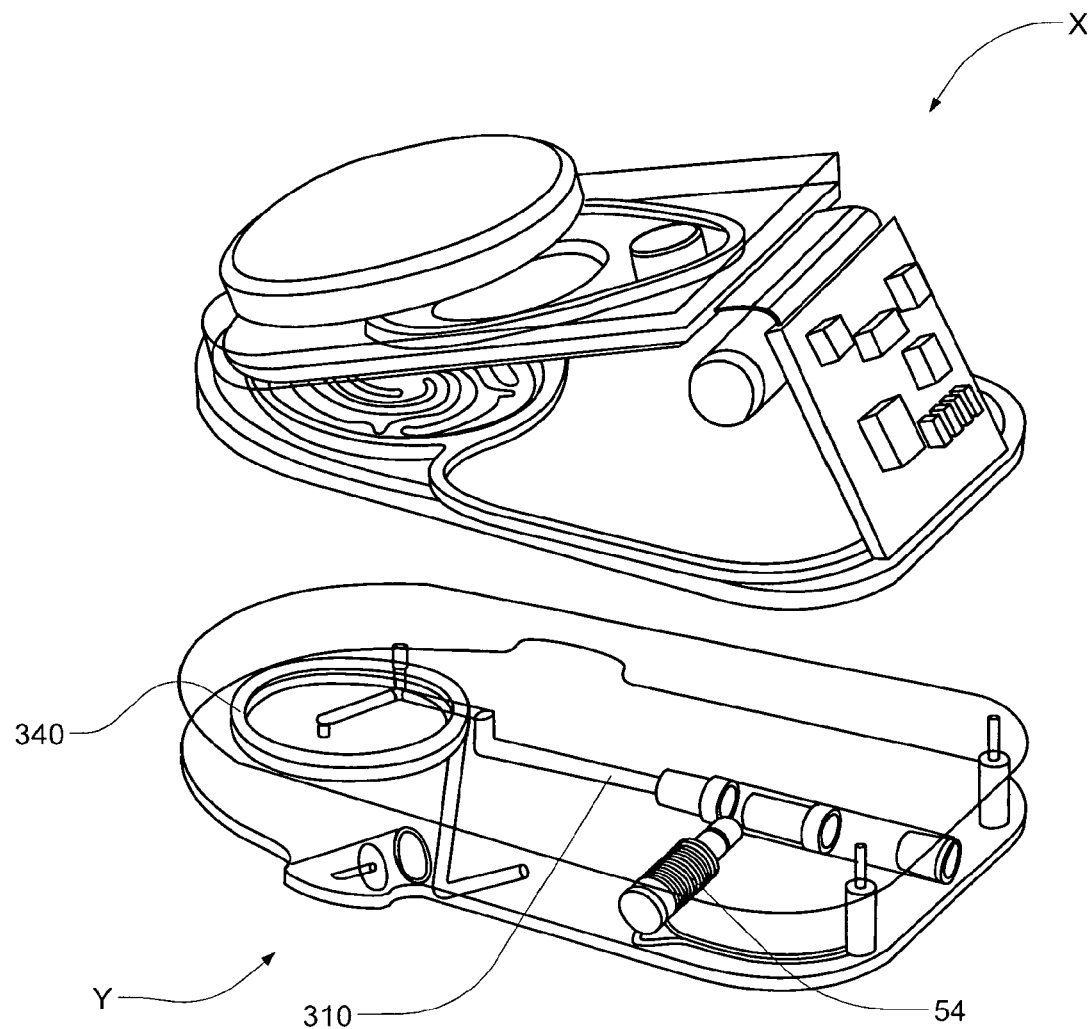
FIG. 76 shows an exploded pictorial view of an embodiment of a fluid delivery device.

Referring now to FIG. 76, an exploded view of the device 10 shown in FIGS. 72, 74 and 75 is shown. The top, non-disposable portion X is shown separated from the base disposable portion Y. In practice, a reservoir (not shown) would be placed in between the top X and base Y portions. Once the top X and base Y are assembled to form a device 10, the reservoir will become connected to the fluid line 310.

Figure 77:
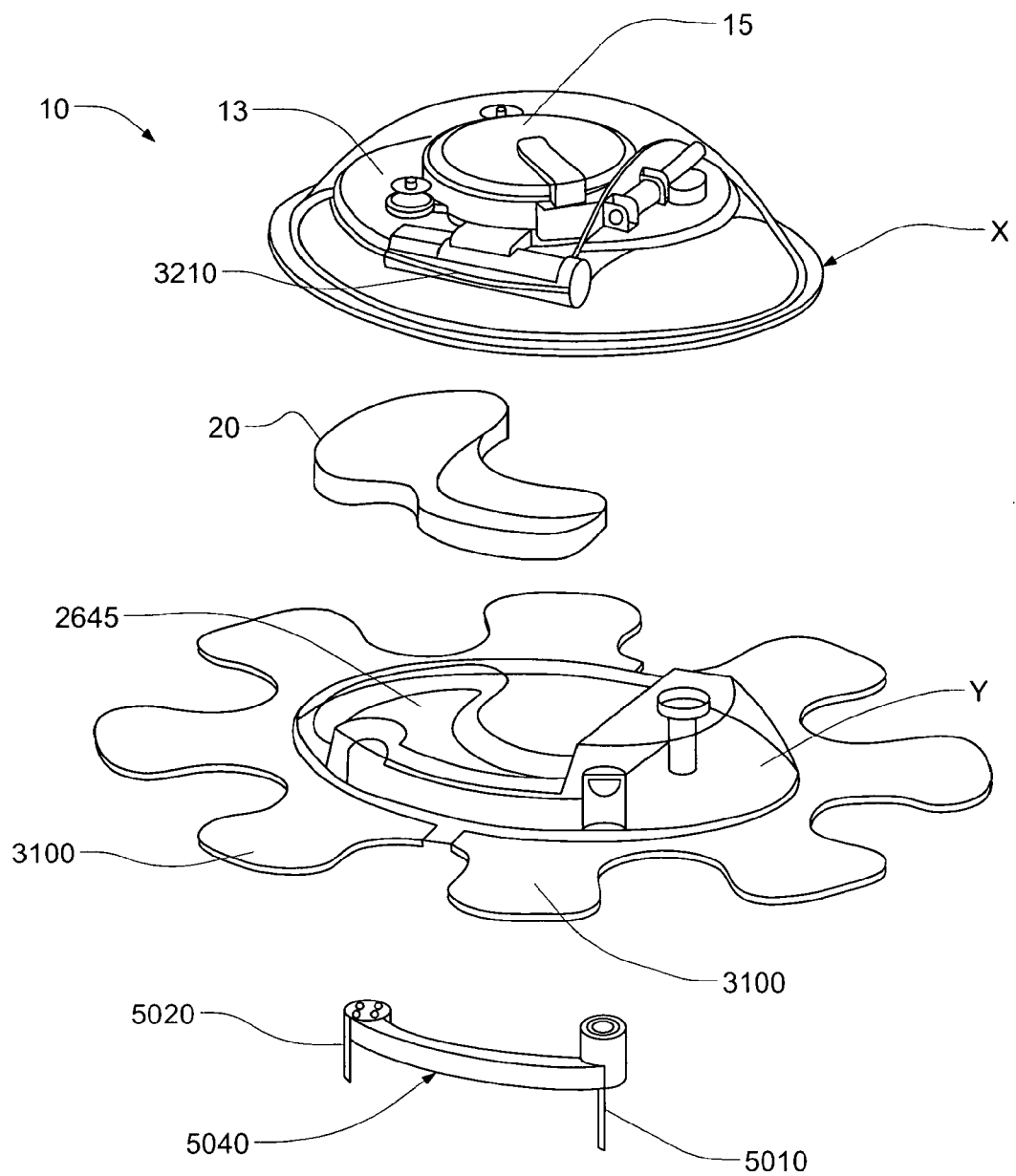
FIG. 77 shows an exploded view of components which may be assembled to create one embodiment of a fluid delivery device.

Referring now to FIG. 77, an exploded view of another embodiment of a device 10 including a disposable base Y and non-disposable top X part is shown. Also included is a reservoir 20, an adhesive 3100 and a bridge 5040 apparatus holding an infusion device 5010 and a sensor 5020. This device 10 includes a more rounded footprint and a dome shape. A battery 15 and a main PCB 13 are shown located on the top X. The base Y includes a reservoir cavity 2645. An adhesive 3100 is shown in a two piece embodiment. The bridge 5040 is used to insert the infusion device 5010 and sensor 5020 through the base Y. The reservoir 20 is shown as having an irregular shape, however, in other embodiments, the reservoir 20 can have any shape and can vary in size according to the fluid capacity desired. In this embodiment of the device 10, the non wetted components are in the top non-disposable X and the wetted components are in the base disposable Y.

When assembled, the device 10 may be adhered together using a center region of the adhesive (not shown). Alternately, the device 10 may be locked together mechanically using any of many embodiments described herein for latching. Although some embodiments are described below herein, many others will be apparent and as the shape of the device varies, in many cases, the latch will also.

Figure 78:
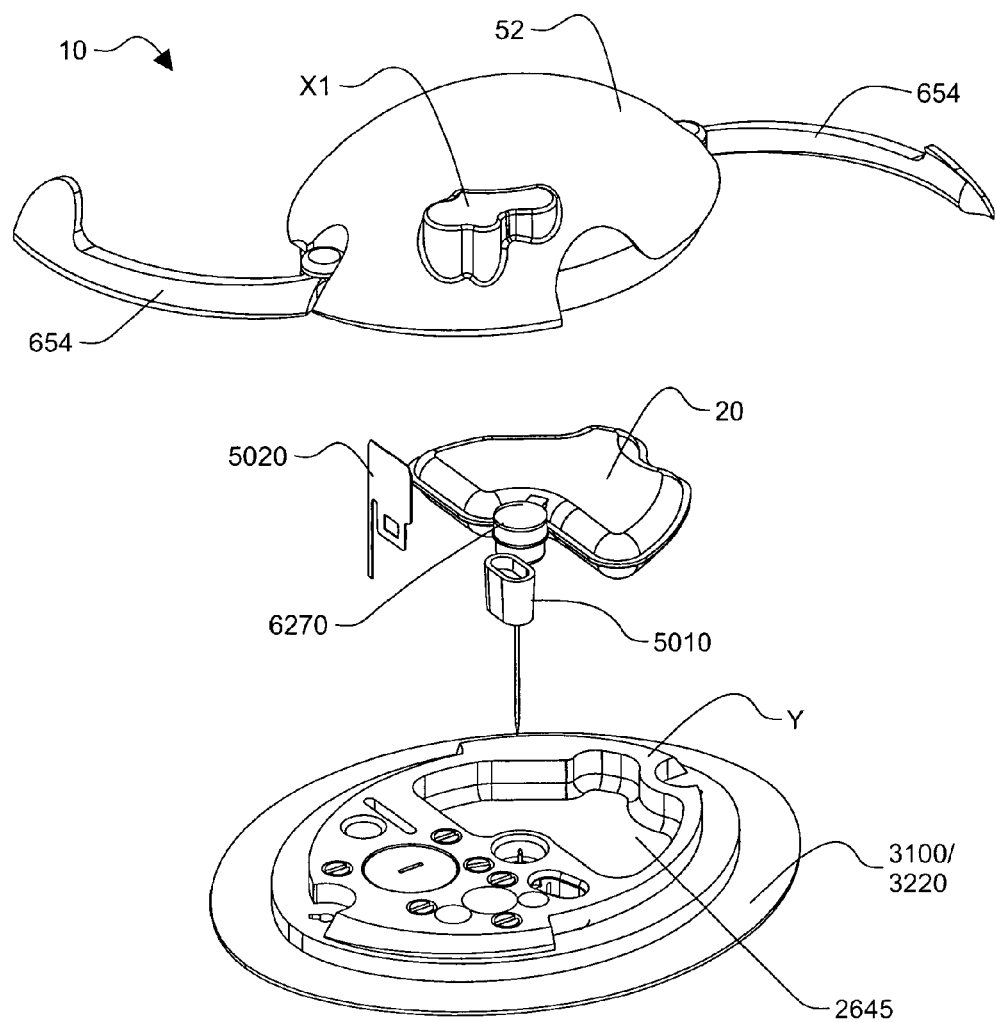
FIG. 78 shows an exploded view of an embodiment of the fluid delivery device.

Referring now to FIG. 78, an exploded view of another embodiment of the device 10 is shown. The top non-disposable portion X is mostly dome shaped, however, a protrusion X1 is shown to accommodate the mechanisms inside the top X. Thus, the shape of the device can vary and can include polyps and protrusions, dimples and other texture-like features to accommodate various designs of the device.

The reservoir 20, infusion device 5010 and sensor 5020 are shown. The infusion device 5010 and sensor 5020 can be inserted through the base Y and into a patient (not shown). The base Y is shown with an adhesive 3100 or pad 3220 underneath. In practice, the adhesive 3100 or pad 3220 can be first adhered to the skin and base Y. Next, the infusion device 5010 and sensor 5020 are inserted through the base Y into a patient (not shown, shown in FIGS. 79 as 5020 and 5010). The reservoir 20 is then placed into the reservoir cavity 2645 either by first placing the reservoir 20 into the top X then sandwiching the top X and the base Y, or, placing the reservoir 20 into the reservoir cavity 2645 and then sandwiching the top X and the base Y. Either way can be used. The final result is the reservoir 20 becomes connected to the fluid line (not shown) located in the base Y through a septum (shown upside down) on the reservoir 20 and a septum needle (not shown, see 6272). The top X is then fastened to the base X either through use of an adhesive, or in this embodiment, mechanically using a latch 654 to clamp the top X and base Y together.

Figure 79:
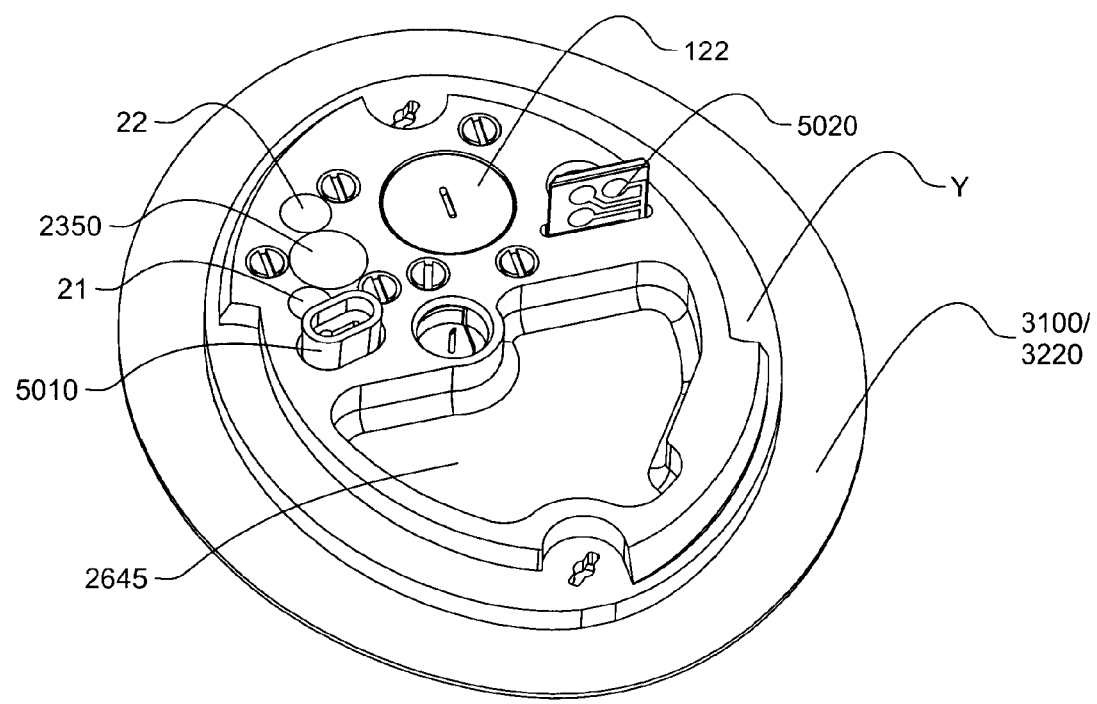
FIG. 79 shows a top view of a base of one embodiment of the fluid delivery device.

The base Y includes those components that are wetted. The base Y is disposable. The top X includes non wetted components. The top X is non-disposable. Referring now to FIG. 79, the base Y includes a variable volume dispensing chamber 122, an inlet valve 21, and exit valve 22 and a pumping chamber 2350. As shown in this figure, those elements are shown as the membrane covering the area that acts as either the chambers or the valves. Thus, the base Y includes the membrane that securely maintains the wetted areas, thus, maintaining the non wetted areas as such in the top (not shown). As shown in FIG. 79, the sensor 5020 and the infusion device 5010 have been inserted into their respective housings and through the base Y to the patient (not shown). The base Y is shown with the reservoir cavity 2645, but the reservoir (not shown) need to be connected so that the fluid lines from the reservoir to the chamber and to the infusion device are connected.

Figure 80:
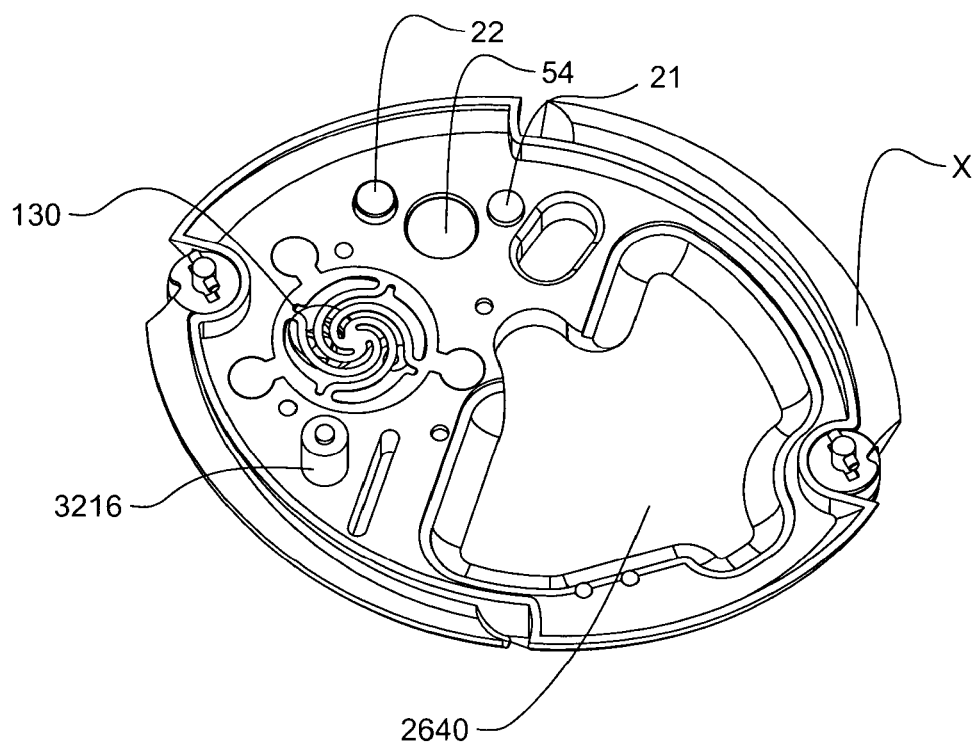
FIG. 80 shows the underside of the top of one embodiment of the fluid delivery device.

Referring now to FIG. 80, the top X of the device is shown. The top X includes those non wetted components including, as shown, a temperature sensor 3216, a diaphragm spring 130, an inlet valve poppet 21, and exit valve poppet 22 and a pumping actuation member 54. The top Y also includes a relief 2640 to accommodate the reservoir (not shown).

Figure 81A:
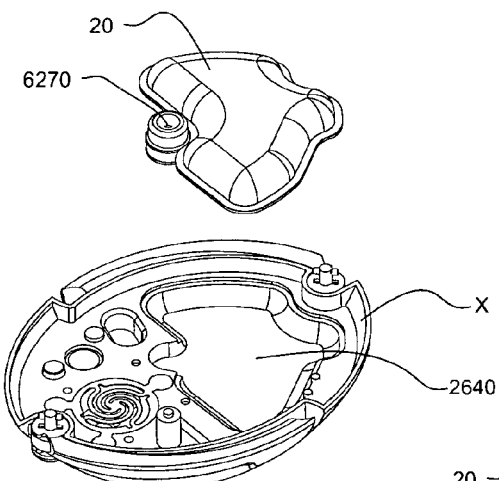
FIGS. 81A-81C show a sequence to illustrate the process of sandwiching the reservoir 20 between the top and base.
Figure 81B:
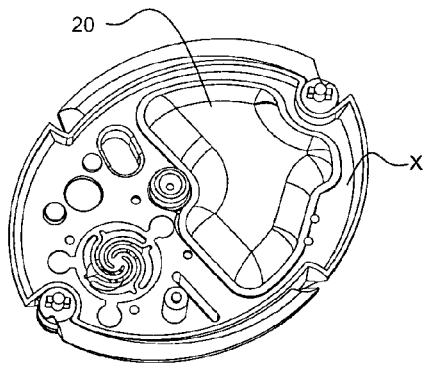
Figure 81C:
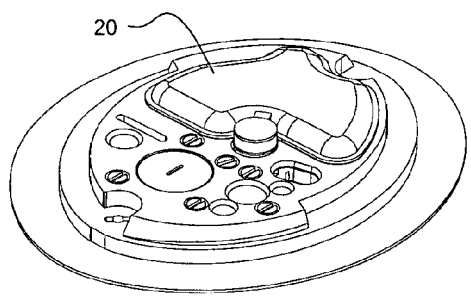

Referring now to FIGS. 81A-81C, a sequence is shown to illustrate the process of sandwiching the reservoir 20 between the top X and base Y. As seen in FIG. 81A, the top X as well as the reservoir 20 outside of the top X are shown. The reservoir includes a septum 6270. The top X includes a reservoir relief 2640. Next, as shown in FIG. 81B, the top is prepared to sandwich with the base Y. Referring now to FIG. 81C, the reservoir 20 is placed, septum side down, inside the base Y. The septum will connect with a cannulated septum needle (not shown) inside the base Y and connect the reservoir to the fluid line (not shown). In alternate embodiments, the reservoir may include a cannulated needle rather than a septum and the fluid path may include a reservoir interface with a septum rather than a cannulated needle.

Figure 82:
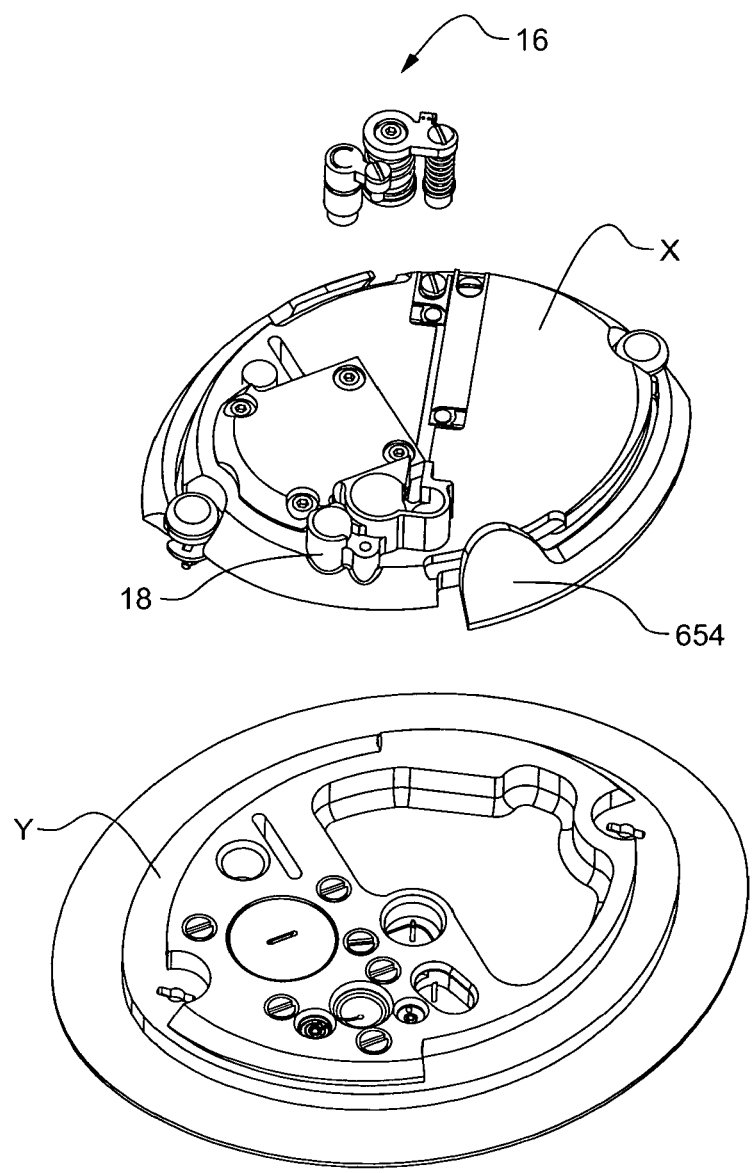
FIG. 82 shows an exploded top view of a device.

Referring next to FIG. 82, the top X is shown with one embodiment of the pumping mechanism 16 exploded. The pumping mechanism 16 fits into the pumping mechanism housing 18 in the top X. The base Y is also shown as well as one part of the latch 654 that will clamp the top X and base Y together.

Figure 83:
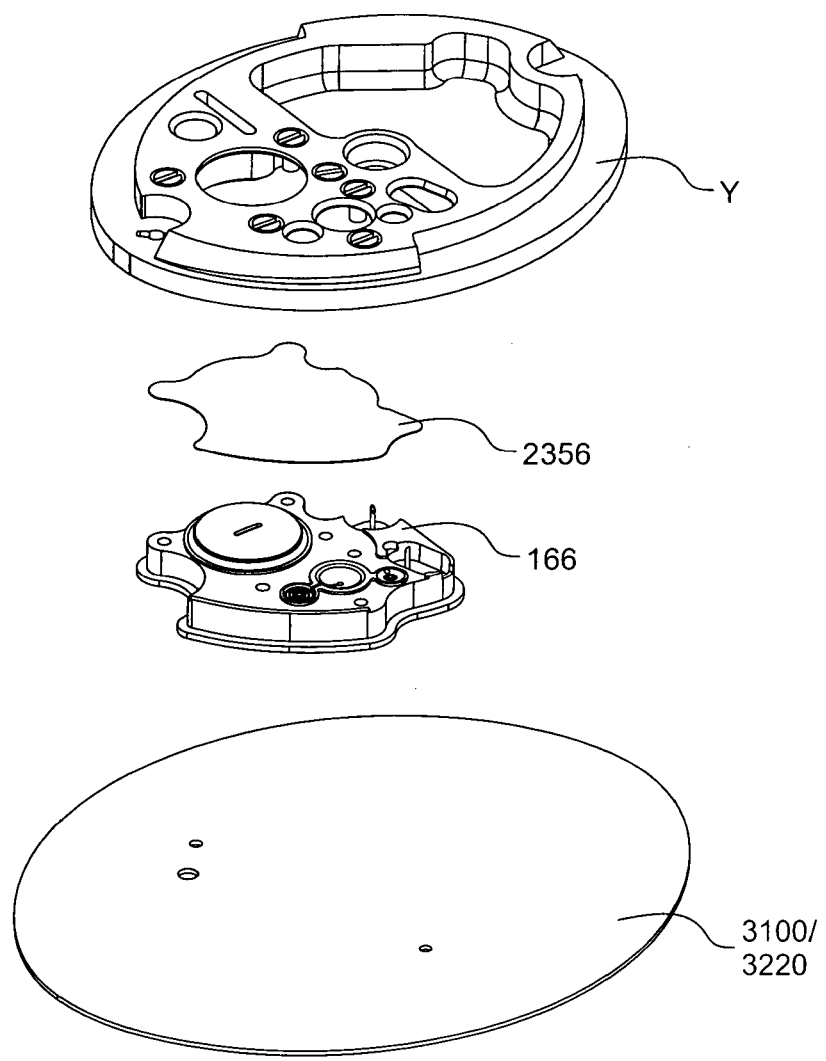
FIG. 83 shows an exploded view of the bottom of one embodiment of the device showing the fluid path assembly, the bottom housing and the membrane and adhesive.
Figure 84:
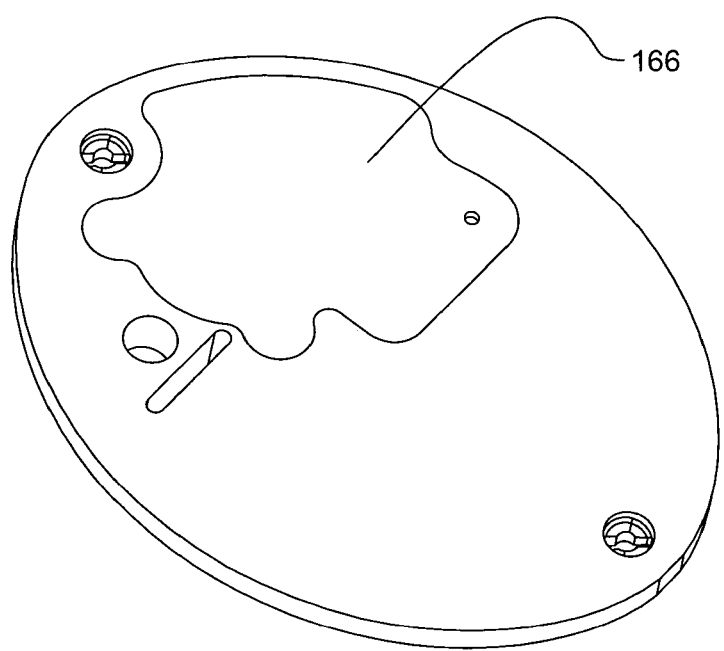
FIG. 84 shows a bottom view of the base showing a bottom view of a fluid path assembly.

Referring now to FIG. 83, the base Y is shown with the fluid path assembly 166 as the membrane 2356 exploded from the base Y. This illustrates that in some embodiments of the device, the fluid path assembly 166 is a separate part that is inserted into the base Y and sandwiched with the membrane 2356. Also shown in this figure, the adhesive or pad 3100/3220 in some embodiments, includes apertures for the infusion device and sensor (not shown). Referring now to FIG. 84, a bottom view of the base Y is shown. The bottom of the fluid path assembly 166.

Figures 85A, 85B:
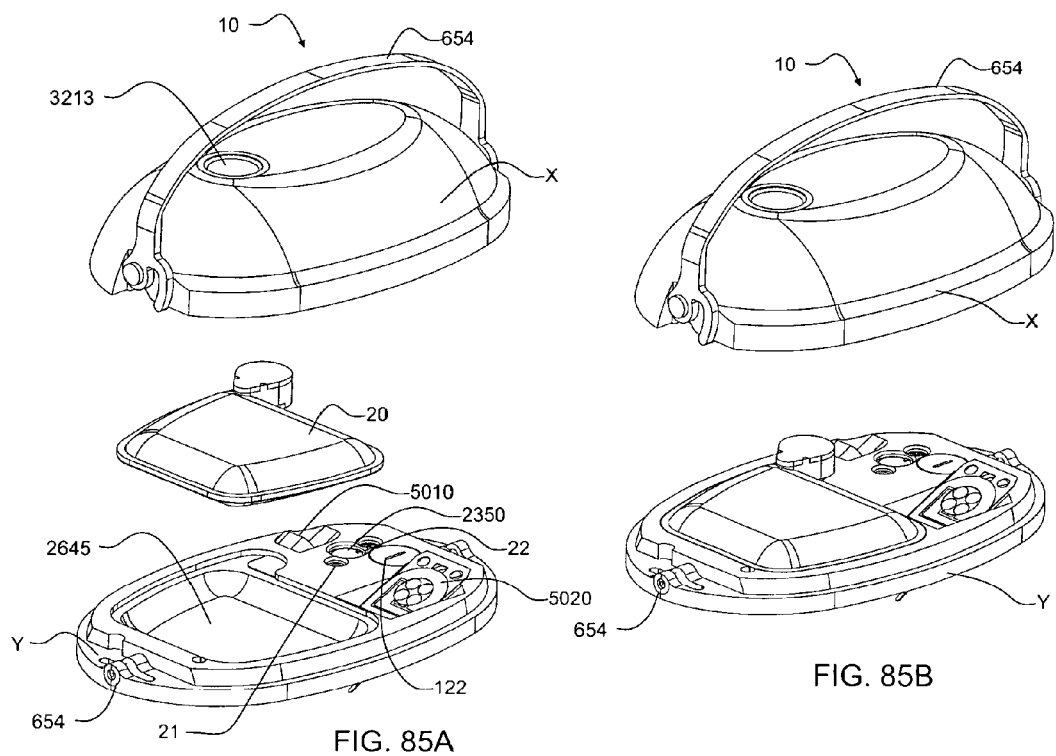
FIGS. 85A-85D show exploded, partially exploded and non-exploded views of an embodiment of a device.

Referring now to FIGS. 85A and 85B, another embodiment of the device is shown. In this embodiment, the top X, also non-disposable, includes a bolus button 654. The reservoir 20 is shown in an exploded view, however, in one embodiment, the reservoir 20 is built into the base Y. In another embodiment, the reservoir 20 is removable and placed into the reservoir cavity 2645 using a process similar to that described above with respect to another embodiment of the device.

The base Y is disposable and includes the wetted parts of the device 10. The sensor 5020, the cannula 5010, the variable volume dispensing chamber 122, the inlet valve area 21, the exit valve area 22 and the pumping chamber 2350. The volume dispensing chamber, the inlet valve area 21, the exit valve area 22 and the pumping chamber 2354 are all covered by membrane material, which may be in the form of a single membrane or distinct membranes.

Figure 85C:
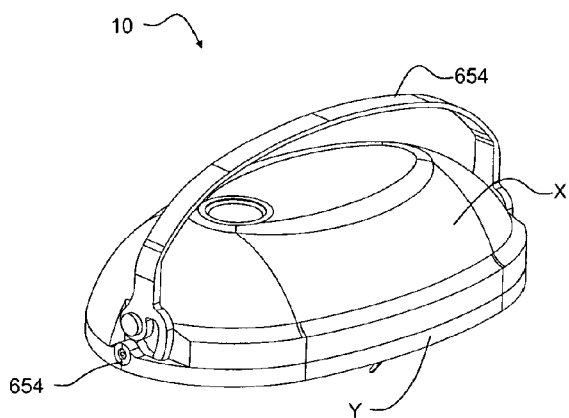
Figure 85D:
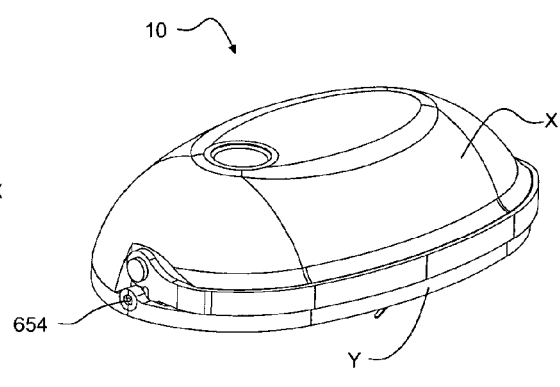

The device 10 is clamped together by a latch mechanism 654 on the top X and the base Y. Referring now to FIGS. 85C-85D, the device 10 is the latching mechanism 654 is shown in an open position (FIG. 85C) and a clamped or closed position (FIG. 85D). The bolus button 3213, as described in further detail above, can also be seen.

A cover (not shown) may be provided for use in any of the embodiments of the device, to replace the reservoir and top portion when the reservoir is removed while the base is connected to the patient. The cover would not contain electrical components, thus, could be used in wet conditions. However, in some instances, the reservoir can be removed without the use of any cover.

Cannula and Inserter

Figure 86A:
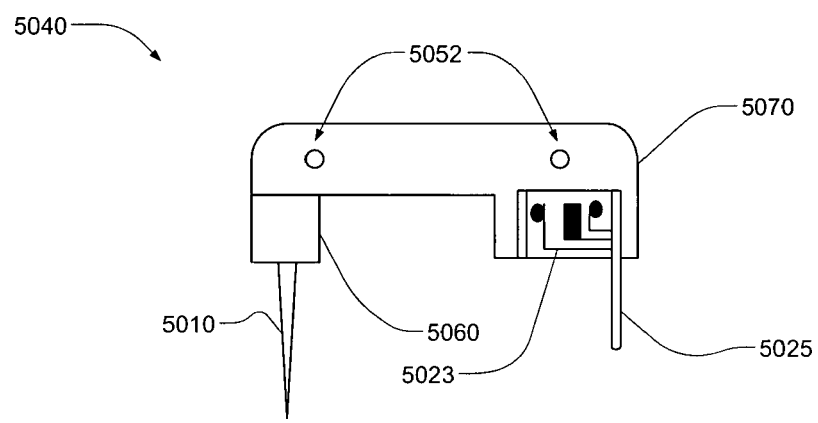
FIG. 86A shows a schematic of an infusion and sensor assembly having an infusion device and analyte sensor connected.

FIG. 86A schematically shows a representative embodiment of the infusion and sensor assembly 5040 including both an infusion device, which can be a cannula or a needle 5010 and an analyte sensor, which includes a sensor probe 5025 and a sensor base 5023. A bridge 5070 rigidly joins an infusion cannula 5010 and the analyte sensor base 5023. The infusion device 5010 is bounded on an upper side by a septum 5060 which allows for fluid to flow from a source and be administered through an infusion device 5010 to a patient. The sensor base 5023 is the section of the analyte sensor that is not inserted into the patient. In one embodiment, the base 5023 contains electronic contacts for the electrochemical analysis of blood glucose. A probe 5025 protrudes from the base 5023 of the analyte sensor 5020.

Figure 86B:
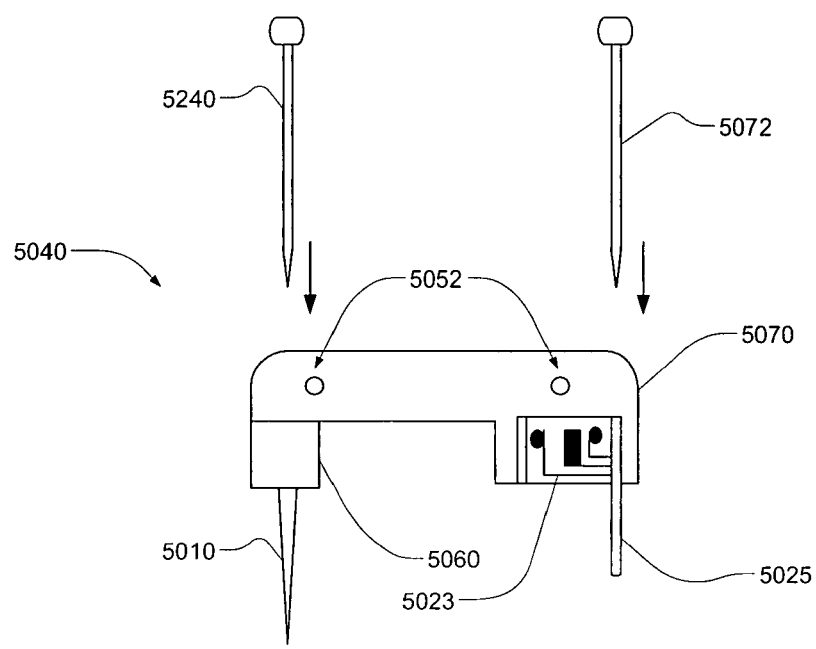
FIG. 86B shows an exploded view of an infusion and sensor assembly as shown in FIG. 86A with introduction needles.

Referring now to FIG. 86B, in this embodiment, the infusion device 5010 is a cannula that is introduced into the patient using an introducing needle 5240. The introduction needle 5240 is inside the cannula 5010 when being inserted into a patient. After insertion of the cannula 5010 into the patient, the introduction needle 5240 is removed and the septum 5060 is sealed to a fluid source, which, in some embodiments of the device described herein, is the fluid line. In some embodiments, the sensor probe 5025 is associated with an introduction needle 5072 which aids in skin puncture for insertion of the sensor probe 5025. The sensor introduction needle 5072, in some embodiments, at least partially surrounds the sensor probe 5025 while the sensor probe 5025 is being inserted into a patient.

In other embodiments, the infusion device 5010 is a needle and does not require an introduction needle 5240. In these embodiments, the infusion device 5010 is inserted into the patient and the septum 5060 seals with a fluid source.

In both FIGS. 86A and 86B, upon both the infusion device 5010 and sensor probe 5025 being lined up appropriately, force is applied to the bridge 5070. This forces both the infusion device 5010 and sensor probe 5025 into the patient. Once in the patient, releases 5052 are actuated through holes, separating the infusion device 5010 and septum 5060, as well as the sensor base 5023, from the bridge 5070. Referring to FIG. 86B, where introduction needles 5240 and 5072 are used, they will typically remain attached to the bridge 5070 following insertion.

The bridge can be made from any material desired, including plastic. The cannula can be any cannula in the art. The septum 5060 can be made from rubber or plastic and have any design capable of imparting the functions desired. In the embodiments where the infusion device is a needle, any needle may be used. In embodiments where introduction needles are used, any needle, needle device or introduction device can be used.

The infusion and sensor assembly requires force be applied in order to be inserted into a patient. As well, the infusion and sensor assembly requires that the infusion device and sensor are released from the infusion and sensor assembly. Thus, both the force and the release can be actuated manually, i.e., a person performs these functions, or an insertion device may be used to actuate the assembly properly. Referring now to FIGS. 87A-87E, an example of an inserter 5011 that can be manually operated is shown. The infusion device 5010 and sensor 5023 are held by the bridge 5070. The inserter 5011 includes covers 5012 for both the infusion device 5010 and the sensor 5023. As shown in FIGS. 87B-87E, using the inserter 5011, both the infusion device 5010 and the sensor 5023 are inserted through a device 10. Although FIG. 87A shows the sharps exposed, in some embodiments, the covers 5012 completely encase the sharps prior to the insertion process.

Figure 88A:
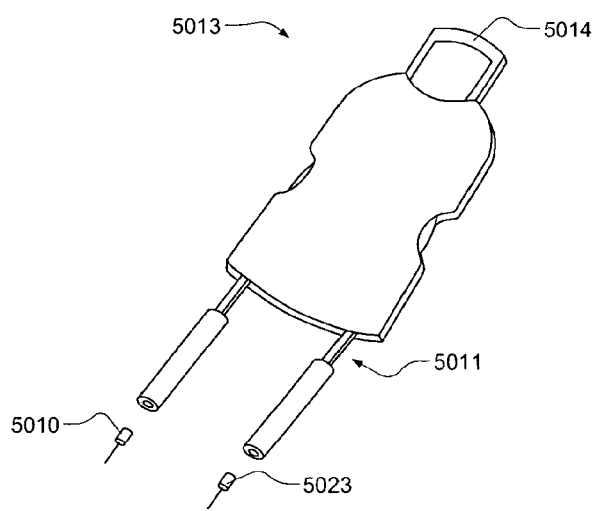
FIGS. 88A-88B show one embodiment of an inserter device in a sequence with an infusion and sensor assembly.
Figure 88B:
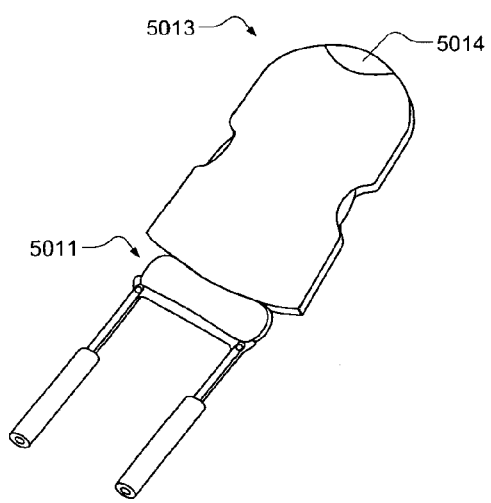
Figure 88C:
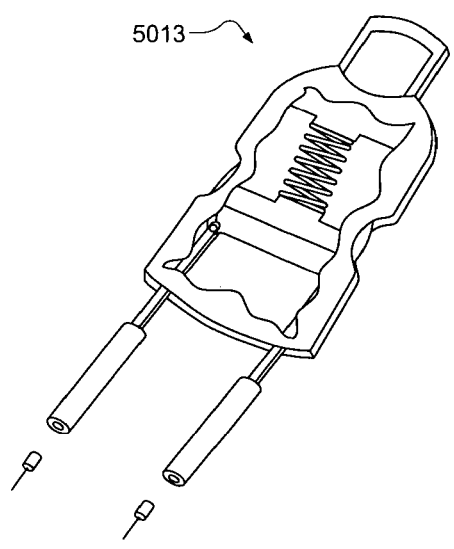
FIGS. 88C-88D show a partial cut away view of the inserter in FIG. 88A-88B.
Figure 88D:
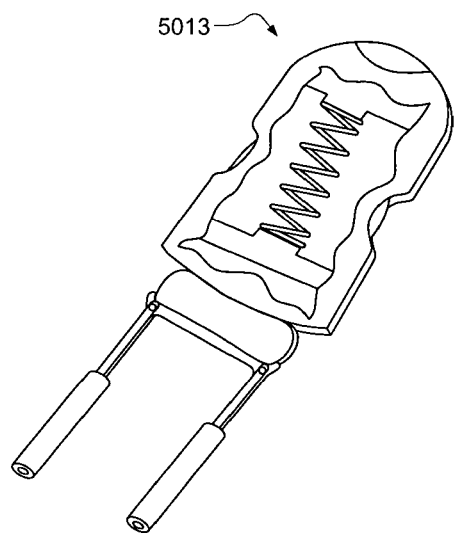

The inserter 5011 could be operated manually, but could also be incorporated into another inserter device such that a mechanical advantage can be applied. Referring now to FIGS. 88A-88B, one embodiment of an inserter device 5013 is used with an apparatus similar to the inserter 5012 shown in FIGS. 87A-87E. The mechanism of the inserter device 5013 is shown in FIGS. 88C-88D. An actuation lever 5014 either releases a spring (as shown in FIGS. 88C-88D) or provides another mechanical advantage that allows for the inserter 5012 to be inserted through a device (not shown). The inserter 5012 will thus release the infusion device 5010 and sensor 5023 and then, the inserter 5012 can either be removed from the inserter device 5013 and the inserter device 5013 refilled, or, the inserter device 5013 and inserter 5012 can be discarded.

Various insertion devices are described herein. However, in other embodiments, different insertion devices are used or the infusion device and sensor are introduced manually.

Features may be included for securing the infusion and sensor assembly 5040 to an automatic inserter. For example, the releases shown in FIGS. 86A-86B as 5052 may receive pins of an automatic insertion device. Referring to both FIGS. 89A and 89B a representative embodiment of an automatic inserter 5100 is shown. As shown in the front view of FIG. 89A, the inserter 5100 includes pins 5130 which travel in pin slots 5140 within an inserting cartridge recess 5120. In practice, the infusion and sensor assembly (not shown, shown in FIGS. 86A and 86B as 5040) is pressed into the cartridge recess 5120, causing pins 5130 to be inserted into the holes in the infusion and sensor assembly (shown as 5052 in FIGS. 86A and 86B). As shown in the rear view of FIG. 89B, a cocking lever 5145 is used to ready the inserter 5100 for firing. The inserter 5100 is then either held against the skin or aligned with a cannula housing and sensor housing on a base (not shown) and fired by pressing a trigger 5110. Upon firing, the pins 5130 travel in their slots 5140, thereby forcing the infusion device and sensor (both not shown) into a patient. Inserter foot 5160 limits the downward travel of the infusion and sensor assembly. The inserter may also automatically withdraw the introduction needles (not shown, see FIGS. 86B) from the infusion and sensor assembly.

The infusion and sensor assembly may be preloaded in the inserter 5100 prior to distribution to an end user. As shown in FIG. 90, in other embodiments, a cartridge 5080 may be used to protect a user and to protect the sharps held in the assembly shown as 5040 in FIGS. 56A and 56B. Referring to both FIG. 90 and FIGS. 86A-86B and FIG. 89A, in the cartridge embodiment 5080, the infusion and sensor assembly 5040 is embedded in the cartridge 5080. The cartridge 5080 is mounted in the cartridge recess 5120. The pins 5130 may project through the holes 5052 and into grooves 5090 in the cartridge 5080. Upon actuation of the inserter 5100, the pins travel within the grooves 5090 as the 5080 travels toward the patient to insert the sharps. The cartridge 5080 may be constructed of a rigid material.

Figure 89A:
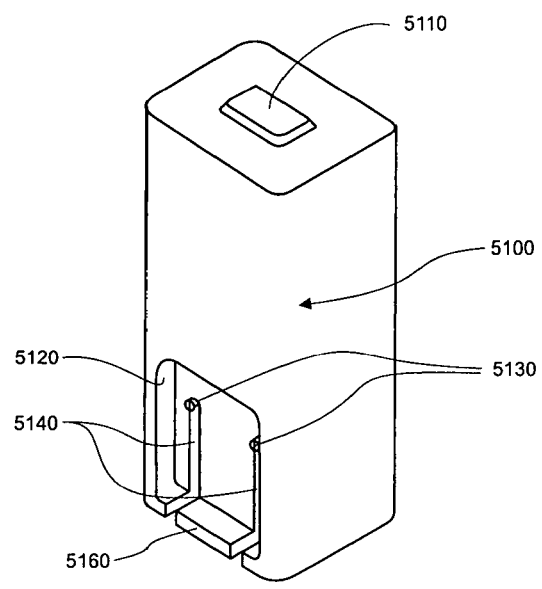
FIG. 89A shows a front view of one embodiment of an inserter device for the insertion of an infusion and sensor assembly.
Figure 89B:
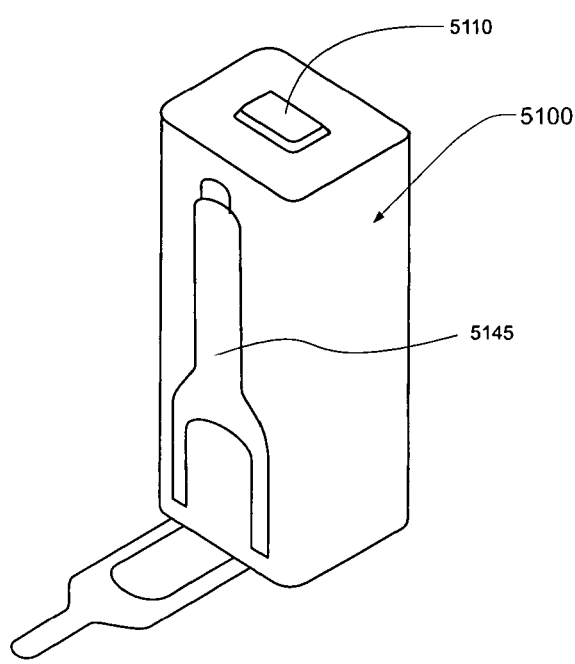
FIG. 89B shows a rear view of insertion device of FIG. 89A.
Figure 90:
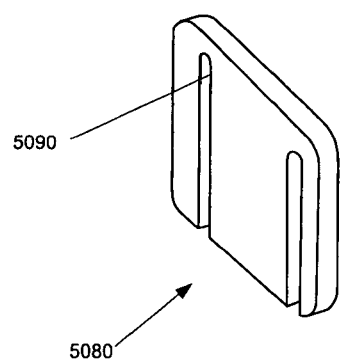
FIG. 90 shows a perspective view of one embodiment of a cartridge for an infusion and sensor assembly.
Figure 91A:
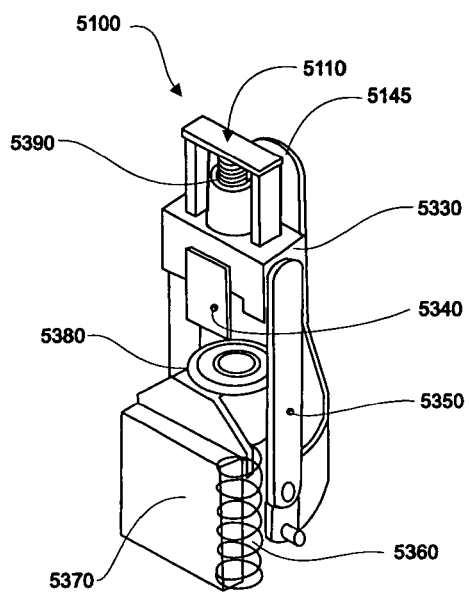
FIGS. 91A-91C show perspective front and side views of an inserter device for insertion of infusion and sensor assembly.
Figure 91B:
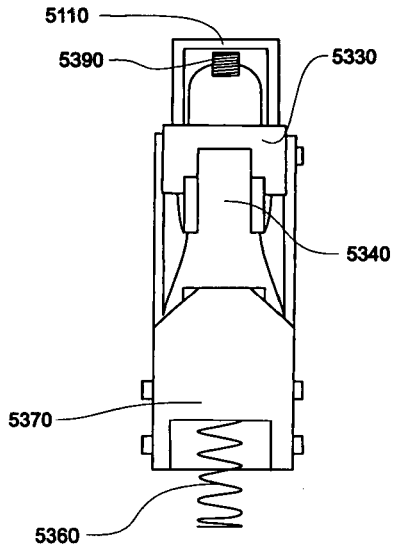
Figure 91C:
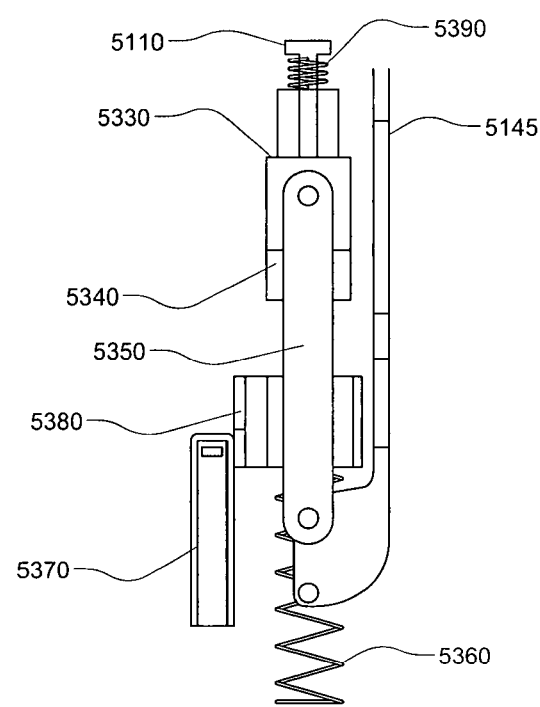

Referring now to FIGS. 91A-91C, several views of an embodiment of an inserter mechanism for an inserter, such as the one shown in FIGS. 89A and 89B as 5100, are shown. FIG. 91A shows a perspective view, FIG. 91B shows a front view, and FIG. 91C shows a side view of one embodiment of an inserter mechanism. The inserter 5100 has a cocking lever 5145, which connects via cocking linkages 5350 to a hammer cocking slide 5330, and is used to move the cocking slide 5330 to a charged position. A power spring 5390 connects the hammer cocking slide 5330 to a trigger 5110 and, when compressed, provides the downward force necessary for insertion of an infusion device or an infusion and sensor assembly (not shown). A trigger hammer 5340 is disposed under the hammer cocking slide 5330 and between a pair of cocking linkages 5350; the trigger hammer 5340 transmits the kinetic energy that is released from the power spring 5390 upon pressing the trigger 5110. The energized trigger hammer 5340 impacts a cartridge bolt 5380, positioned below. The cartridge bolt 5380 is linked to a cartridge housing 5370, which holds the cartridge, for example, the one shown in FIG. 90. The cartridge bolt 5380 is also disposed atop a return spring 5360 for returning the cartridge housing 5350 to a retracted position.

Figures 92A, 92B, 92C:
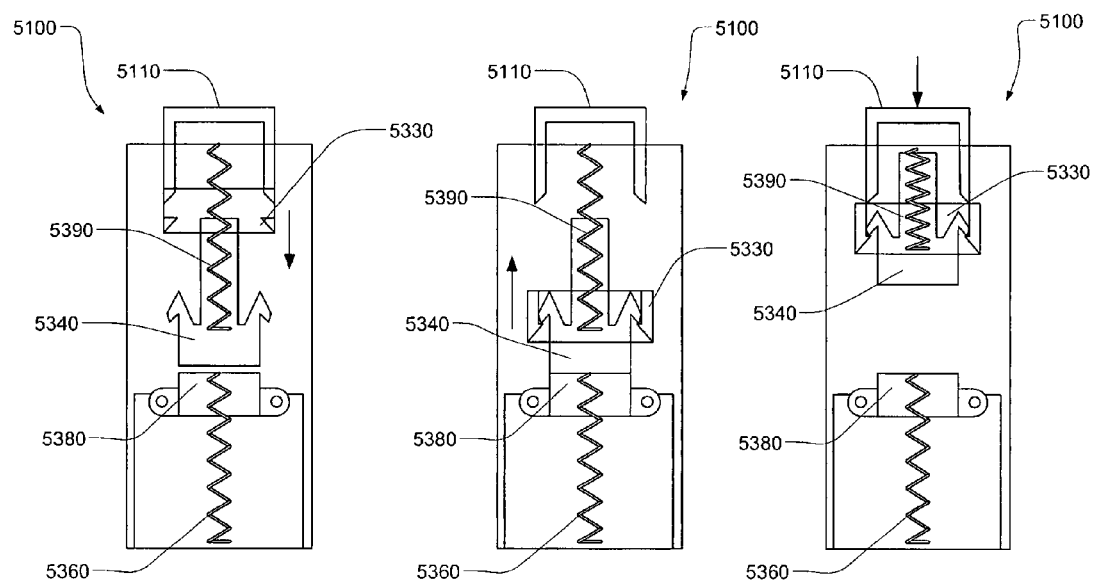

FIGS. 92A-92F schematically show a time sequence for the cocking and firing of an inserter 5100 of the type described with reference to FIGS. 91A-91C. FIG. 92A shows the inserter 5100 in a resting position. Lowering the cocking lever (not shown, see FIG. 91A 5145) causes the hammer cocking slide 5330 to lower and engage the trigger hammer 5340. FIG. 92B shows the hammer cocking slide 5330 in a lowered position in which it is engaged with the trigger hammer 5340. Raising the cocking lever causes the hammer cocking slide 5330 and hammer 5340 to be raised, thus compressing the power spring 5390; the resulting position is shown in FIG. 92C. After ensuring the proper positioning of the inserter 5100 with respect to a base (not shown) and/or the skin of a patient, the trigger is pressed, thereby sending the trigger hammer 5340 downward; FIG. 92D shows the trigger hammer 5340 in transit. As shown in FIG. 92E, the trigger hammer 5340 impacts the cartridge bolt 5380, causing it to travel downward, insert the needle or needles held in the cartridge housing (not shown) and compress the return spring 5360. FIG. 92F shows the return spring 5360 in the process of forcing the cartridge bolt 5380 upward; this causes retraction of the cartridge housing and the cartridge contained therein (not shown) and any associated introduction needles used.

Figure 93A:
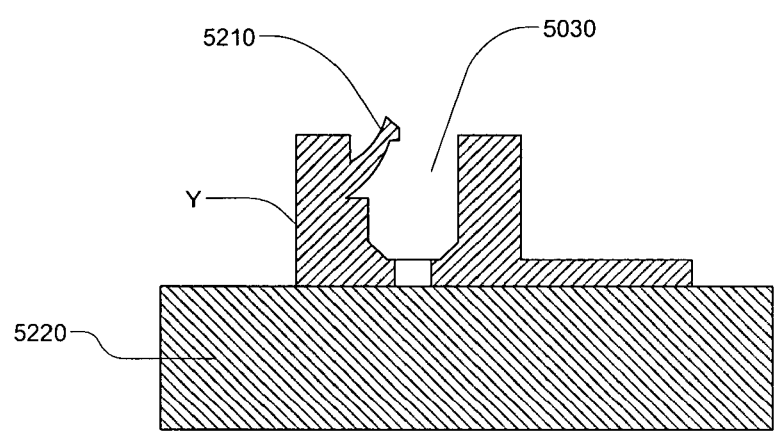
FIGS. 93A-93C show a time-series for the insertion of a cannula into a base of a fluid delivery device.
Figure 93B:
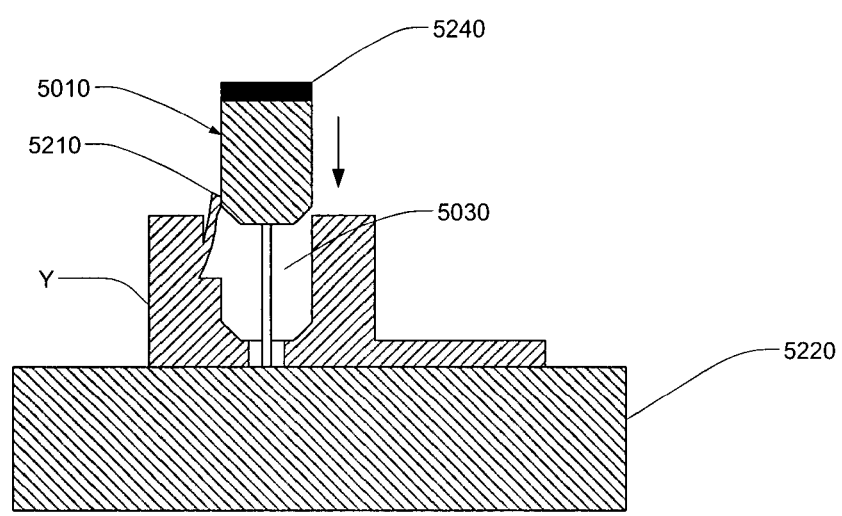
Figure 93C:
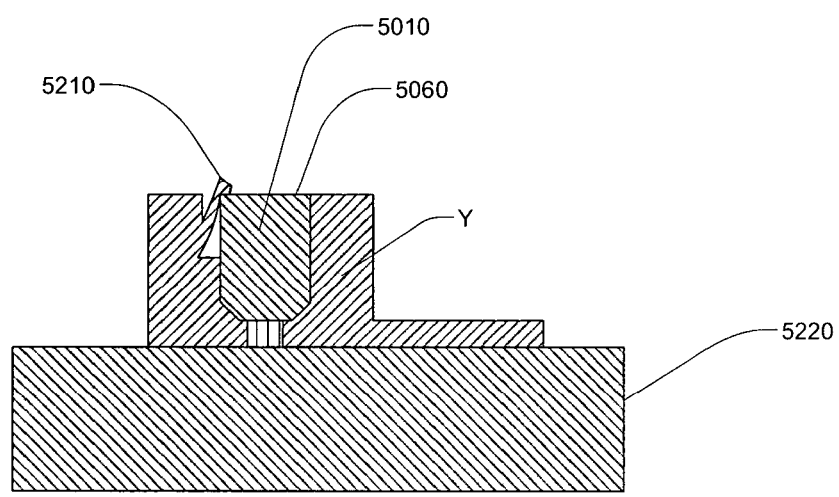

Referring now to FIGS. 93A-93C, one embodiment of a temporal sequence for inserting and securing an infusion device (i.e., cannula or needle 5010) into a base Y is shown. FIG. 93A shows a base Y with a locking feature 5210 positioned above a cannula housing 5030. The base Y is typically positioned against the skin of a patient 5220 when inserting an infusion device or cannula 5010. FIG. 93B shows a cannula 5010 being forced through the cannula housing 5030 in the base Y. In this figure, an introduction needle 5240 is used that traverses a septum (not shown) and is positioned coaxially in the cannula 5010; a sharp point of the introduction needle 5240 emerges from the tip (not shown) of the cannula 5010 to help puncture a patient 5220. The resilient locking feature 5210 is pushed aside during insertion of the cannula 5010. FIG. 93C shows the cannula 5010 fully inserted through the cannula housing 5030 of the base Y, with the tip of the cannula fully inserted into the patient 5220. The introduction needle 5240 has been removed and the septum 5060 has self-sealed to a fluid source or fluid line (not shown). The resilient locking feature 5210 is engaged with the cannula 5010, thereby preventing the cannula 5010 from moving in relation to the base Y. Although FIGS. 93A-93C show a cannula 5010, the infusion and sensor assembly shown in FIGS. 86B can be inserted using the locking feature 5210 and method shown and described in FIGS. 93A-93C.

Figure 92G:
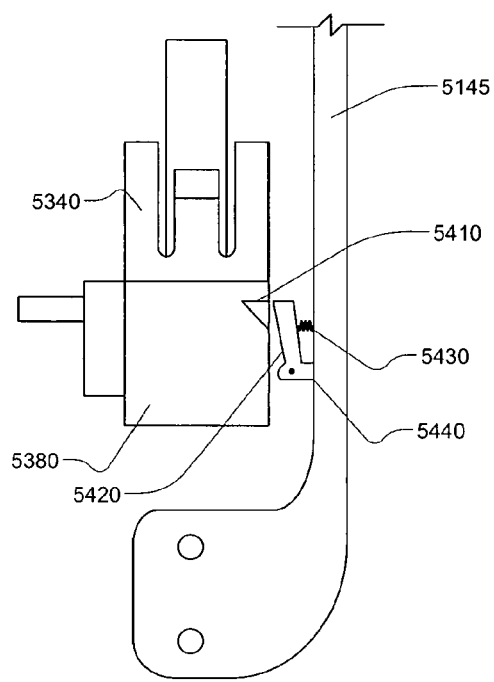
FIG. 92G shows an inserter mechanism having a catch and a cocking lever in a closed position.
Figure 92H:
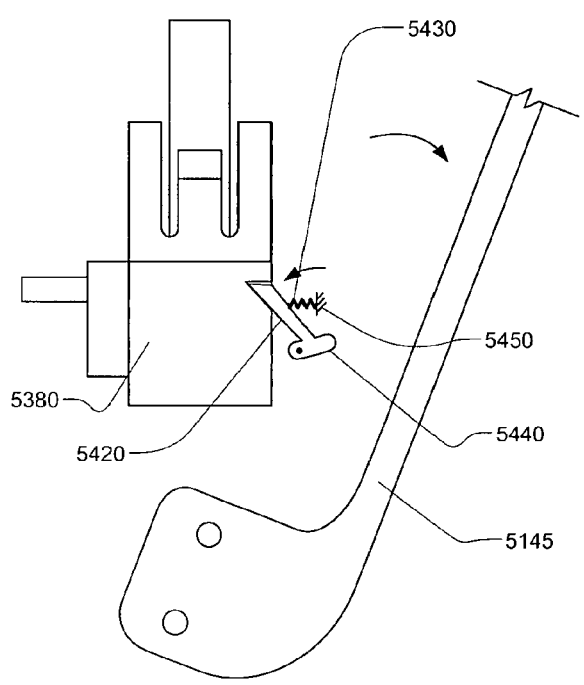
FIG. 92H shows an inserter mechanism with a catch and a cocking lever in an open position.

Referring now to FIGS. 92G-92H, an inserting cartridge bolt locking mechanism for use with an inserter, such as the one shown in FIGS. 91A-92F, as 5100 is shown. The cartridge bolt locking mechanism can function as an interlock to prevent accidental firing while the mechanism is being cocked. The locking mechanism includes a catch 5420, which when engaged in a catch recess 5410, prevents downward movement of the cartridge bolt 5380. As shown in FIG. 92G, when the cocking lever 5145 is in a closed position, the cocking lever 5145 contacts a catch lever 5440, which rotates the catch 5420 and prevents the catch 5420 from inserting into the catch recess 5410. A catch spring 5430, disposed between the catch 5420 and a catch spring support 5450, is in a compressed positioned. The cartridge bolt 5380 and trigger hammer 5340 are free to move. As shown in FIG. 92H, when the cocking lever 5145 is rotated into a downward position, the catch lever 5440 is released, thereby allowing the catch spring 5430 to force the catch 5420 to insert into the recess (here the catch 5420 is shown inside the recess, but the recess is shown in FIG. 92G as 5410); downward movement of the cartridge bolt 5380 is thereby prevented. Return of the cocking lever 5145 then returns the catch 5420 to an unlocked position. The cartridge bolt 5380 is then free for downward movement in the triggering process.

Figure 94A:
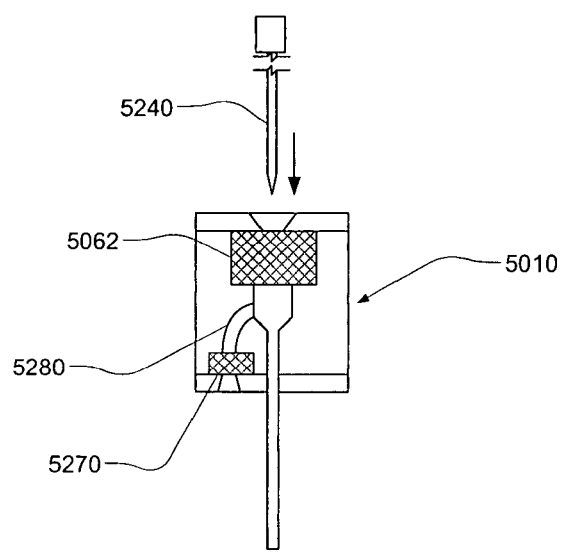
FIGS. 94A-94C shows a temporal sequence for the insertion of a cannula into a base with co-incident connection of the cannula to a fluid line.
Figure 94B:
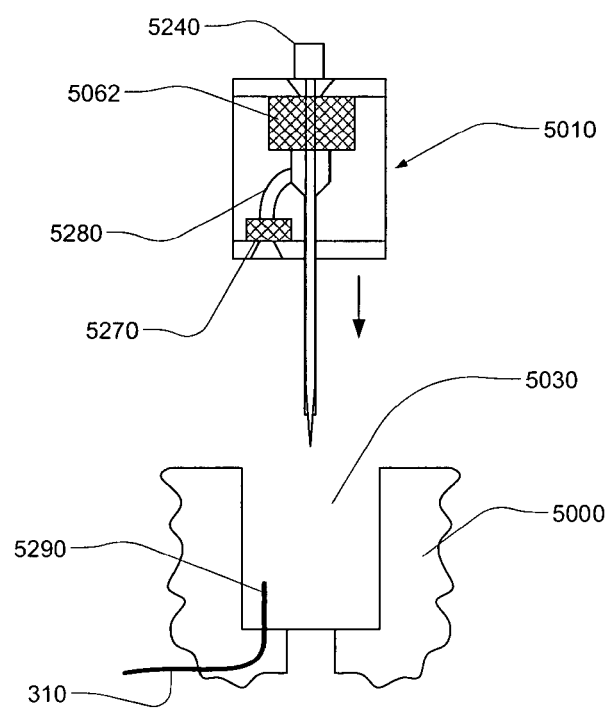
Figure 94C:
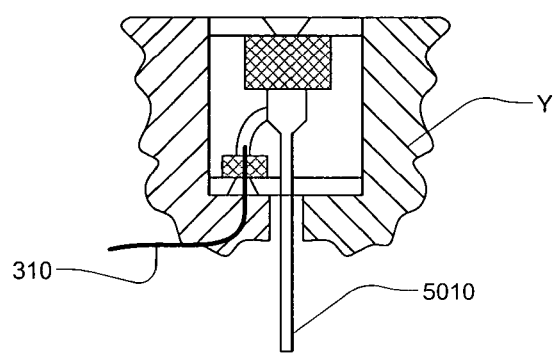

Referring now to FIGS. 94A-94C, one embodiment of the process of mating a cannula 5010, where the cannula is a traditional cannula requiring an introduction needle (as shown in FIG. 86B) to the base Y and establishes fluid communication with a fluid line 310 is shown. FIG. 94A shows a sectional view of a cannula 5010 with two septa: an introduction needle septum 5062 and a fluid line septum 5270. The introduction needle septum 5062 seals a passageway 5280 leading to the hollow needle (not shown, shown in FIG. 94B as 5290) of the cannula 5010. A cannula introduction needle 5240 is shown positioned above the introduction needle septum 5062 and just prior to insertion of the introduction needle 5240.

Referring now to FIG. 94B, the introduction needle 5240 is shown inserted through the introduction needle septum 5062. A user mates the cannula 5010 into the base Y, which has an upwardly-pointing rigid, hollow needle 5290. During insertion of the cannula 5010 into the base Y, the introduction needle 5240 punctures the fluid line septum 5270 to establish fluid communication between the fluid line 310 and the passageway 5280. If the base Y is held against a patient (not shown) during insertion of the cannula 5010 into the base Y, fluid communication between the fluid line 310 and the passageway 5280 will be established at about the same time that the patient's skin is pierced. Referring now to FIG. 94C, the cannula 5010 is shown, fully inserted into the base Y, with the introduction needle removed and fluid communication established with the fluid line 310.

In an alternate embodiment, insertion of an infusion device and/or sensor is assisted by a vibration motor coordinated with a fluid delivery device. Simultaneously with the insertion of the infusion device and/or sensor, a vibration motor may be activated.

Adhesion

Figure 95:
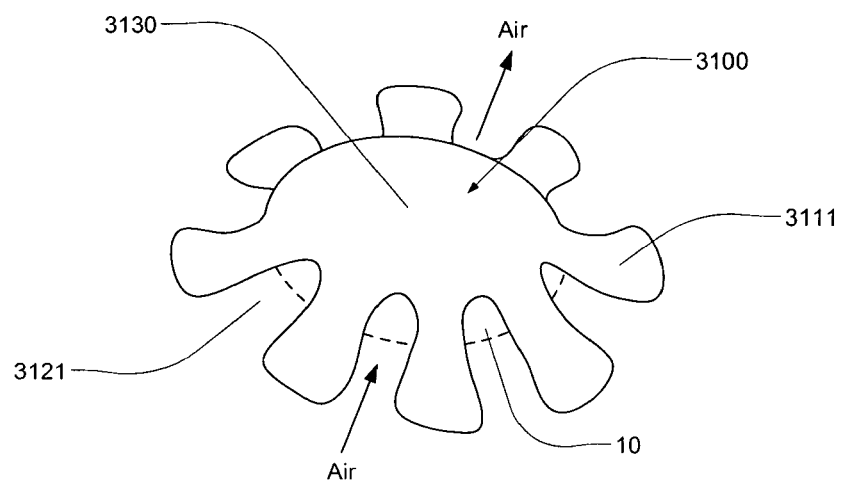
FIG. 95 shows a top view of an adhesive patch for holding a fluid delivery device.

Referring now to FIG. 95 a top perspective view of one embodiment of an adhesive patch 3100 for securing an object, such as a fluid delivery device 10, to the skin of a patient (not shown) is shown. Although the adhesive patch 3100 is shown in the present shape, other shapes can be used. Any adhesive patch 3100 that can securely hold a fluid delivery device can be used.

Fluid delivery device 10 is securely held under a central region 3130 of the adhesive patch 3100, which is attached to the skin of a patient by adhesive members 3111. These adhesive members 3111 emanate from a central region 3130 in a radial pattern and are spaced apart from each other by intervening regions 3121. The radial arrangement of the adhesive members 3111 allows for attachment of the device 10 to the patient in secure manner. In some embodiments, the central region 3130 covers the entire device 10, however, in other embodiments, the central region 3130 covers a portion of the device 10. The central region 3130 may also include interlocking attachment features (not shown) that may be held by complementary interlocking features (not shown) of the device 10. In an alternate embodiment, the device 10 is securely attached atop the central region 3130 (for example, by an adhesive or interlocking feature).

The adhesive patch 3100 is typically flat and composed of a polymeric sheet or fabric. The adhesive patch 3100 may be supplied with adhesive affixed on one side and protected by a peelable backing such as a peelable sheet of plastic to which the adhesive will adhere more loosely that to the patch 3100. The backing may be a single continuous piece, or may be divided into regions that may be removed separately.

In an illustrative embodiment, the backing for the central region 3130 may be removable without removing the backing to the adhesive members 3111. To use the adhesive patch 3100, a user removes the backing of the central region 3130 and presses the device 10 against the newly exposed adhesive of the central region to attach the device 10 to the central region 3130. The user then places the device against the skin, removes the backing from an adhesive member 3111, affixes the adhesive member to the skin, and repeats the affixation process with additional members. A user may affix all of the adhesive members 3111 or only some of the members, and save additional adhesive members 3111 for application on another day. Since adhesives typically used for attachment to skin only remain securely attached for several days, application of sets of adhesive members 3111 on different days (for example, staggered by 3 to 5 days) should extend the amount of time that the device 10 remains securely attached to the skin and reduce the of time, expense and discomfort that is often involved in reapplication of the device. The varying tabs may have indicia such as different colors or numbers to indicate to the appropriate time to affix the various adhesive members 3111. The adhesive members 3111 may include perforations to render them frangible with respect to the central region 3130 so that used adhesive members may be removed after use. Additional embodiments for extending the duration during which device 10 remains affixed are discussed above with reference to FIGS. 79-83.

Figure 96:
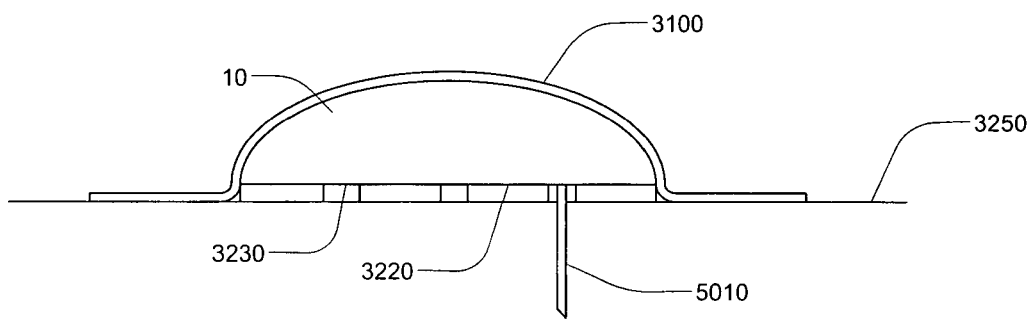
FIG. 96 schematically shows a sectional view of a fluid-delivery device under an adhesive patch.

FIG. 96 schematically shows a sectional view of a fluid delivery device 10, with an inserted cannula 5010, held securely under an adhesive patch 3100. A pad 3220 may be included between the device 10 and a patient's skin 3250 and allow air to flow to the skin. Air flow to skin may be increased by the inclusion of passageways 3230 in the pad 3220. Passageways 3230 may also be formed by using multiple pads that are spaced apart or by constructing pad 3220 from a highly porous material. Thus, the pad 3220 can be any shape and size and in some embodiments, the pad 3220 is made up of a number of separate pieces. Pads 3220 may be either adhered to the underside of the device 10 during manufacture or may be adhered to the device 10 by a user. Alternately, the pad 3220 may be loosely placed onto the skin by a user prior to application of the adhesive patch 3100. The pad 3220 may include a compliant material, such as porous polymeric foam.

Figure 97:
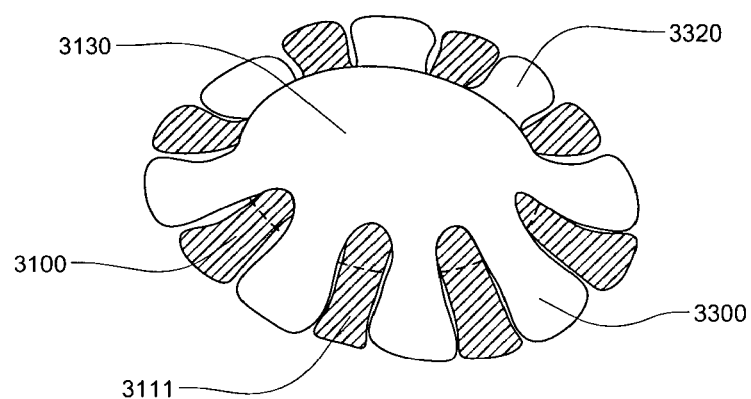
FIG. 97 shows a perspective view of two overlapping adhesive patches for holding a fluid delivery device.

FIG. 97 shows an embodiment of the invention that uses a first adhesive patch 3100 and an additional adhesive patch 3300 to secure a device (not shown) to a patient. First, a device (not shown) is positioned for use and secured to the skin (not shown) of a patient with an adhesive patch 3100 using tab-like adhesive members 3111. The central region 3130 may be positioned atop (as shown), or secured below, the device. After a period of time, either prolonged or short, a second adhesive patch 3300 is positioned so that its central region sits atop the first adhesive patch 3100 and the second adhesive patch's adhesive members 3320 are secured to the skin of the patient in the intervening regions between the first adhesive patch's adhesive members 3111. Frangible regions may be provided to aid in the removal of loose or unwanted adhesive members 3111 associated with the earlier placed patch 3100.

Figure 98:
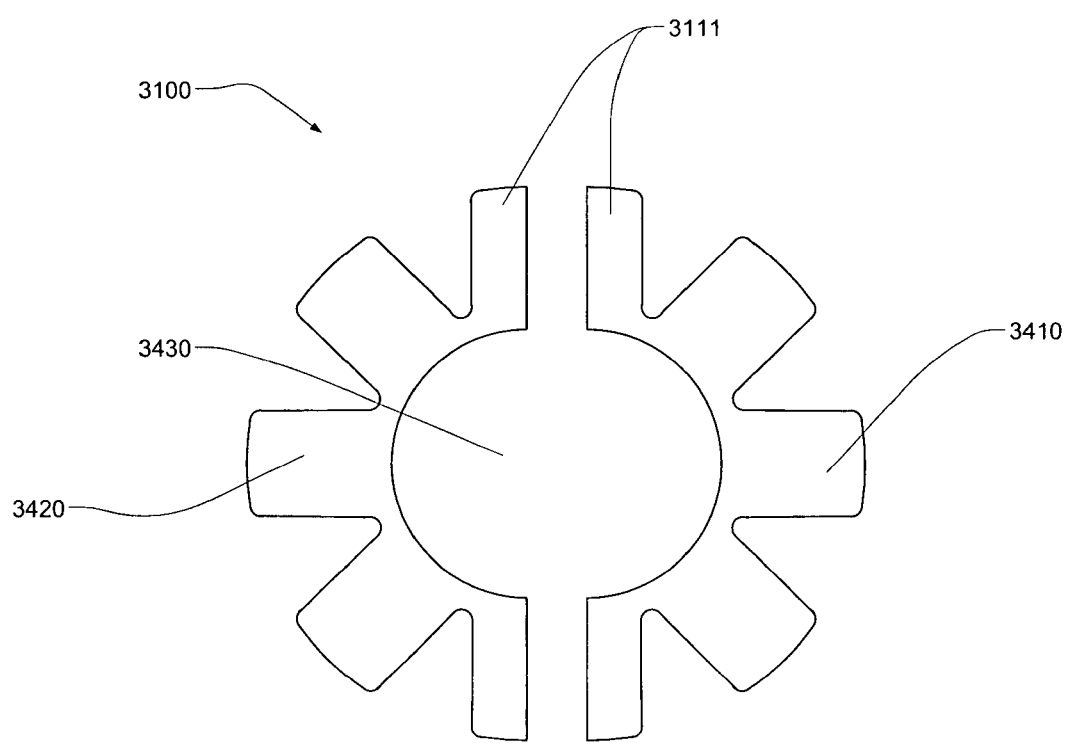
FIG. 98 shows a top view of two semicircular adhesive patch portions.
Figure 99:
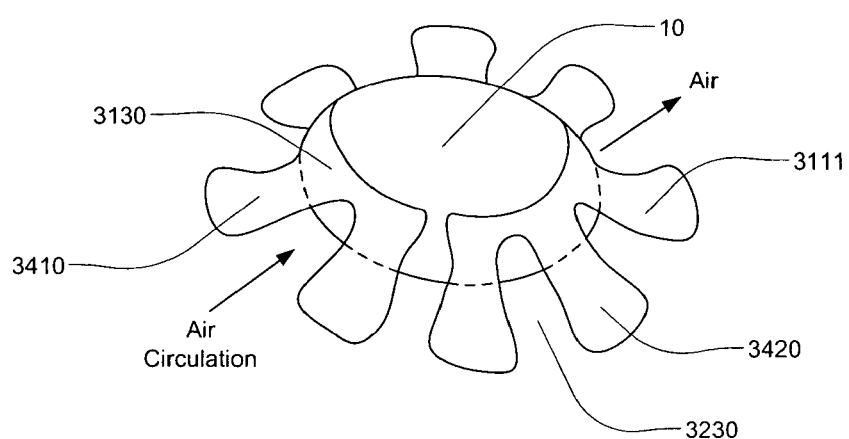
FIG. 99 shows a perspective view of two semicircular adhesive patch portions holding a fluid delivery device.

Referring now to both FIGS. 98 and 99, embodiments in which an adhesive patch 3100 has been divided into at least two smaller adhesive patches are shown. In these embodiments, the adhesive patch 3100 is divided into two adhesive patches, 3410 and 3420, each having adhesive members 3111 radially arranged around a central void 3430. The two adhesive patches, 3410 and 3420, each span a semi-circle of about 180°, but other configurations could be used such as: three patches, each spanning 120°, or four patches each spanning 90°. In some embodiments, the adhesive can include greater than four patches. The configurations described with respect to these embodiments follow the formula 360°/n where n is the number of patches. But, in other embodiments, depending on the shape of the device, the formula shown and described here does not apply. In still other embodiments, the patches may also cover more than 360°, and thus overlap.

As shown in the perspective view of FIG. 99, due to the presence of a central void (not shown, shown in FIG. 98), the central region 3130 is in the form of a thin strip for adherently positioning along the perimeter of the device 10. The two patches, 3410 and 3420, together securely attach the device 10 to the skin (not shown). As in the embodiment described with reference to FIG. 95, air may flow between the adhesive members 3111 and under the device 10, especially if passageways 3230 are provided.

Figure 100:
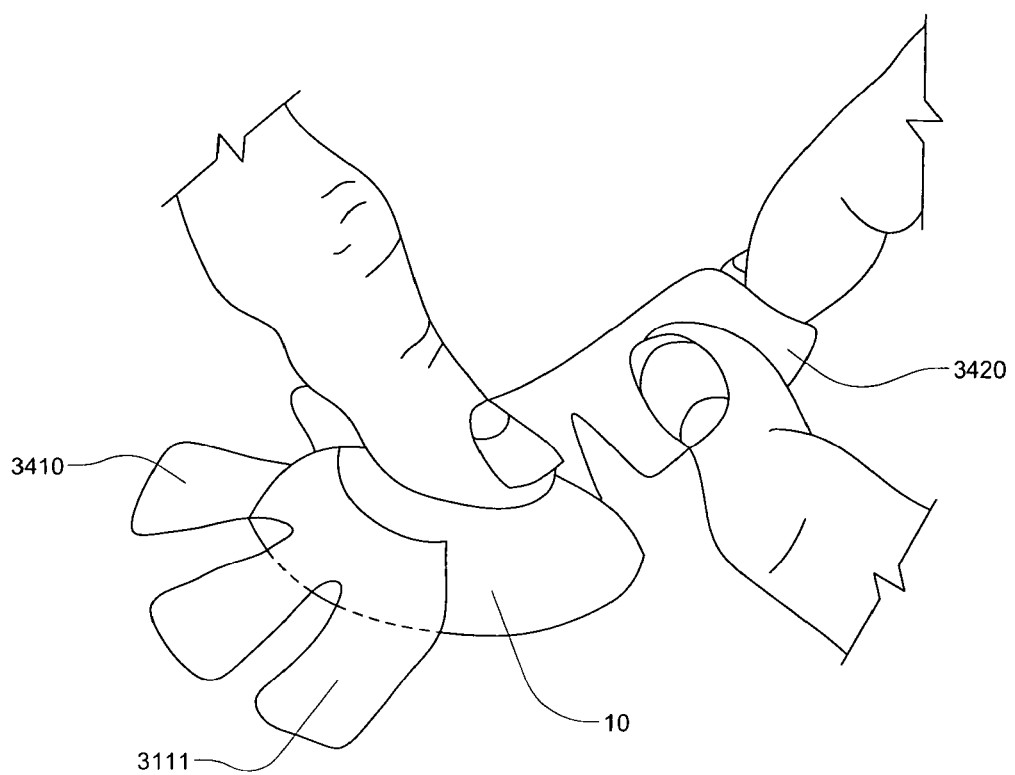
FIG. 100 shows a perspective view of a semicircular adhesive patch portion being removed by a patient.

FIG. 100 shows a perspective view of an embodiment that includes using the multiple adhesive patches to extend the time during which a device 10 remains adhered to a patient (not shown) before removal. One of the multiple partial adhesive pads 3420 is removed while the device 10 is held in place (either by a remaining adhesive patch 3410 and/or by a user). The removed adhesive patch 3420 is then replaced with a fresh replacement adhesive patch (not shown). The replacement adhesive patch may be identical to the removed pad 3420 or may have adhesive members 3111 that are positioned in an alternate configuration to allow adhesion to the fresh skin between the areas previously covered by adhesive patch 3420. The remaining adhesive patch 3410 may then be replaced in a similar manner. Indicia such as color coding may be used to indicate the age of the adhesive patches. The patches may also have a color change mechanism to indicate that their useful life has expired. Decorative patterns, such as images and designs, may be included on the patches.

Figure 101:
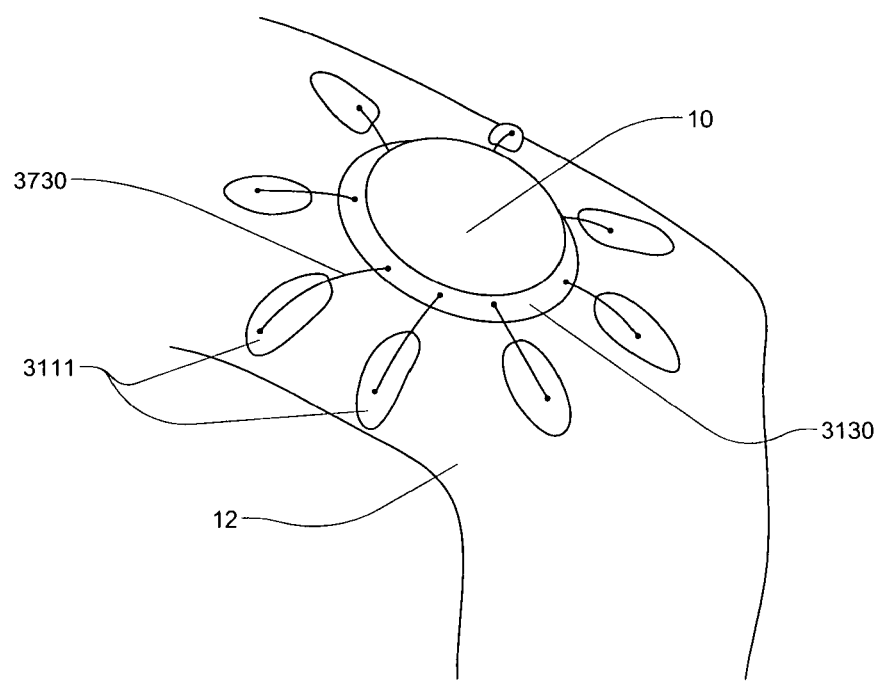
FIG. 101 shows a perspective view of a fluid-delivery device being held against a patient using multiple adhesive members and tethers.

FIG. 101 schematically shows an embodiment in which multiple adhesive members 3111 are affixed to a patient 12 and also connected to a ring like central region 3130 via tethers 3730. The tethers 3730 may be fibers or cords and may be resilient to decrease the movement of the device 10 in response to movement of the patient 12. The use of tethers 3730 also increases options available for skin positions of the adhesive members 3111.

The adhesive used in the embodiments described in FIGS. 95-101 can be any effective and safe adhesive available for use on a patient's skin. However, in one embodiments, the adhesive used is 3M product number 9915, value spunlace medical non woven tape.

Clamping and Latching

Figure 102A:
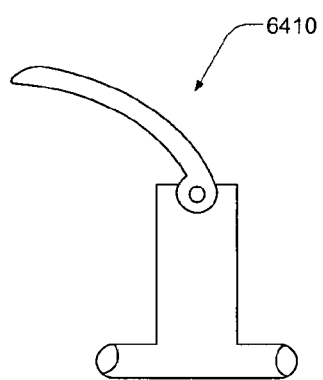
FIG. 102A shows a clamp for assembling a device.
Figure 102B:
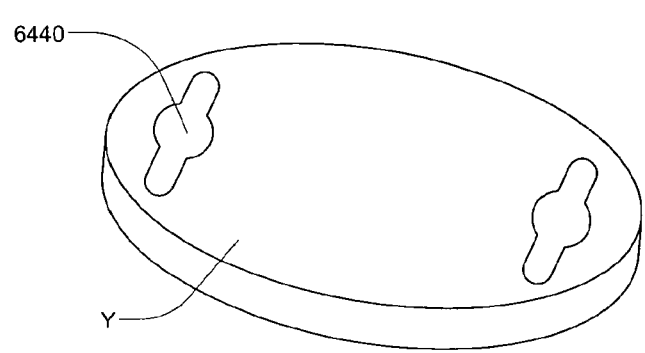
FIG. 102B shows a base of a fluid delivery device having keyholes for inserting clamps.
Figure 102C:
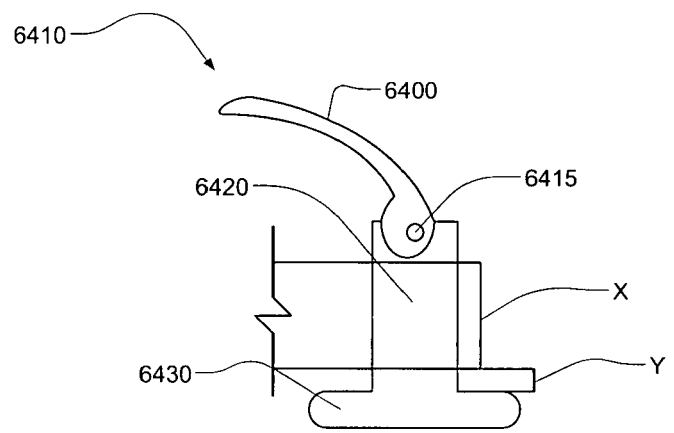
FIG. 102C shows a sectional view of a fluid delivery device assembled with a clamp.

FIGS. 102A-102C schematically show one mechanism for clamping or latching together a top portion and a base portion of a fluid delivery device. Referring first to FIG. 102A, an elevation view of a clamp 6410 is shown. FIG. 102B shows a base portion Y with keyholes 6440 for two clamps; corresponding keyholes may also be included in the top portion (not shown). Referring now to FIG. 102C, the top X and the base Y may be aligned and a clamp 6410 may be inserted through the keyholes (not shown, shown in FIG. 102B as 6440). Rotating the clamp 6410 by 90° causes a stud bar 6430 to move into a locking position. Depressing a cam lever 6400 engages a cam 6415, that is hingedly connected to a clamp pin 6420, to push against the top X. As a result, the top X and the base Y are held with a clamping force between the cam 6415 and the stud bar 6430. Raising the cam lever 6400 releases the clamping force and the clamp 6410 may be rotated by 90° and withdrawn to allow disassembly of the top X and base Y. In some embodiments, the lever may act as a protective cover for the top X.

Figure 103C:
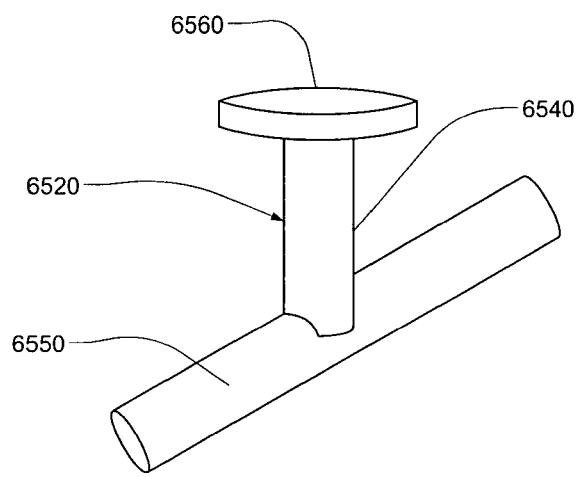
FIG. 103C shows a perspective view of a clamp pin for use in assembling a fluid delivery device.
Figure 103D:
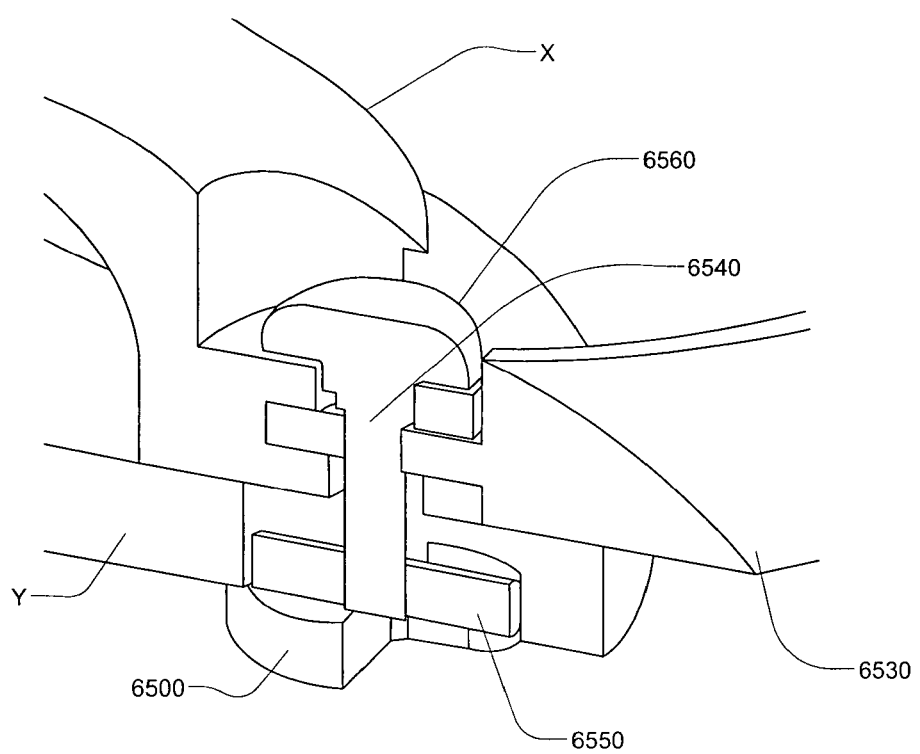
FIG. 103D shows an embodiment of a fluid delivery device assembled using a clamp pin and cam guide.

An alternate embodiment for clamping together the portions of a device is shown in FIGS. 103A-103D. FIG. 103A shows a perspective view and FIG. 103B shows a top view of a cam guide 6500. The cam guide 6500 has a keyhole 6440 and sloped surfaces 6510. FIG. 103C shows a cam follower 6520 having a central pin 6540 with a head 6560 attached at a first end and a bar 6550 attached to an opposite end. As shown in the sectional view of FIG. 103D, the cam follower (not shown, shown in FIG. 103C) may be inserted into keyholes (not shown, shown in FIG. 103C) in the top X, base Y, and cam guide 6500. Movement of a lever 6530 attached to the central pin 6540 causes rotation of the cam follower (not shown, shown in FIG. 103C), causing the bar 6550 to travel along the sloped surface (not shown, shown in FIG. 103C as 6510) and thereby transforming the rotational force to a force which clamps the base Y and top X firmly between the cam follower head 6560 and the bar 6550.

Reservoir

Exemplary embodiments of collapsible reservoirs for holding fluids are shown in FIGS. 104-106C. The collapsible reservoir has at least one section or wall that collapses as fluid is withdrawn, thereby maintaining ambient pressure in its interior.

In most embodiments, a sealable port (e.g., a septum) is included in the reservoir. The port allows the reservoir to be filled with fluid by a syringe and also, for a leak free connection to a fluid line. Alternately, an adaptor may be used to connect the reservoir with the fluid line. Alternately, as shown above with reference to FIG. 71, a needle may be associated with the reservoir and a septum may be associated with the terminus of the fluid line. The reservoir may be constructed of a plastic material known to be compatible, even if for a very short duration, with the fluid contained in the reservoir. In some embodiments, the reservoir is entirely collapsible, i.e., the reservoir does not include any rigid body surfaces.

Figure 104:
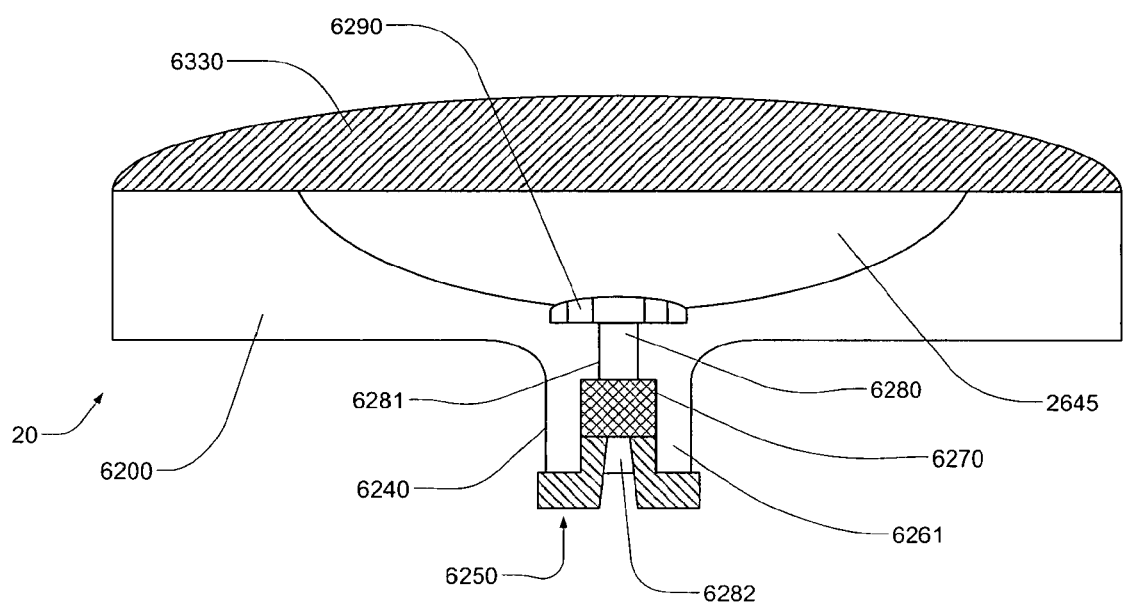
FIG. 104 shows a sectional view of a collapsible reservoir in accordance with one embodiment.

Referring now to FIG. 104 a sectional view of a reservoir 20 is shown. A cavity 2645 for holding a volume of fluid is formed between a rigid reservoir body 6200 and a flexible reservoir membrane 6330. The flexible membrane 6330 is sealingly attached around the periphery of the cavity 2645 to hold fluid within the cavity 2645. The flexible membrane 6330 imparts collapsibility to the reservoir 20; it deforms inwardly as fluid is pumped from the cavity 2645.

A septum 6270 is seated in a neck 6240 extending from the body 6200. The septum 6270 serves as an interface between the cavity 2645 and a fluid line. In some devices, the fluid line terminates in a needle (not shown). In these embodiments, the needle may be inserted through the septum 6270 to access a needle chamber 6280 portion of the cavity 2645. The septum 6270 location can be maintained by its location between a cap 6250 and a ledge (not shown) formed at the junction of the inner wall 6281 of the needle chamber 6280 and the cap bore 6282. The cap 6250 may be held by a friction fit within the cap bore 6282. Upon insertion of the cap 6250, its position is limited by the wall 6261 of the cap bore 6282. The portion of the cap 6250 closest to the septum 6270 may have a central aperture to allow insertion of the needle through the cap 6250 and into the septum 6270. Alternately, the cap 6250 may be punctured by the needle.

Figure 105:
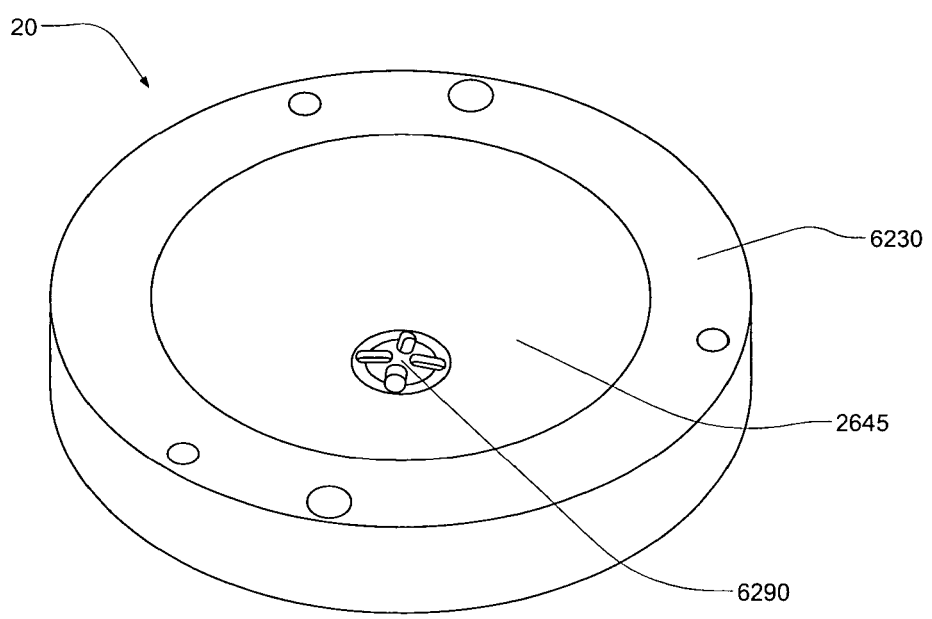
FIG. 105 shows a perspective view the reservoir of FIG. 104.

FIG. 105 shows a perspective view of the inside of the collapsible reservoir 20. A rim 6230 allows attachment of the flexible reservoir membrane, which may be attached by welding, clamping, adhering, or other suitable method to create a fluid tight seal. A guard structure 6290 may be included to allow fluid to flow to or from the cavity 2645, but prevents a needle from entering the cavity, thereby preventing it from possible puncture of the reservoir membrane.

Figure 106A:
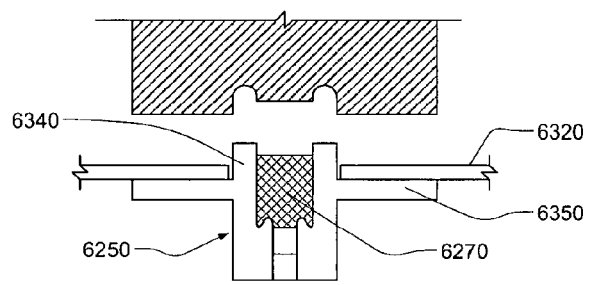
FIG. 106A-106C shows a series of steps for securing a septum to a cap to produce a reservoir in accordance with one embodiment.
Figure 106B:
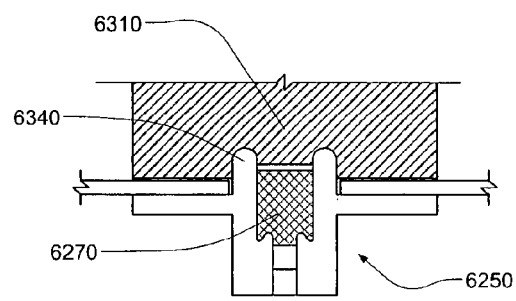
Figure 106C:
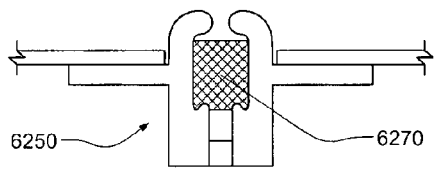

FIGS. 106A-106C show an alternate embodiment of a reservoir in which a cap 6250 sealingly attaches a septum 6270 to a wall 6320 of a reservoir. The wall 6320 could be constructed, for example, from a flexible sheet such as PVC, silicone, polyethylene or from an ACLAR film. In some embodiments, the wall 6320 may be constructed from a heat formable polyethylene laminate formed with an ACLAR firm. The flexible sheet is compatible with the fluid. The wall may be attached to a rigid housing, or part of a flexible plastic pouch, such as may be formed by folding and welding the ends of a plastic sheet. FIG. 106A shows the cap 6250 sealed to a wall 6320 via a circular fin 6350. The septum 6270 may be inserted into a turret 6340 that protrudes from the cap 6250. The turret 6340 may be constructed from a material that is deformable at high temperature, but rigid at room temperature, for example, low density polyethylene. Referring now to FIG. 106B, a hot press 6310, or another apparatus or process for melting, is used to melt or bend the turret 6340 over the septum 6270. Referring now to FIG. 106C, the septum 6270 is shown immobilized to the cap 6250.

Certain fluids are sensitive to storage conditions. For example, insulin may be somewhat stable in the glass vials in which it is typically shipped, but may be unstable when left in prolonged contact with certain plastics. In some embodiments, the reservoir 20 is constructed of such a plastic. In this case, the reservoir 20 may be filled with fluid just prior to use so that the fluid and plastic are in contact for a shorter period time.

Reservoir Filling Station

Figure 107:
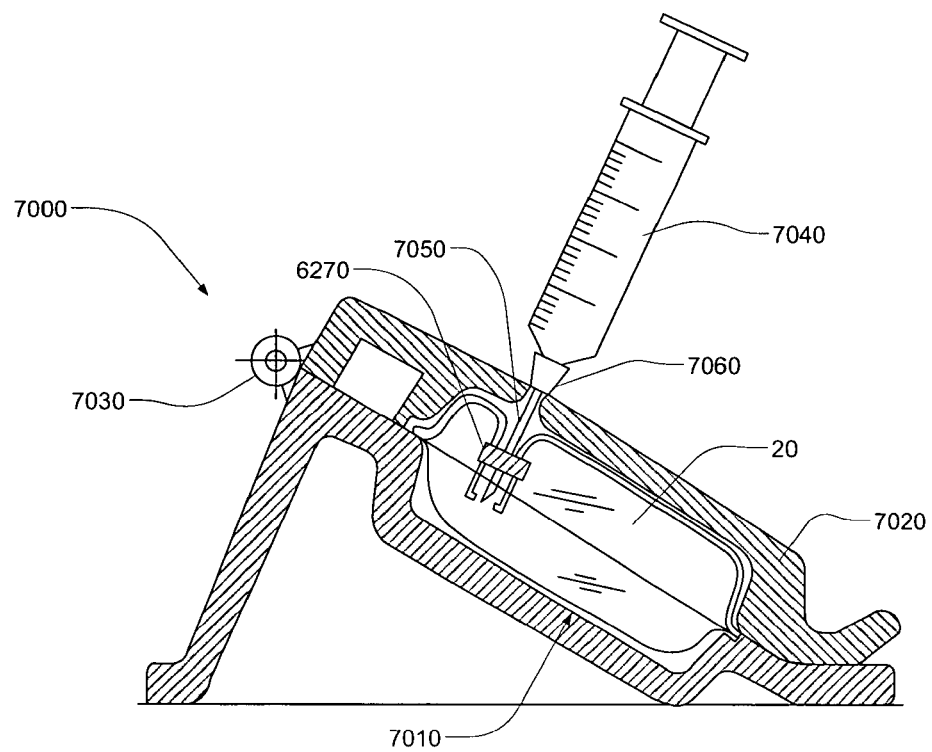

Referring now to FIG. 107 a reservoir filling station 7000 for filling a reservoir 20 with a fluid is shown. The fluid may be withdrawn from its original container with a syringe 7040 and introduced into the reservoir 20 by using the fill station 7000. The fill station 7000 may include a substantially rigid fill station base 7010 hinged to a substantially rigid fill station cover 7020 via a hinge 7030. Accordingly, the station 7000 may be opened and closed to accept and hold the reservoir 20. A needle 7050 attached to the syringe 7040 may then be inserted through a filling aperture 7060 in the cover 7020, and through the reservoir septum 6270. Since the fill station cover 7020 is rigid, it establishes a limit of travel upon the syringe 7040 and therefore controls the depth of needle 7050 penetration into the reservoir 20 to discourage puncture of the underside of the reservoir 20. A leg 7070 holds the station 7000 in a tilted position when supported on a surface. Since the station 7000 is tilted, as the fluid is injected from the syringe 7040 into the reservoir 20, air will tend to rise upwardly toward the septum 6270. After the syringe 7040 injects the desired amount of fluid into the reservoir 20, the syringe 7040 may be used to remove any remaining air in the reservoir 20. Since the fill station base 7010 and cover 7020 are rigid, the flexible reservoir 20 generally cannot be distended past a fixed volume and overfilling of the reservoir 20 is discouraged. The base 7010 and cover 7020 may be locked together with a clasp, or a heavy cover may be used to further discourage overexpansion and overfilling of the reservoir.

Figure 108A:
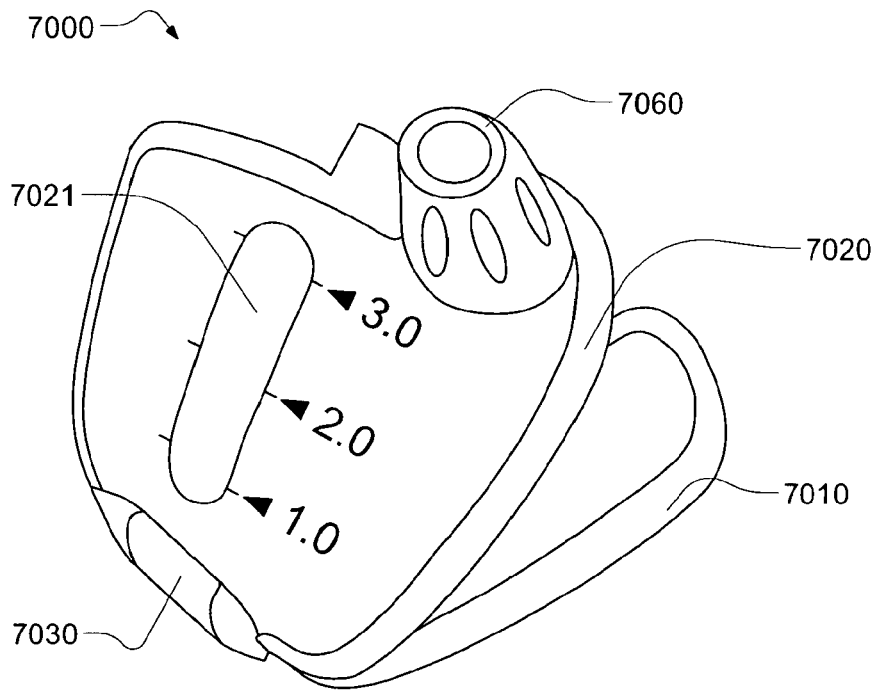
Figure 108B:
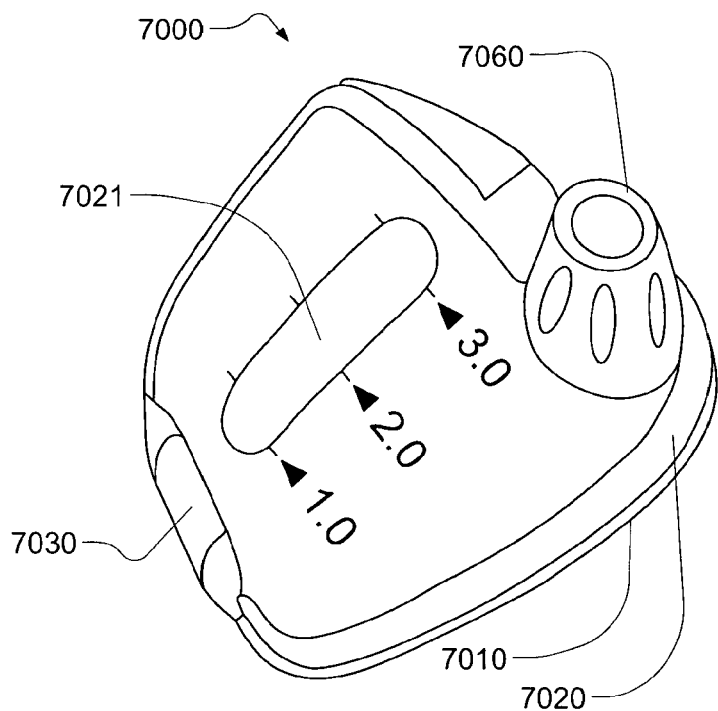

Referring now to FIGS. 108A and 108B, an alternate embodiment of the reservoir filling station 7000 is shown. In this embodiment, the reservoir (not shown) is placed in the space between the cover 7020 and the base 7010. A hinge 7030 attached the cover 7020 and the base 7010. As shown in FIG. 108B, the reservoir (not shown) is inside, and a syringe (not shown) needle (not shown) is inserted into the filling aperture 7060. The filling aperture 7060 connects directly to the reservoir's septum (not shown). A viewing window 7021 indicates the fluid line in terms of the volume of fluid that has been injected into the reservoir.

A fluid delivery system typically includes a fluid delivery device and an external user interface, although in some embodiments a complete or partial internal user interface is included in the device. The device can be any device as described herein or a variation thereof.

Figure 109A:
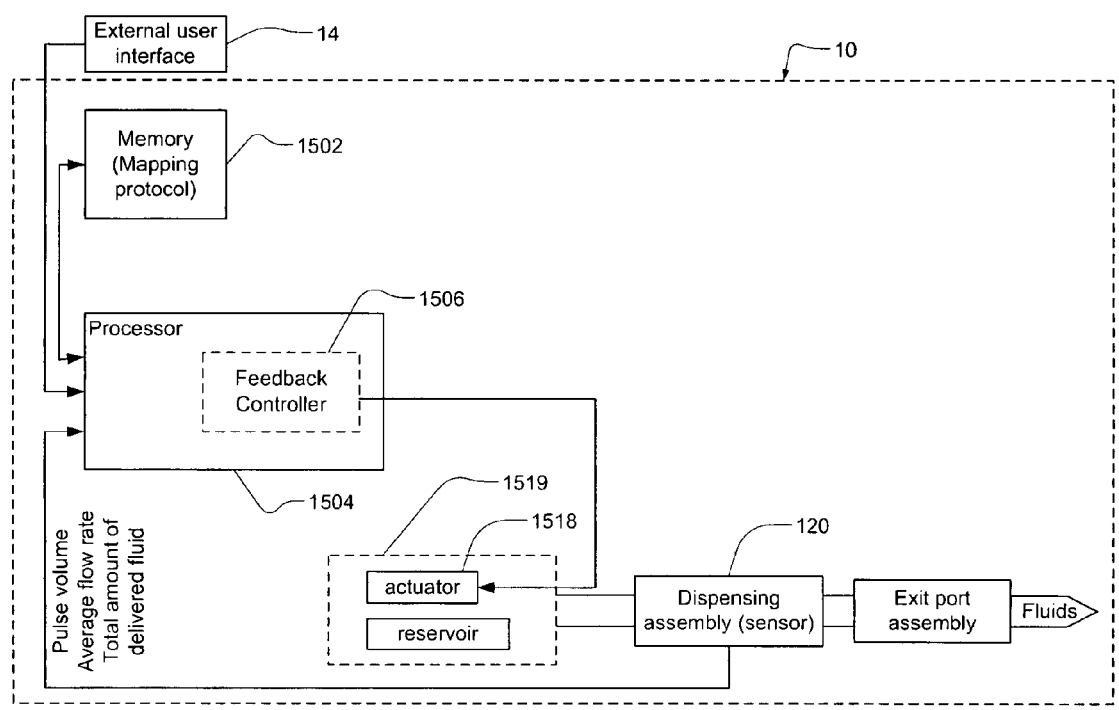

FIG. 109A shows a flow diagram of a data acquisition and control scheme for an exemplary embodiment of a fluid delivery system. A patient or caregiver utilizes an external user interface 14 which is typically a base station or hand held unit housed separately from the fluid delivery device 10. In some embodiments, the user interface 14 is integrated with a computer, cell phone, personal digital assistance, or other consumer device. The user interface assembly may be in continuous or intermittent data communication with the fluid delivery device 10 via wireless radio frequency transmission (for example, via LF, RF, or standard wireless protocols such as "Bluetooth") but could also be connected via data cable, optical connection or other suitable data connection. The external user interface 14 communicates with a processor 1504 to input control parameters such as body mass, fluid dose ranges or other data and receives status and function updates such as the presence of any error conditions resulting from occluded flow, leaks, empty reservoir, poor battery condition, need for maintenance, passage of an expiration date, total amount of fluid delivered or remaining or unauthorized disposable component. The interface 14 may transmit error signals to a patient's guardian or medical professional through a telephone, email, pager, instant messaging, or other suitable communication medium. A reservoir actuator assembly 1519 includes an actuator 1518 and a reservoir 1520. The dispensing assembly 120 transmits data related to flow through the flow line to the processor 1504. The processor 1504 uses the flow data to adjust the action of the actuator 1518 in order to increase or decrease flow from the reservoir pump assembly 1519 to approximate the desired dosage and timing. Optionally, a feedback controller 1506 of the processor 1504 may receive data related to the operation of the reservoir pump assembly 1519 for detection of conditions such as open or short circuit faults, or actuator temperature.

Figure 109B:
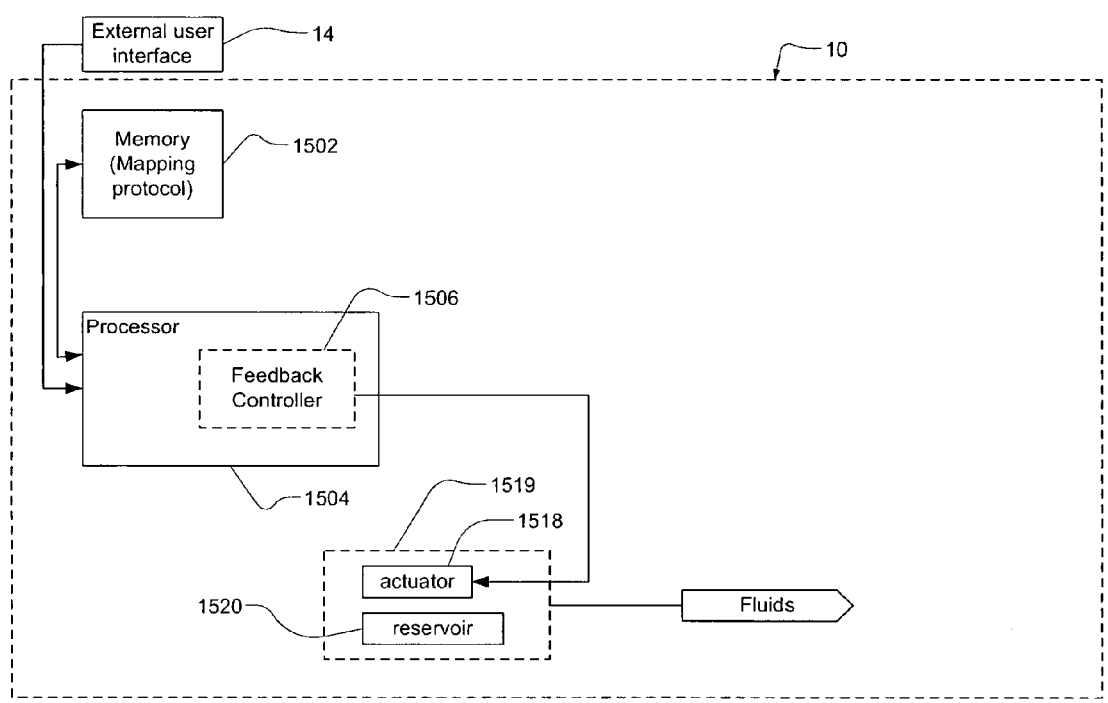

FIG. 109B shows an alternate embodiment of the flow diagram in FIG. 102A. In this embodiment, the lack of dispensing assembly/sensor removes the feedback based on volume of fluid.

Figure 110A:
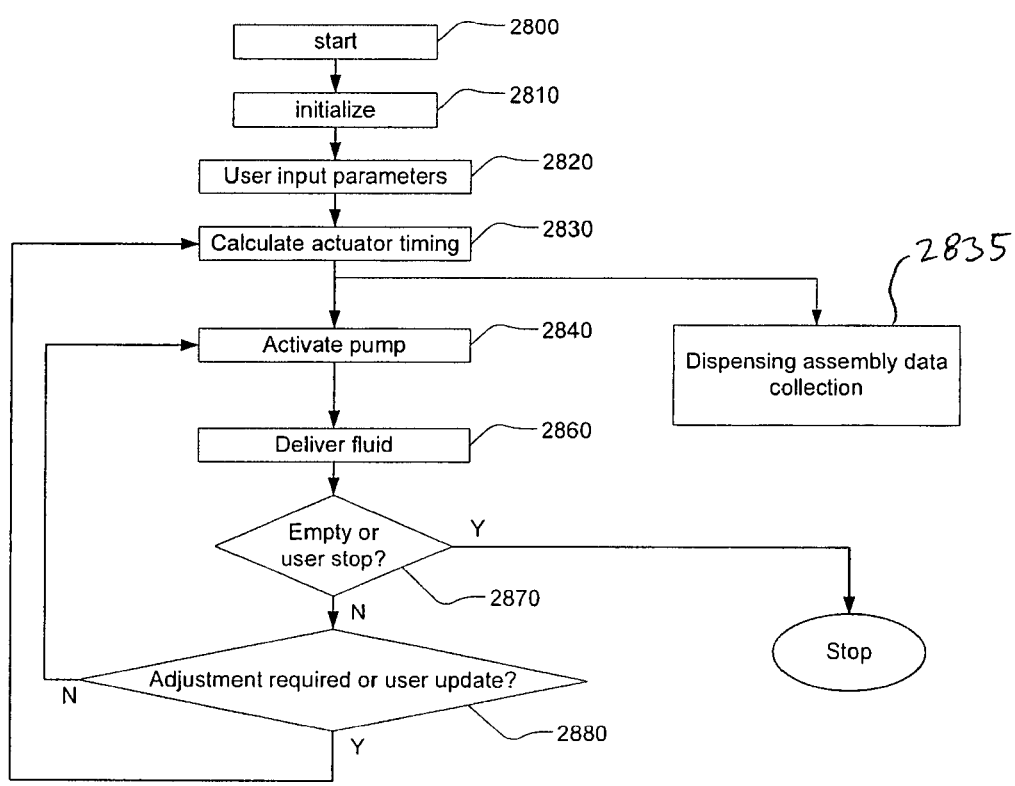

Referring now to FIG. 110A, a flow chart of one embodiment of the overall operation of a fluid delivery device within the fluid delivery system is shown. A user starts 2800 the system using a switch or from an external user interface (step 2800). The system initializes by loading default values, running system tests (step 2810) and obtaining variable parameters such as desired basal and bolus doses. Variable parameters may be selected by the user using the user interface, either using an input device such as a touch screen on the user interface or by loading saved parameters from memory (step 2820). The actuator timing is calculated based on the predicted or calibrated performance of the fluid delivery device (step 2830). The dispensing assembly is initiated at the start of the fluid delivery device activation (step 2840). Dispensing assembly data collection 2835 continues through actuation and delivery. During operation, the dispensing assembly provides data that allows determination of the cumulative volume of fluid that has flowed through the dispensing chamber as well as the flow rate for one or more time periods. The fluid delivery device is activated to cause fluid to flow through the flow line into the dispensing chamber (step 2840). Drug flows from the dispensing chamber to the patient at a rate determined by the impedance of the exit, and in some embodiments, the force exerted by a diaphragm spring, and the force exerted by the pumping assembly (step 2860). The system will stop and the user will be notified if there is a user stop interrupt, a low flow condition, the reservoir is determined to be empty based on predicted cumulative flow or detection by an additional reservoir volume sensor, or any other alarm operation either part of the system or user specified (step 2870). If there is no user stop signal, determination of an empty reservoir or another alarm indicator, then a check is made to determine if an adjustment to the actuator timing is needed due to a deviation between the actual and desired flow rate or due to a change in desired flow rate by the user (step 2880). If no adjustment is needed, the process returns to step 2840. If an adjustment is needed, the process instead returns to step 2830.

Figure 110B:
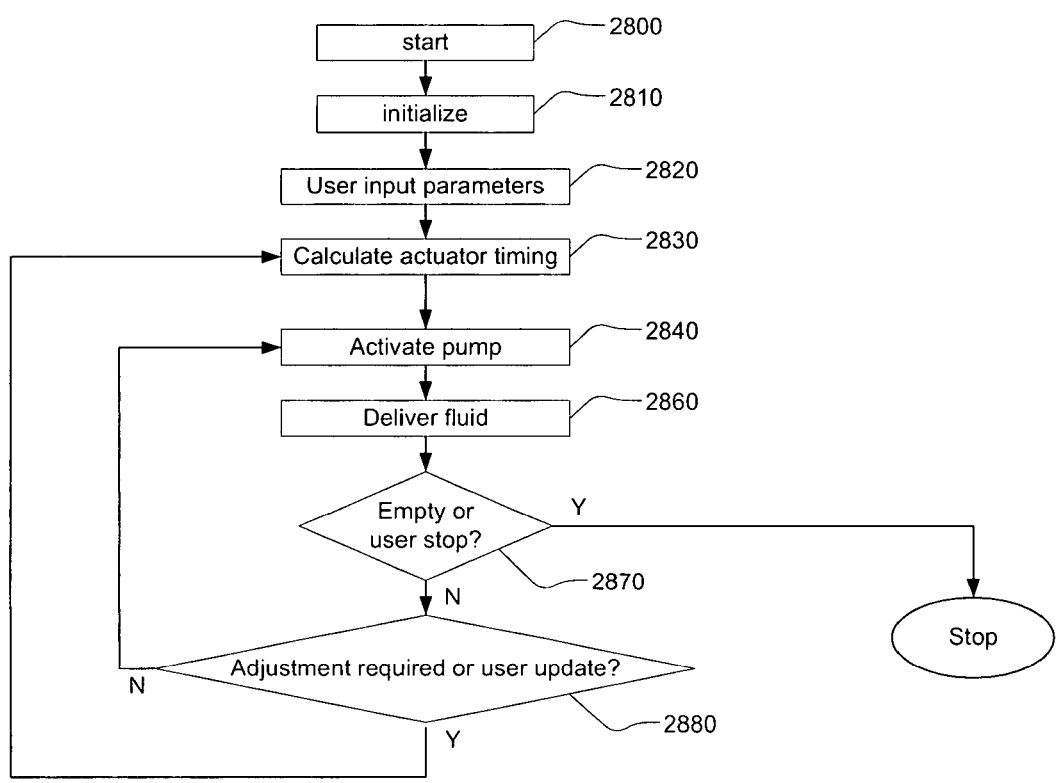

Referring now to FIG. 110B, a flow chart of another embodiment of the overall operation of a fluid delivery device within the fluid delivery system is shown. In this embodiment, the decision to adjust the actuation timing is made based on a user inputted variation or on another feedback. In this embodiment, a dispensing assembly with a sensor for determining volume is not included; thus the adjustments are made based on alternative feedback mechanisms.

Wireless Communication

Figure 111:
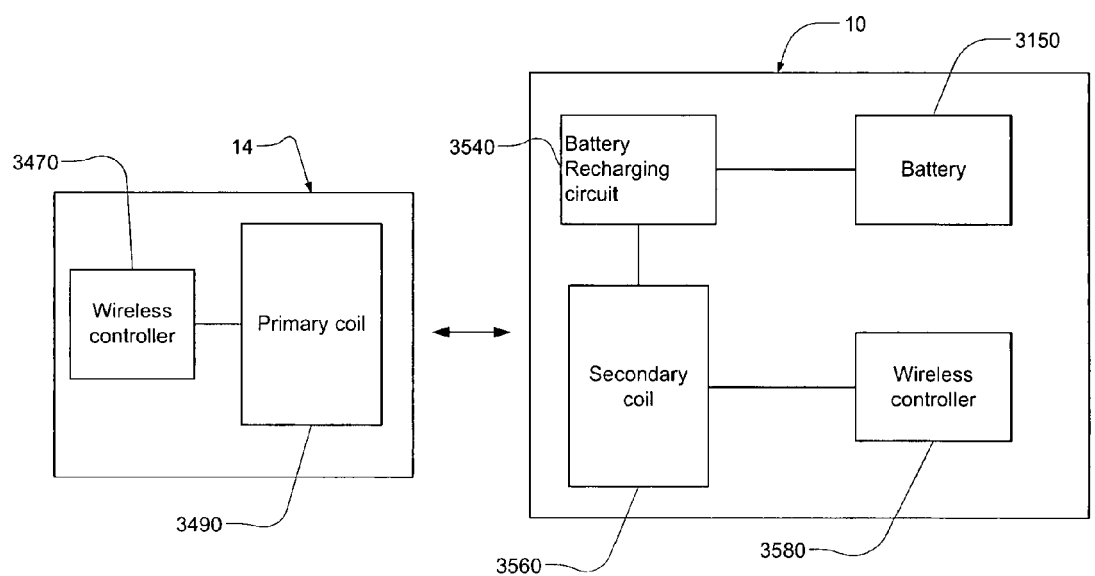

Referring now to FIG. 111 a layout of an embodiment using coils for inductive charging and wireless communication in a fluid delivery system is shown. As previously described, the user interface assembly 14 can be embodied as a hand held user interface assembly 14 that wirelessly communicates with the fluid delivery device 10. A secondary coil (i.e. a solenoid) 3560 may be employed in the fluid delivery device 10 as a wireless transceiver antenna in conjunction with wireless controller 3580. The secondary coil 3560 may also serve as a secondary transformer for recharging the device battery 3150, at least partially, in conjunction with a battery recharging circuit 3540. In this embodiment, the user interface assembly 14 contains a primary coil 3490 for inductively coupling energy to a secondary coil 3560. When the user interface assembly 14 is in close proximity to the fluid delivery device 10, the primary coil 3490 energizes the secondary coil 3560. The energized secondary coil 3560 powers a battery recharging circuit 3540 for recharging the battery 3150 in the fluid delivery device 10. In some embodiments, the primary coil 3490 also functions as an antenna to transmit and receive information from the fluid delivery device 10 in conjunction with a wireless controller 3470.

Figure 112:
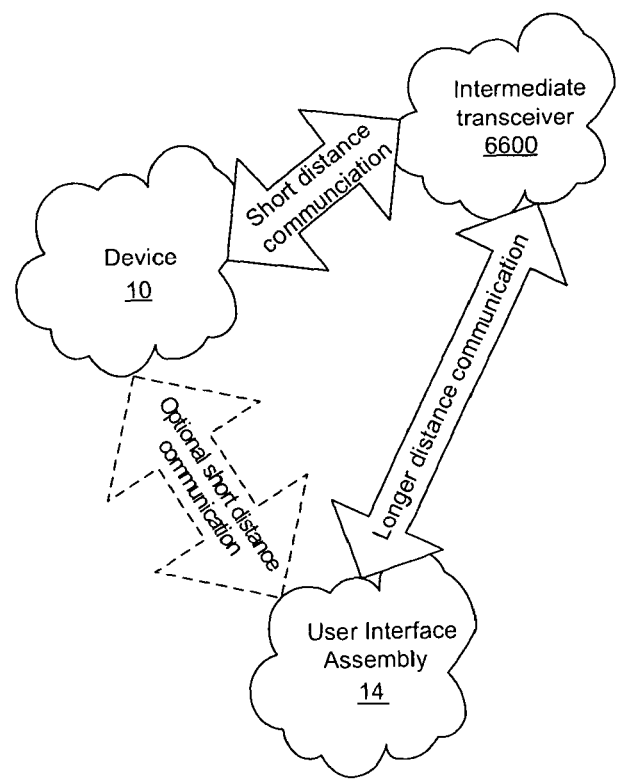

Referring now to FIG. 112, some embodiments include long range wireless communication (e.g., 20-200 ft or more) hardware in the fluid delivery device 10. Thus, the fluid delivery device 10 could be monitored from a distance.

Still referring to FIG. 112, an intermediate transceiver 6600, typically carried by the patient, can provide the benefits of long range communication without increasing the size, weight and power consumption of the fluid delivery device 10. As shown in the data flow diagram of FIG. 112, a wearable fluid delivery device 10 uses short range hardware and associated software to transmit data to, or receive data from, the intermediate transceiver 6600. For example, the device 10 may be equipped to transmit data over distances of approximately 3-10 ft. The intermediate transceiver 6600 may then receive this data and use long range hardware and software to relay this data to a user interface assembly 14. The intermediate transceiver 6600 may also accept control signals from the user interface assembly 14 and relay these signals to the device 10. Optionally, the user interface assembly 14 may also be capable of communicating directly with the fluid delivery device 10, when in range. This direct communication may be configured to occur only when the intermediate transceiver 6600 is not detected, or alternatively, anytime the user interface assembly 14 and the fluid delivery device are within range of each other.

Many types of data may be transmitted in this way, which include, but are not limited to:

Data related to the timing of pump actuation and volume measurements and other data from the dispensing assembly may be transmitted to the intermediate transceiver 6600 and, in turn, to the user interface assembly 14;

Alarm signals may be transmitted to and from the fluid delivery device 10;

Signals to confirm the receipt of data may be transmitted from the user interface 14 to the intermediate transceiver 6600 and from the intermediate transceiver 6600 to the fluid delivery device 10;

Control signals to change the operating parameters of the device 10 may be transmitted from the user interface assembly 14 to the fluid delivery device 10 using the intermediate transceiver 6600.

Figure 113:
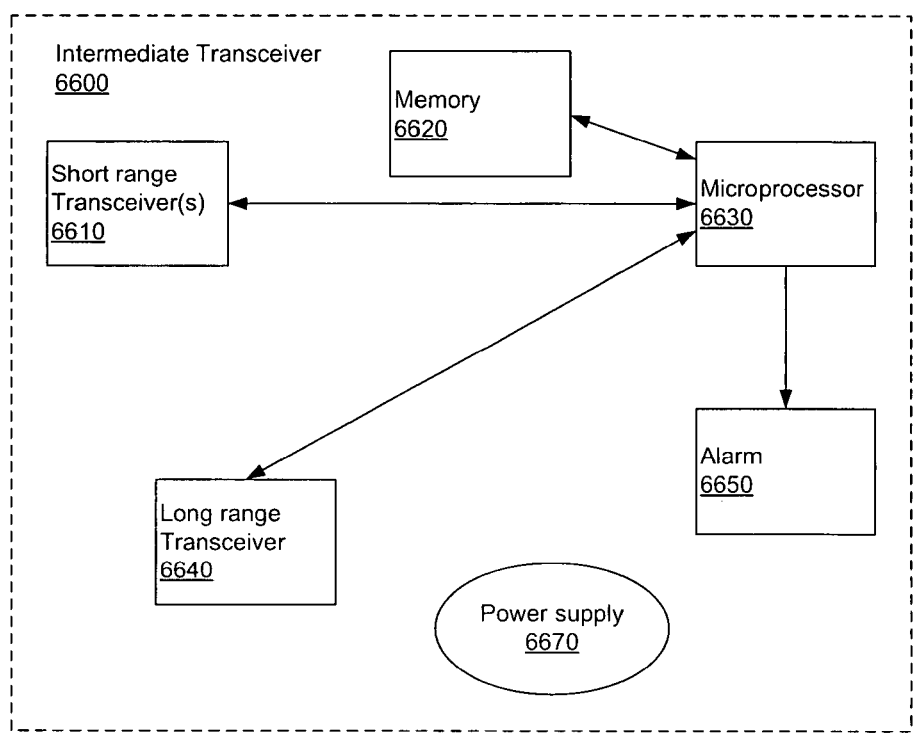

Referring now to FIG. 113, a plan diagram of a specific embodiment of an intermediate transceiver 6600 is shown. A short range transceiver 6610 communicates with a nearby fluid delivery device. The short range transceivers of the device and the intermediate transceiver 6600 may communicate using one or more of many protocols and transmission frequencies known to be useful for short range communication, e.g. radio frequency transmission. Data received by the intermediate transceiver 6600 is conveyed to a microprocessor 6630, which may store the data in memory 6620 (e.g., a flash memory chip), and retrieve the data as needed. The microprocessor 6630 is also connected to a long range transceiver 6640, which is in data communication with the user interface. For example, the intermediate transceiver 6600 and user interface assembly may operate on the Bluetooth standard which is a spread-spectrum protocol that uses a radio frequency of about 2.45 MHz and may operate over a distance of up to about 30 feet. The Zigbee standard is an alternative standard that operates in the ISM bands around 2.4 GHz, 915 MHz, and 868 MHz. However, any wireless communication could be used.

Optionally, the microprocessor 6630 analyzes received data to detect the presence of malfunctions or maintenance needs associated with the device. Some examples of fault conditions include, but are not limited to:

a lack of received data for a time period that exceeds a set limit;
a lack of data receipt confirmation signal from the device or the user interface assembly;
an overflow or near overflow condition of the appliance memory 6620; low power;
overly high, low or improperly timed volume measurements received from the fluid delivery device 10.

Based on this fault analysis, the microprocessor 6630 may trigger an alarm 6650 (e.g., a bell or buzzer). The microprocessor 6630 may also communicate an alarm condition to a remote device. The remote device may be, for example, the user interface assembly using the long range transceiver 6640, the fluid delivery device 10 using the short range transceiver, or both the user interface assembly and fluid delivery device. Upon receiving an alarm signal, the user interface assembly may then relay the alarm signal over longer distances to a medical professional or patient guardian (e.g., by pager or telephone call or other methods of communication).

The power supply 6670 may be rechargeable, and may store sufficient energy to operate continuously for a period of time, for example, at least 10 hours. However, the operation time will vary based on use and device. The size of the fluid delivery device may be reduced so that it may easily be carried in a pocket, purse, briefcase, backpack or the like. One embodiment of the device includes a means to withstand routine shocks or spills. Additional features may be included in some embodiments, including, but not limited to, decorative features, or any of a wide range of consumer electronics capabilities such as the ability to play video games, send and receive instant messages, watch digital video, play music, etc. Third party controls may be included to remove or limit the use of such functions during some or all hours of the day. Alternately, the device may be as small and simple as possible, and only serve to repeat short range signals over a longer range. For example, the memory and analysis capability may be omitted.

Figure 114:
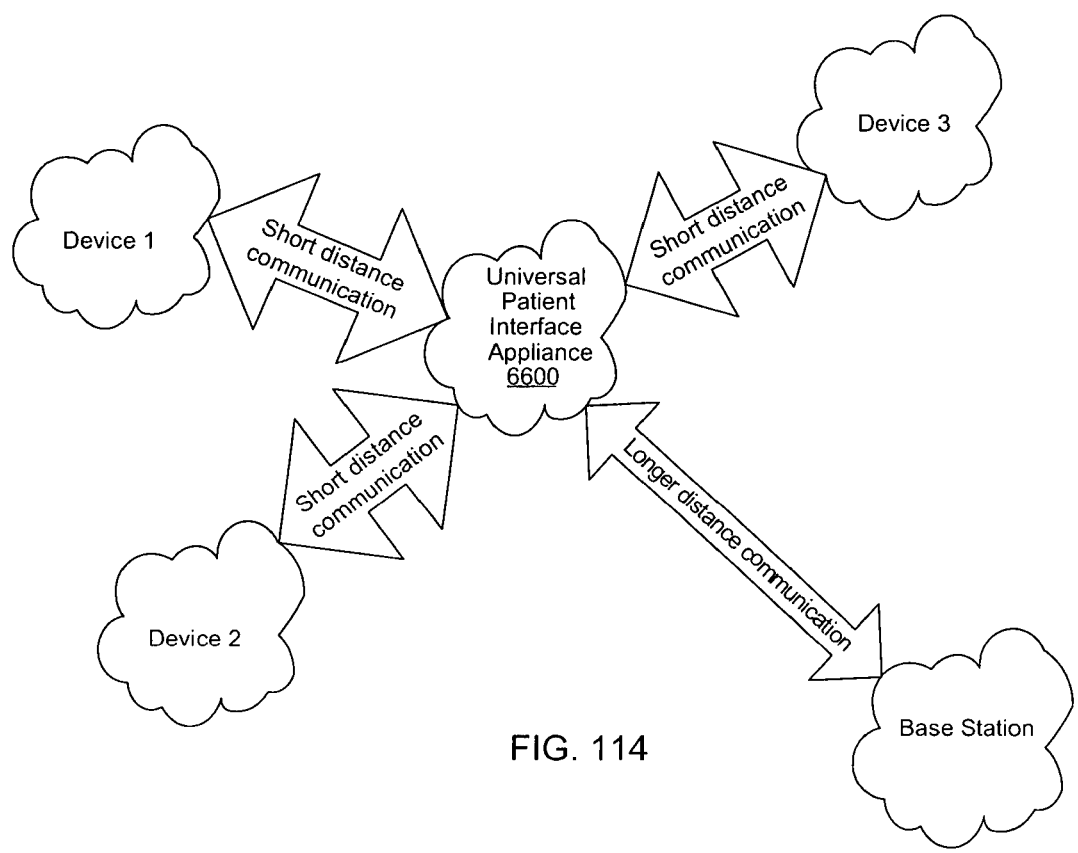

Referring now to FIG. 114, a data flow diagram for an embodiment of the system is shown. An intermediate transceiver 6600 is shown operating as a universal patient interface that engages in short range communication with multiple devices and relays information from those devices over a long range to one or more user interfaces associated with those devices. Examples of devices include wearable, implantable or internal medical devices including a fluid delivery system, a glucose sensor, a knee joint with an integrated strain sensor, an instrumented enteric probe in pill form, a defibrillator, a pacemaker, and other wearable therapeutic delivery devices. Since different types of devices and devices from different manufacturers may utilize differing short range communication standards and frequencies, the intermediate transceiver 6600 may include hardware (e.g., multiple antennas and circuitry), and software to support multiple protocols.

Battery Recharger

Figure 115:
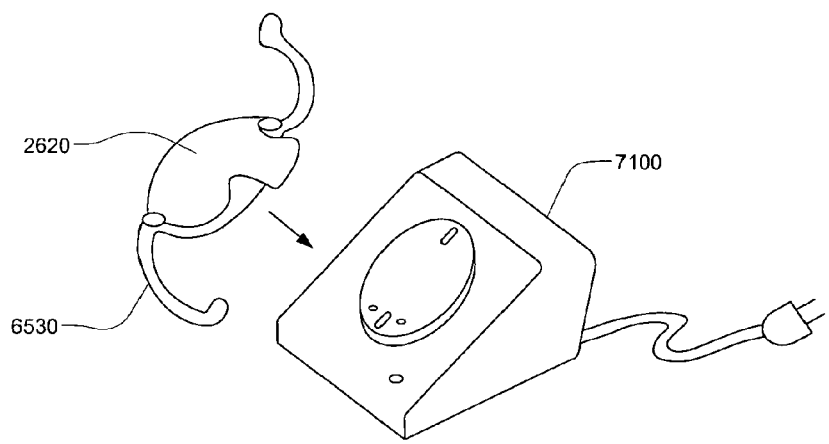
Figure 116:
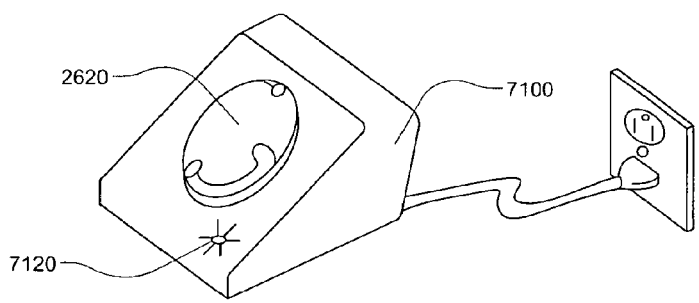

Referring now to FIGS. 115 and 116. One embodiment of an apparatus is shown for recharging the battery 7100. In FIG. 15, the top, non-disposable portion of a fluid delivery device 2620 is shown disconnected from the base, disposable portion of a fluid delivery device. The battery recharger 7100 is used to recharge the battery (not shown) in the top 2620. In FIG. 116, the top 2620 is shown on the battery recharger 7100. The latches 6530 are shown closed, connecting the top 2620 to the battery recharger 7100. Thus, the latch 6530 used to connect a top portion 2620 to a base portion (not shown) is also used to connect the top 2620 to the battery recharger 7100. Docking may establish a direct power connection, or power may be transferred by way of inductive coupling. Also, in some embodiments of the system, the patient employs multiple non-disposable portions 2620 in rotation; i.e., recharging one non-disposable portion 2620, while using a second non-disposable portion (not shown).

The various embodiments described herein include different types and configurations of elements such as, for example, pump architectures, pump actuators, volume sensors, flow restrictors, reservoirs (and reservoir interfaces), sharps inserters, housings, latching mechanisms, user interfaces, on-board peripherals (e.g., controllers, processors, power sources, network interfaces, sensors), and other peripherals (e.g., handheld remote controller, base station, repeater, filling station). It should be noted that alternative embodiments may incorporate various combinations of such elements. Thus, for example, a pump architecture described with reference to one embodiment (e.g., the pump shown and described with reference to FIGS. 15A-15D) may be used with any of the various configurations of pump actuators (e.g., single shape-memory actuator with single mode of operation, single shape-memory actuator with multiple modes of operation, multiple shape-memory actuators of the same size or different sizes), and may be used in devices with various combinations of other elements (or absence of other elements) and/or any of the various flow restrictors.

Furthermore, while various embodiments are described herein with reference to a non-pressurized reservoir, it should be noted that a pressurized reservoir may be used in certain embodiments or under certain conditions (e.g., during priming and/or air purging). Among other things, a pressurized reservoir might facilitate filling of the pump chamber, for example, following retraction of the pump actuation member 54 shown and described with reference to FIGS. 15A-15D.

Additionally, while various embodiments are described herein with reference to a pump motor disposed in a reusable portion of a housing, it should be noted that a pump and/or a pump motor may alternatively be situated in the disposable portion, for example, along with various components that come into contact with the fluid. As with some of the other motors described herein, a motor disposed in the disposable portion may include one or more shape-memory actuators.

It should be noted that section headings are included for convenience and are not intended to limit the scope of the invention.

In various embodiments, the herein disclosed methods including those for controlling and measuring flow of a fluid and for establishing communication amongst linked components may be implemented as a computer program product for use with a suitable controller or other computer system (referred to generally herein as a "computer system"). Such implementations may include a series of computer instructions fixed either on a tangible medium, such as a computer readable medium (e.g., a diskette, CD-ROM, ROM, EPROM, EEPROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions may embody desired functionalities previously described herein with respect to the system. Those skilled in the art should appreciate that such computer instructions can be written in a number of programming languages for use with many computer architectures or operating systems.

Furthermore, such instructions may be stored in any memory device, such as semiconductor, magnetic, optical or other memory devices, and may be transmitted using any communications technology, such as optical, infrared, acoustic, radio, microwave, or other transmission technologies. It is expected that such a computer program product may be distributed as a removable medium with accompanying printed or electronic documentation (e.g., shrink wrapped software), preloaded with a computer system (e.g., on system ROM, EPROM, EEPROM, or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or substantially in software (e.g., a computer program product).

It should be noted that dimensions, sizes, and quantities listed herein are exemplary, and the present invention is in no way limited thereto. In an exemplary embodiment of the invention, a patch-sized fluid delivery device may be approximately 6.35 cm (~2.5 in) in length, approximately 3.8 cm (~1.5 in) in width, and approximately 1.9 cm (~0.75 in) in height, although, again, these dimensions are merely exemplary, and dimensions can vary widely for different embodiments.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. An inserter system for connection of an infusion device in fluid-flow communication with the inlet or outlet port of a reservoir and for insertion of a sensor, the insertion system comprising:

a bridge comprising a cover for the infusion device and a cover for the sensor;

an infusion device introduction needle and a sensor introduction needle supported by the bridge for movement between a retracted position and an extended position;

an inserter housing for accommodating the bridge and for movement of the infusion device introduction needle and the sensor introduction needle between the retracted position and the extended position, the covers having a needle passage through which the infusion device introduction needle and a sensor introduction needle extends when the infusion device introduction needle and a sensor introduction needle are in the retracted position and moving toward the extended position;

an infusion device about the infusion device introduction needle and moveable with the infusion device introduction needle between the retracted position and the extended position, the infusion device having a central passage through which the infusion device introduction needle extends when the infusion device introduction needle is in the retracted position and moving toward the extended position;

a sensor about the sensor introduction need and moveable with the sensor introduction needle between the retracted position and the extended position, the sensor having a central passage through which the sensor introduction needle extended when the sensor introduction needle is in the retracted position and moving toward the extended position;

an infusion device release located on the bridge for releasing the infusion device in the extended position upon the infusion device introduction needle and infusion device being moved to the extended position; and a sensor release located on the bridge for releasing the sensor in the extended position upon the sensor introduction needle and sensor being moved to the extended position, wherein the infusion device introduction needle and the sensor introduction needle remain attached to the bridge.

2. The inserter system of claim 1, wherein the infusion device is located in a position adapted to extend into a user's when the infusion device introduction needle and infusion device are locked in the extended position.

3. The inserter system of claim 1, wherein the infusion device introduction needle is located in a position adapted to pierce a user's skin wherein the infusion device introduction needle is moved to the extended position, and wherein the infusion device introduction needle is located in a position external to a user's skin, when the infusion device introduction needle is in the retracted position.

4. The inserter system of claim 1, wherein the inserter housing a spring.

5. The inserter system of claim 1, wherein the bridge configured to be removably attached to the inserter housing wherein the inserter housing for imparting a force on the bridge in a direction for moving the infusion device introduction needle and the sensor introduction needle needle from the a retracted position to the extended position.

6. The inserter system of claim 1, wherein:

The inserter housing comprising an actuation lever for releasing a spring to impart a force on the bridge and wherein the force moves the infusion device introduction needle and the sensor introduction needle in a direction for moving the infusion device introduction needle and the sensor introduction needle from the a retracted position to the extended position.

7. The inserter system of claim 1, wherein the inserter device configured to actuate the infusion device release and the sensor release when the infusion device introduction needle and the sensor introduction needle are in the extended position.

8. The inserter system of claim 1, wherein the infusion device release and the sensor release are actuated through apertures and release the infusion device and the sensor device from the bridge when the infusion device introduction needle and the sensor introduction needle are moved to the extended position.

9. The inserter system of claim 1, wherein the bridge comprises:
 a body having two ends, an infusion device end and a sensor end, wherein the infusion device and the sensor removably attach to the infusion device end and the sensor end respectively; and
 the infusion device introduction needle and the sensor introduction attached to the needle infusion device end and the sensor end respectively.

10. A delivery device for delivery of infusion medium, the delivery device comprising a reservoir for containing an infusion medium and having an outlet port, a fluid conduit connected in fluid flow communication with the outlet port of the reservoir, a drive device operatively connectable to the reservoir, for selectively driving the infusion medium from the reservoir and an inserter system according to claim 1, wherein the infusion device is connected in fluid flow communication with the fluid conduit when the infusion device introduction needle the infusion device are in the extended position.

11. The inserter system of claim 1, wherein the inserter housing further comprising an actuation lever operable from outside of the inserter housing, for selectively releasing the bridge to move under the force of a spring from the retracted position to the extended position.

12. The inserter system of claim 11, wherein the inserter housing further comprising a cocking lever connecting cocking linkages to a hammer cocking slide, wherein the cocking lever moves the cocking slide to a charged position.

13. The inserter system of claim 12, wherein the inserter housing further comprising a power spring connected to the hammer cocking slide to a trigger, wherein the trigger, when compressed, provides downward force for moving the bridge from the retracted position to the extended position.

14. The inserter system of claim 13, wherein the inserter housing further comprising a trigger hammer disposed under the hammer cocking slide and between a pair of cocking linkages, wherein the trigger hammer transmits energy released from the power spring when the trigger is released and the trigger hammer impacts a bridge bolt, linked to the bridge.

\* \* \* \* \*